(12) United States Patent
Otsu et al.

(10) Patent No.: US 10,017,691 B2
(45) Date of Patent: Jul. 10, 2018

(54) ORGANIC ELECTROLUMINESCENT ELEMENT, DISPLAY DEVICE AND LIGHTING DEVICE

(71) Applicant: KONICA MINOLTA, INC., Tokyo (JP)

(72) Inventors: Shinya Otsu, Tokyo (JP); Masato Nishizeki, Tokyo (JP); Eisaku Katoh, Tokyo (JP); Tomohiro Oshiyama, Tokyo (JP); Dai Ikemizu, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 407 days.

(21) Appl. No.: 14/795,588

(22) Filed: Jul. 9, 2015

(65) Prior Publication Data

US 2015/0318499 A1 Nov. 5, 2015

Related U.S. Application Data

(63) Continuation of application No. 12/598,774, filed as application No. PCT/JP2008/058939 on May 15, 2008, now abandoned.

(30) Foreign Application Priority Data

May 16, 2007 (JP) ................. 2007-130329
Oct. 31, 2007 (JP) ................. 2007-283247

(51) Int. Cl.
| | | |
|---|---|---|
| H01L 51/54 | (2006.01) |
| H01L 51/56 | (2006.01) |
| C09K 11/06 | (2006.01) |
| H01L 51/00 | (2006.01) |
| H01L 51/50 | (2006.01) |
| C07F 15/00 | (2006.01) |
| H05B 33/14 | (2006.01) |

(52) U.S. Cl.
CPC .......... *C09K 11/06* (2013.01); *C07F 15/0033* (2013.01); *H01L 51/0072* (2013.01); *H01L 51/0073* (2013.01); *H01L 51/0085* (2013.01); *H01L 51/0087* (2013.01); *H01L 51/504* (2013.01); *H01L 51/5016* (2013.01); *H01L 51/5036* (2013.01); *H01L 51/56* (2013.01); *H05B 33/14* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *C09K 2211/1466* (2013.01); *C09K 2211/1475* (2013.01); *C09K 2211/185* (2013.01); *H01L 51/0037* (2013.01); *H01L 2251/308* (2013.01); *H01L 2251/552* (2013.01); *Y02B 20/181* (2013.01)

(58) Field of Classification Search
None
See application file for complete search history.

(56) References Cited

U.S. PATENT DOCUMENTS

| | | |
|---|---|---|
| 2,130,262 A | 3/1938 | Burlin |
| 2,723,430 A | 11/1955 | Paillard |
| 3,884,403 A | 5/1975 | Brewer |
| 3,938,166 A | 2/1976 | Sloop |
| 4,058,242 A | 11/1977 | Brewer |
| 4,328,917 A | 5/1982 | Reeberg |
| 4,416,405 A | 11/1983 | Caillouet |
| 4,419,794 A | 12/1983 | Horton, Jr. et al. |
| 4,461,411 A | 7/1984 | Harrow |
| 4,473,177 A | 9/1984 | Parandes |
| 4,714,184 A | 12/1987 | Young et al. |
| 5,014,892 A | 5/1991 | Copeland |
| 5,172,838 A | 12/1992 | Rowell et al. |
| 5,251,800 A | 10/1993 | Leenders |
| 5,343,050 A * | 8/1994 | Egusa et al. .......... H01L 51/005 257/103 |
| 5,375,749 A | 12/1994 | Oliva |
| 5,850,954 A | 12/1998 | Kim |
| 5,850,996 A | 12/1998 | Liang |
| 6,097,147 A | 8/2000 | Baldo et al. |
| 7,147,937 B2 | 12/2006 | Lussier et al. |
| 7,162,281 B2 | 1/2007 | Kim |
| 7,624,901 B1 | 12/2009 | Mozes |
| 7,795,799 B2 | 9/2010 | Mishima |
| 8,007,927 B2 | 8/2011 | Lin et al. |
| 8,080,658 B2 | 12/2011 | Iwakuma et al. |
| 8,815,415 B2 | 8/2014 | Tsai et al. |

(Continued)

FOREIGN PATENT DOCUMENTS

| | | |
|---|---|---|
| GB | 871489 A | 6/1961 |
| JP | 63264692 A | 11/1988 |

(Continued)

OTHER PUBLICATIONS

Office Action dated Feb. 11, 2016, issued in the U.S. Appl. No. 12/598,965; Applicant(s): Otsu et al; Total of 14 pages.
Non-Final Office Action (for U.S. Appl. No. 12/598,965) dated Mar. 15, 2012; total of 13 pages.
Final Office Action (for U.S. Appl. No. 12/598,965) dated Jul. 17, 2012; total of 10 pages.
Non-Final Office Action (for U.S. Appl. No. 12/598,965) dated Nov. 19, 2014; total of 20 pages.
Final Office Action (for U.S. Appl. No. 12/598,965) dated May 28, 2015; total of 8 pages.
Non-Final Office Action (for U.S. Appl. No. 12/598,965) dated Sep. 24, 2015; total of 12 pages.

(Continued)

*Primary Examiner* — Marie R. Yamnitzky
(74) *Attorney, Agent, or Firm* — Lucas & Mercanti, LLP

(57) ABSTRACT

A wet process using an organic solvent is used to produce an organic EL element, which has high light emission efficiency, a long light emission life and a small color change when continuously driven, an illuminating device and a display device are provided. Especially, an organic EL element which emits white light and can be manufactured at low cost is provided.

6 Claims, 2 Drawing Sheets

(56) References Cited

U.S. PATENT DOCUMENTS

| | | |
|---|---|---|
| 2001/0019782 A1 | 9/2001 | Igarashi et al. |
| 2001/0053462 A1 | 12/2001 | Mishima |
| 2002/0045061 A1 | 4/2002 | Hosokawa |
| 2003/0072964 A1 | 4/2003 | Kwong et al. |
| 2003/0098323 A1 | 5/2003 | Taylor et al. |
| 2004/0200867 A1 | 10/2004 | Chee |
| 2005/0123792 A1 | 6/2005 | Deaton et al. |
| 2005/0147843 A1 | 7/2005 | Kobayashi et al. |
| 2007/0190359 A1 | 8/2007 | Knowles et al. |
| 2009/0096360 A1 | 4/2009 | Tanaka et al. |
| 2009/0196596 A1 | 8/2009 | Chamberlayne |
| 2010/0054724 A1 | 3/2010 | Chamberlayne |
| 2015/0295184 A1* | 10/2015 | Kaiser et al. ....... H01L 51/0067 257/40 |

FOREIGN PATENT DOCUMENTS

| | | | |
|---|---|---|---|
| JP | 3093796 | B2 | 10/2000 |
| JP | 2000321655 | A | 11/2000 |
| JP | 2001247859 | A | 9/2001 |
| JP | 2003109758 | | 4/2003 |
| JP | 2003116621 | A | 4/2003 |
| JP | 2004067658 | | 3/2004 |
| JP | 2004085450 | | 3/2004 |
| JP | 2004131463 | A | 4/2004 |
| JP | 2004214050 | A | 7/2004 |
| JP | 2005053912 | A | 3/2005 |
| JP | 2005108572 | A | 4/2005 |
| JP | 2005255986 | A | 9/2005 |
| JP | 2005255992 | A | 9/2005 |
| JP | 2005259687 | A | 9/2005 |
| JP | 2006028101 | A | 2/2006 |
| JP | 2006032883 | A | 2/2006 |
| JP | 2006290988 | A | 10/2006 |
| JP | 2007091718 | A | 4/2007 |
| JP | 2008072538 | A | 3/2008 |
| JP | 2008075517 | A | 4/2008 |
| JP | 2009526071 | A | 7/2009 |
| JP | 2010515255 | A | 5/2010 |
| WO | 8301370 | A1 | 4/1983 |
| WO | 9406157 | A1 | 3/1994 |
| WO | 9736516 | A1 | 10/1997 |
| WO | 2004085450 | A2 | 10/2004 |
| WO | 2007077810 | A1 | 7/2007 |
| WO | 2007095118 | A2 | 8/2007 |
| WO | 2008072538 | A1 | 6/2008 |
| WO | 2008075517 | A1 | 6/2008 |
| WO | 2008156879 | A1 | 12/2008 |
| WO | 09039292 | A1 | 3/2009 |
| WO | 2009030981 | A2 | 3/2009 |

OTHER PUBLICATIONS

Japanese Notice of Reasons for Refusal—Application #2009-514178. dated Aug. 8, 2012. English translation of Japanese Notice of Reasons for Refusal.

Japanese Notice of Reasons for Refusal—Application #2009-514179. dated Aug. 6, 2012. English translation of Notice of Reasons for Refusal.

Japanese Notice of Reasons for Refusal—Application #2007-283244. dated Aug. 15, 2012. English translation of Reasons for Refusal.

Japanese Notice of Reasons for Refusal—Application #2007-283243. dated Aug. 15, 2012. English translation of Reasons for Refusal.

Japanese Notice of Reasons for Refusal—Application #2009-515131. dated Aug. 8, 2012. English translation of Reasons for Refusal.

Japanese Notice of Reasons for Refusal—Patent Application #2009-514161. dated Feb. 4, 2013. English translation of Reasons for Refusal.

Notification of Reasons for refusal for Japanese Patent Application No. 2009-514178, dated Nov. 12, 2012 together with English translation.

Notification of Reasons for refusal for Japanese Patent Application No. 2009-514179, dated Nov. 12, 2012 together with English translation.

Notification of Reasons for refusal for Japanese Patent Application No. 2009-515131, dated Nov. 8, 2012 together with English translation.

Notification of Reasons for refusal for Japanese Patent Application No. 2009-514178, dated Apr. 8, 2013 together with English translation.

Notification of Reasons for refusal for Japanese Patent Application No. 2009-514179, dated Apr. 8, 2013 together with English translation.

Japanese Office Action for Patent Application No. JP 2009-515161, dated Feb. 4, 2013 together with English translation.

* cited by examiner

ORGANIC ELECTROLUMINESCENT ELEMENT, DISPLAY DEVICE AND LIGHTING DEVICE

CROSS REFERENCE TO RELATED APPLICATIONS

This is a continuation of U.S. application Ser. No. 12/598,774 filed Nov. 4, 2009, which was a 371 of PCT/JP2008/058939 filed May 15, 2008, which claimed the priority of Japanese application Nos. 2007130329 filed May 16, 2007, and 2007283247 filed Oct. 31, 2007, the priority of each of these applications is claimed and each of these applications are incorporated herein by reference.

TECHNICAL FIELD

The present invention relates to an organic electroluminescent element, a display device and a lighting device.

BACKGROUND

Conventionally, an emission type electronic display device includes an electroluminescence display (hereinafter, referred to as an ELD). A constituent element of an ELD includes such as an inorganic electroluminescent element and an organic electroluminescent element (hereinafter, referred to as an organic EL element).

An inorganic electroluminescent element has been utilized as a flat light source, however, it requires a high voltage of alternating current to operate an emission element.

On the other hand, an organic electroluminescent element is an element provided with a constitution comprising an emitting layer containing a emitting substance being sandwiched with a cathode and an anode, and an exciton is generated by an electron and a positive hole being injected into the emitting layer to be recombined, resulting emission utilizing light release (fluorescence phosphorescence) at the time of deactivation of said exciton; the emission is possible at a voltage of approximately a few to a few tens volts, and an organic electroluminescent element is attracting attention with respect to such as superior viewing angle and high visual recognition due to a self-emission type as well as space saving and portability due to a completely solid element of a thin layer type.

However, in an organic electroluminescence in view of the future practical application, desired has been development of an organic EL element which efficiently emits at a high luminance with a low electric consumption.

In Japanese Patent No. 3093796, a slight amount of a fluorescent substance has been doped in a stilbene derivative, a distyrylarylene derivative or a tristyrylarylene derivative, to achieve improved emission luminance and a prolonged lifetime of an element.

Further, there are known such as an element having an organic emitting layer comprising a 8-hydroxyquinoline aluminum complex as a host compound which is doped with a slight amount of a fluorescent substance (for example, JP-A 63-264692) and an element having an organic emitting layer comprising a 8-hydroxyquinoline aluminum complex as a host compound which is doped with quinacridone type dye (for example, JP-A 3-255190).

In the case of utilizing emission from an excited singlet as described above, since a generation ratio of a singlet exciton to a triplet exciton is ⅓, that is, a generation probability of an emitting exciton species is 25% and a light taking out efficiency is approximately 20%, the limit of an external quantum efficiency ($\eta$ext) of taking out light is said to be 5%.

However, since an organic EL element which utilizes phosphorescence from an excited triplet has been reported from Princeton University (M. A. Baldo et al., Nature vol. 395, pp. 151-154 (1998)), researches on materials exhibiting phosphorescence at room temperature have come to be active.

For example, it is also disclosed in A. Baldo et al., Nature, vol. 403, No. 17, pp. 750-753 (2000), and U.S. Pat. No. 6,097,147.

Since the upper limit of internal quantum efficiency becomes 100% by utilization of an excited triplet, which is principally 4 times of the case of an excited singlet, it may be possible to achieve almost the same ability as a cooled cathode ray tube to attract attention also for an illumination application.

For example, in such as S. Lamansky et al., J. Am. Chem. Soc., vol. 123, p. 4304 (2001), many compounds mainly belonging to heavy metal complexes such as iridium complexes have been synthesized and studied.

Further, in the aforesaid, A. Baldo et al., Nature, vol. 403, No. 17, pp. 750-753 (2000), utilization of tris(2-phenylpyridine)iridium as a dopant has been studied.

In addition to these, M. E. Tompson et al., at The 10th International Workshops on Inorganic and Organic Electroluminescence (EL'00, Hamamatsu), have studied to utilize $L_2Ir(acac)$ such as $(ppy)_2Ir(acac)$ as a dopant, Moon-Jae Youn. Og., Tetsuo Tsutsui et al., also at The 10th International Workshops on Inorganic and Organic Electroluminescence (EL'00, Hamamatsu), have studied utilization of such as tris(2-(p-tolyl)pyridine)iridium ($Ir(ptpy)_3$) and tris(benzo[h]quinoline)iridium ($Ir(bzq)_3$) (herein, these metal complexes are generally referred to as orthometalated iridium complexes.).

Further, in also the aforesaid, S. Lamansky et al., J. Am. Chem. Soc., vol. 123, p. 4304 (2001), or in JP-A No. 2001-247859, studies have been carried out to prepare an element utilizing various types of iridium complexes.

Further, to obtain high emission efficiency, Ikai et al., at The 10th International Workshops on Inorganic and Organic Electroluminescence (EL'00, Hamamatsu) utilized a hole transporting compound as a host of a phosphorescent compound. Further, M. E. Tompson et al. utilized various types of electron transporting materials as a host of a phosphorescent compound doped with a new iridium complex.

An orthometalated complex provided with platinum instead of iridium as a center metal is also attracting attention. With respect to these types of complexes, many examples having a characteristic ligand are known.

In any case, emission luminance and emission efficiency are significantly improved compared to conventional elements because the emitting light arises from phosphorescence, however, there has been a problem of a poor emission lifetime of the element compared to conventional elements.

Thus described, it is hard to achieve an emission of a short wavelength and an improvement of an emission lifetime of the element for a phosphorescent emission material provided with a high efficiency. At present state, it cannot be achieved a level of a practical use.

In order to realize a short wavelength, the following were disclosed: to incorporate an electron withdrawing group such as a fluorine atom, a trifluoromethyl group or a cyano group in phenyl pyridine ring as a substituent; and to introduce a picolinic acid ligand or a pyrazabole ligand.

However, although a short wavelength blue emission was achieved by using the aforesaid ligand in the light emitting material with high emission efficiency, the lifetime of the element was found to be greatly decreased. As a result, the improvement of a trade-off of these properties has been required.

There was disclosed that a metal complex containing phenylpyrazole as a ligand was a light emitting material which emits light of a short wavelength (for example, refer to Patent Documents 1 and 2). Further, there was disclosed a metal complex formed with a ligand having a partial structure in which a five-membered ring of phenylpyrazole is condensed with a six-membered ring (for example, refer to Patent Documents 3 and 4).

Recently, it was reported that complexes with a ligand of a condensed aromatic compound having 18π electrons exhibited to be effective as a blue emitting material (US 2007/0190359). It was that the basic molecular structure of these complexes can produce an emission light of a short wavelength. There is no need to incorporate an electron withdrawing substituent, which is a factor to destabilize the exited state of the molecule, for realizing a dopant to produce a blue light. As a result the complex was found to be stable.

In addition, when a mixed color or a white color is intended to produce by using an EL element containing two or more dopants, it was a problem to adjust the ratio of each dopant while emitting of light with high efficiency. I particular, when an element was continuously driven, it was a problem that it is easy to produce a color shift.

Conventionally, as a way of acquiring a white light, the following two ways are known. One way of acquiring a white light is by arranging plural EL elements emitting two color or 3 color or more at a plane, and making light emitting simultaneously. The other way is to incorporate emitting bodies to produce two color or 3 color or more into a single element, and acquiring a white light from a single element. A white light emitting element by using the latter way was desired from the viewpoints of the design of apparatus and a manufacturing cost.

Patent Document 1: WO 2004/085450
Patent Document 2: JP-A NO. 2005-53912
Patent Document 3: JP-A No. 2006-28101
Patent Document 4: U.S. Pat. No. 7,147,937

DISCLOSURE OF THE INVENTION

Problems to be Solved by the Invention

The present invention was achieved by considering the above-described problems. An object of the present invention is to provide an organic EL element material which has high emission efficiency and long emission lifetime with a decreased color shift after prolonged continuous driving, and to provide a lighting device and a display device.

Means to Solve the Problems

An object of the present invention described above has been achieved by the following constitutions.
1. An organic electroluminescent element comprising a light emitting layer sandwiched between an anode and a cathode, wherein the light emitting layer contains at least two phosphorescence emitting metal complexes, provided that one of the two phosphorescence emitting metal complexes has a ligand made of a six-membered aromatic compound condensed with three or more rings each having a five or a six-membered aromatic ring.
2. The organic electroluminescent element of the aforesaid item 1, wherein the one of the two phosphorescence emitting metal complexes has a partial structure represented by one of the following Formulas (1) to (4).

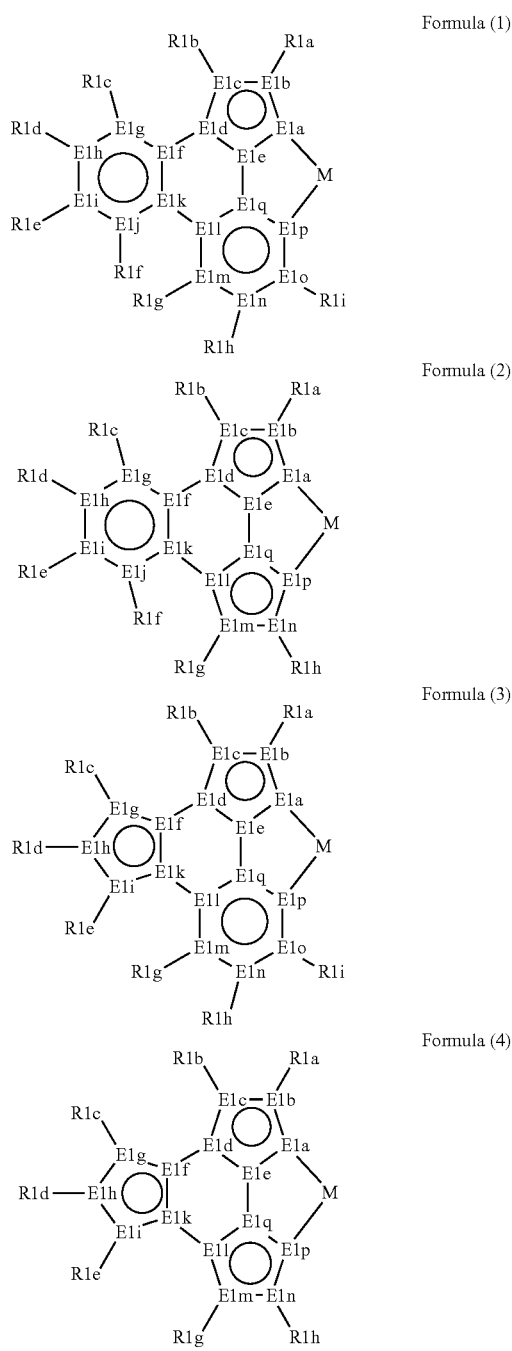

Formula (1)

Formula (2)

Formula (3)

Formula (4)

(In Formula (1): E1a represents a nitrogen atom; E1b and E1c represent a carbon atom, a nitrogen atom, an oxygen atom or a sulfur atom; E1d and E1e represent a carbon atom or a nitrogen atom; E1f represents a carbon atom; E1g to E1j represent a carbon atom or a nitrogen atom; E1k and E1l represent a carbon atom; E1m to E1o represent a carbon atom or a nitrogen atom; E1p and E1q represent a carbon atom;

R1a and R1b represent a hydrogen atom or a substituent when E1b and E1c represent the carbon atom or the nitrogen atom having a bond of —N<, R1a and R1b represent null when E1b and E1c represent the nitrogen atom having a bond of —N=, the oxygen atom or the sulfur atom; and R1c to R1i represent a hydrogen atom or a substituent; and M represents a transition metal of Group 8 to Group 10 in the periodic table, in Formula (2): E1a represents a nitrogen atom; E1b and E1c represent a carbon atom, a nitrogen atom, an oxygen atom or a sulfur atom; E1d and E1e represent a carbon atom or a nitrogen atom; E1f represents a carbon atom; E1g to E1j represent a carbon atom or a nitrogen atom; E1k represents a carbon atom; E1l represents a carbon atom or a nitrogen atom; E1m and E1n represent a carbon atom, a nitrogen atom, an oxygen atom or a sulfur atom; E1p represents a carbon atom; E1q represents a carbon atom or nitrogen atom;

R1a, R1b, R1g and R1h represent a hydrogen atom or a substituent when E1b, E1c, E1m and E1n represent the carbon atom or the nitrogen atom having a bond of —N<, R1a, R1b, R1g and R1h represent null when E1b, E1c, E1m and E1n represent the nitrogen atom having a bond of —N=, the oxygen atom or the sulfur atom; and R1c to R1f represent a hydrogen atom or a substituent; and M represents a transition metal of Group 8 to Group 10 in the periodic table, in Formula (3): E1a represents a nitrogen atom; E1b and E1c represent a carbon atom, a nitrogen atom, an oxygen atom or a sulfur atom; E1d and E1e represent a carbon atom or a nitrogen atom; E1f and E1k represent a carbon atom or nitrogen atom; E1g to E1i represent a carbon atom, a nitrogen atom, an oxygen atom or a sulfur atom; E1l represent a carbon atom; E1m to E1o represent a carbon atom or a nitrogen atom; E1p and E1q represent a carbon atom;

R1a, R1b, R1c, R1d and R1e represent a hydrogen atom or a substituent when E1b, E1c, E1g, E1h and E1i represent the carbon atom or the nitrogen atom having a bond of —N<, R1a, R1b, R1c, R1d and R1e represent null when E1b, E1c, E1g, E1h and E1i represent the nitrogen atom having a bond of —N=, the oxygen atom or the sulfur atom; and R1g to R1i represent a hydrogen atom or a substituent; and M represents a transition metal of Group 8 to Group 10 in the periodic table, in Formula (4): E1a represents a nitrogen atom; E1b and E1c represent a carbon atom, a nitrogen atom, an oxygen atom or a sulfur atom; E1d and E1e represent a carbon atom or a nitrogen atom; E1f and E1k represents a carbon atom or nitrogen atom; E1g to E1i represent a carbon atom, a nitrogen atom, an oxygen atom or a sulfur atom; E1l represents a carbon atom or nitrogen atom; E1m and E1n represent a carbon atom, a nitrogen atom, an oxygen atom or a sulfur atom; E1p represent a carbon atom; E1q represents a carbon atom or a nitrogen atom;

R1a to R1e, R1g and R1h represent a hydrogen atom or a substituent when E1b, E1c, E1g, E1h, E1i, E1m and E1n represent the carbon atom or the nitrogen atom having a bond of —N<, R1a to R1e, R1g and R1h represent null when E1b, E1c, E1g, E1h, E1i, E1m and E1n represent the nitrogen atom having a bond of —N=, the oxygen atom or the sulfur atom; and M represents a transition metal of Group 8 to Group 10 in the periodic table.)

3. The organic electroluminescent element of the aforesaid items 1 or 2, wherein the two phosphorescence emitting metal complexes each emits a light of a different hue, and the phosphorescence emitting metal complex having a ligand made of a six-membered aromatic compound condensed with three or more rings each having a five or a six-membered aromatic ring emits a blue light.

4. The organic electroluminescent element of any one of the aforesaid items 1 to 3, wherein a difference of highest occupied molecular orbitals (HOMO) of the at least two phosphorescence emitting metal complexes is 0.5 eV or less.

5. The organic electroluminescent element of any one of the aforesaid items 1 to 4, comprising at least two light emitting layers as constituting layers, provided that each of the two phosphorescence emitting metal complexes are contained in a different light emitting layer.

6. The organic electroluminescent element of any one of the aforesaid items 1 to 5, wherein the aforesaid M represents platinum or iridium.

7. The organic electroluminescent element of any one of the aforesaid items 1 to 6, wherein at least one of the light emitting layer is produced with a wet process.

8. The organic electroluminescent element of any one of the aforesaid items 1 to 7, emitting a white light.

9. A display device comprising the organic electroluminescent element of any one of the aforesaid items 1 to 8.

10. A lighting device comprising the organic electroluminescent element of any one of the aforesaid items 1 to 8.

11. A method for producing an organic electroluminescent element comprising a light emitting layer sandwiched between an anode and a cathode, the method comprising a step of:

preparing the light emitting layer with a wet process using an organic solvent selected from the group consisting of a ketone, a fatty acid ester, a halogenated hydrocarbon, an aromatic hydrocarbon, an aliphatic hydrocarbon, dimethylformamide (DMF) and dimethylsulfoxide (DMSO), wherein the light emitting layer emits a white light and contains at least two phosphorescence emitting metal complexes, provided that one of the phosphorescence emitting metal complexes has a partial structure represented by one of the following Formulas (1) to (4):

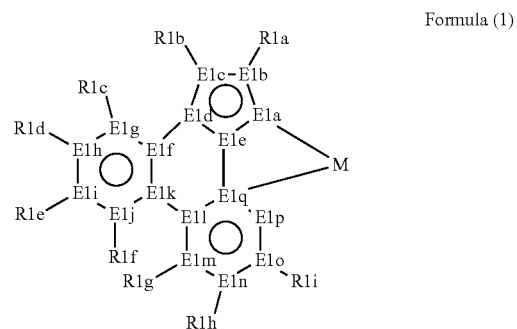

Formula (1)

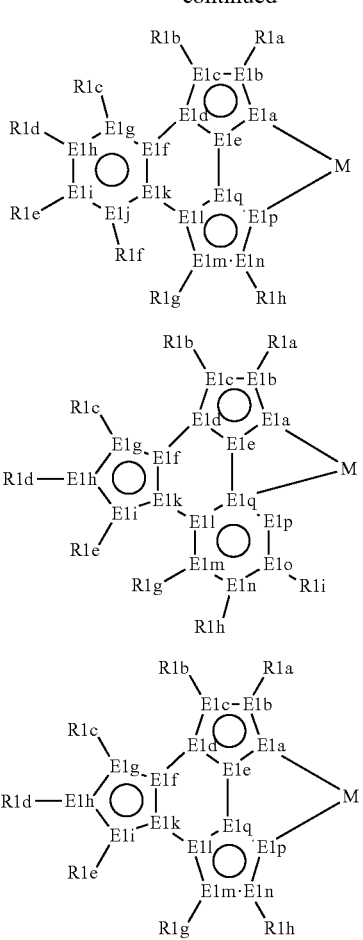

wherein, in Formula (1): E1a represents a nitrogen atom; E1b and E1c represent a carbon atom, a nitrogen atom, an oxygen atom or a sulfur atom; E1d and E1e represent a carbon atom or a nitrogen atom; E1f represents a carbon atom; E1g to E1j represent a carbon atom or a nitrogen atom; E1k and E1l represent a carbon atom; E1m to E1o represent a carbon atom or a nitrogen atom; E1p and E1q represent a carbon atom;

R1a and R1b represent a hydrogen atom or a substituent when E1b and E1c represent the carbon atom or the nitrogen atom having a bond of —N<, R1a and R1b represent null when E1b and E1c represent the nitrogen atom having a bond of —N═, the oxygen atom or the sulfur atom; and R1c to R1i represent a hydrogen atom or a substituent; and M represents a transition metal of Group 8 to Group 10 in the periodic table, in Formula (2): E1a represents a nitrogen atom; E1b and E1c represent a carbon atom, a nitrogen atom, an oxygen atom or a sulfur atom; E1d and E1e represent a carbon atom or a nitrogen atom; E1f represents a carbon atom; E1g to E1j represent a carbon atom or a nitrogen atom; E1k represents a carbon atom; E1l represents a carbon atom or a nitrogen atom; E1m to E1n represent a carbon atom, a nitrogen atom, an oxygen atom or a sulfur atom; E1p represents a carbon atom; E1q represents a carbon atom or nitrogen atom;

R1a, R1b, R1g and R1h represent a hydrogen atom or a substituent when E1b, E1c, E1m and E1n represent the carbon atom or the nitrogen atom having a bond of —N<, R1a, R1b, R1g and R1h represent null when E1b, E1c, E1m and E1n represent the nitrogen atom having a bond of —N═, the oxygen atom or the sulfur atom; and R1c to R1f represent a hydrogen atom or a substituent; and M represents a transition metal of Group 8 to Group 10 in the periodic table, in Formula (3): E1a represents a nitrogen atom; E1b and E1c represent a carbon atom, a nitrogen atom, an oxygen atom or a sulfur atom; E1d and E1e represent a carbon atom or a nitrogen atom; E1f and E1k represent a carbon atom or a nitrogen atom; E1g to E1i represent a carbon atom, a nitrogen atom an oxygen atom or a sulfur atom; E1l represents a carbon atom; E1m to E1o represent a carbon atom or a nitrogen atom; E1p and E1q represent a carbon atom;

R1a, R1b, R1c, R1d and R1e represent a hydrogen atom or a substituent when E1b, E1c, E1g, E1h and E1i represent the carbon atom or the nitrogen atom having a bond of —N<, R1a, R1b, R1c, R1d and R1e represent null when E1b, E1c, E1g, E1h and E1i represent the nitrogen atom having a bond of —N═, the oxygen atom or the sulfur atom; and R1g to R1i represent a hydrogen atom or a substituent; and M represents a transition metal of Group 8 to Group 10 in the periodic table, in Formula (4): E1a represents a nitrogen atom; E1b and E1c represent a carbon atom, a nitrogen atom, an oxygen atom or a sulfur atom; E1d and E1e represent a carbon atom or a nitrogen atom; E1f and E1k represent a carbon atom or a nitrogen atom; E1g to E1i represent a carbon atom, a nitrogen atom, an oxygen atom or a sulfur atom; E1l represents a carbon atom or a nitrogen atom; E1m and E1n represent a carbon atom, a nitrogen atom, an oxygen atom or a sulfur atom; E1p represents a carbon atom; E1q represents a carbon atom or nitrogen atom;

R1a to R1e, R1g and R1h represent a hydrogen atom or a substituent when E1b, E1c, E1g, E1h, E1i, E1m and E1n represent the carbon atom or the nitrogen atom having a bond of —N<, R1a to R1e, R1g and R1h represent null when E1b, E1c, E1g, E1h, E1i, E1m and E1n represent the nitrogen atom having a bond of —N═, the oxygen atom or the sulfur atom; and M represents a transition metal of Group 8 to Group 10 in the periodic table, and wherein the two phosphorescence emitting metal complexes each emits a light of a different hue, and the phosphorescence emitting metal complex having the partial structure represented by one of Formulas (1) to (4) emits a blue light.

12. The organic electroluminescent element of item 11, wherein a difference of highest occupied molecular orbitals (HOMO) of the at least two phosphorescence emitting metal complexes is 0.5 eV or less.

13. The organic electroluminescent element of item 11, comprising at least two light emitting layers as constituting layers, provided that each of the two phosphorescence emitting metal complexes are contained in a different light emitting layer.

14. The organic electroluminescent element of item 11, wherein M represents platinum or iridium.

15. A display device comprising the organic electroluminescent element of item 11.

16. A lighting device comprising the organic electroluminescent element of item 11.

17. An organic electroluminescent element comprising a light emitting layer sandwiched between an anode and a cathode, wherein the light emitting layer is prepared with a wet process using an organic solvent selected from the group consisting of a ketone, a fatty acid ester, a halogenated hydrocarbon, an aromatic hydrocarbon, an aliphatic hydrocarbon, dimethylformamide (DMF) and dimethylsulfoxide (DMSO), wherein the light emitting layer emits a white light and contains at least two phosphorescence emitting metal complexes, provided that one of the phosphorescence emitting metal complexes has a partial structure represented by one of the following Formulas (1) to (4):

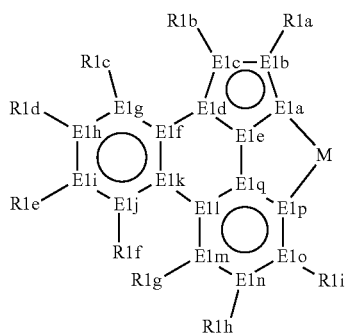

Formula (1)

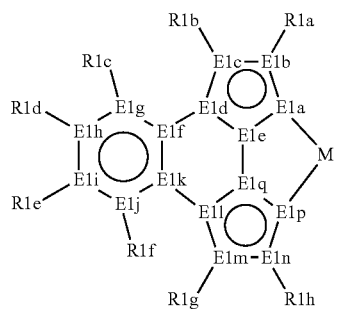

Formula (2)

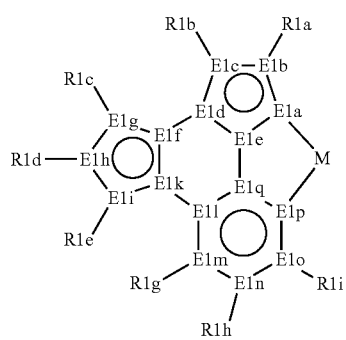

Formula (3)

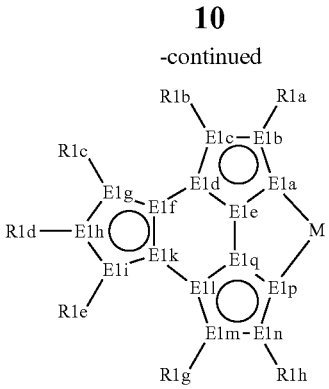

Formula (4)

wherein, in Formula (1): E1a represents a nitrogen atom; E1b and E1c represent a carbon atom, a nitrogen atom, an oxygen atom or a sulfur atom; E1d and E1e represent a carbon atom or a nitrogen atom; E1f represents a carbon atom; E1g to E1j represent a carbon atom or a nitrogen atom; E1k and E1l represent a carbon atom; E1m to E1o represent a carbon atom or a nitrogen atom; E1p and E1q represent a carbon atom;

R1a and R1b represent a hydrogen atom or a substituent when E1b and E1c represent the carbon atom or the nitrogen atom having a bond of —N<, R1a and R1b represent null when E1b and E1c represent the nitrogen atom having a bond of —N═, the oxygen atom or the sulfur atom; and R1c to R1i represent a hydrogen atom or a substituent; and M represents a transition metal of Group 8 to Group 10 in the periodic table.

in Formula (2): E1a represents a nitrogen atom; E1b and E1c represent a carbon atom, a nitrogen atom, an oxygen atom or a sulfur atom; E1d and E1e represent a carbon atom or a nitrogen atom; E1f represents a carbon atom; E1g to E1j represent a carbon atom or a nitrogen atom; E1k represents a carbon atom; E1l represents a carbon atom or a nitrogen atom; E1m and E1n represent a carbon atom, a nitrogen atom, an oxygen atom or a sulfur atom; E1p represents a carbon atom; E1q represents a carbon atom or nitrogen atom;

R1a, R1b, R1g and R1h represent a hydrogen atom or a substituent when E1b, E1c, E1m and E1n represent the carbon atom or the nitrogen atom having a bond of —N<, R1a, R1b, R1g and R1h represent null when E1b, E1c, E1m and E1n represent the nitrogen atom having a bond of —N═, the oxygen atom or the sulfur atom; and R1c to R1f represent a hydrogen atom or a substituent; and M represents a transition metal of Group 8 to Group 10 in the periodic table.

in Formula (3): E1a represents a nitrogen atom; E1b and E1c represent a carbon atom, a nitrogen atom, an oxygen atom or a sulfur atom; E1d and E1e represent a carbon atom or a nitrogen atom; E1f and E1k represent a carbon atom or a nitrogen atom; E1g to E1i represent a carbon atom, a nitrogen atom, an oxygen atom or a sulfur atom; E1l represents a carbon atom; E1m to E1o represent a carbon atom or a nitrogen atom; E1p and E1q represent a carbon atom;

R1a, R1b, R1c, R1d and R1e represent a hydrogen atom or a substituent when E1b, E1c, E1g, E1h and E1i represent the carbon atom or the nitrogen atom having a bond of —N<, R1a, R1b, R1c, R1d and R1e represent null when E1b, E1c, E1g, E1h and E1i represent the nitrogen atom having a bond of —N=, the oxygen atom or the sulfur atom; and R1g to R1i represent a hydrogen atom or a substituent; and M represents a transition metal of Group 8 to Group 10 in the periodic table.

in Formula (4): E1a represents a nitrogen atom; E1b and E1c represent a carbon atom, a nitrogen atom, an oxygen atom or a sulfur atom; E1d and E1e represent a carbon atom or a nitrogen atom; E1f and E1k represent a carbon atom or a nitrogen atom; E1g to E1i represent a carbon atom, a nitrogen atom, an oxygen atom or a sulfur atom; E1l represents a carbon atom or a nitrogen atom; E1m and E1n represent a carbon atom or a nitrogen atom, an oxygen atom or a sulfur atom; E1p represents a carbon atom; E1q represents a carbon atom or a nitrogen atom;

R1a to R1e, R1g and R1h represent a hydrogen atom or a substituent when E1b, E1c, E1g, E1h, E1i, E1m and E1n represent the carbon atom or the nitrogen atom having a bond of —N<, R1a to R1e, R1g and R1h represent null when E1b, E1c, E1g, E1h, E1i, E1m and E1n represent the nitrogen atom having a bond of —N=, the oxygen atom or the sulfur atom; and M represents a transition metal of Group 8 to Group 10 in the periodic table, and wherein the two phosphorescence emitting metal complexes each emits a light of a different hue, and the phosphorescence emitting metal complex having the partial structure represented by one of Formulas (1) to (4) emits a blue light.

Effects of the Invention

The present invention has enabled to provide an organic EL element, a lighting device and a display device having high emission efficiency and long emission lifetime.

Figure 1:
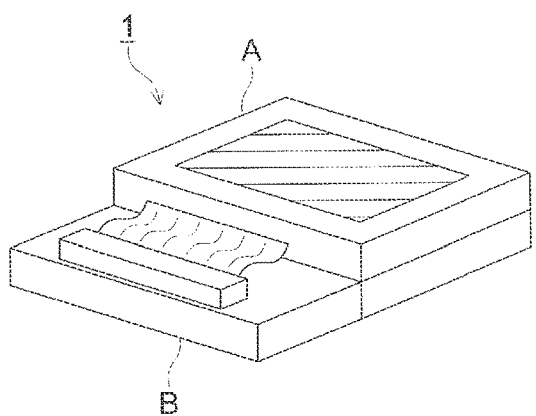
FIG. 1 is a schematic drawing to show an example of a display device constituted of an organic EL element.
Figure 2:
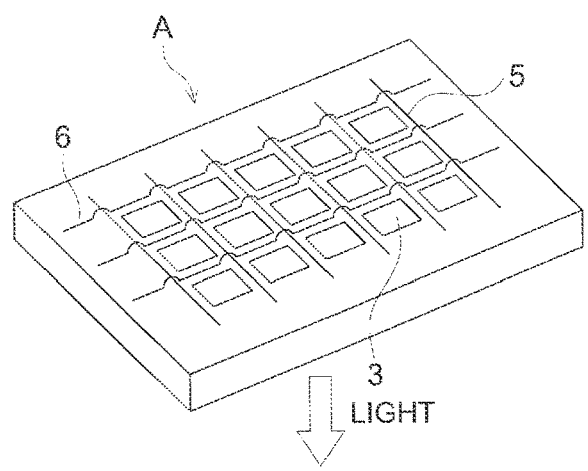
FIG. 2 is a schematic drawing of display section.

DESCRIPTION OF SYMBOLS 1 display
3 pixel
5 scanning line
6 data line
A display section
B control section
101 organic EL element
107 glass substrate having a transparent electrode
106 organic EL layer
105 cathode
102 glass cover
108 nitrogen gas
109 desiccant

BEST MODES TO CARRY OUT THE INVENTION

In the organic EL element of the present invention, by using any one of the aforementioned embodiments of items 1-8, there has been provided an organic EL element exhibiting high emission taking out quantum efficiency and having a prolonged emission lifetime with high stability. And further, a lighting equipment and a display device of high luminance can be successfully provided.

The inventors of the present focused attention to organic EL element materials used for a light emission layer of an organic EL element, in particular, the inventors examined various aspects of the metal complex compounds used as a light emitting dopant.

As a result, it was found that the phosphorescence emitting metal complex having a ligand made of a six-membered aromatic compound condensed with three or more rings each having a five or a six-membered aromatic ring emits a light of relatively short wavelength and the foresaid metal complex is relatively stable in its exited state.

Further, it was revealed that this dopant produces a white light with high efficiency and with a small amount of color shift under prolonged continuous drive when it is used in combination with the conventionally known green dopant and red dopant.

The reason of this property is not clearly identified. However, this property is assumed to be originated from the fact that when the phosphorescence emitting metal complex having a ligand made of a six-membered aromatic compound condensed with three or more rings each having a five or a six-membered aromatic ring is used as a blue dopant, its HOMO and LUMO levels are not widely different from those of a red dopant and a green dopant.

As a luminescence mechanism of a phosphorescent dopant in an organic EL element, there was proposed a carrier trap type mechanism in which a positive hole or an electron enters directly into a light emitting dopant contained in a light emitting layer.

The orbital into which a positive hole or an electron enters is considered to be HOMO or LUMO, respectively.

Although phosphorescence luminescence is considered to be luminescence from the lowest exited triplet state (T1), the difference of HOMO level and LUMO level (S1) has a relation of: S1>T1.

As compared with the conventional phosphorescence luminescence metal complex, the phosphorescence emitting metal complex of the present invention having a ligand made of a six-membered aromatic compound condensed with three or more rings each having a five or a six-membered aromatic ring has a small amount of difference between S1 and T1. In addition, since there is no need to introduce an electron withdrawing substituent which extremely changes electric potential, it is possible to locate the levels of HOMO and LUMO closer to those of green and red dopant which emits a light of longer wavelength.

As a result, a large amount of load is not required for carrier transportation between dopants. This is presumed to easily produce an element exhibiting high efficiency and a small amount of color shift. Furthermore, it was revealed that: the fact that the difference between S1 and T1 is small will mean that the minimum energy required for transporting the charge generated from the cathode and the anode is little; and it will also contribute to a lower voltage.

Hereafter, the details of each structural element concerning the present invention are described sequentially.
<Phosphorescence Emitting Metal Complex>

At least one of the phosphorescence emitting metal complexes contained in a light emitting layer of an organic EL element of the present invention is a phosphorescence emitting metal complex having a ligand made of a six-membered aromatic compound condensed with three or more rings each having a five or a six-membered aromatic ring.

<Aromatic Compound Condensed with Three or More Rings Each Having a Five or a Six-Membered Aromatic Ring>

An aromatic compound condensed with three or more rings each having a five or a six-membered aromatic ring indicates, in particular, a compound which is formed by a ring (such as: a benzene ring, a pyridine ring, a pyridazine ring, a pyrimidine ring, a pyrazine ring, an s-triazine ring, and an as-triazine ring) to which are condensed three or more rings each having a five or a six-membered aromatic ring.

Among these rings, preferred rings are aromatic compounds derived from a pyridine ring or a benzene ring with which other rings are condensed. There is not specific limitation to a five or a six-membered aromatic ring which is condensed. Specific examples of a five-membered aromatic ring include: a pyrrole ring, a furan ring, a thiophene ring, an imidazole ring, a pyrazole ring, an oxazole ring, the triazole ring, an isoxazole ring, an isothiazole ring and a triazole ring. Among these, preferable rings are an imidazole ring and a pyrazole ring.

Moreover, specific examples of a six-membered aromatic ring include: a benzene ring, a pyridine ring, a pyridazine ring, a pyrimidine ring, a pyrazine ring, an s-triazine ring and an as-triazine ring. Among these six-membered aromatic rings, a benzene ring and a pyridine ring are preferable. These aromatic compounds may have any substituents. (Transition Metal of Group 8 to Group 10 in the Periodic Table)

The metal atom which forms the phosphorescence emitting metal complex concerning the present invention is preferably a transition metal of Group 8 to Group 10 in the periodic table from the viewpoint of light emission property. Particularly preferable are iridium and platinum.

In addition, in the partial structure represented by one of Formulas (1)-(4), the transition metal element represented by M corresponds to the above-mentioned metal atom.
(Partial Structure Represented by One of Formulas (1)-(4))

A phosphorescence emitting metal complex of the present invention having a ligand made of a six-membered aromatic compound condensed with three or more rings each having a five or a six-membered aromatic ring is preferably a compound (it is also called as a metal complex or a metal complex compound) having a partial structure represented by one of the above-described Formulas (1) to (4).

Here, the partial structure represented by one of Formulas (1) to (4) is described.
(Molecular Structure Having 18π Electrons)

In the partial structure of the present invention represented by one of Formulas (1) to (4), the molecular structure composed of E1a to E1q contains 18π electrons in total.

In the partial structure represented by one of Formulas (1) to (4), the ring formed by E1a to E1e represents a five-membered aromatic heterocycle. Examples thereof include: an oxazole ring, a thiazole ring, an oxadiazole ring, the oxatriazole ring, an isoxazole ring, a tetrazole ring, a thiadiazole ring, a thiatriazole ring, an isothiazole ring, a thiophene ring, a furan ring, a pyrrole ring, an imidazole ring, a pyrazole ring and a triazole ring.

Among the foresaid rings, preferable rings are: a pyrazole ring, an imidazole ring, an oxazole ring and a thiazole ring. These rings each may further have a substituent which will be described later.

In the partial structure of represented by one of the Formulas (1) to (4), the ring formed with E1l to E1q represents a six-membered aromatic hydrocarbon ring, or a five or six-membered aromatic heterocycle.

An example of a six-membered aromatic hydrocarbon ring formed with E1l to E1q is a benzene ring. It may further have a substituent which will be described later.

Examples of a five or six-membered aromatic heterocycle formed with E1l to E1q include: a furan ring, a thiophene ring, an oxazole ring, a pyrrole ring, a pyridine ring, a pyridazine ring, a pyrimidine ring, a pyrazine ring, a triazine ring, an oxadiazole ring, a triazole ring, an imidazole ring, a pyrazole ring and a thiazole ring.

These rings each may further have a substituent which will be described later.

In the partial structure of represented by one of the Formulas (1) to (4), the ring formed with E1f to E1k represents a six-membered aromatic hydrocarbon ring, or a five or six-membered aromatic heterocycle. These rings are the same as the six-membered aromatic hydrocarbon ring, or the five or six-membered aromatic heterocycle formed with E1i to E1q in the partial structure of represented by one of Formulas (1) to (4).

In a partial structure represented by one of Formulas (1) to (4), examples of the substituents represented by R1a through R1i each include: an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group); a cycloalkyl group (for example, a cyclopentyl group, and a cyclohexyl group); an alkenyl group (for example, a vinyl group and an allyl group); an alkynyl group (for example, an ethynyl group and a propargyl group); an aromatic hydrocarbon ring group (also called an aromatic carbon ring or an aryl group, for example, a phenyl group, a p-chlorophenyl group, a mesityl group, a tolyl group, a xylyl group, a naphthyl group, an anthryl group, an azulenyl group, an acenaphthenyl group, a fluorenyl group, a phenantolyl group, an indenyl group, a pyrenyl group, and a biphenyryl group); an aromatic heterocyclic group (for example, a pyridyl group, a pyrimidinyl group, a furyl group, a pyrrolyl group, an imidazolyl group, a benzoimidazolyl group, a pyrazolyl group, a pyradinyl group, a triazolyl group (for example, 1,2,4-triazole-1-yl group and 1,2,3-triazole-1-yl group), an oxazolyl group, a benzoxazolyl group, a thiazolyl group, an isooxazolyl group, an isothiazolyl group, a furazanyl group, a thienyl group, a quinolyl group, a benzofuryl group, a dibenzofuryl group, a benzothienyl group, a dibenzothenyl group, an indolyl group, a carbazolyl group, a carbolynyl group, a diazacarbazolyl group (which is a group in which one of the carbon atoms constituting the carboline ring of the above carbolynyl group is replaced with a nitrogen atom), a quinoxalinyl group, a pyridazinyl group, a triazinyl group, a quinazolinyl group, a phthalazinyl group); a heterocyclic group (for example, a pyrrolidyl group, an imidazolidyl group, a morpholyl group, and an oxazolidyl group); an alkoxyl group (for example, a methoxy group, an ethoxy group, a propyloxy group, a pentyloxy group, an hexyloxy group, an octyloxy group, and a dodecyloxy group); a cycloalkoxy group (for example, a cyclopentyloxy group and a cyclohexyloxy group); an aryloxy group (for example, a phenoxy group and a naphthyloxy group); an alkylthio group (for example, a methylthio group, an ethylthio group, a propylthio group, a pentylthio group, a hexylthio group, an octylthio group, and a dodecylthio group); a cycloalkylthio group (for example, a cyclopentylthio group and a cyclohexylthio group); an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group and a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group); an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, and a 2-pyridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-oyridylaminoureido group); a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, and a 2-pyridylsulfinyl group); an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group, an arylsulfonyl group or a heteroarylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a dodecylamino group, an anilino group, a naphthylamino group, and a 2-pyridylamino group); a cyano group; a nitro group; a hydroxyl group; a mercapto group; and a silyl group (for example, a trimethylsilyl group, a triisopropylsilyl group, a triphenylsilyl group, and a phenyldiethylsilyl group).

These substituents may be further substituted with the aforesaid substituents. Further, a plurality of these substituents may be mutually joined to form a ring.

In the present invention, among the partial structures represented by the above-described Formulas (1) to (4), the partial structures represented by one of the following Formulas (5) to (8) are preferable.

<Partial Structure Represented by One of Formulas (5) to (8)>

The partial structure represented by one of Formulas (5) to (8) will be described.

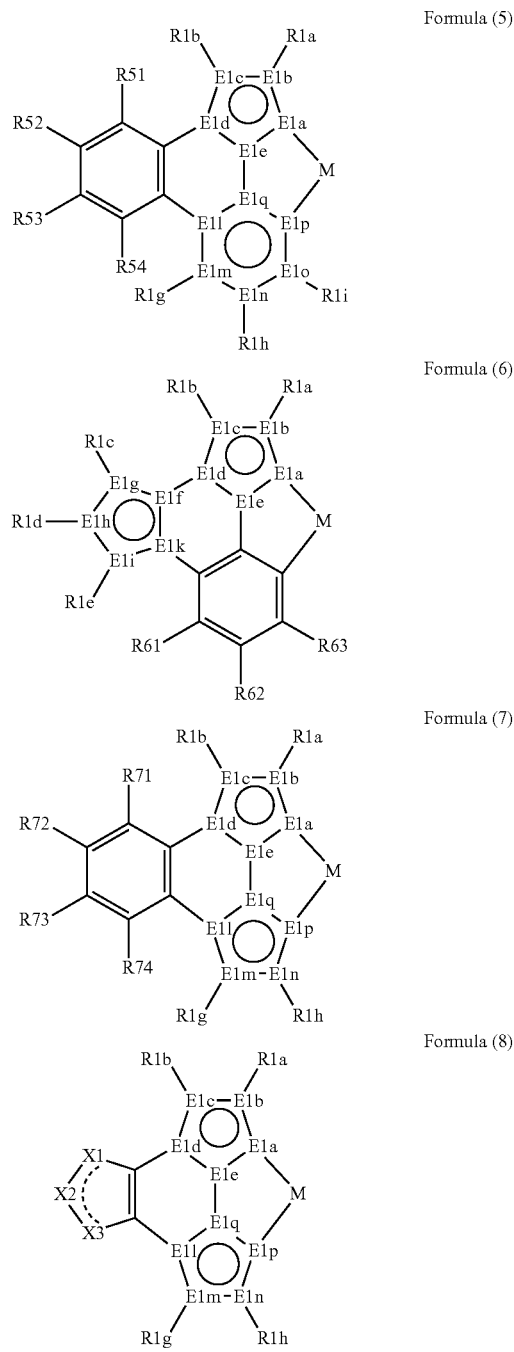

In Formulas, E1a to E1q each represent a carbon atom, a nitrogen atom, an oxygen atom or a sulfur atom. The ring formed with E1a to E1e represents a five-membered aromatic heterocycle. The ring formed with E1l to E1p represents a six-membered aromatic hydrocarbon ring, or a five or six-membered aromatic heterocycle. E1a and E1p are different with one another and each represent a carbon atom or a nitrogen atom. R1a to R1i, R51 to R54 and R71 to R74 each represent a hydrogen atom or a substituent, provided that at least one of them is a group represented by the following Formula (A) or Formula (B). M represents a transition metal of Group 8 to Group 10 in the periodic table. X1, X2 and X3 each represent a carbon atom or a nitrogen atom.

In the partial structure represented by one of Formulas (5) to (8), the five-membered aromatic heterocycle formed with E1a to E1e is the same five-membered aromatic heterocycle formed with E1a to E1e in the partial structure represented by one of Formulas (1) to (4).

In the partial structure represented by one of Formulas (5) to (8), the six-membered aromatic hydrocarbon ring formed with E1l to E1p is the same six-membered aromatic hydrocarbon ring formed with E1l to E1p in the partial structure represented by one of Formulas (1) to (4).

In the partial structure represented by one of Formulas (5) to (8), the five or six-membered aromatic heterocycle formed with E1l to E1p is the same six-membered aromatic heterocycle formed with E1l to E1p in the partial structure represented by one of Formulas (1) to (4).

In the partial structure represented by one of Formulas (5) to (8), the five-membered aromatic heterocycle formed with E1f to E1k is the same five-membered aromatic heterocycle formed with E1a to E1e in the partial structure represented by one of Formulas (1) to (4).

In the partial structure represented by one of Formulas (5) to (8), R1a to R1i, R51 to R54 and R71 to R74 each represent a hydrogen atom or a substituent, and the substituent is the same as indicated by R1a to R1i in the partial structure in represented by one of Formulas (1) to (4). In one of the preferred embodiments, at least one of the substituents is preferably represented by the following Formulas (A) or (B).
(Group Represented by Formulas (A) or (B))

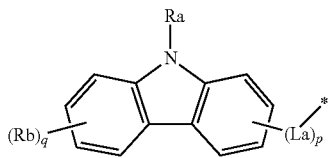

Formula (A)

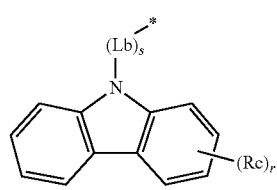

Formula (B)

In Formulas, Ra, Rb and Rc each represent a hydrogen atom or a substituent. La and Lb each represent a divalent linking group. p and s each represent an integer of 0 or 1. q represents an integer of 0 to 7. r represents an integer of 0 to 8. (*) indicates a linking position.

In the partial structure represented by one of Formulas (5) to (8), the preferable embodiments are cited as follows: the group represented by Formulas (A) or (B) is bonded to the ring formed with E1a to E1e; the group represented by Formulas (A) or (B) is bonded to the ring formed with E1l to E1q; and the group represented by Formulas (A) or (B) is bonded to one of the groups represented by R51 to R54 or R71 to R74, or it is bonded to the ring formed with E1f to E1k, or it is bonded to the ring formed with X1, X2, X3 and —C=C—.

In the present invention, among the partial structures represented by one of the above-described Formulas (5) to (8), the partial structures represented by one of the following Formulas (9) to (12) are preferable.

<Partial Structure Represented by One of Formulas (9) to (12)>

The partial structure represented by one of Formulas (9) to (12) will be described.

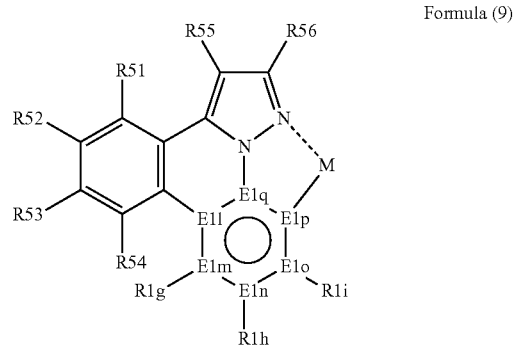

Formula (9)

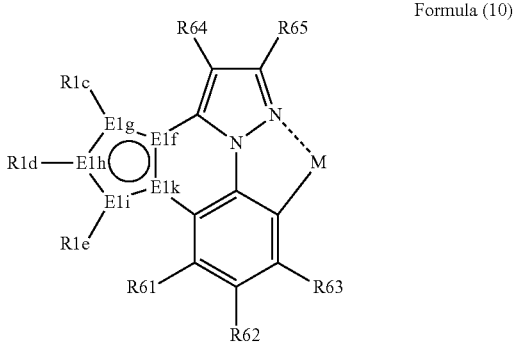

Formula (10)

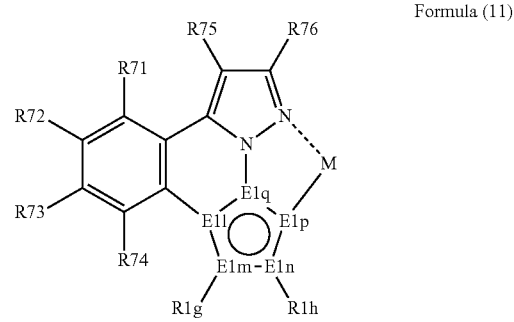

Formula (11)

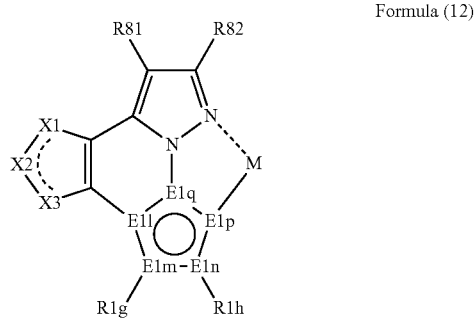

Formula (12)

In Formulas, E1f to E1q each represent a carbon atom, a nitrogen atom, an oxygen atom or a sulfur atom. The ring formed with E1f to E1k represents a five-membered aromatic heterocycle. The ring formed with E1l to E1p represents a six-membered aromatic hydrocarbon ring, or a five or six-membered aromatic heterocycle. R51 to R56, R61 to R65, R71 to R76, R81, R82 and R1c to R1h each represent a hydrogen atom or a substituent, provided that at least one of them is a group represented by Formula (A) or Formula (B). M represents a transition metal of Group 8 to Group 10 in the periodic table. X1, X2 and X3 each represent a carbon atom or a nitrogen atom which may have a substituent.

In the partial structure represented by one of Formulas (9) to (12), the five-membered aromatic heterocycle formed with E1f to E1k is the same five-membered aromatic heterocycle formed with E1a to E1e in the partial structure represented by one of Formulas (1) to (4).

In the partial structure represented by one of Formulas (9) to (12), the six-membered aromatic hydrocarbon ring formed with E1l to E1p is the same six-membered aromatic hydrocarbon ring formed with E1l to E1p in the partial structure represented by one of Formulas (1) to (4).

In the partial structure represented by one of Formulas (9) to (12), the five or six-membered aromatic heterocycle formed with E1l to E1p is the same five or six-membered aromatic heterocycle formed with E1l to E1p in the partial structure represented by one of Formulas (1) to (4).

In the partial structure represented by one of Formulas (9) to (12), the substituent represented by R51 to R56, R61 to R65, R71 to R76, R81, R82 or R1c to R1h is the same substituent as indicated by R1a to R1i in the partial structure in represented by one of Formulas (1) to (4).

In the partial structure represented by one of Formulas (9) to (12), the substituent which may be possessed on the carbon atom or the nitrogen atom represented by X1, X2, and X3 is the same substituent as indicated by R1a to R1i in the partial structure in represented by one of Formulas (1) to (4).

In the partial structure represented by one of Formulas (9) to (12), the preferable embodiments are cited as follows: at least one of R55, R56, R64, R65, R75, R76, R81 and R82 is a group represented by the aforesaid Formulas (A) or (B); at least one of R1g, R1h, R1i, R61, R62, R63, R1g and R1h is a group represented by the aforesaid Formulas (A) or (B); at least one of R51 to R54, R1c to R1e and R71 to R74 is a group represented by the aforesaid Formulas (A) or (B); and at least one of X1 to X3 is a group represented by the aforesaid Formulas (A) or (B).

In the present invention, among the partial structures represented by one of the above-described Formulas (5) to (8), the partial structures represented by one of the following Formulas (13) to (16) are cited as preferable embodiments.
<Partial Structure Represented by One of Formulas (13) to (16)>

The partial structure represented by one of Formulas (13) to (16) will be described.

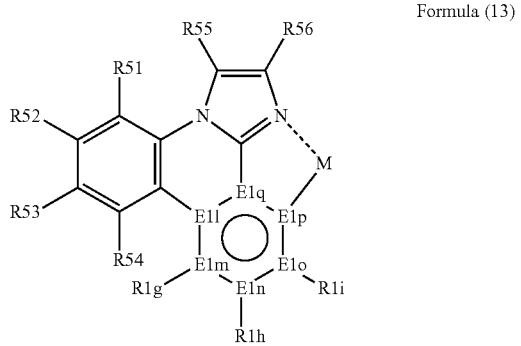

Formula (13)

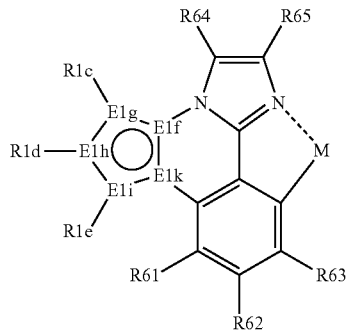

Formula (14)

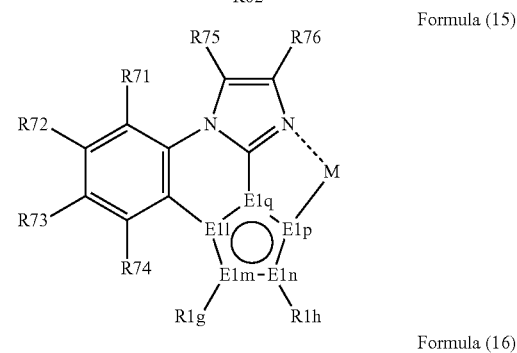

Formula (15)

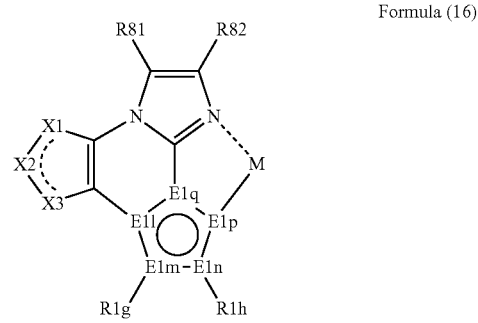

Formula (16)

In Formulas, E1f to E1q each represent a carbon atom, a nitrogen atom, an oxygen atom or a sulfur atom. The ring formed with E1f to E1k represents a five-membered aromatic heterocycle. The ring formed with E1l to E1p represents a six-membered aromatic hydrocarbon ring, or a five or six-membered aromatic heterocycle. R51 to R56, R61 to R65, R71 to R76, R81, R82 and R1c to R1h each represent a hydrogen atom or a substituent, provided that at least one of them is a group represented by Formula (A) or Formula (B). M represents a transition metal of Group 8 to Group 10 in the periodic table. X1, X2 and X3 each represent a carbon atom or a nitrogen atom which may have a substituent.

In the partial structure represented by one of Formulas (13) to (16), the five-membered aromatic heterocycle formed with E1f to E1k is the same five-membered aromatic heterocycle formed with E1a to E1e in the partial structure represented by one of Formulas (1) to (4).

In the partial structure represented by one of Formulas (13) to (16), the six-membered aromatic hydrocarbon ring formed with E1l to E1p is the same six-membered aromatic hydrocarbon ring formed with E1l to E1p in the partial structure represented by one of Formulas (1) to (4).

In the partial structure represented by one of Formulas (13) to (16), the five or six-membered aromatic heterocycle formed with E1l to E1p is the same five or six-membered aromatic heterocycle formed with E1l to E1p in the partial structure represented by one of Formulas (1) to (4).

In the partial structure represented by one of Formulas (13) to (16), the substituent represented by R51 to R56, R61 to R65, R71 to R76, R81, R82 or R1c to R1h is the same substituent as indicated by R1a to R1i in the partial structure in represented by one of Formulas (1) to (4).

In the partial structure represented by one of Formulas (13) to (16), the substituent which may be possessed on the carbon atom or the nitrogen atom represented by X1, X2, and X3 is the same substituent as indicated by R1a to R1i in the partial structure in represented by one of Formulas (1) to (4).

In the partial structure represented by one of Formulas (13) to (16), the preferable embodiments are cited as follows: at least one of R55, R56, R64, R65, R75, R76, R81 and R82 is a group represented by Formulas (A) or (B); at least one of R1g, R1h, R1i, R61, R62, R63, R1g and R1h is a group represented by Formulas (A) or (B); at least one of R51 to R54, R1c to R1e and R71 to R74 is a group represented by Formulas (A) or (B); and at least one of X1 to X3 is a group represented by Formulas (A) or (B).

Examples of a compound (it is also called also as a metal complex or a metal complex compound) containing a partial structure represented by one of the aforesaid Formulas (1) to (4), Formulas (5) to (8), Formulas (9) to (12), or Formulas (13) to (16) are shown in the followings. However, the present invention is not limited to them.

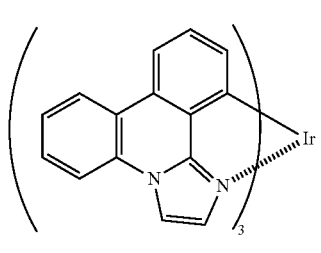
(1)

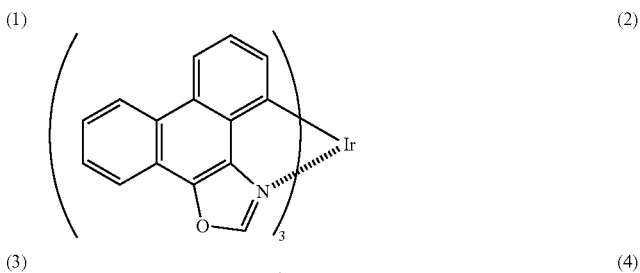
(2)

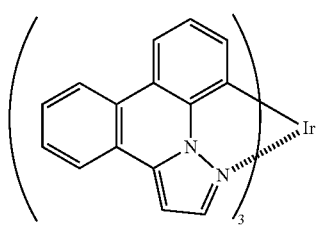
(3)

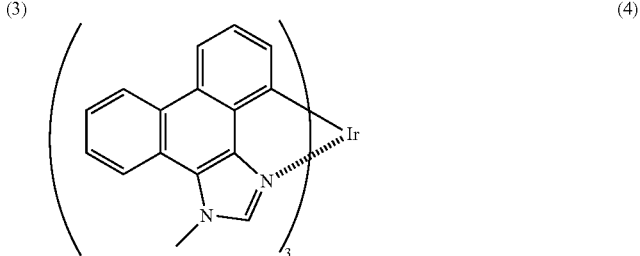
(4)

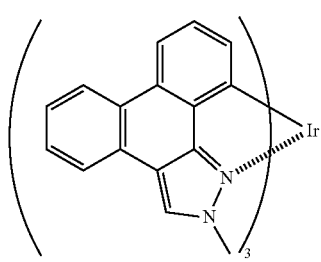
(5)

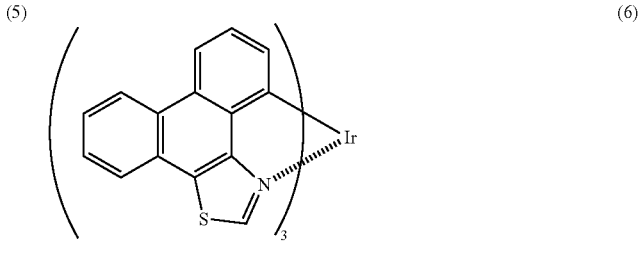
(6)

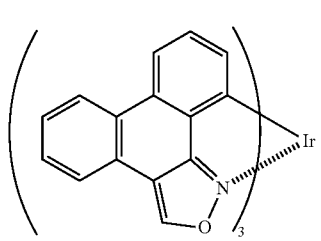
(7)

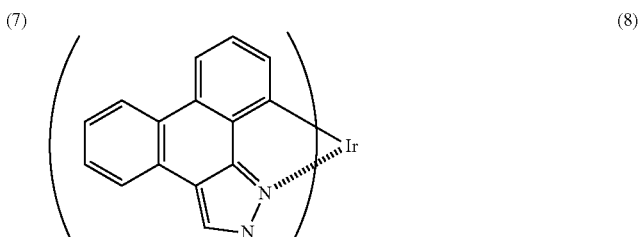
(8)

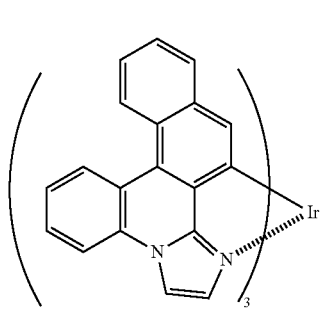
(13)

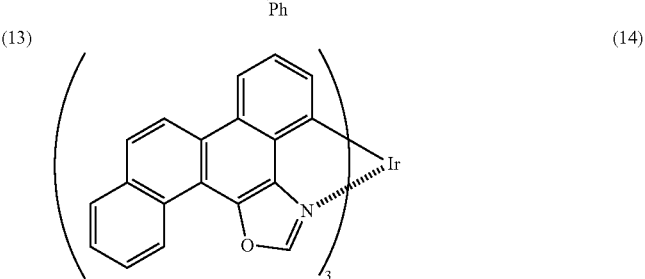
(14)

-continued
(15)
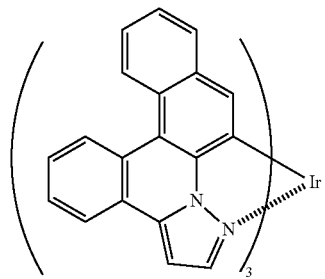
(16)
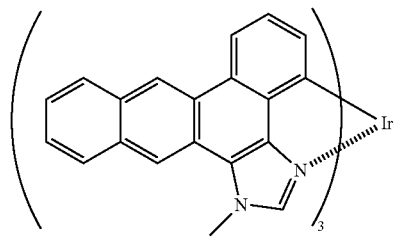
(17)
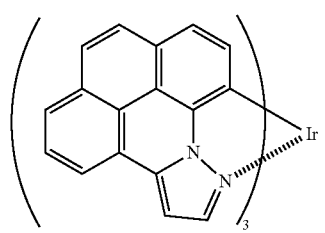
(18)
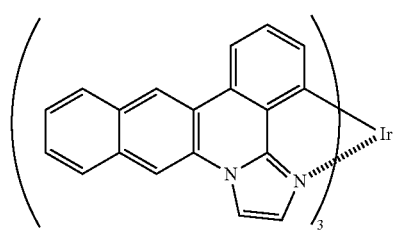
(19)
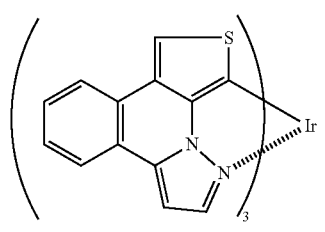
(20)
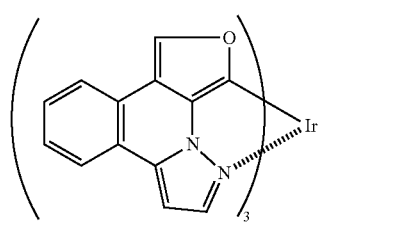
(21)
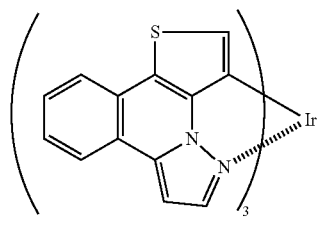
(22)
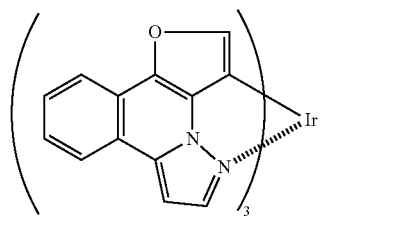
(23)
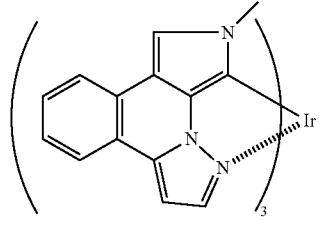
(24)
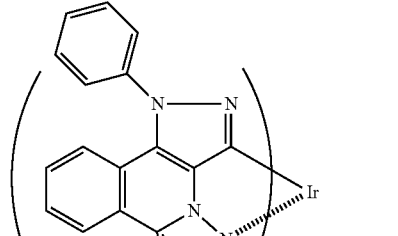
(25)
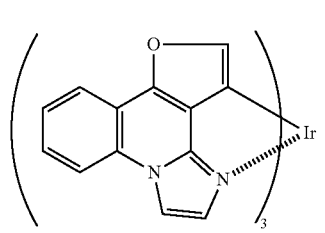
(26)
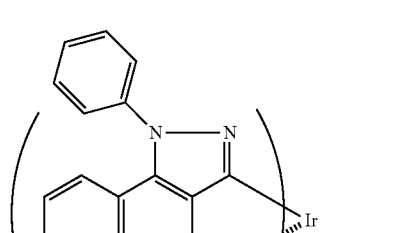

-continued
(27)
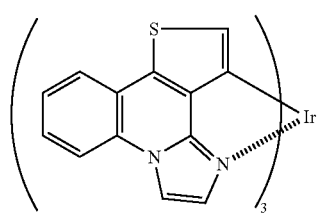
(28)
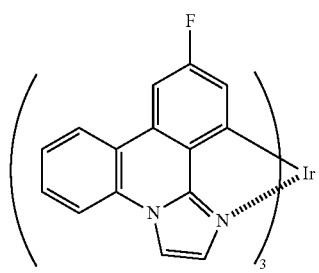
(29)
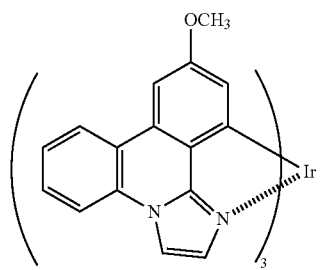
(30)
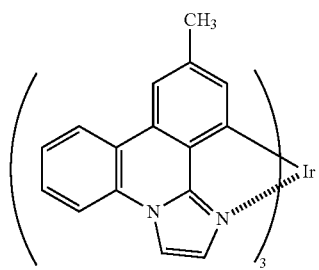
(31)
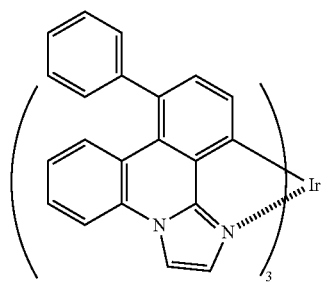
(32)
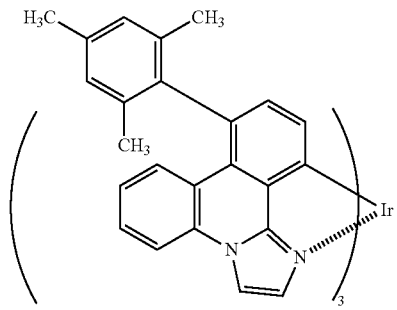
(33)
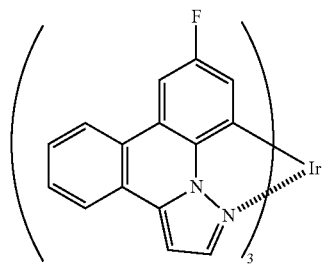
(34)
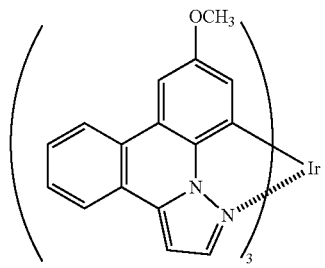
(35)
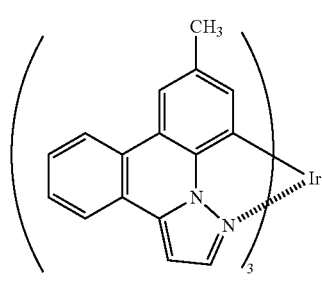
(36)
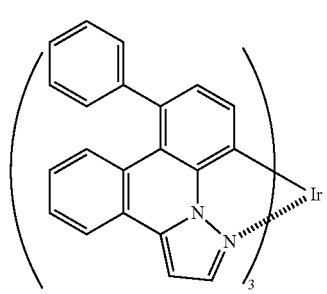

-continued
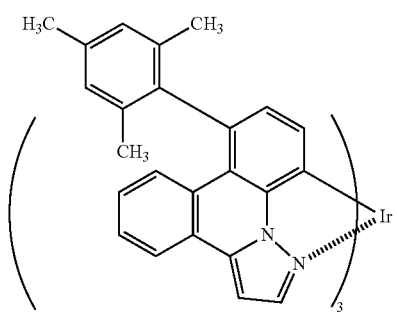
(37)
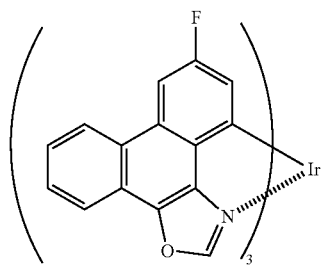
(38)
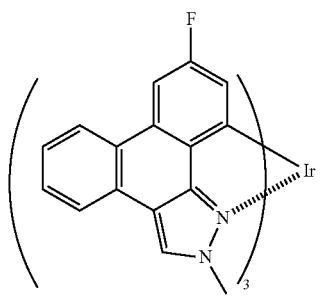
(39)
(40)
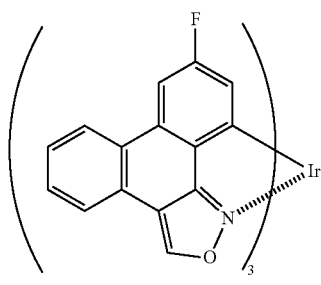
(41)
(42)
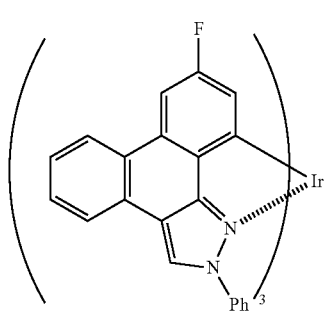
(43)
(44)
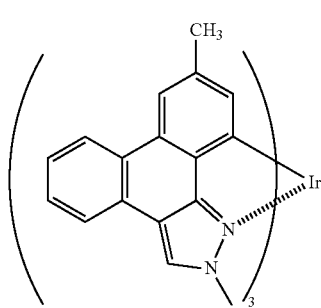
(45)
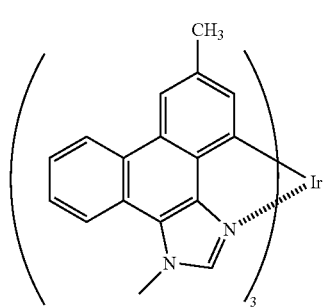
(46)

(47) 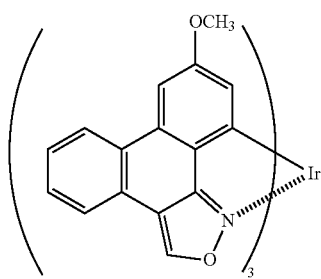
(48) 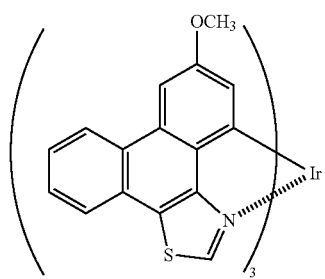
(49) 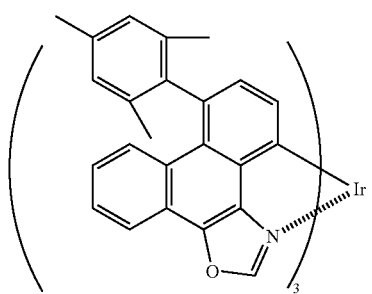
(50) 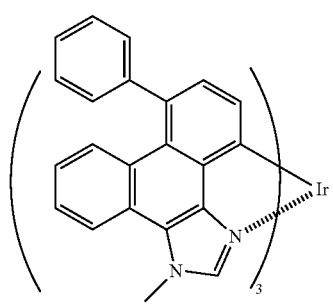
(51) 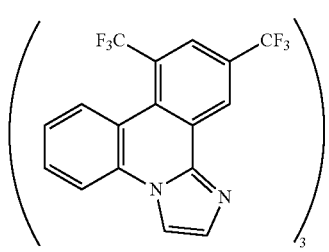
(52) 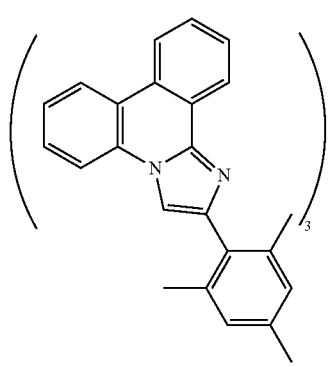
(53) 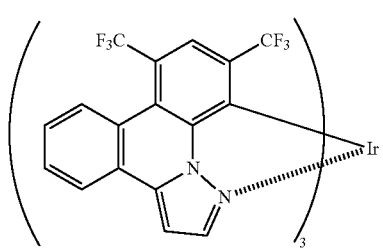
(54) 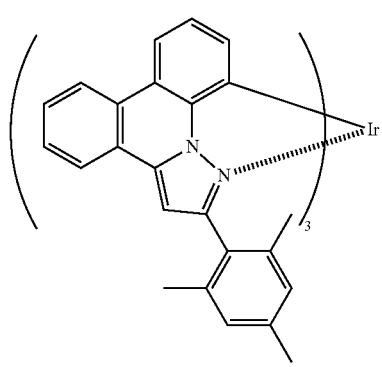
(55) 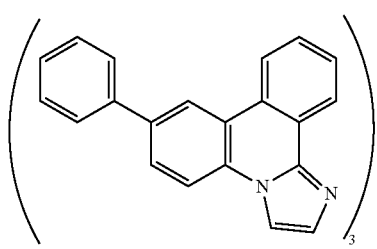
(56) 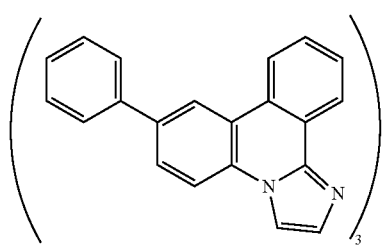

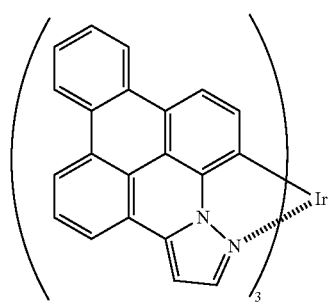
(57)
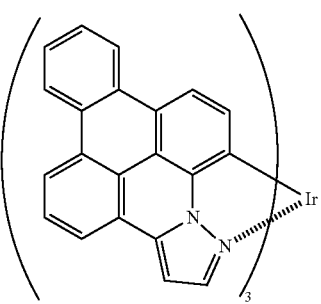
(58)
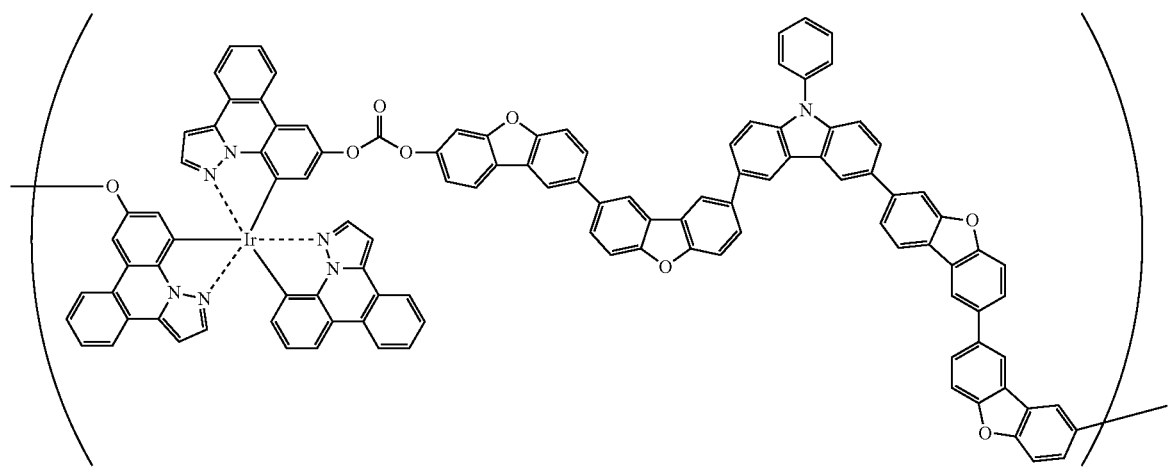
(59)
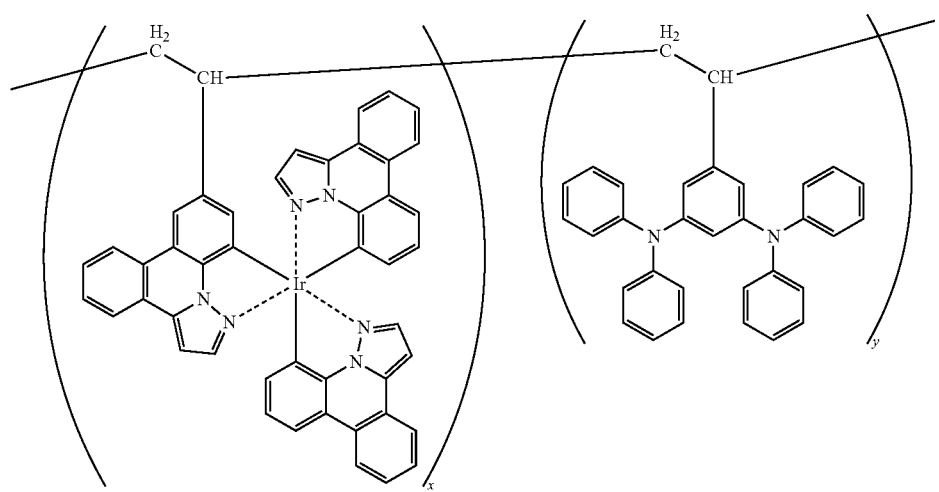
(60)
x:y = 1:10
random co-polymer -continued
(61)
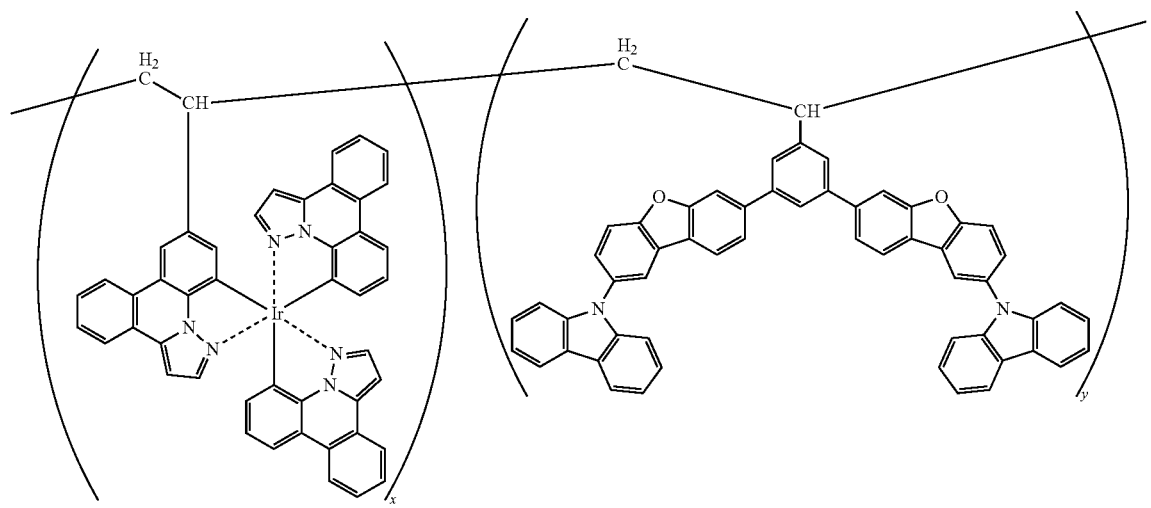
x:y = 1:10
random co-polymer
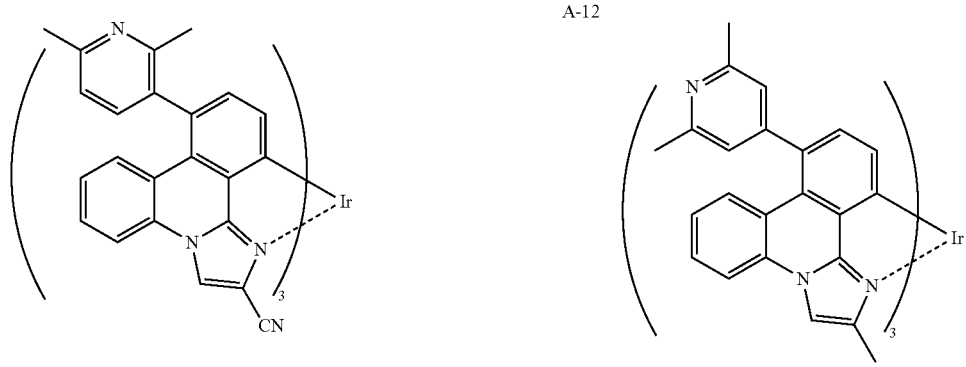
A-12　　　　　　　　　　　A-13
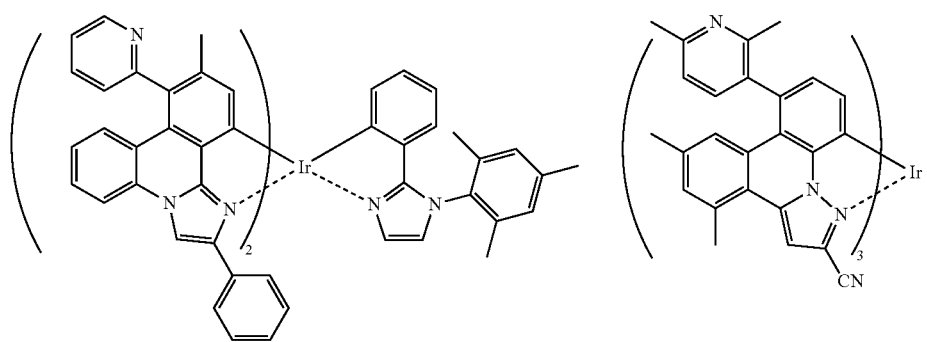
A-14　　　　　　　　　　　A-15
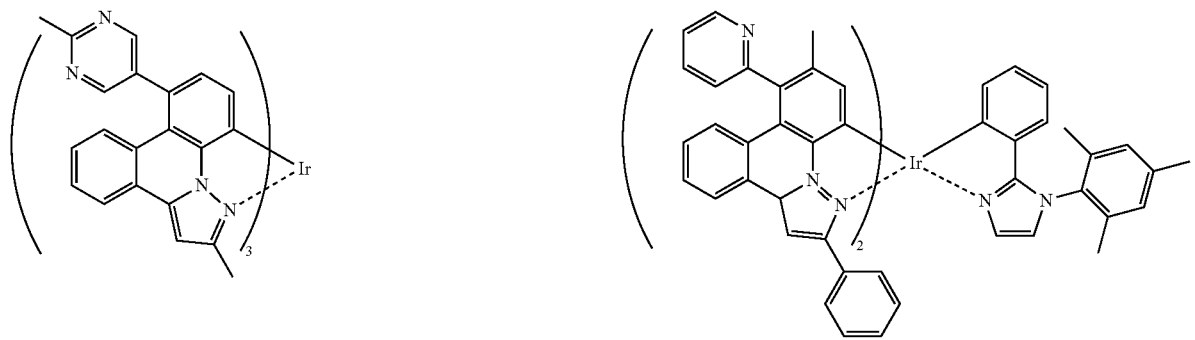
A-16　　　　　　　　　　　A-17

-continued
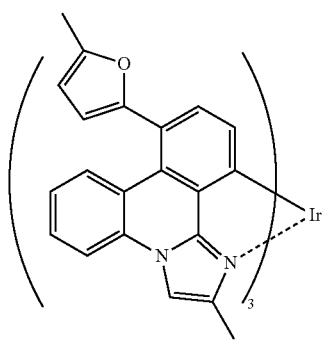
A-18
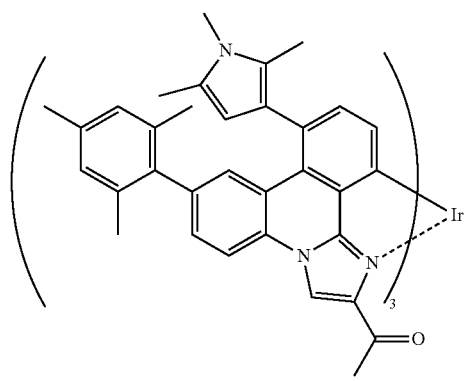
A-19
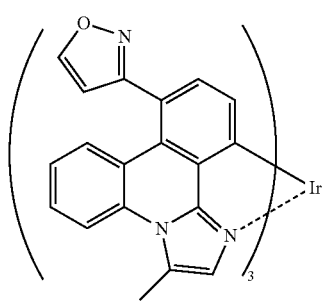
A-20
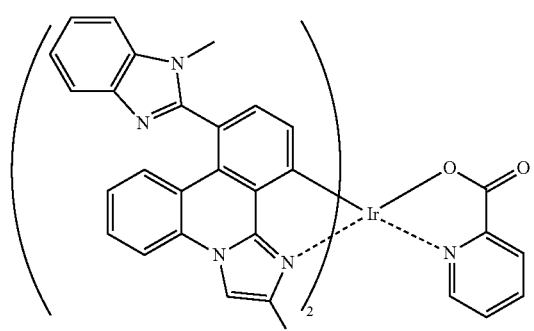
A-21
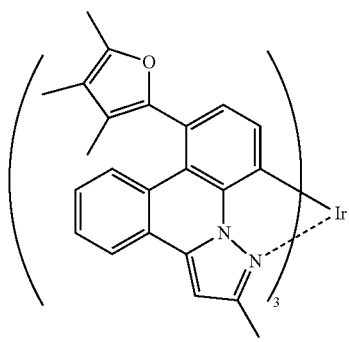
A-22
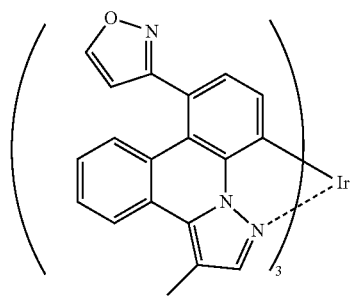
A-23
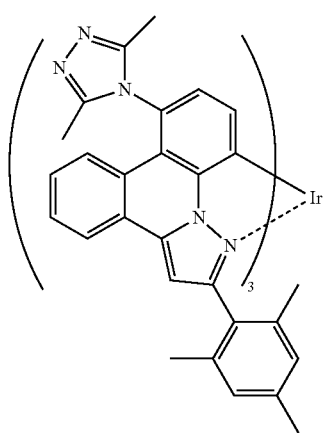
A-24
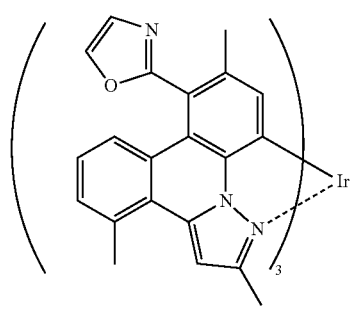
A-25

-continued
A-26
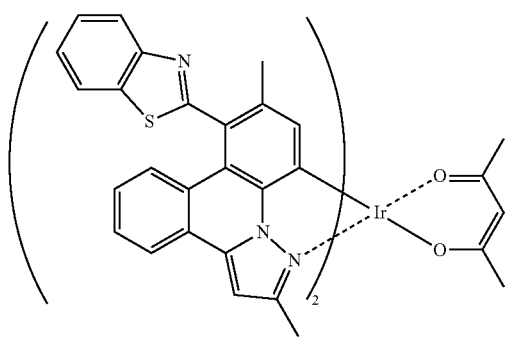
A-27
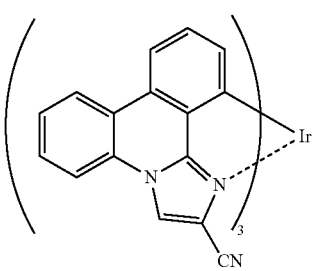
A-28
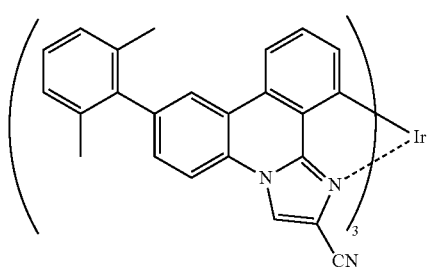
A-29
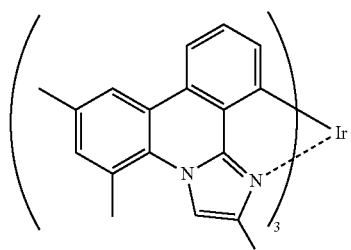
A-30
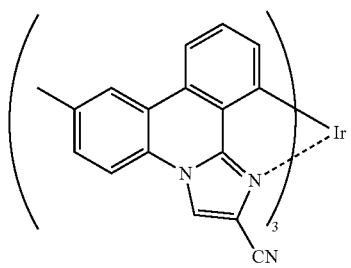
A-31
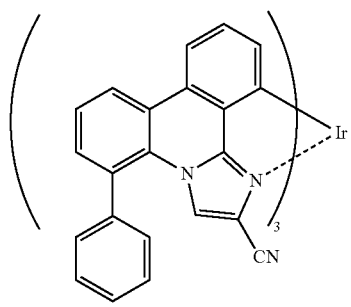
A-32
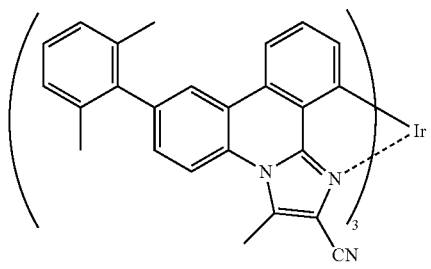
A-33
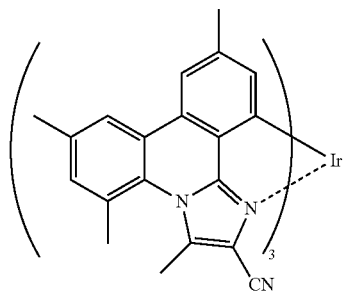
A-34
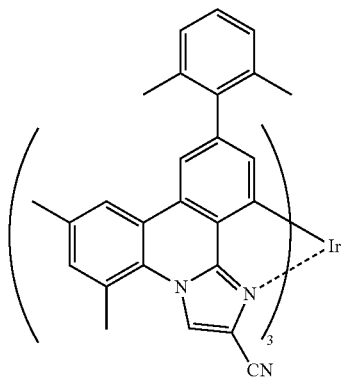
A-35
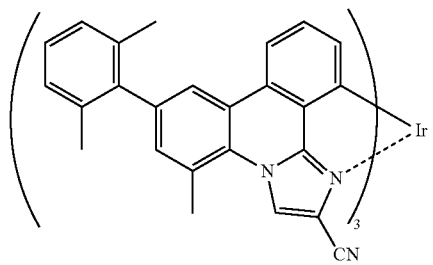

-continued
| | |
|---|---|
| 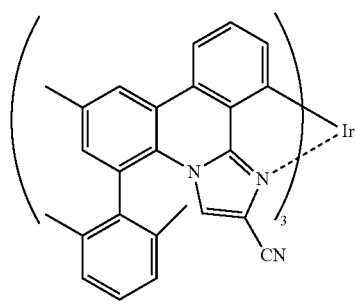 A-36 | 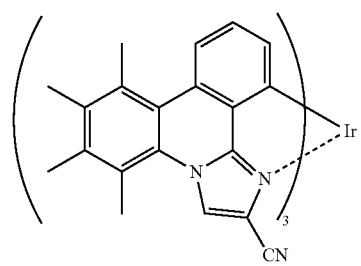 A-37 |
| 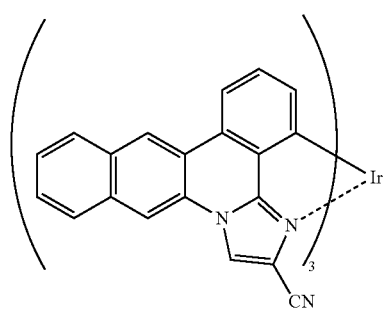 A-38 | 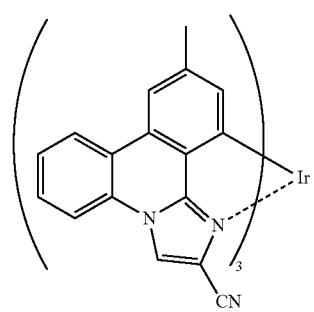 A-39 |
| 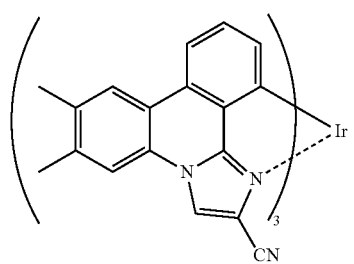 A-40 | 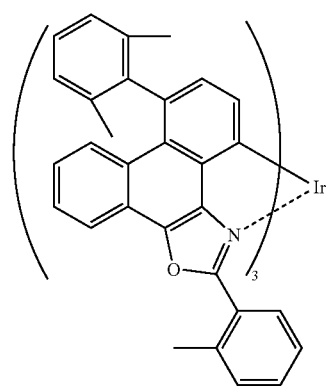 A-41 |
| 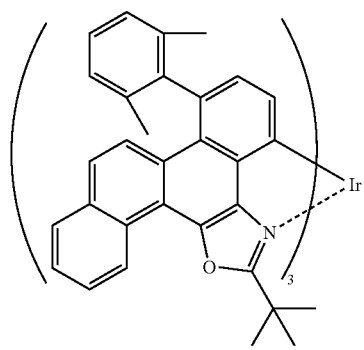 A-42 | 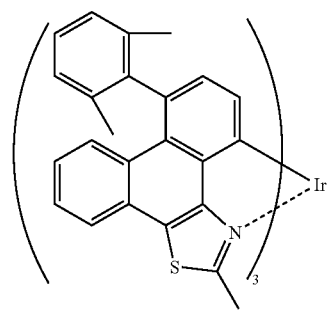 A-43 |

-continued
A-44 A-45
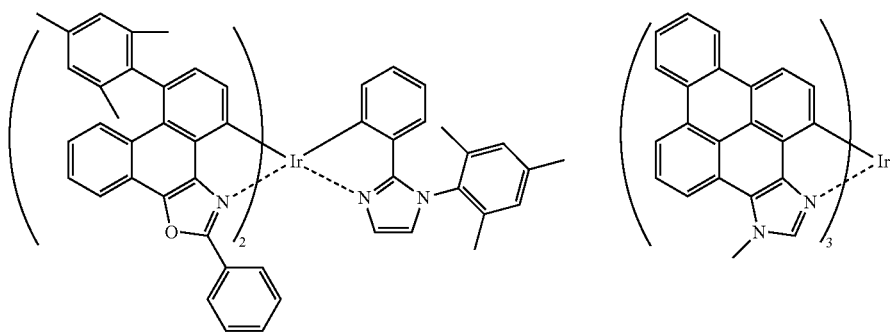
A-46 A-47
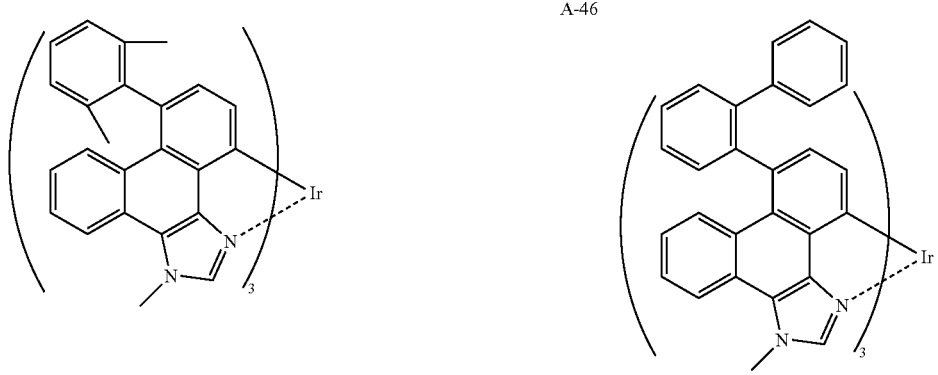
A-48 A-49
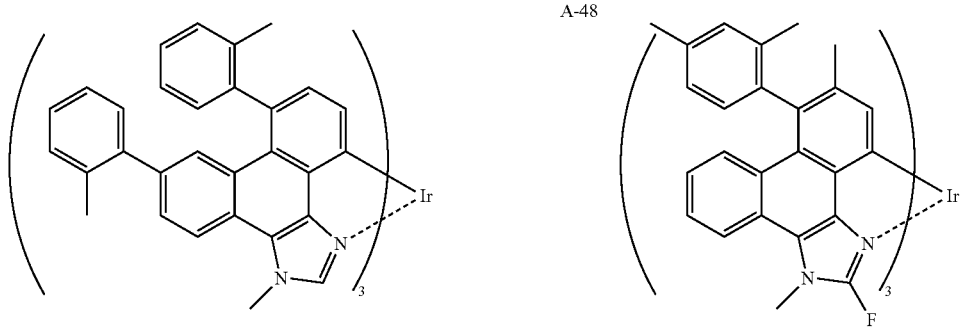
A-50 A-51
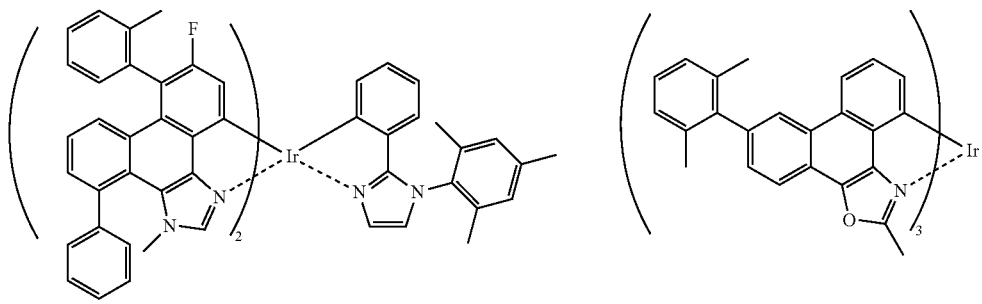

-continued
A-52
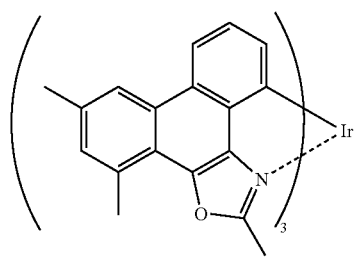
A-53
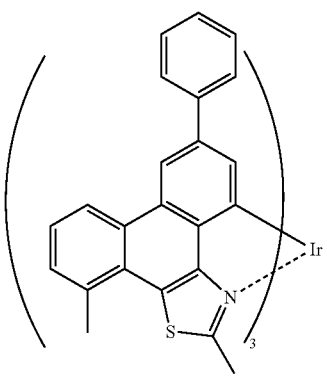
A-54
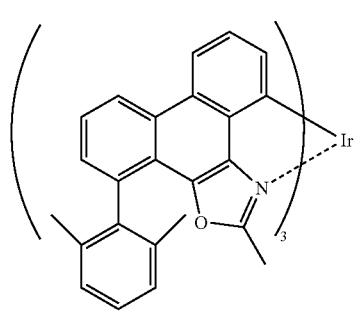
A-55
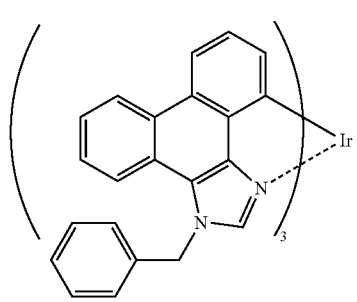
A-56
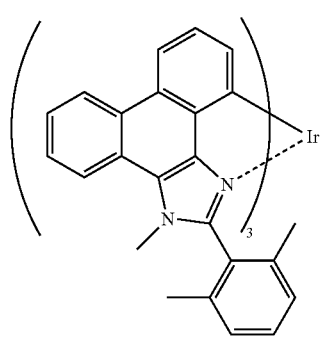
A-57
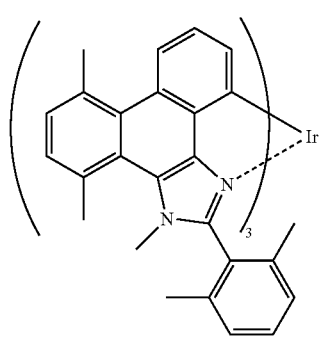
A-58
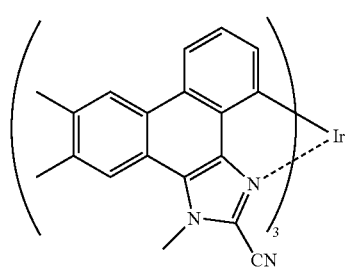
A-59
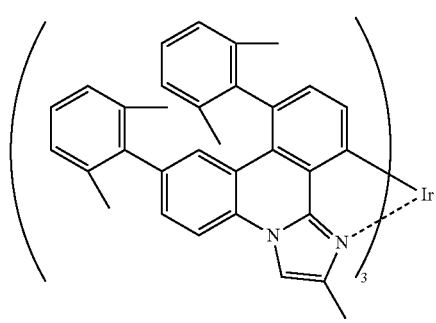

-continued
A-60
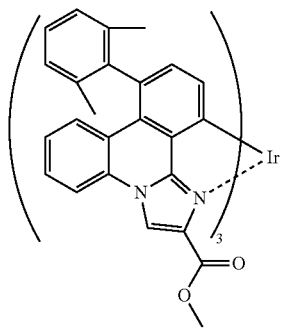
A-61
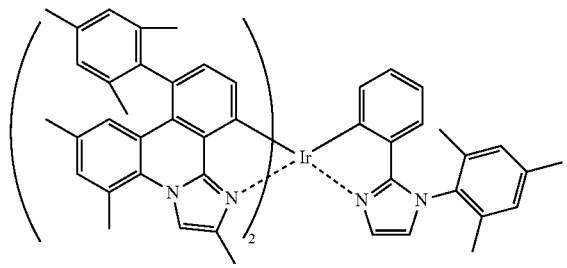
A-62
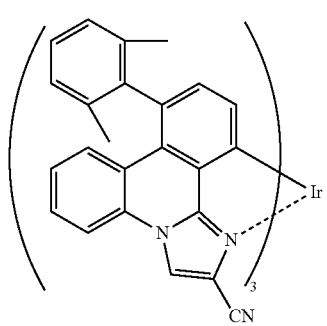
A-63
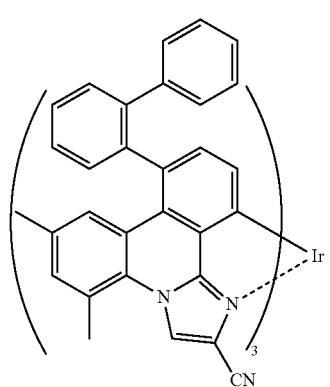
A-64
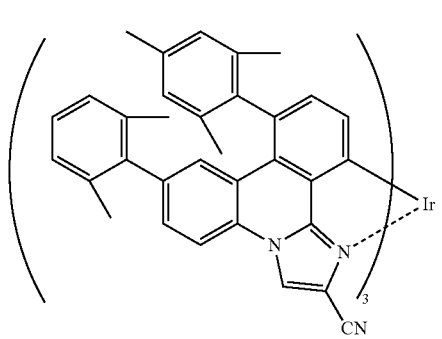
A-65
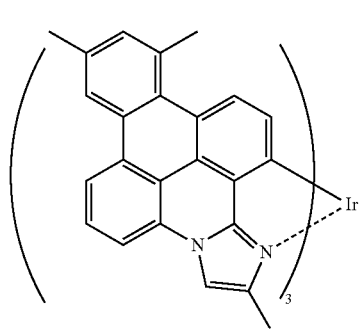
A-66
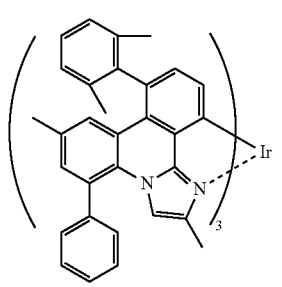
A-67
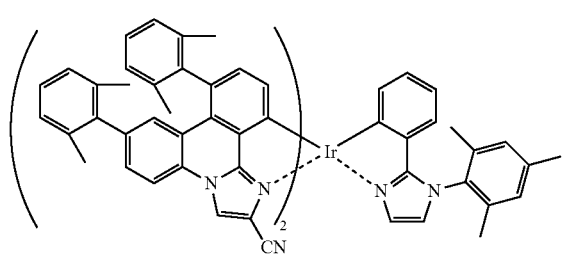

-continued
| | |
|---|---|
| A-68 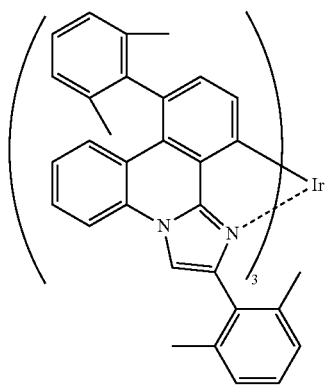 | A-69 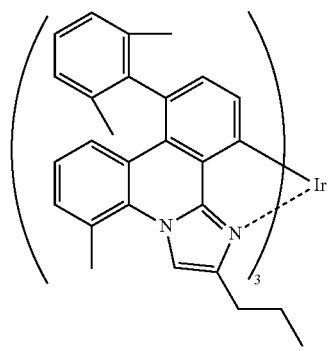 |
| A-70 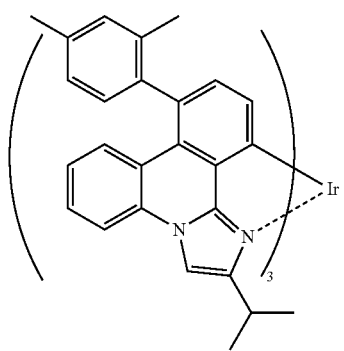 | A-71 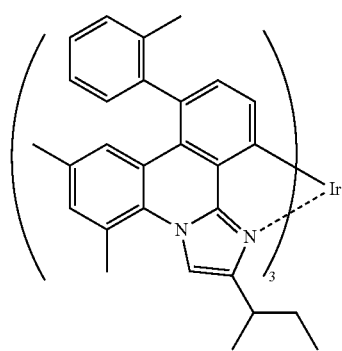 |
| A-72 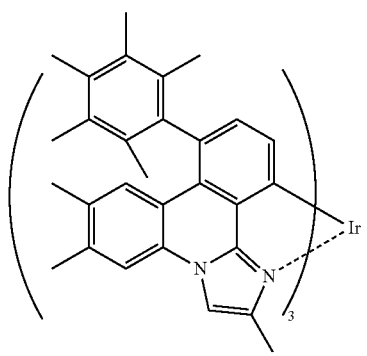 | A-73 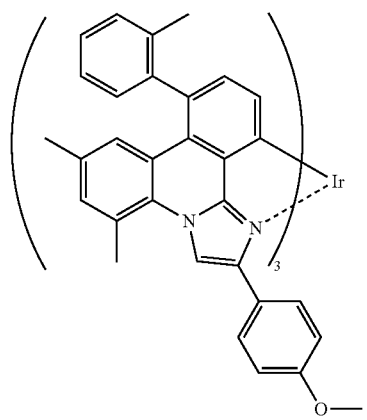 |
| A-74 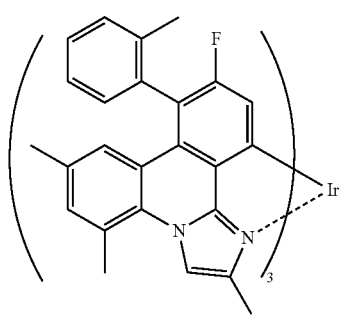 | A-75 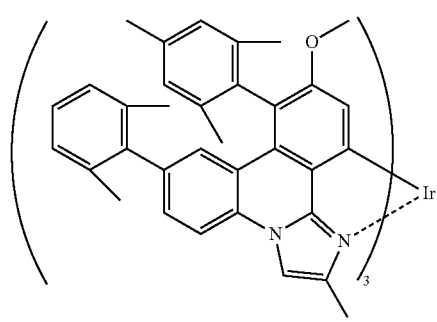 |

-continued
A-76
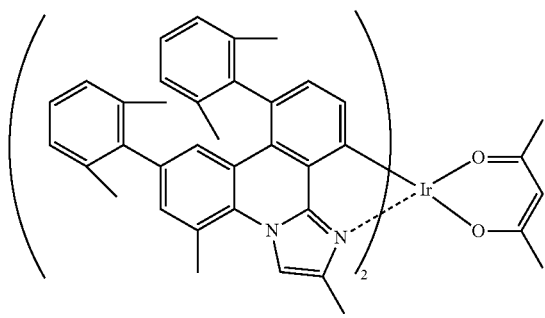
A-77
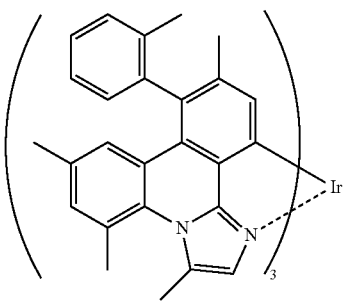
A-78
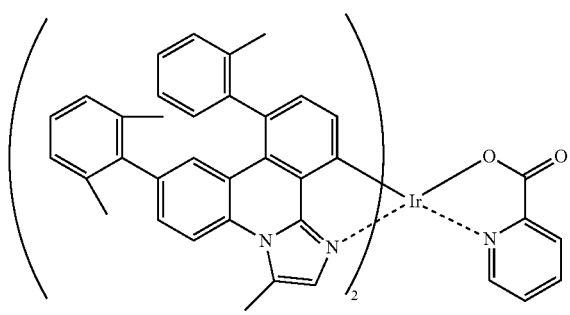
A-79
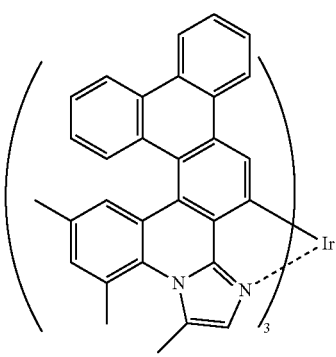
A-80
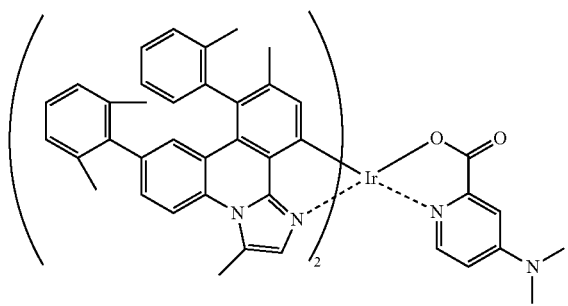
A-81
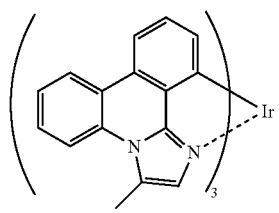
A-82
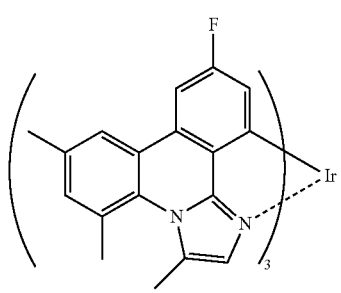
A-83
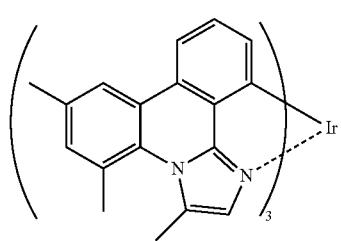
A-84
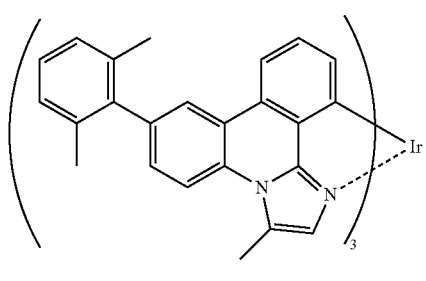
A-85
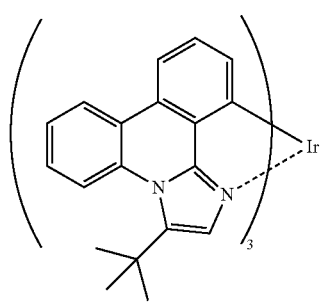

-continued
A-86
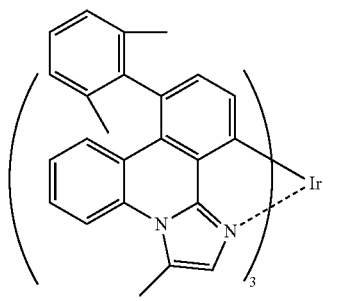
A-87
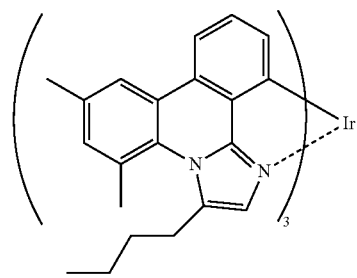
A-88
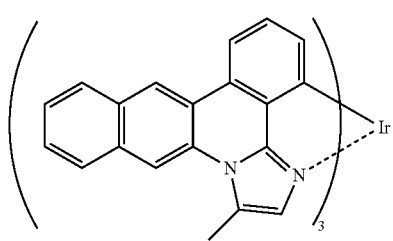
A-89
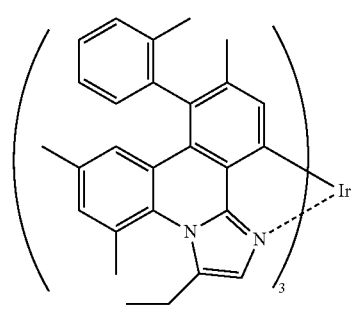
A-90
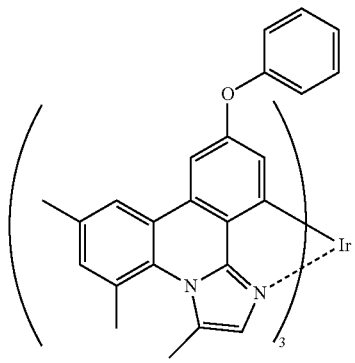
A-91
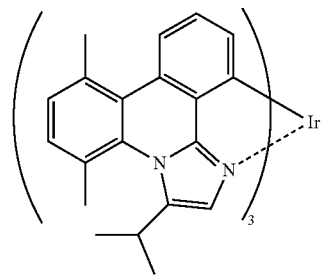
A-92
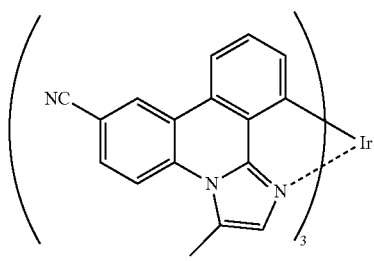
A-93
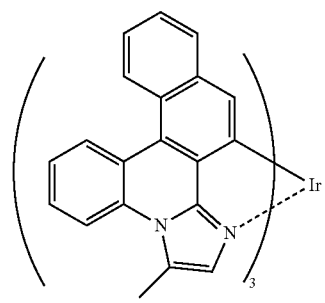
A-94
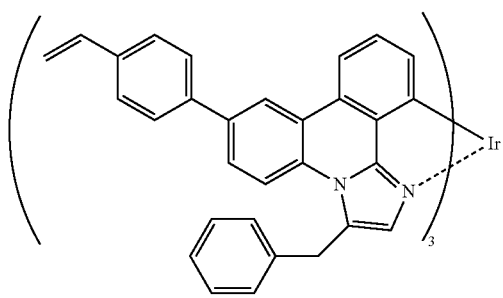
A-95
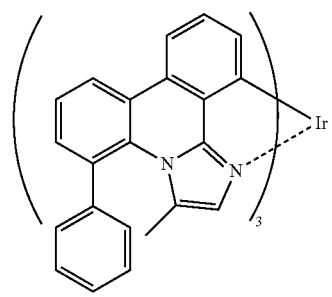

-continued
A-96
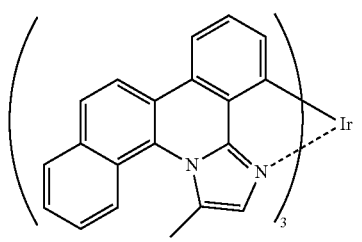
A-97
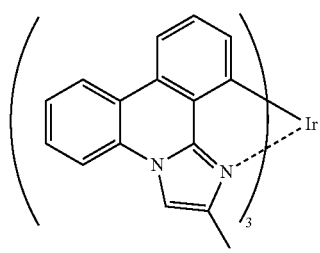
A-98
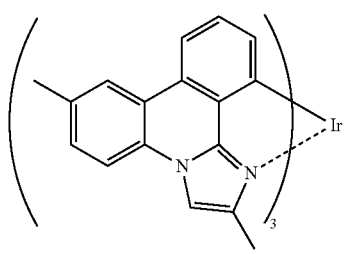
A-99
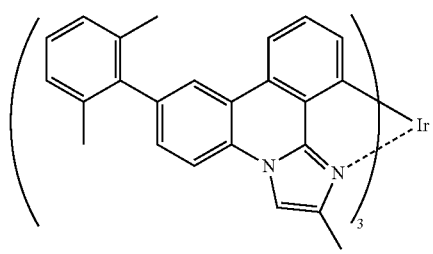
A-100
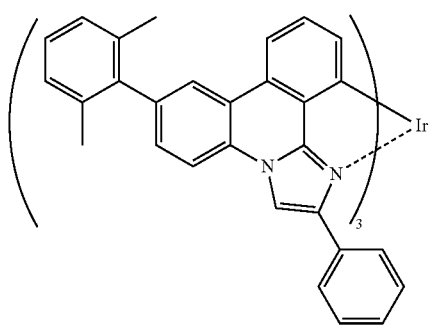
A-101
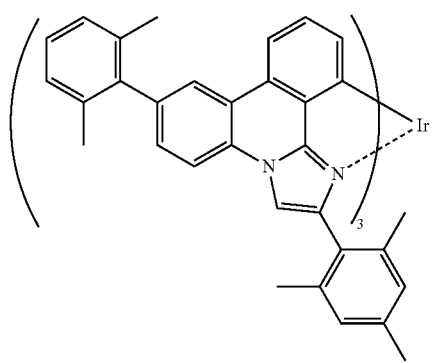
A-102
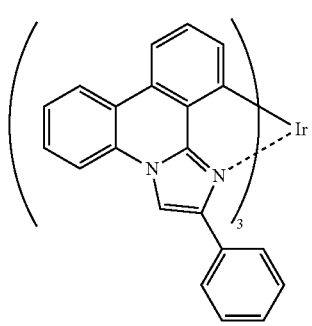
A-103
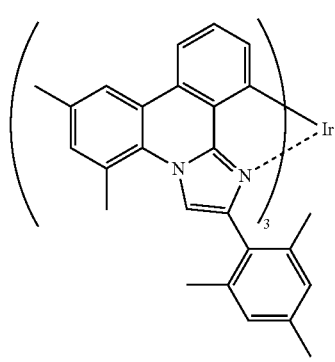
A-104
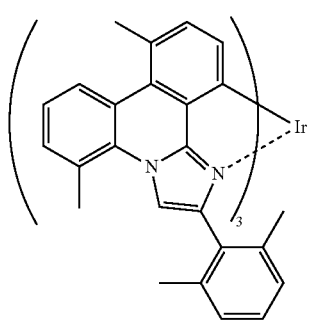
A-105
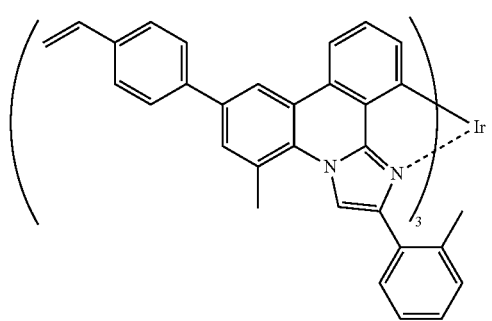

-continued
| A-106 | A-107 |
|---|---|
| 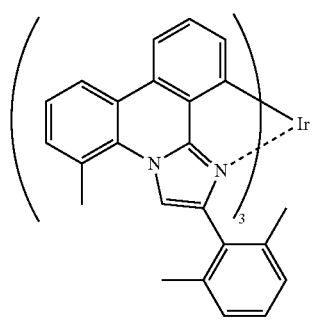 | 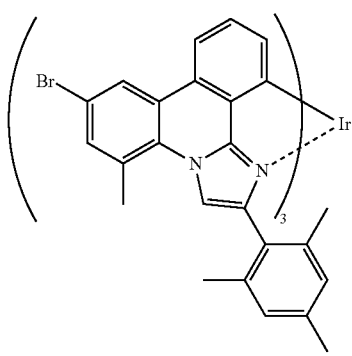 |
| A-108 | A-109 |
| 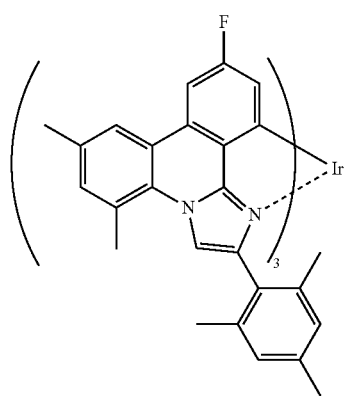 | 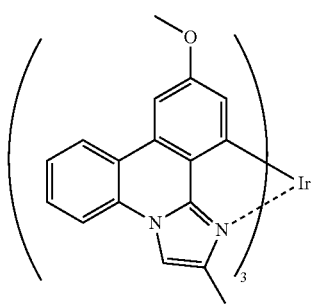 |
| A-110 | A-111 |
| 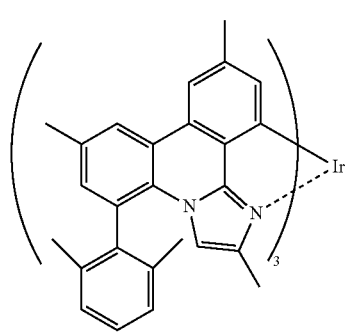 | 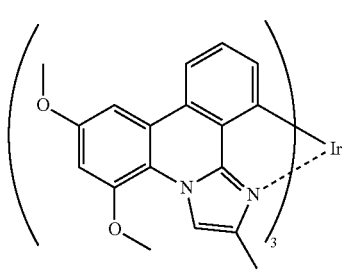 |
| A-112 | A-113 |
| 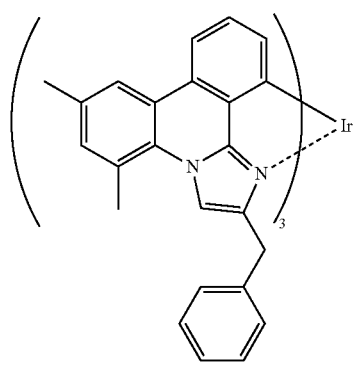 | 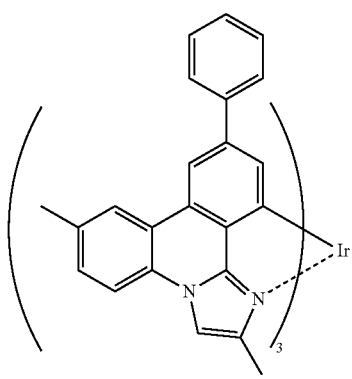 |

-continued
| | |
|---|---|
| A-114 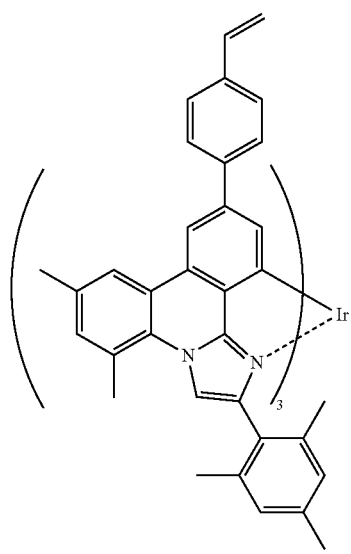 | A-115 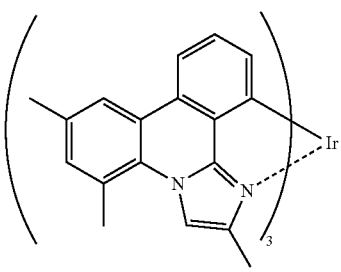 |
| A-116 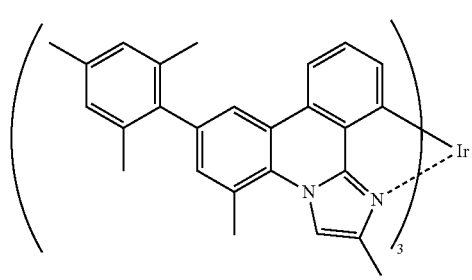 | A-117 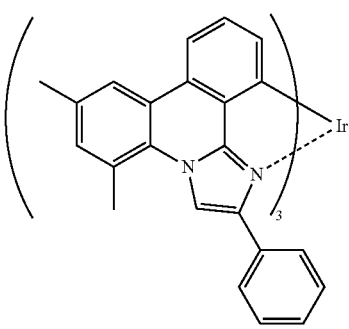 |
| A-118 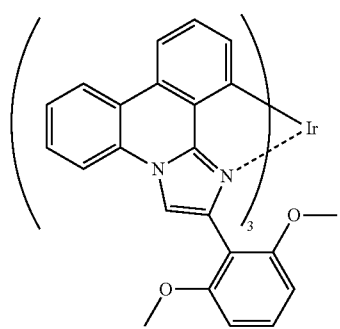 | A-119 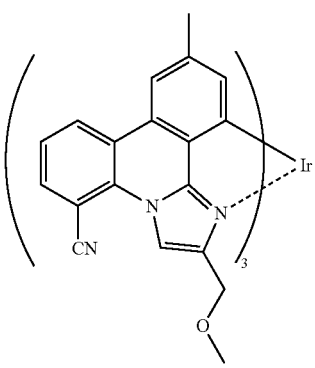 |
| A-120 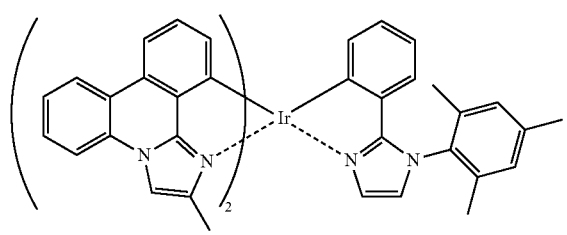 | A-121 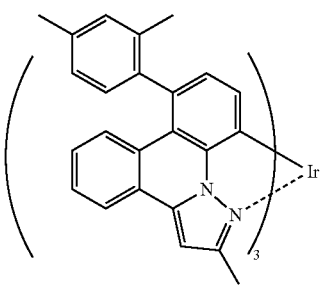 |

-continued
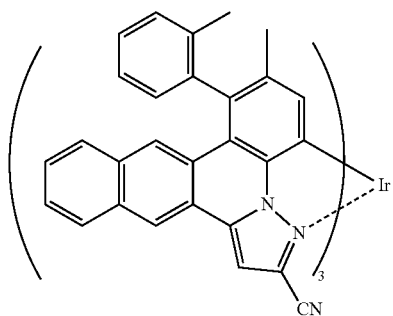
A-122
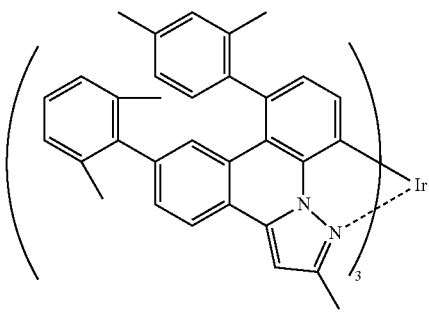
A-123
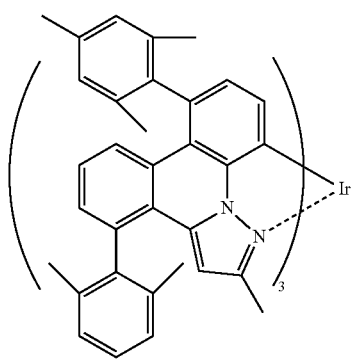
A-124
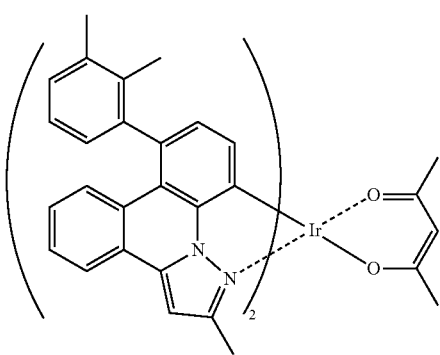
A-125
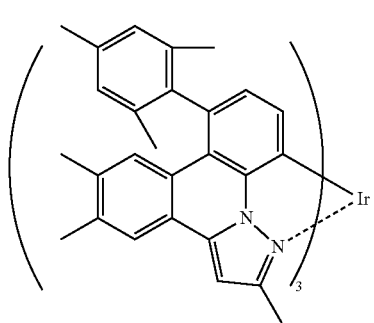
A-126
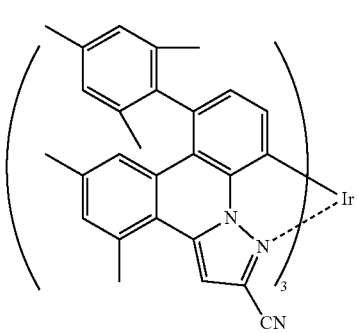
A-127
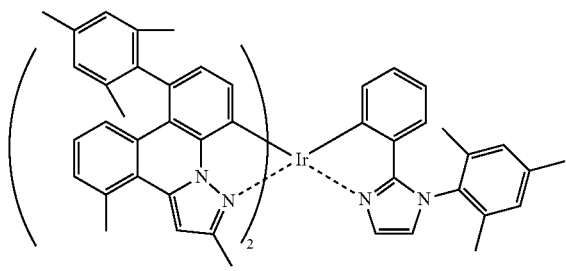
A-128
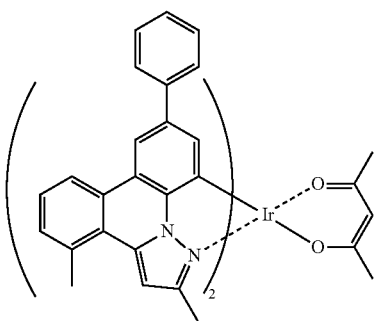
A-129

-continued
| A-130 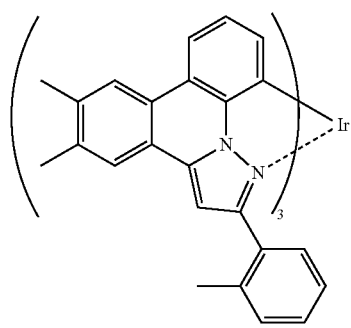 | A-131 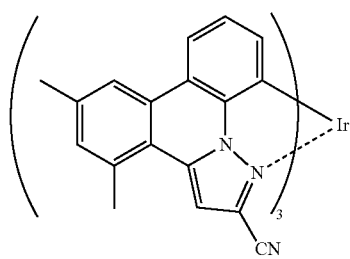 |
| A-132 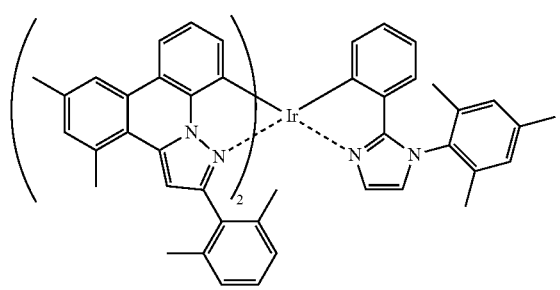 | A-133 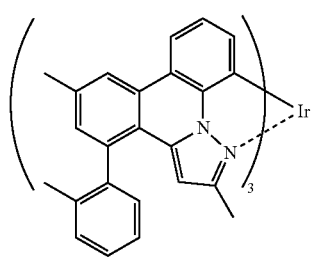 |
| A-134 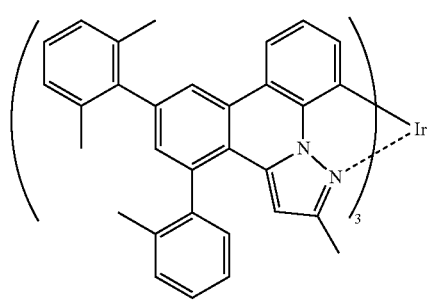 | A-135 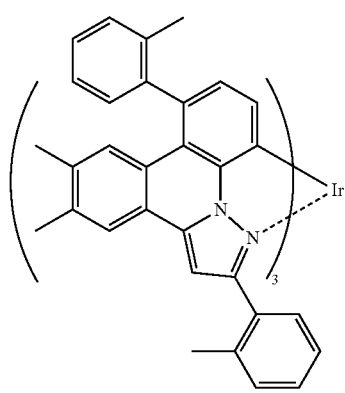 |
| A-136 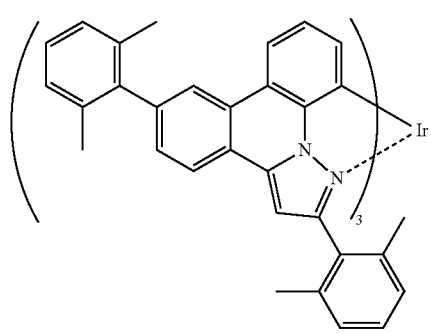 | A-137 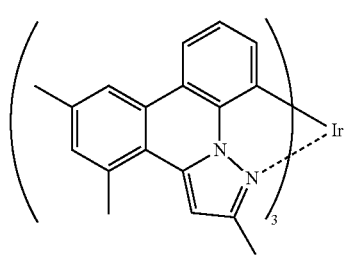 |

-continued
A-138
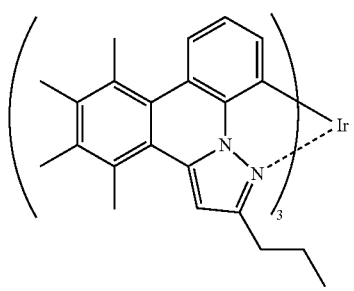
A-139
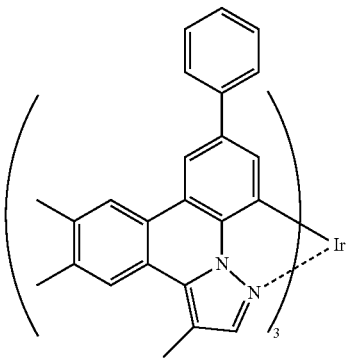
A-140
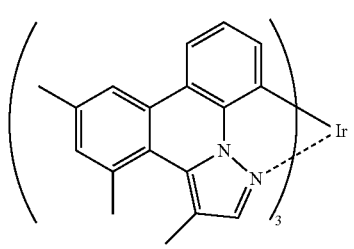
A-141
A-142
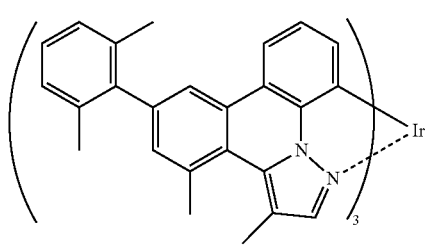
A-143
A-144
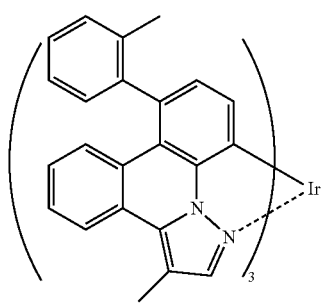
A-145
A-146
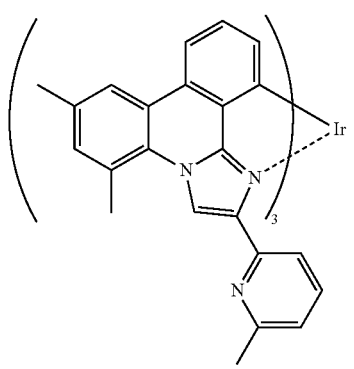
A-147
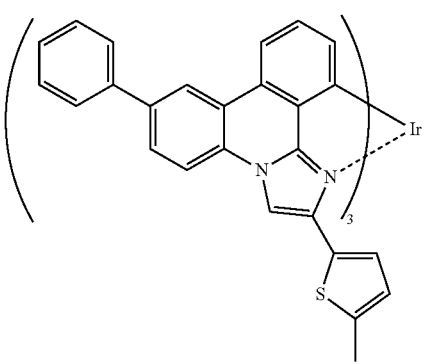

-continued
| A-148 | A-149 |
|---|---|
| 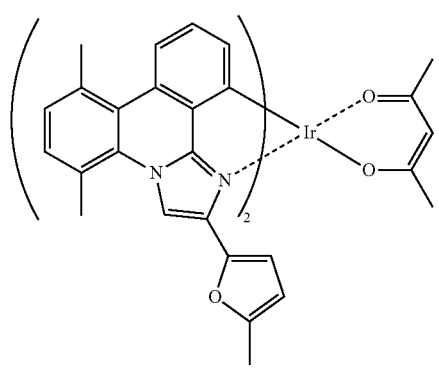 | 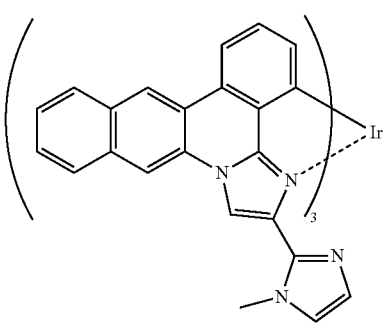 |
| A-150 | A-151 |
| 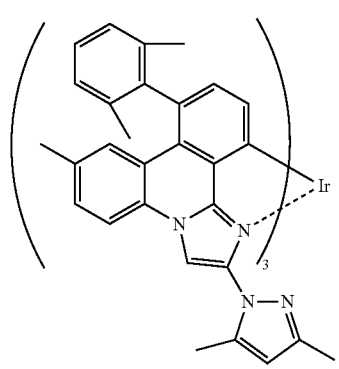 | 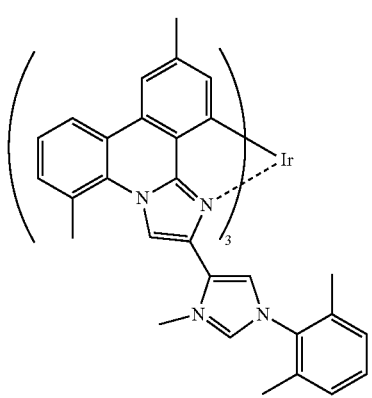 |
| A-152 | A-153 |
| 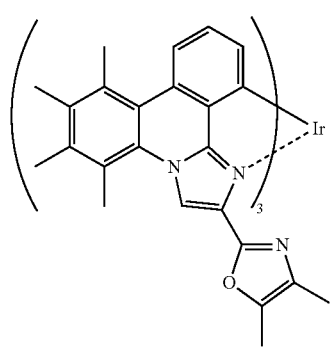 | 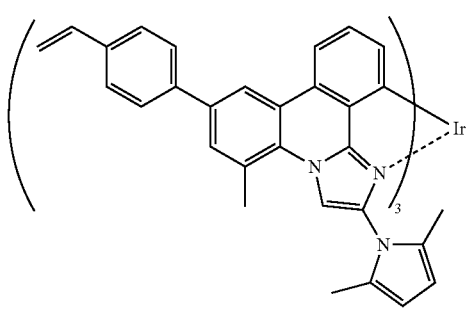 |
| A-154 | A-155 |
| 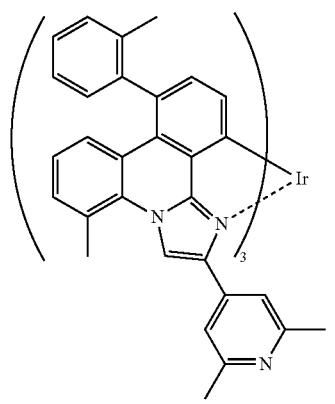 | 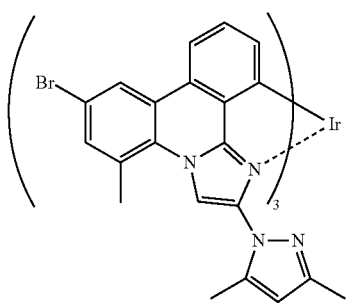 |

-continued
| A-156 | A-157 |
|---|---|
| 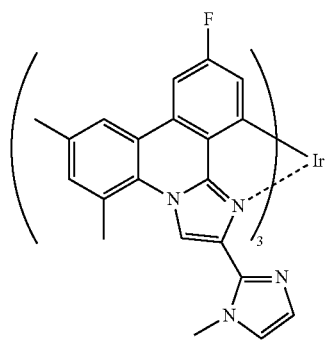 | 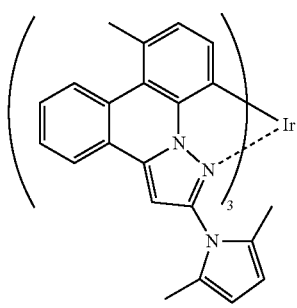 |
| A-158 | A-159 |
| 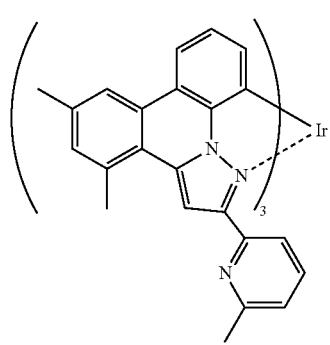 | 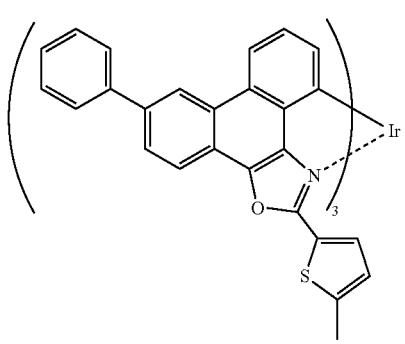 |
| A-160 | A-161 |
| 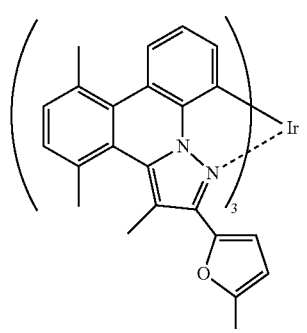 | 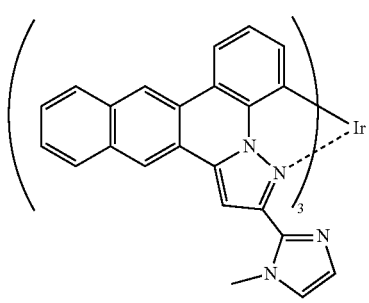 |
| A-162 | A-163 |
| 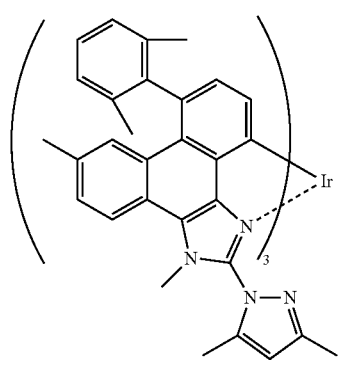 | 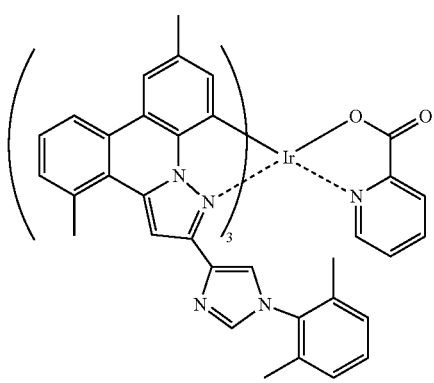 |

-continued
A-164
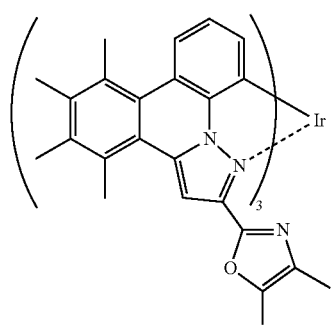
A-165
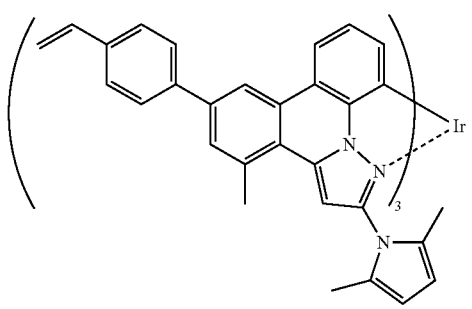
A-166
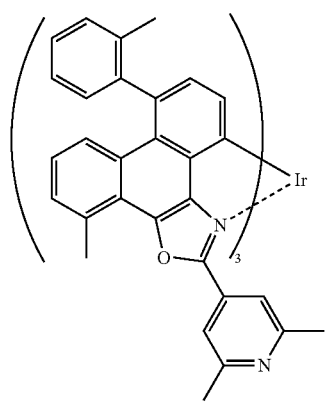
A-167
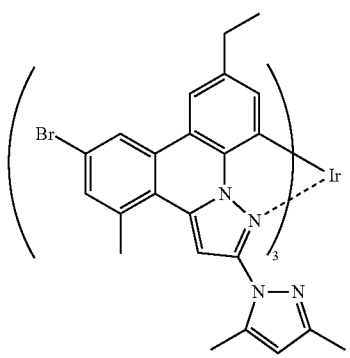
A-168
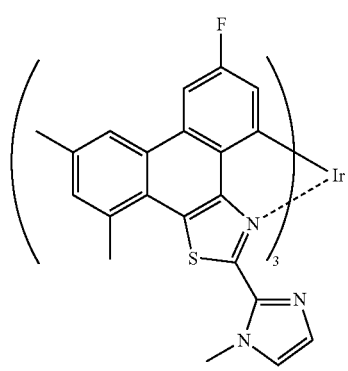
A-169
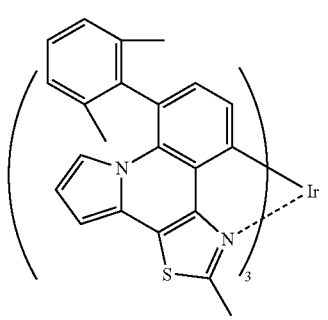
A-170
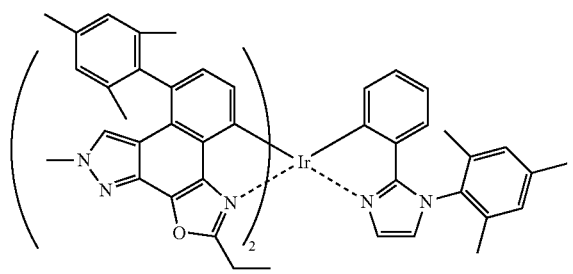
A-171
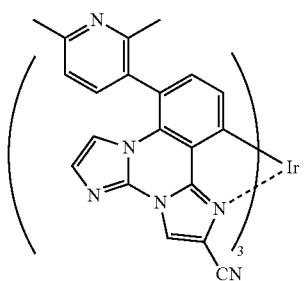

-continued
A-172
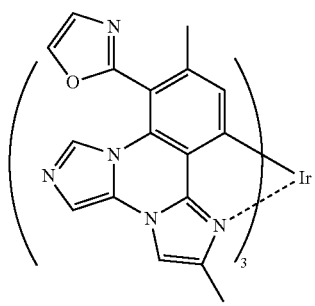
A-173
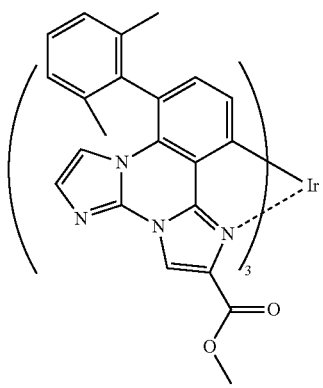
A-174
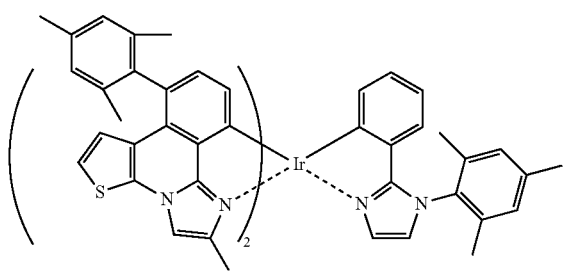
A-175
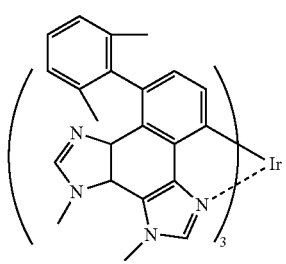
A-176
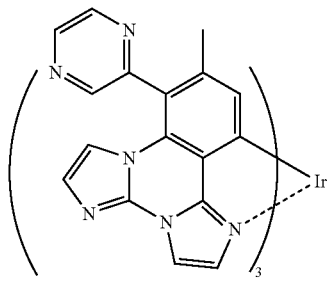
A-177
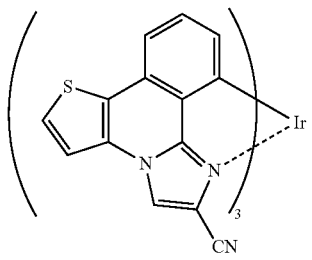
A-178
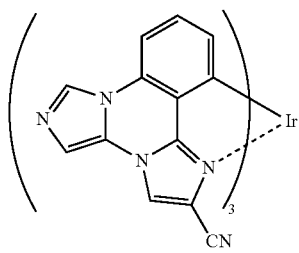
A-179
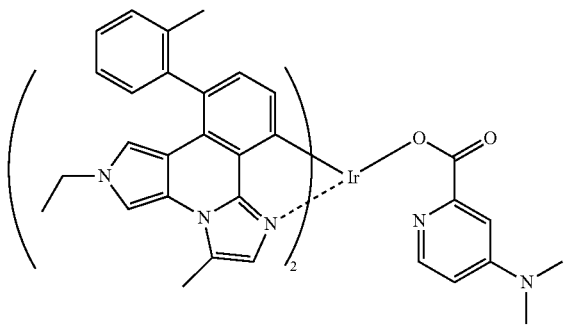
A-180
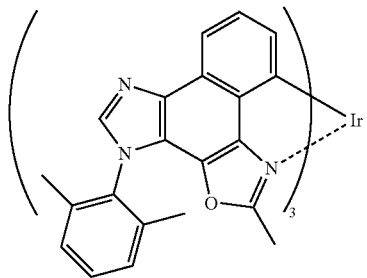
A-181
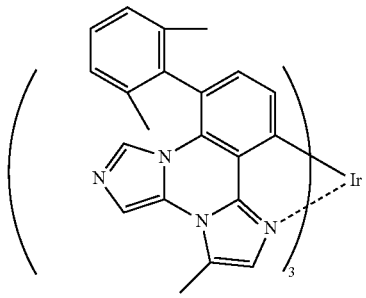

-continued
A-182
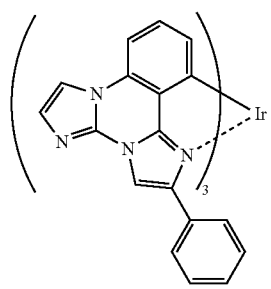
A-183
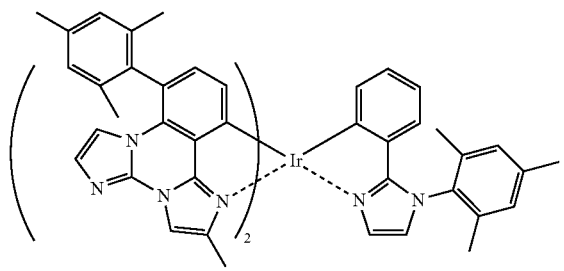
A-184
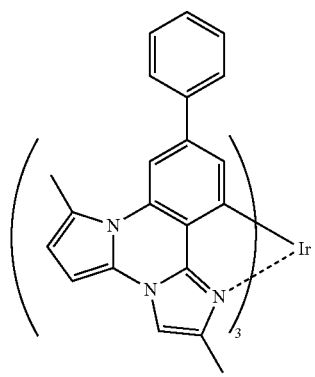
A-185
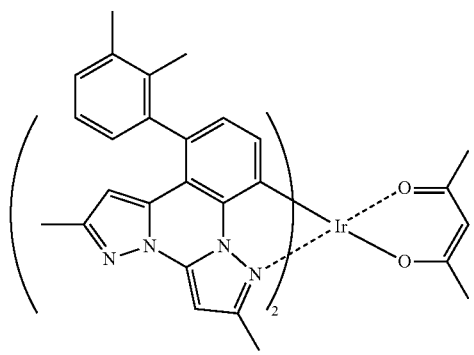
A-186
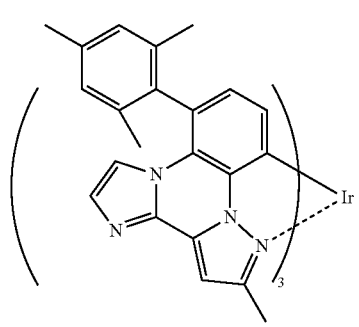
A-187
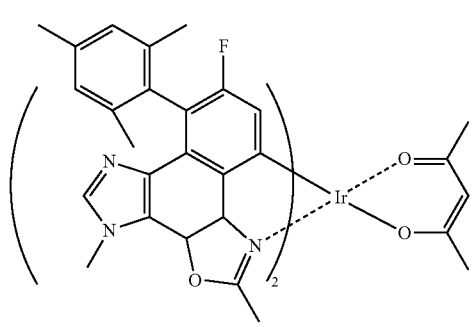
A-188
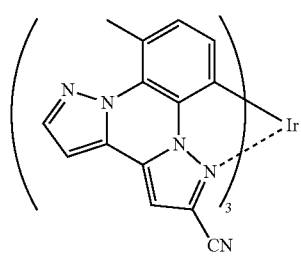
A-189
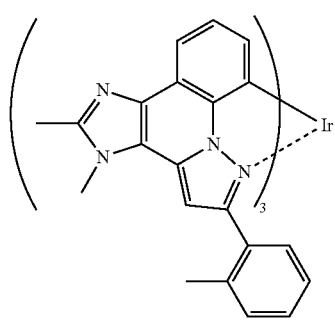

-continued
A-190
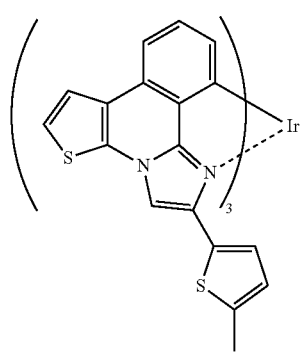
A-191
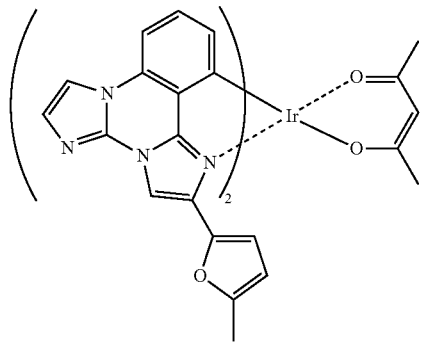
A-192
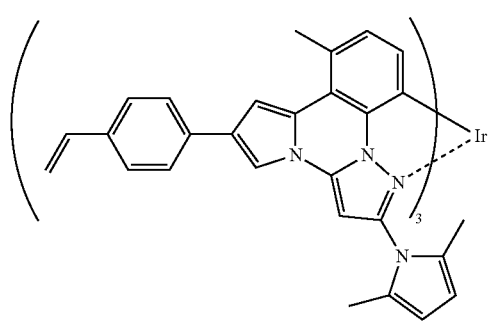
A-193
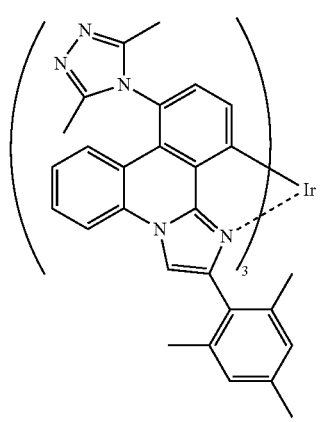
A-194
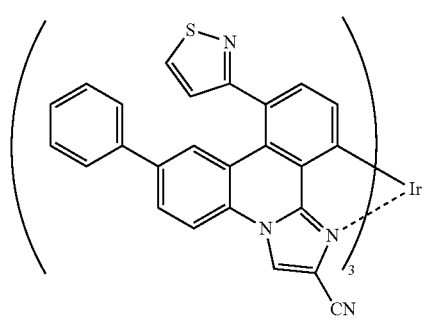
A-195
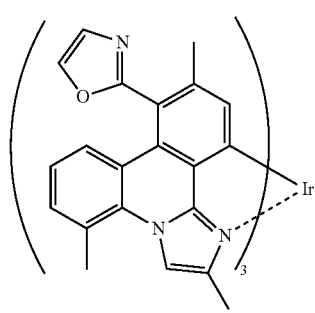
A-196
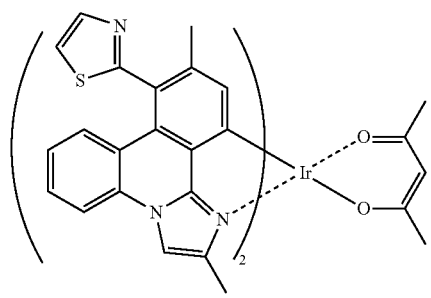
A-197
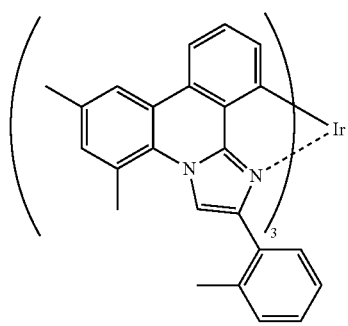

-continued
A-198
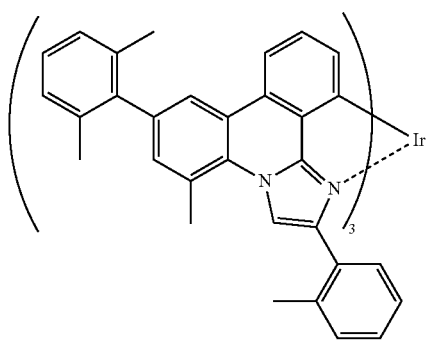
A-199
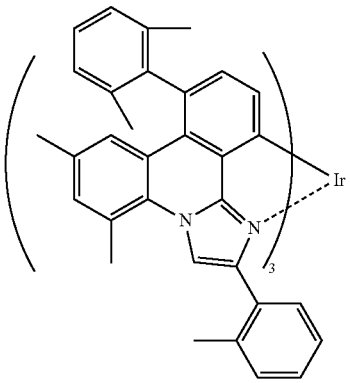
A-200
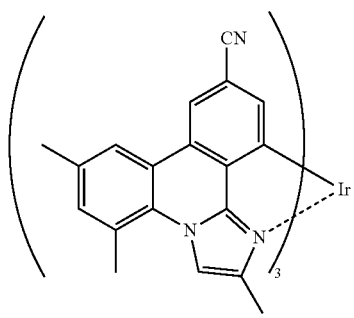
A-201
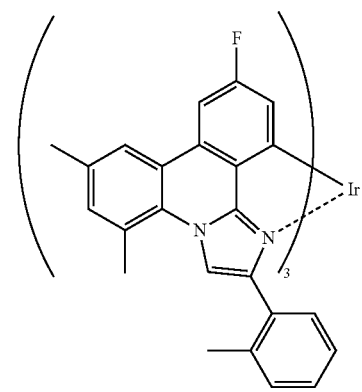
A-202
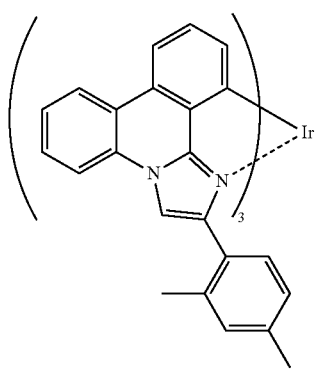
A-203
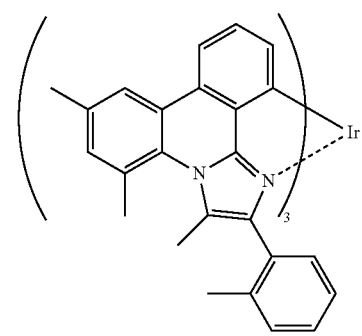
A-204
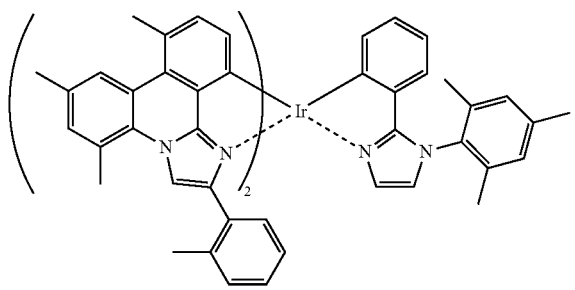
B-8
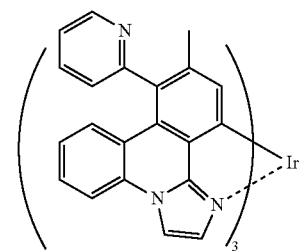

-continued
B-11
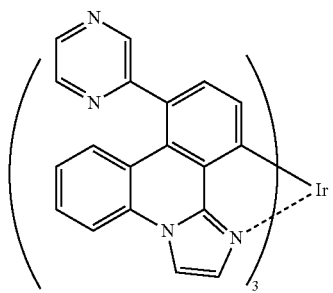
B-12
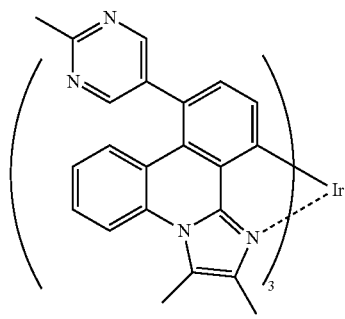
B-13
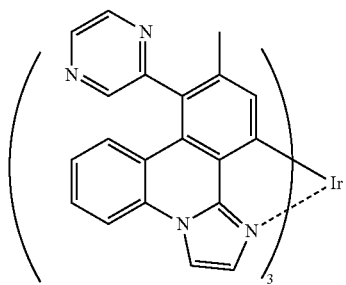
B-14
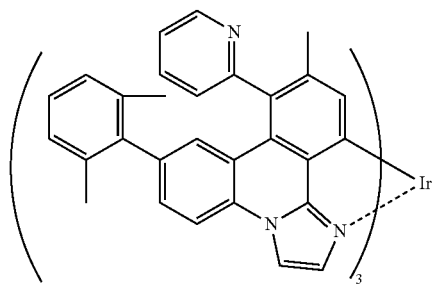
B-15
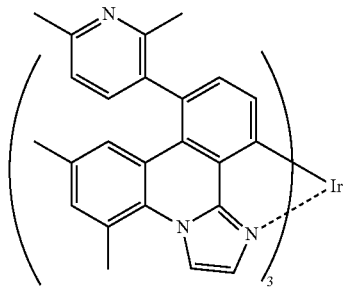
B-16
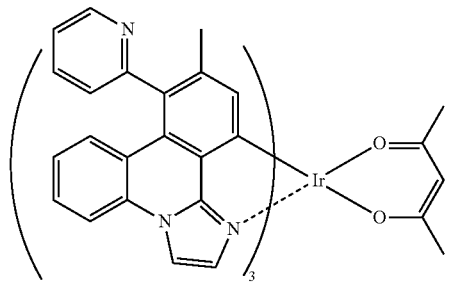
B-17
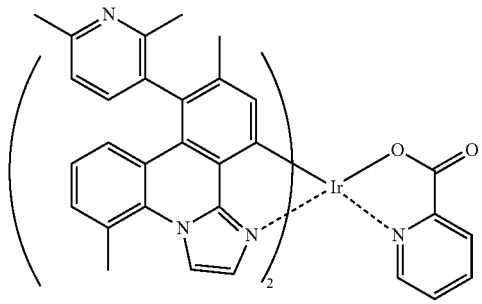
B-19
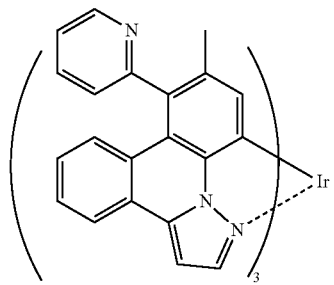
B-20
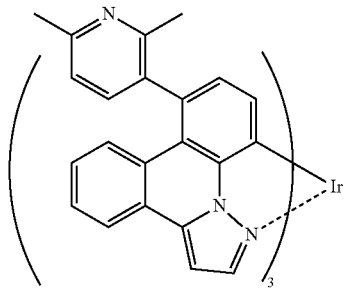
B-21
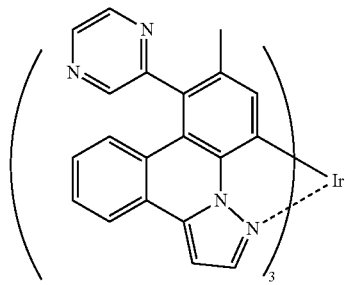

-continued
B-24
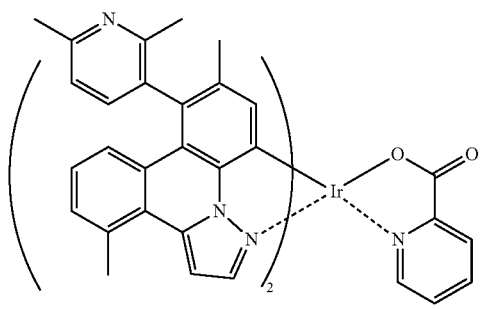
B-26
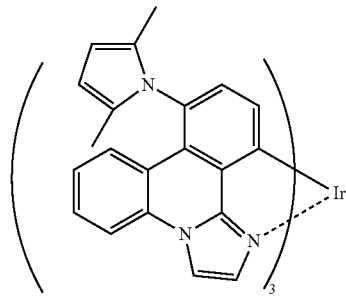
B-28
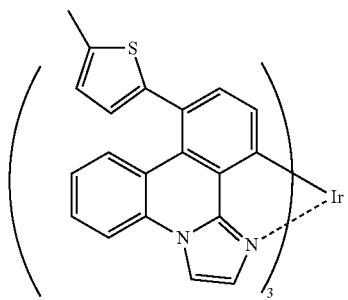
B-30
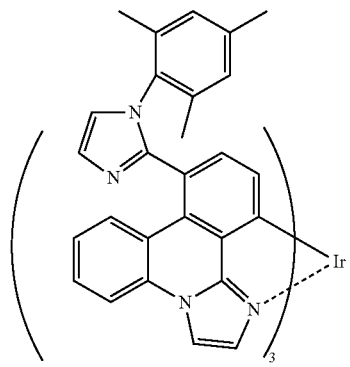
B-32
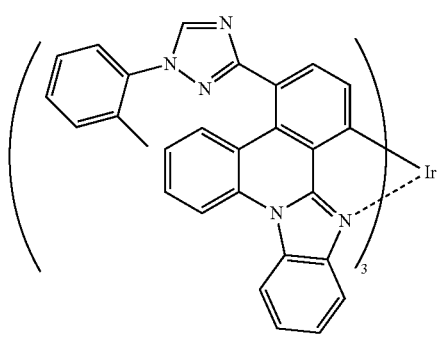
B-35
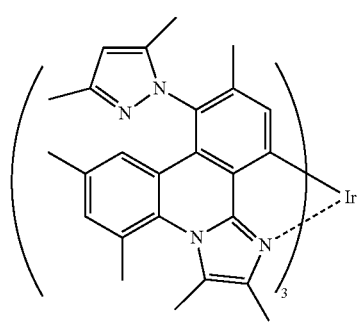
B-36
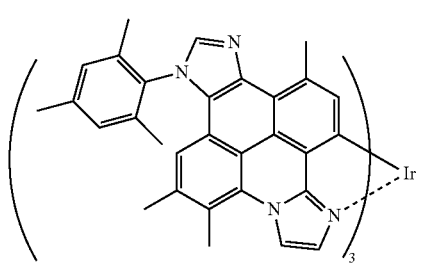
B-40
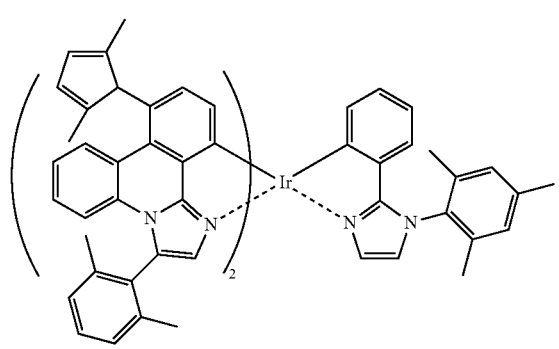

-continued
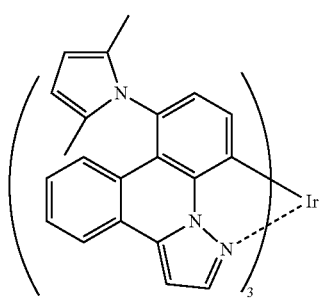
B-41
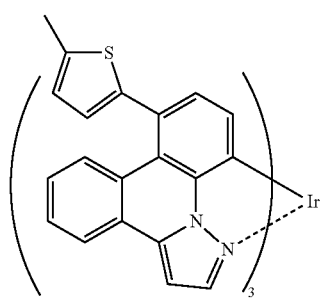
B-43
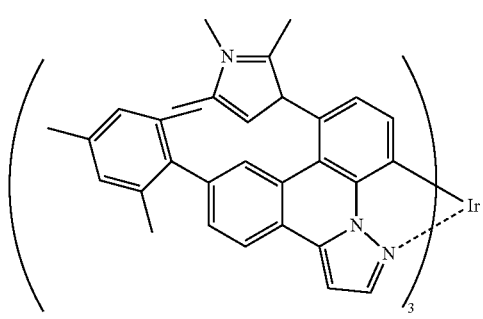
B-44
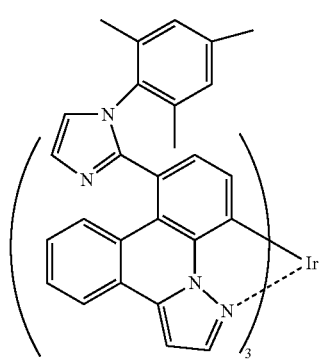
B-45
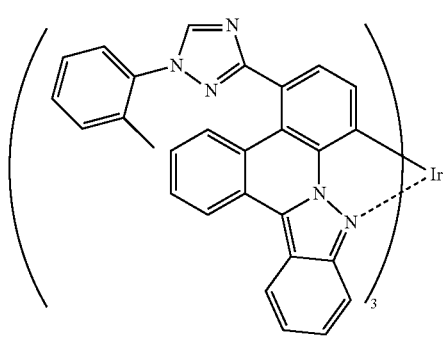
B-47
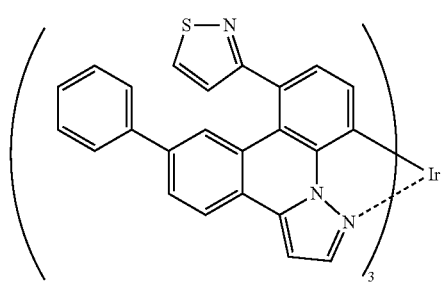
B-49
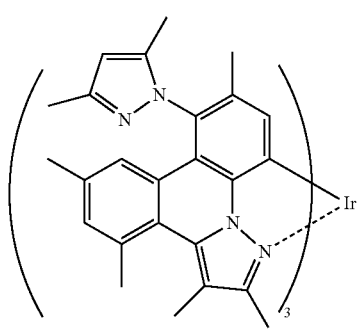
B-50
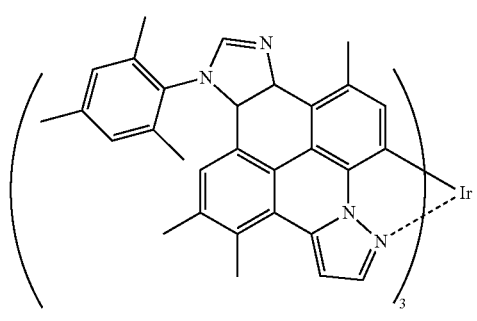
B-51

-continued
B-54
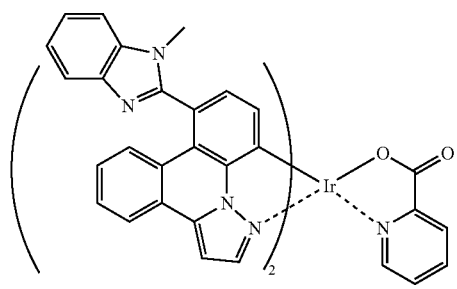
B-55
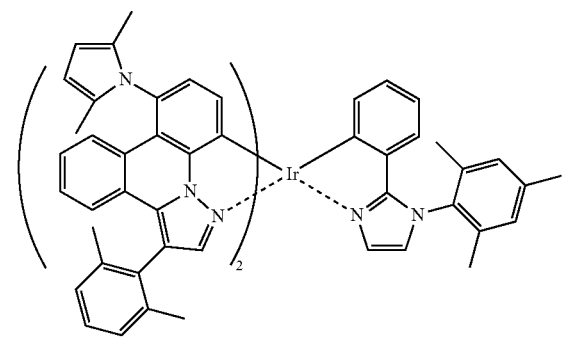
B-56
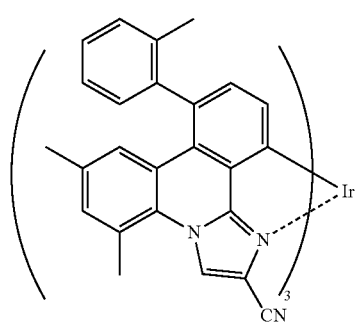
B-57
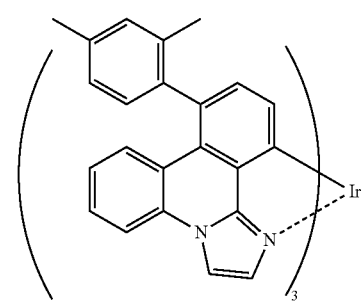
B-59
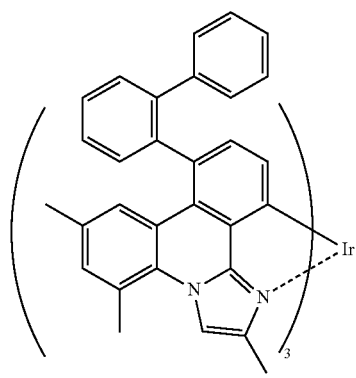
B-60
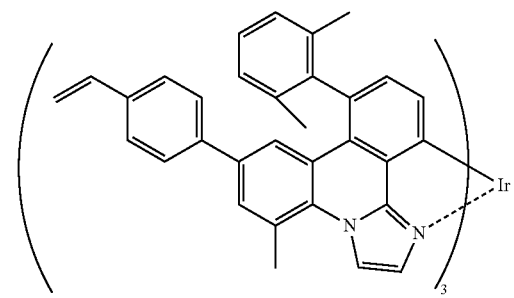
B-61
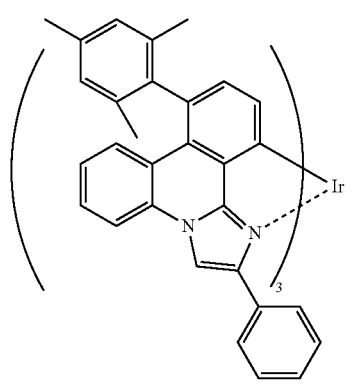
B-62
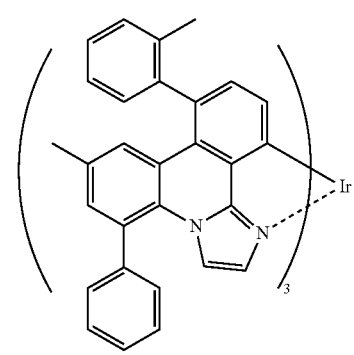

-continued
B-63
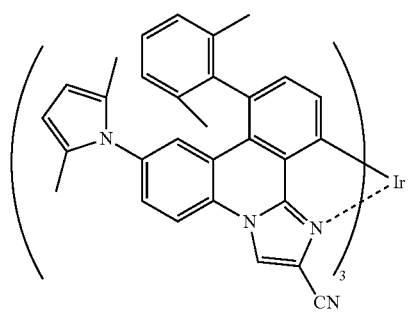
B-34
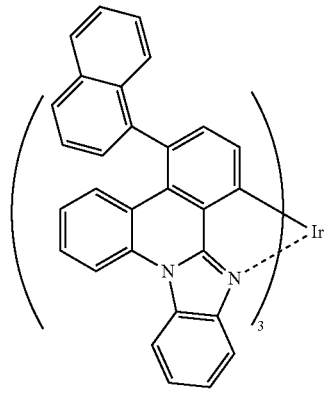
B-66
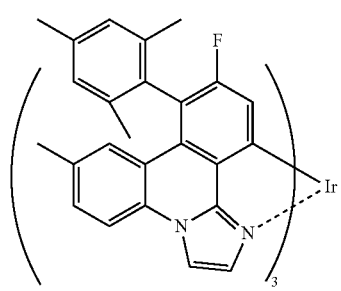
B-68
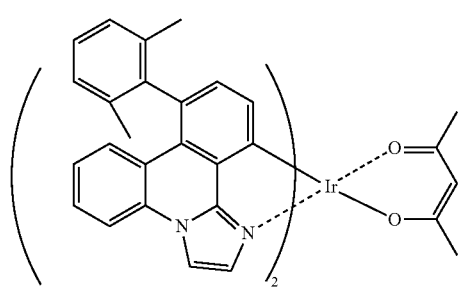
B-72
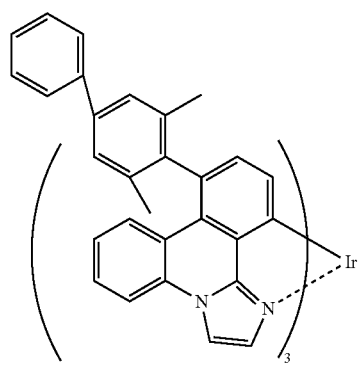
B-73
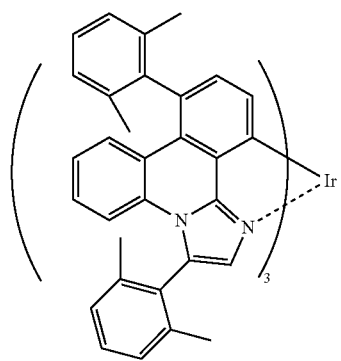
B-79
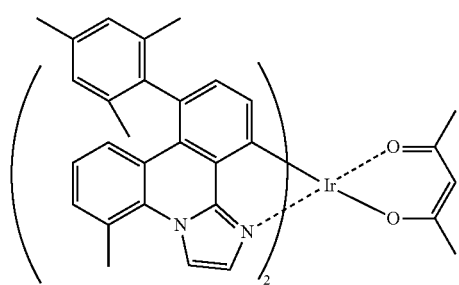
B-82
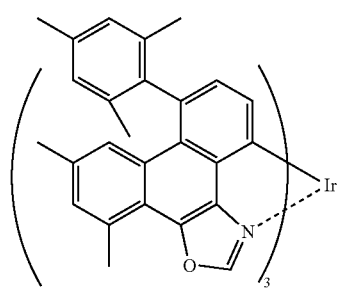

-continued
B-84
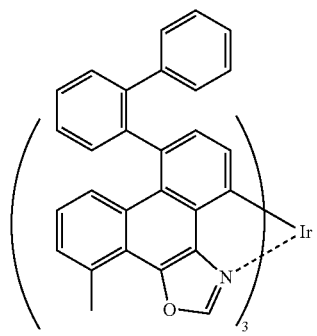
B-86
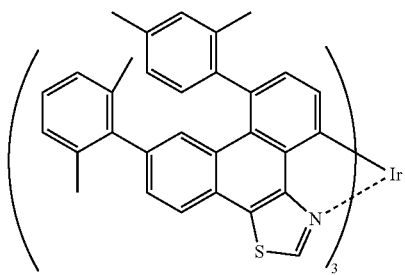
B-88
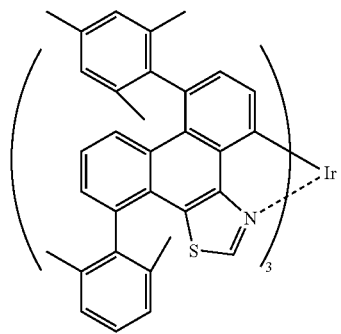
B-89
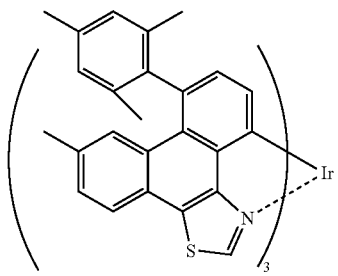
B-90
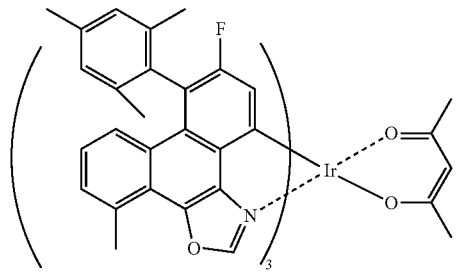
B-91
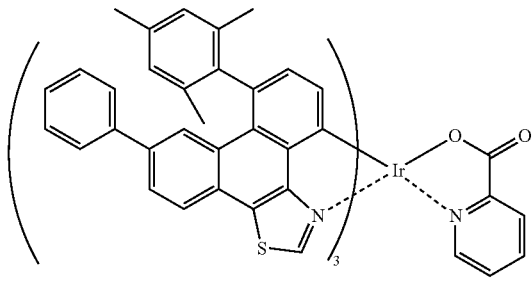
B-95
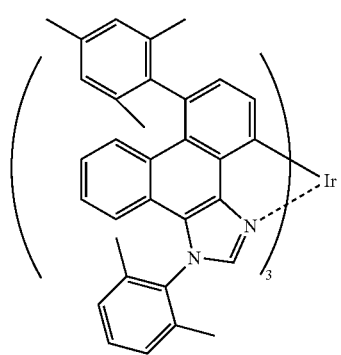
B-98
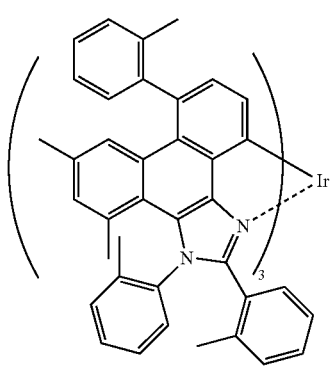

B-100
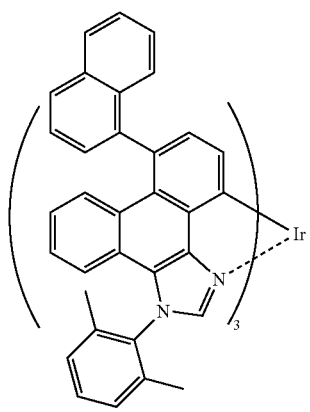
B-101
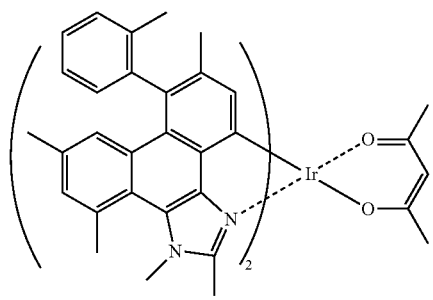
B-102
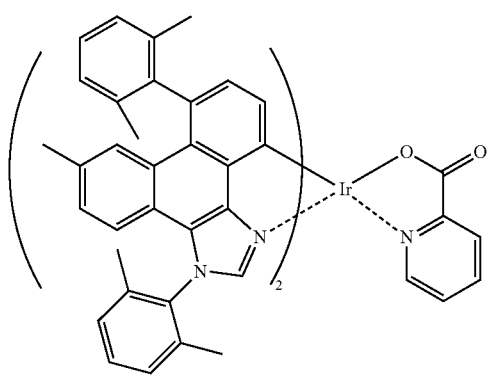
B-104
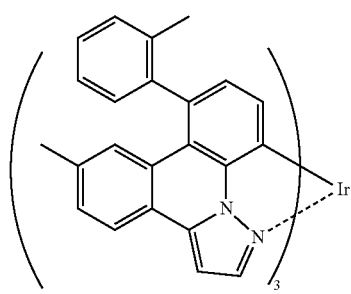
B-106
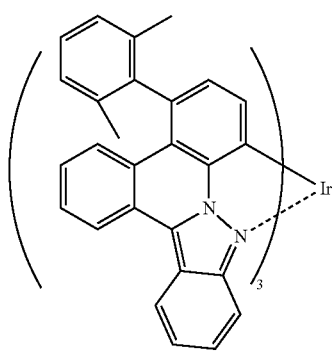
B-107
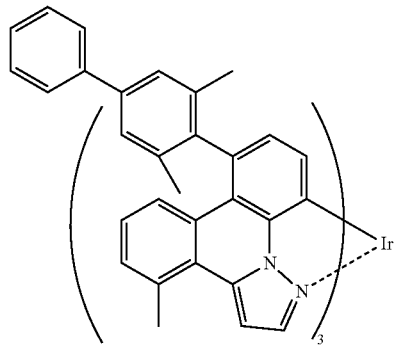
B-108
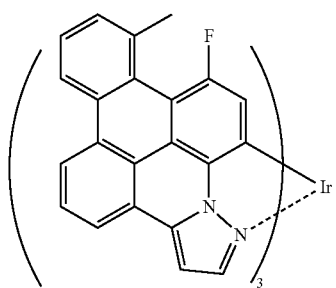
B-110
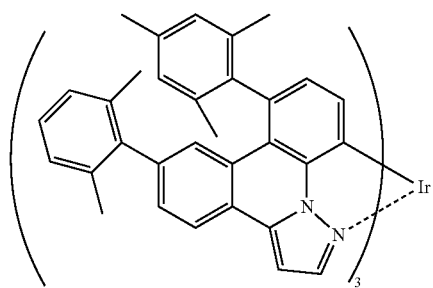

-continued
B-111
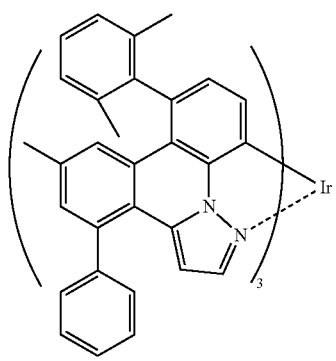
B-113
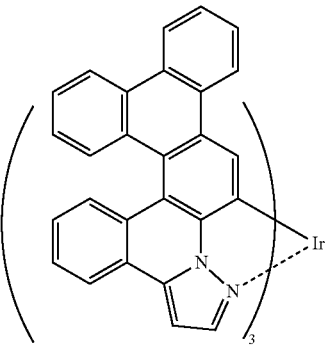
B-114
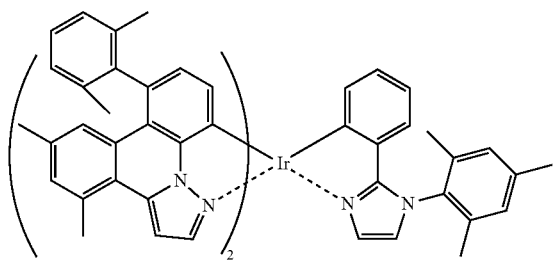
B-115
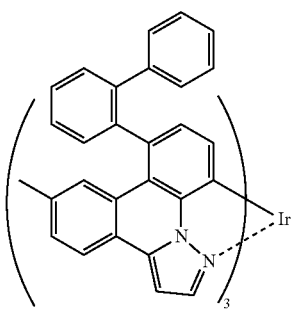
B-116
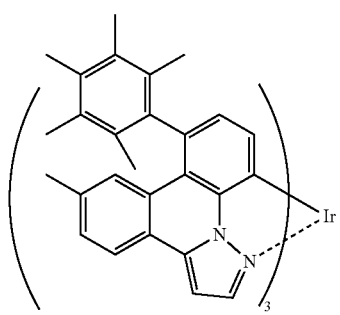
B-117
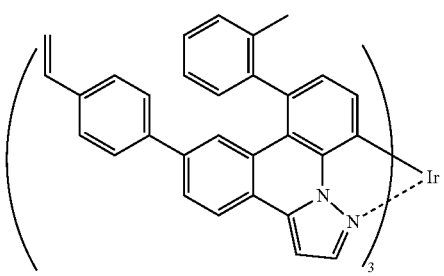
B-118
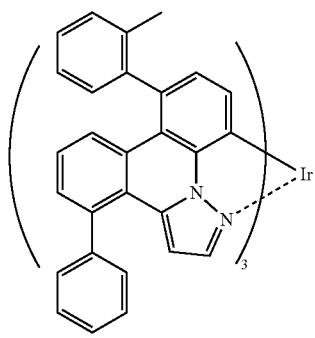
B-119
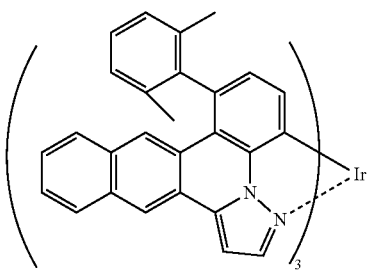

-continued
B-120 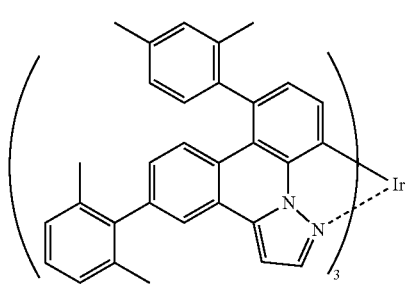 B-123 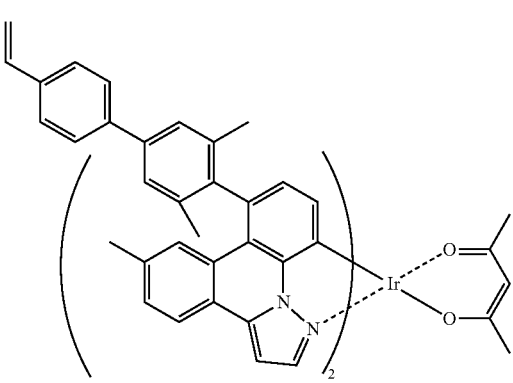
B-124 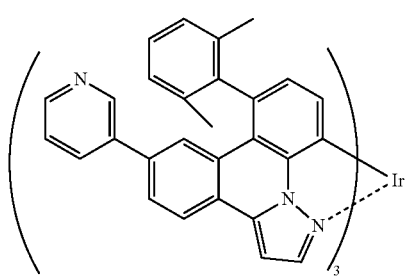 B-128 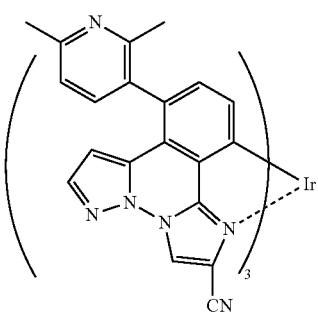
B-129 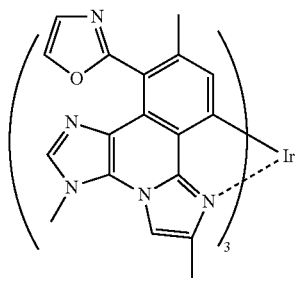 B-130 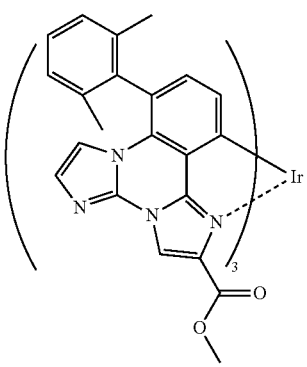
B-135 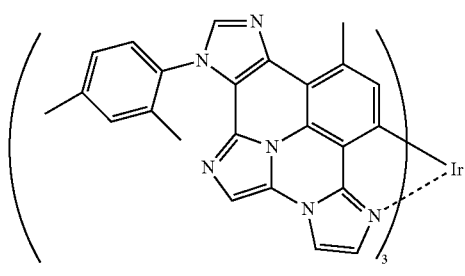 B-136 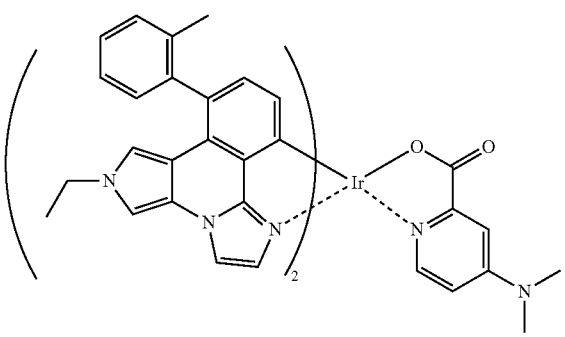

-continued
B-138
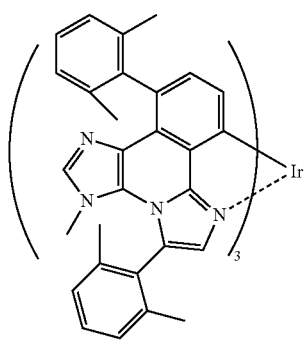
B-139
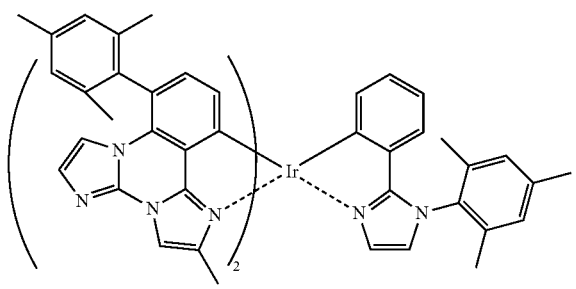
B-144
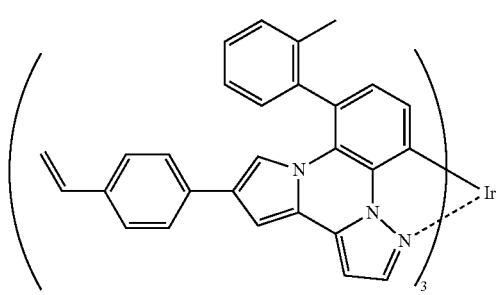
B-145
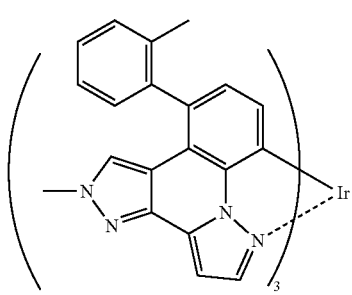
B-146
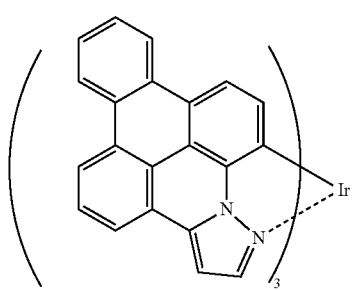
C-1
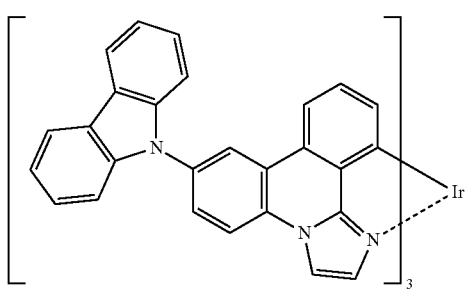
C-2
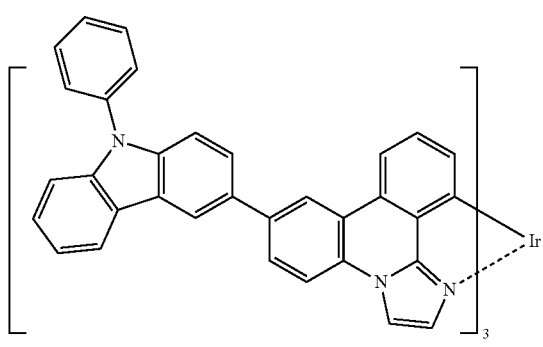
C-3
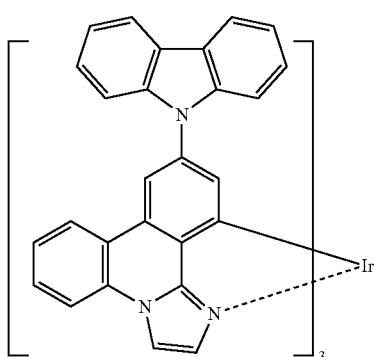

-continued
C-4
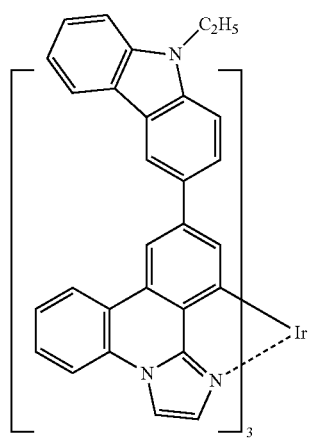
C-5
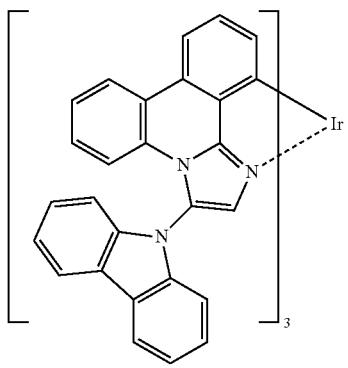
C-6
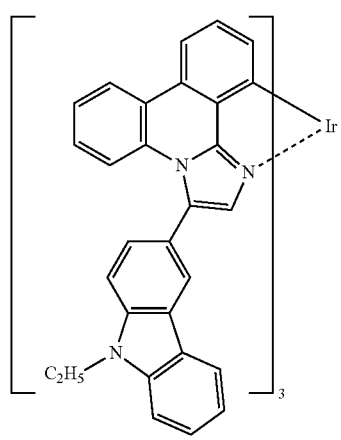
C-7
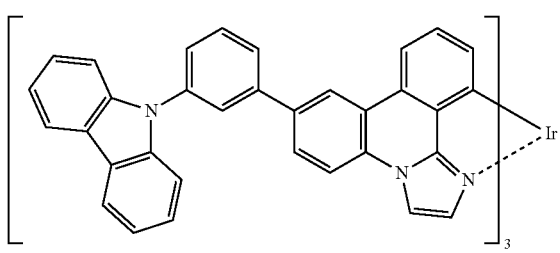
C-8
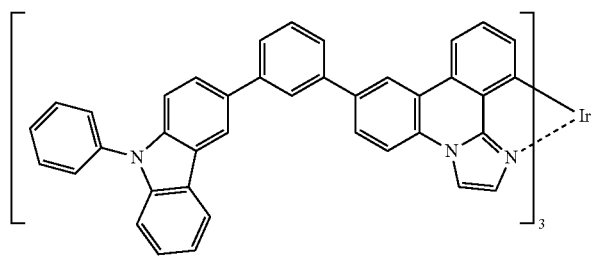
C-9
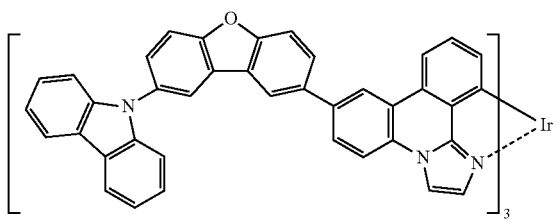
C-10
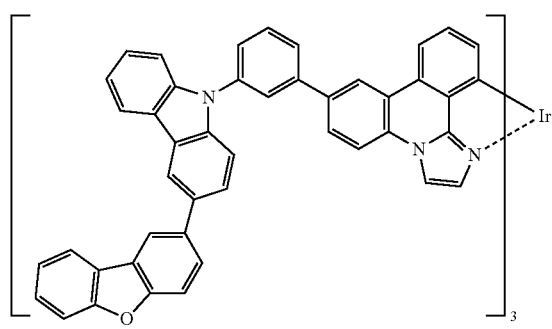
C-11
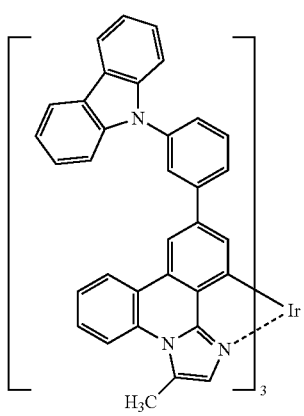

-continued
C-12
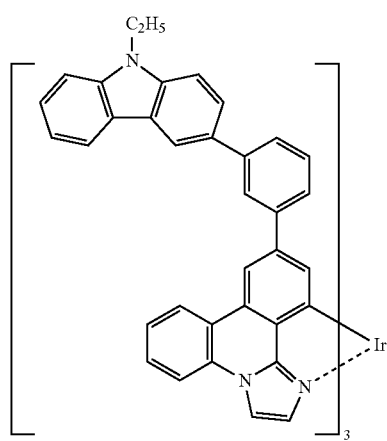
C-13
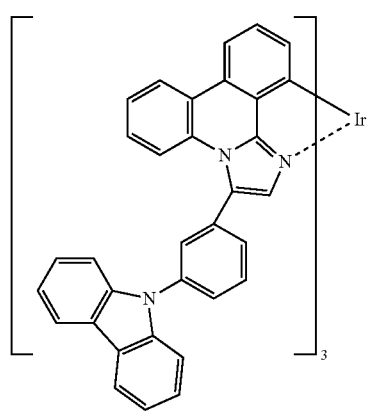
C-14
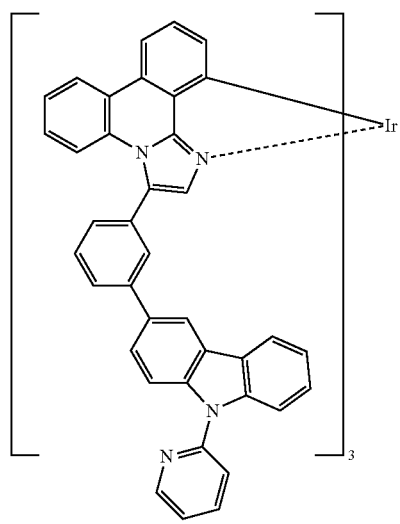
C-15
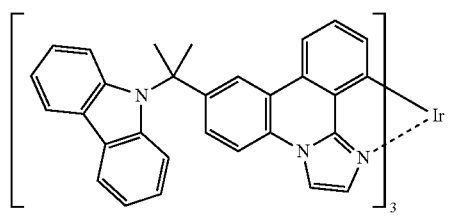
C-16
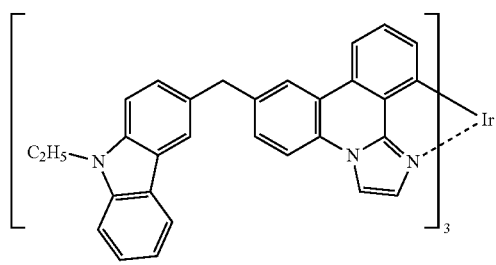
C-17
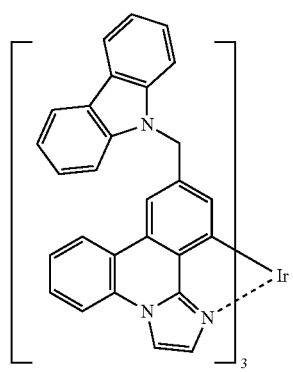

-continued
C-18
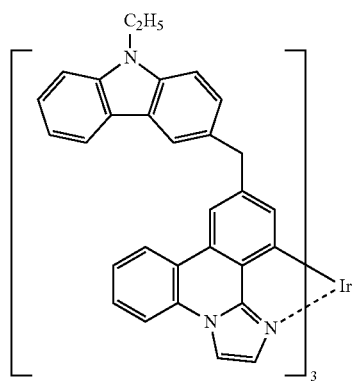
C-19
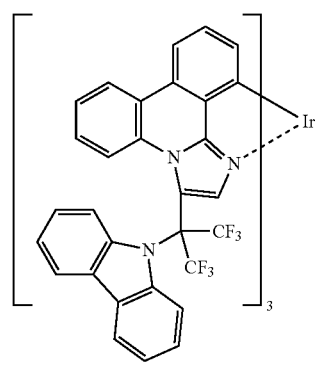
C-20
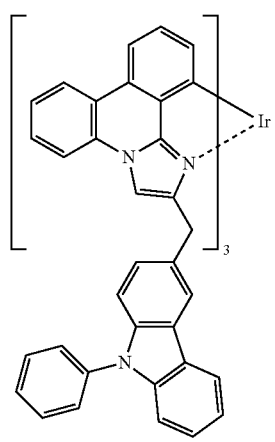
C-21
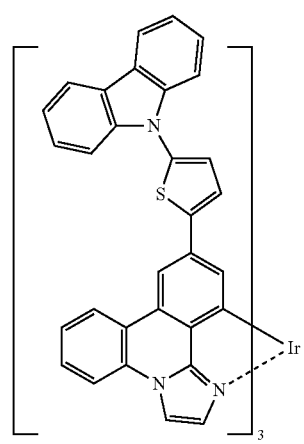
C-22
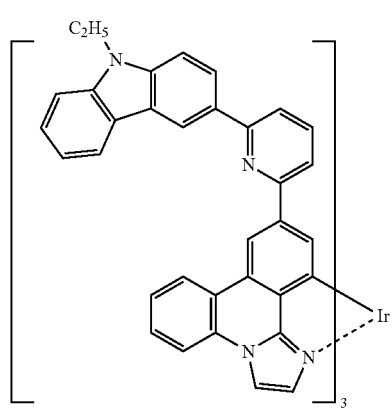
C-23
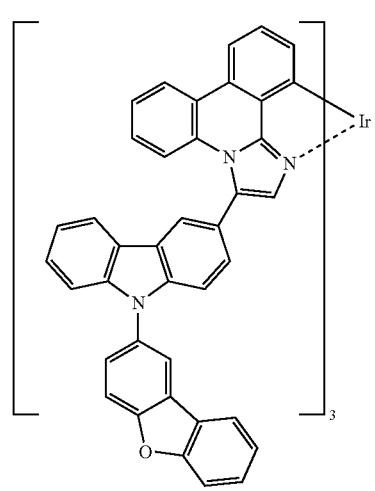

-continued
C-24
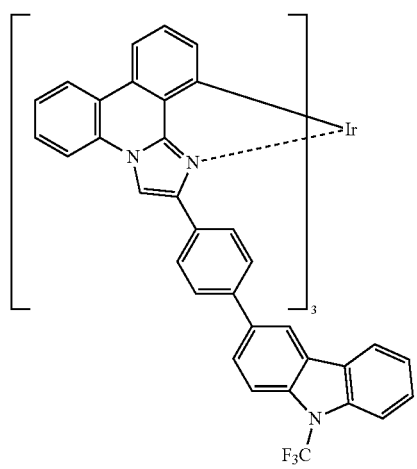
C-25
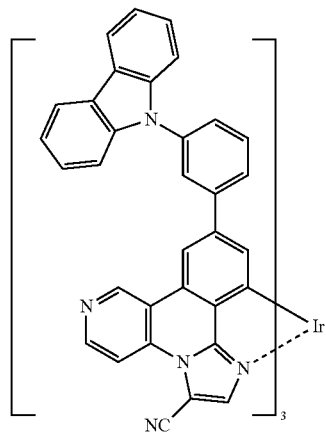
C-26
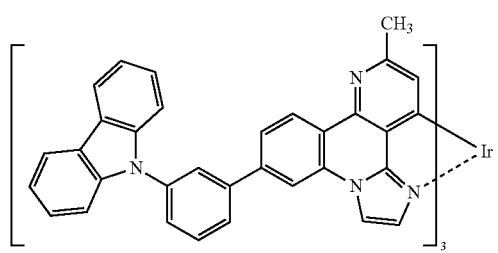
C-27
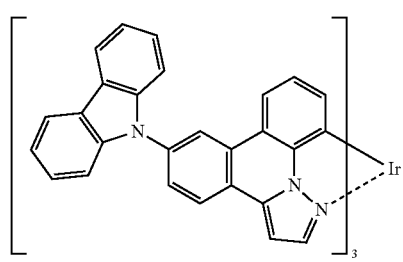
C-28
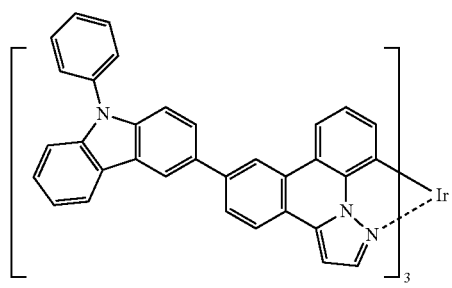
C-29
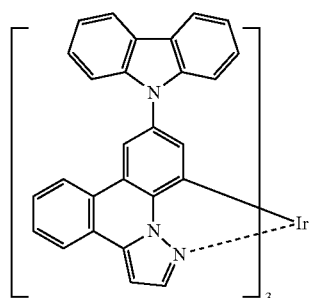
C-30
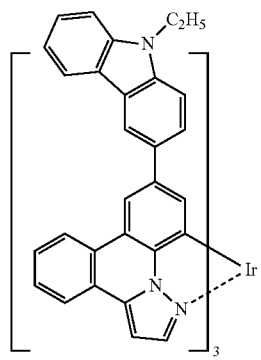
C-31
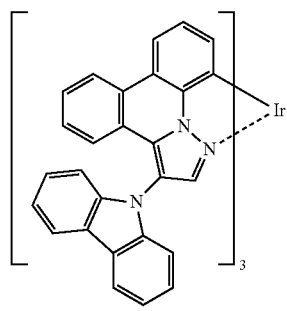

-continued
C-32 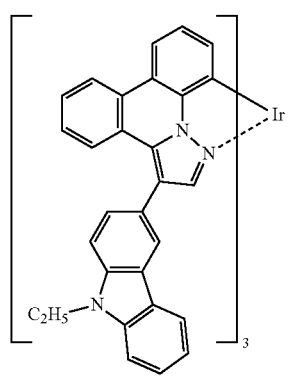
C-33 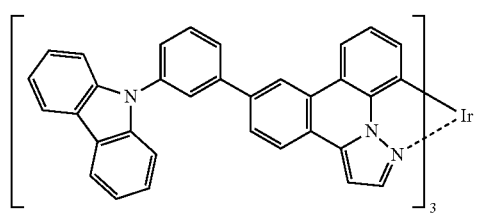
C-34 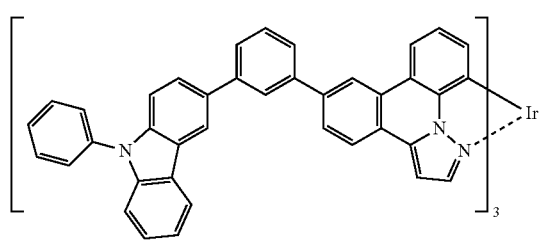
C-35 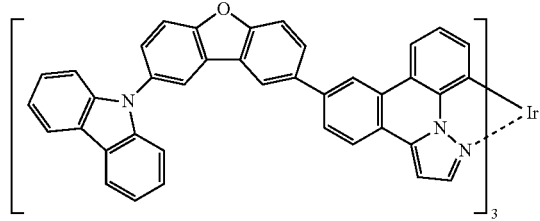
C-36 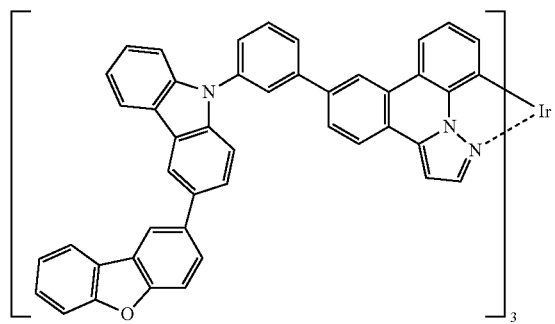
C-37 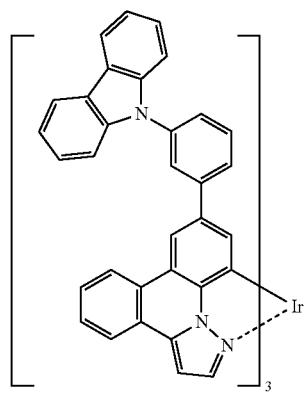
C-38 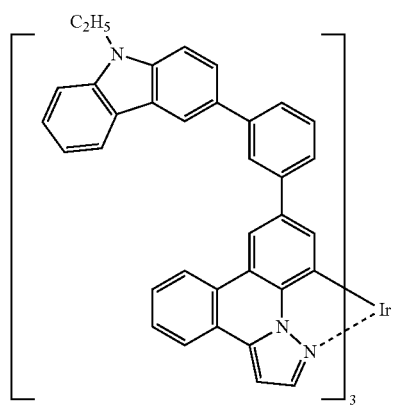
C-39 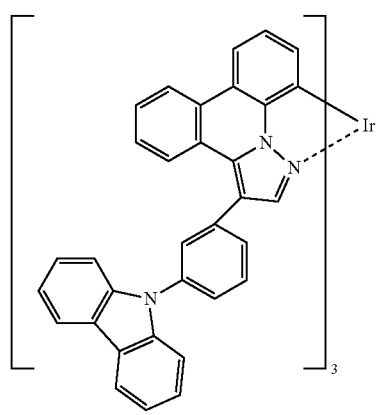

-continued
C-40
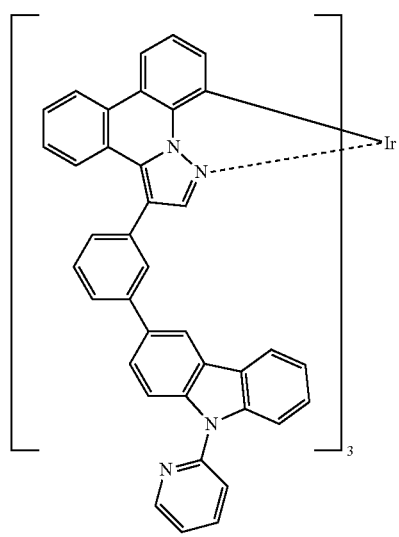
C-41
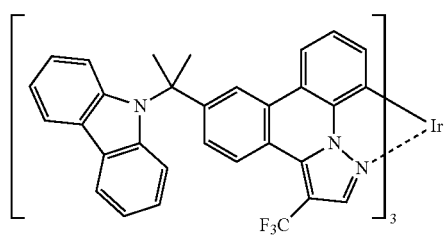
C-42
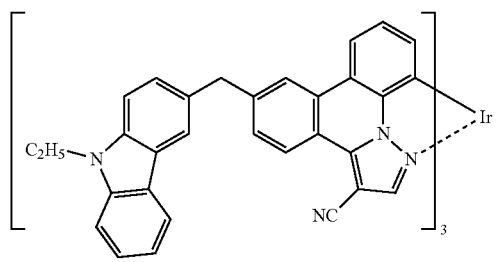
C-43
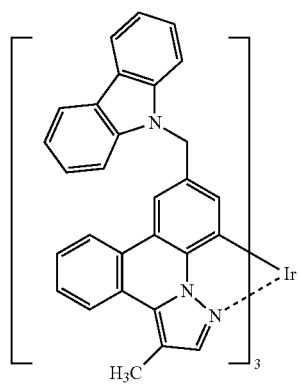
C-44
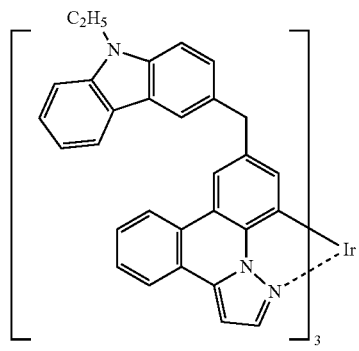
C-45
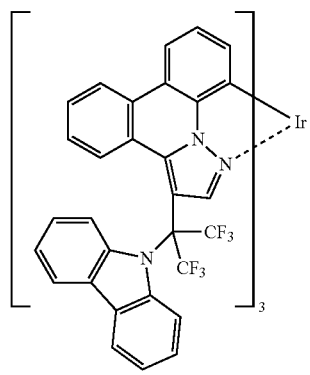

-continued
C-46
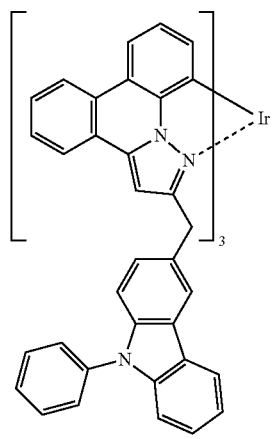
C-47
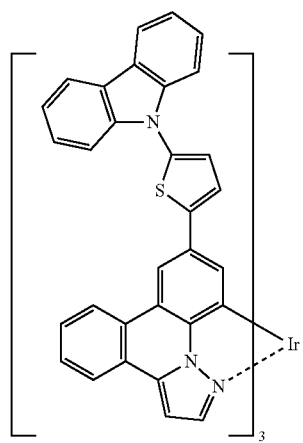
C-48
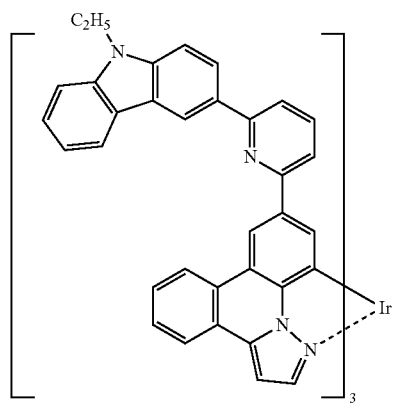
C-49
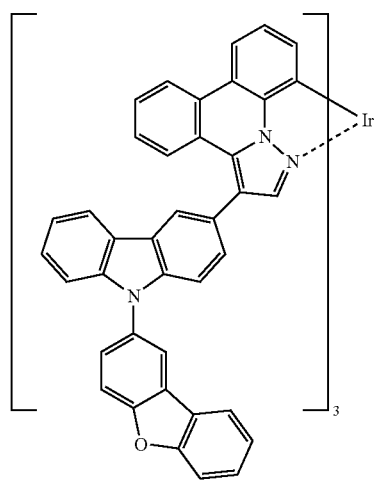
C-50
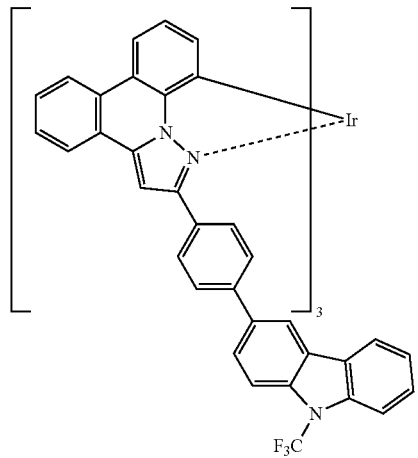
C-51
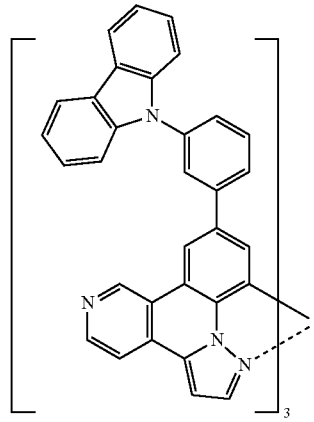
C-52
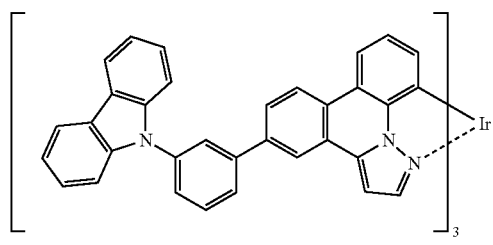
C-53
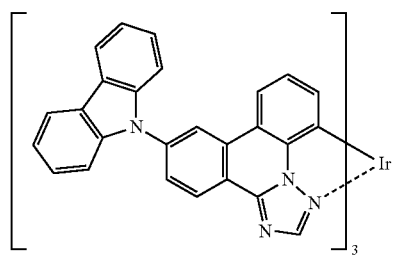

-continued
C-54
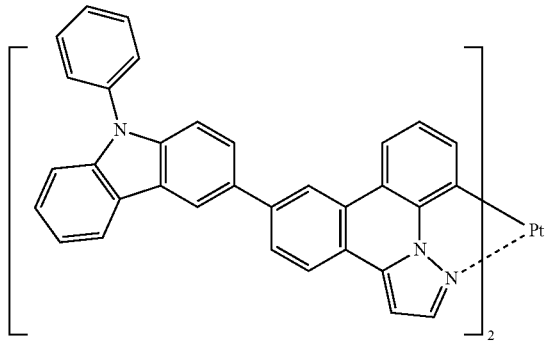
C-55
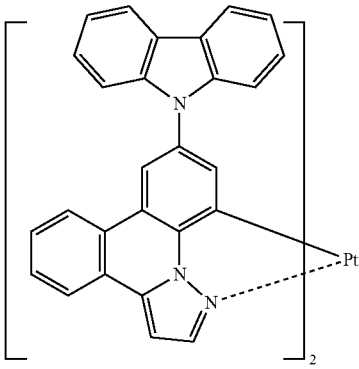
C-56
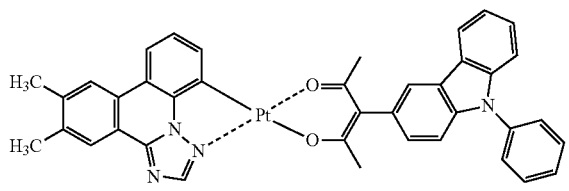
C-57
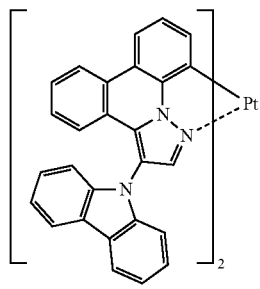
C-58
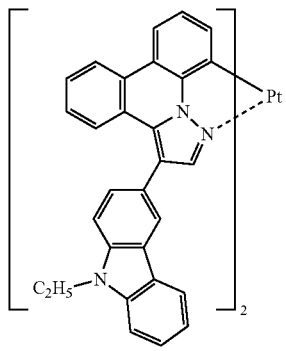
C-59
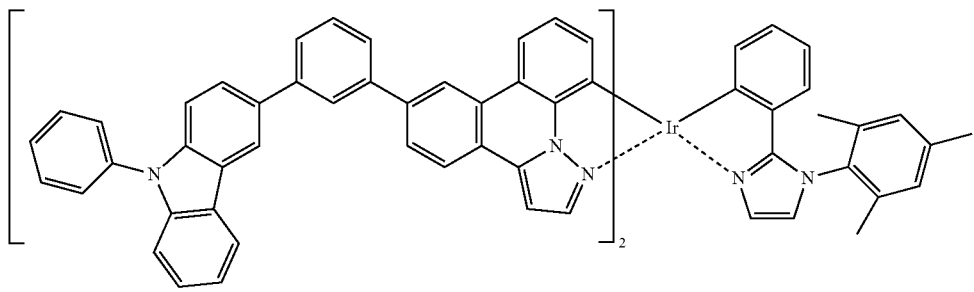
C-60
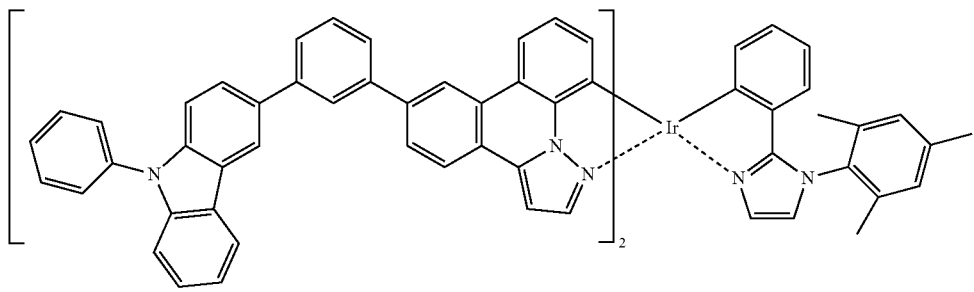
C-61
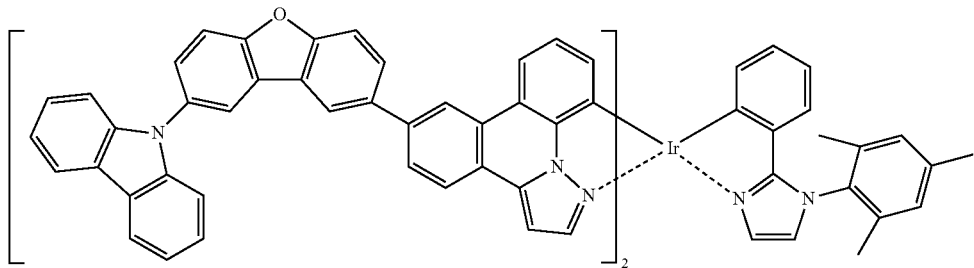

-continued
C-62
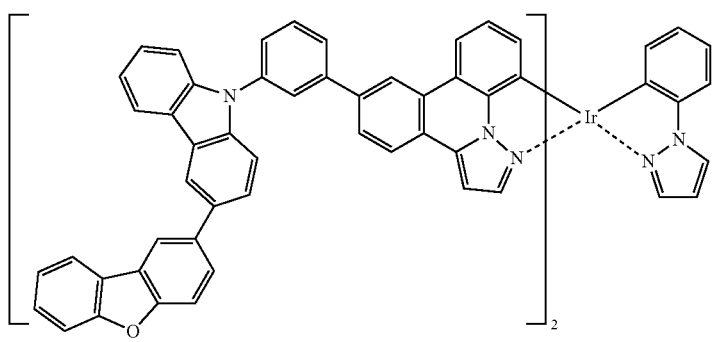
C-63
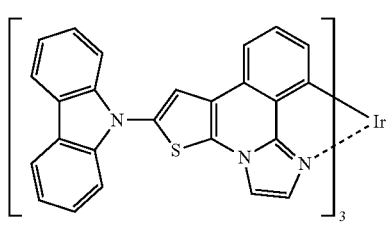
C-64
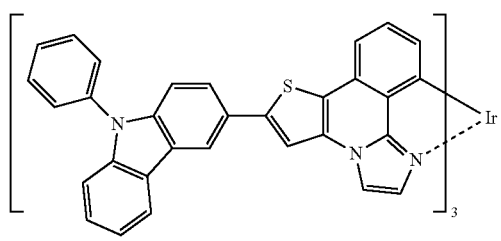
C-65
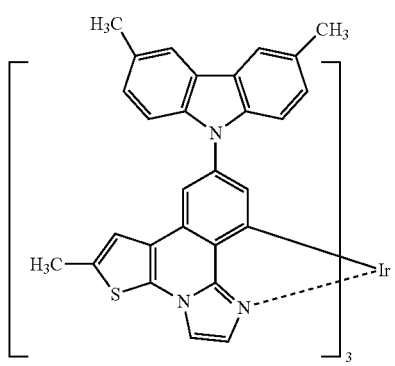
C-66
C-67
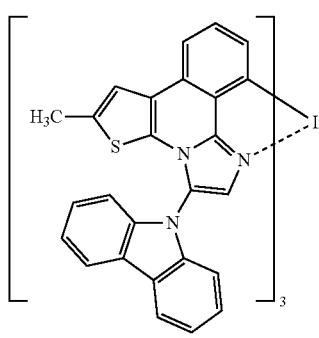
C-68
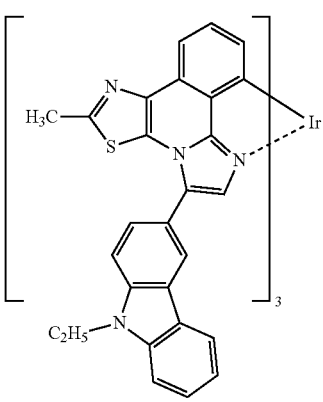
C-69
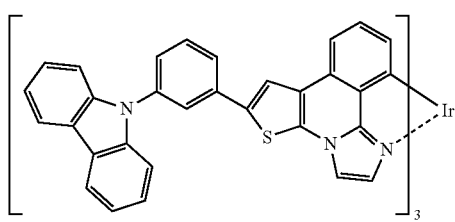
C-70
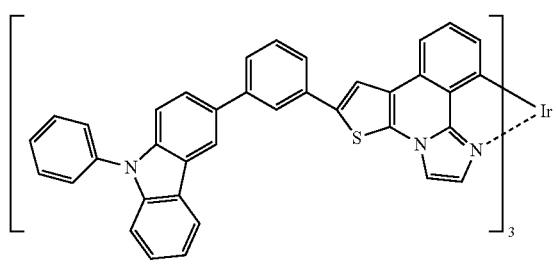

-continued
C-71
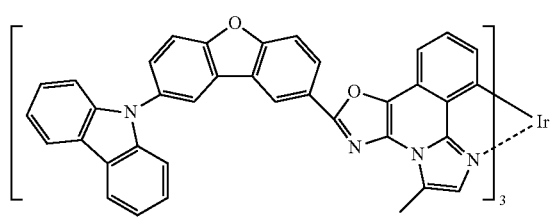
C-72
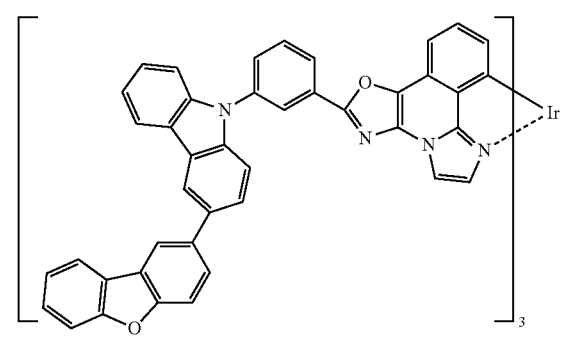
C-73
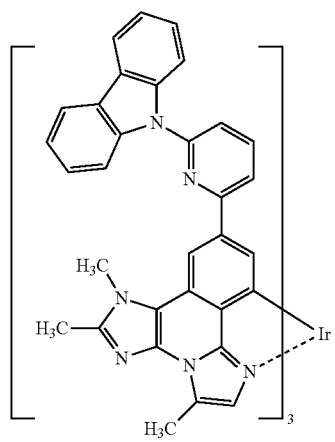
C-74
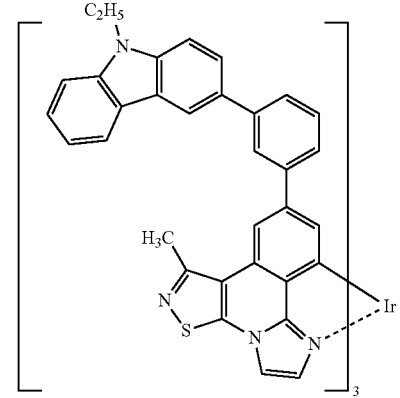
C-75
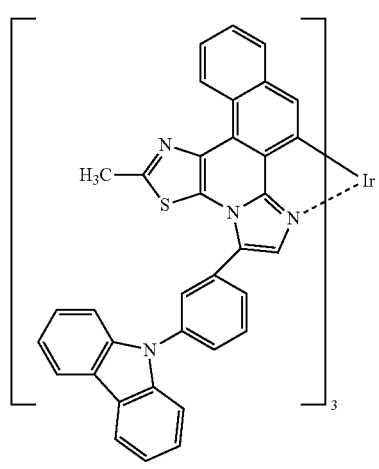
C-76
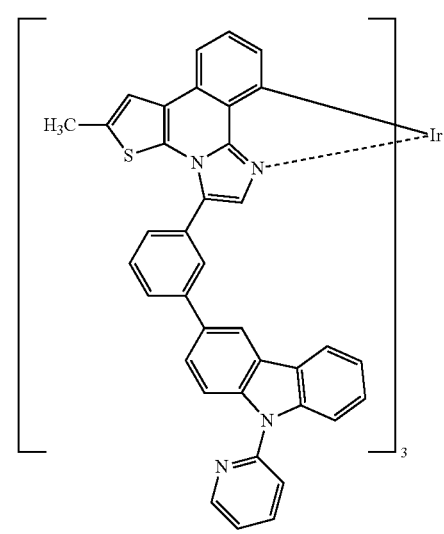
C-77
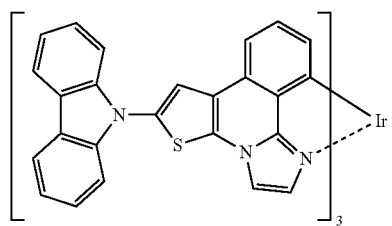
C-78
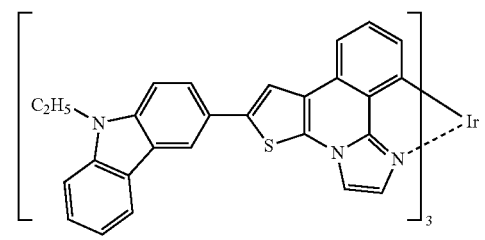

-continued
C-79
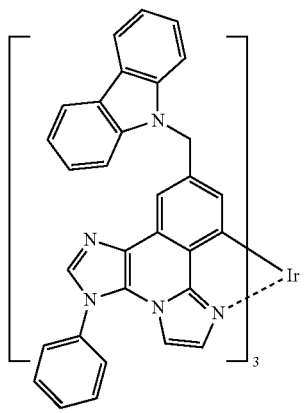
C-80
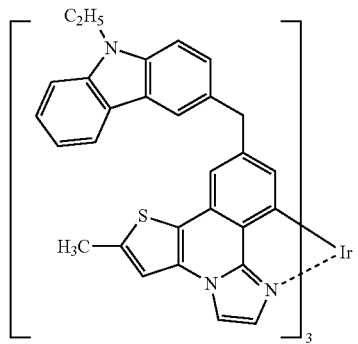
C-81
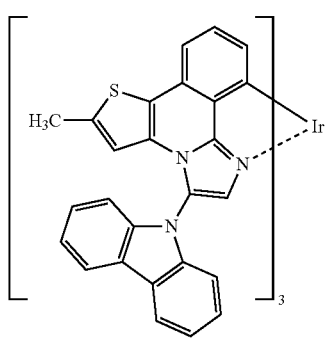
C-82
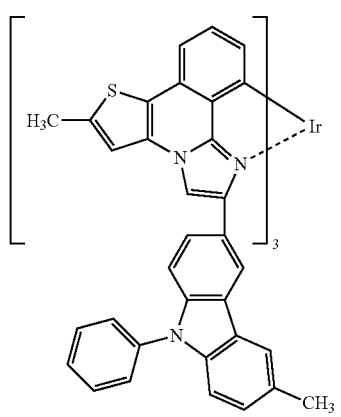
C-83
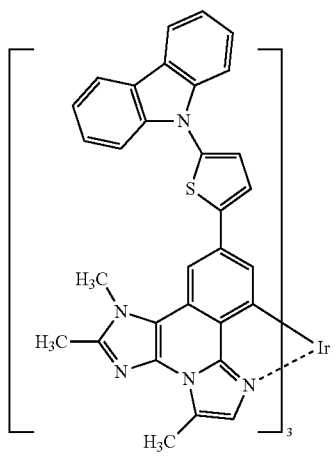
C-84
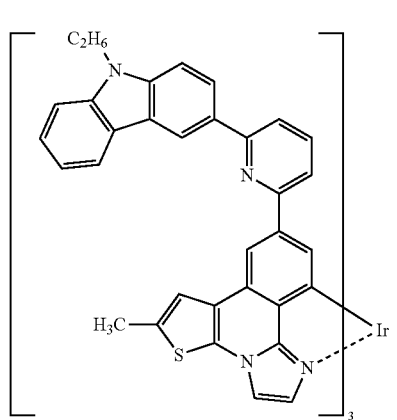

-continued
C-85
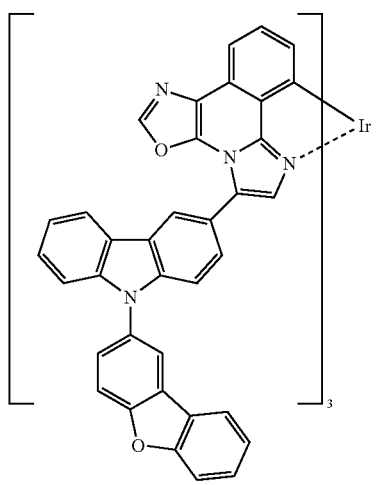
C-86
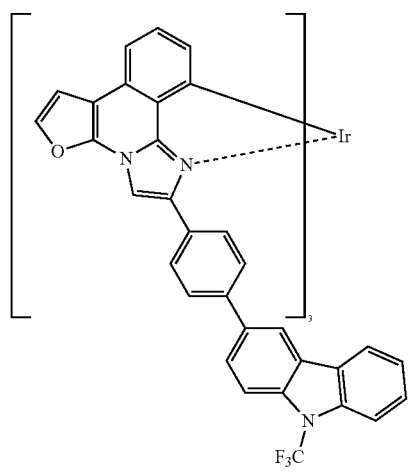
C-87
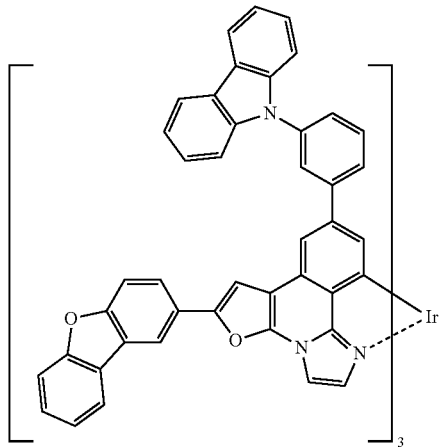
C-88
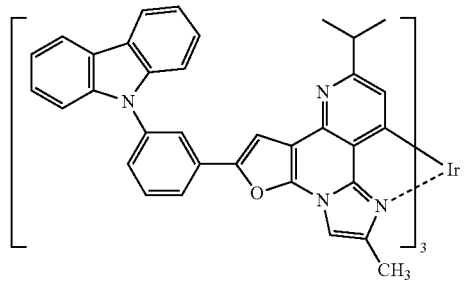
C-89
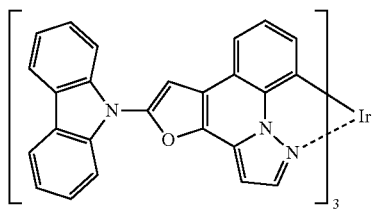
C-90
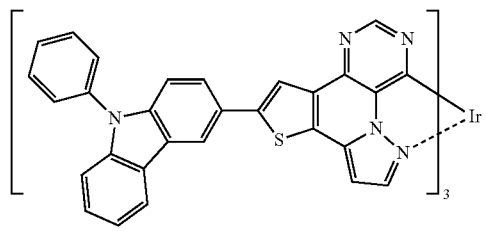
C-91
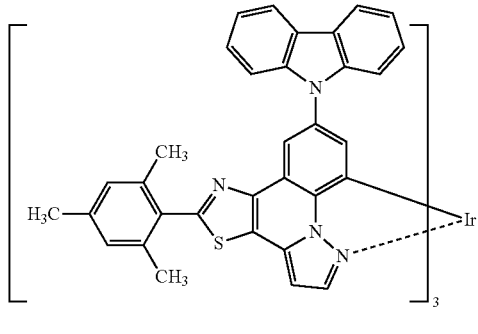
C-92
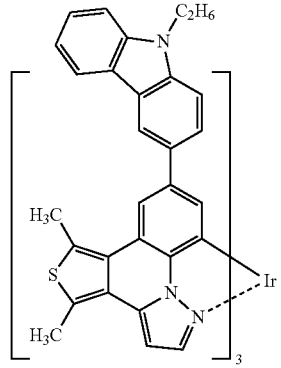

-continued
C-93
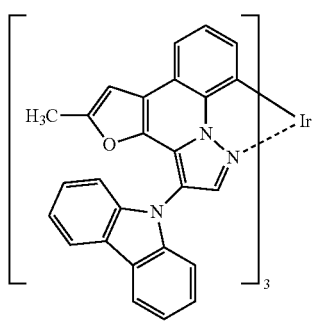
C-94
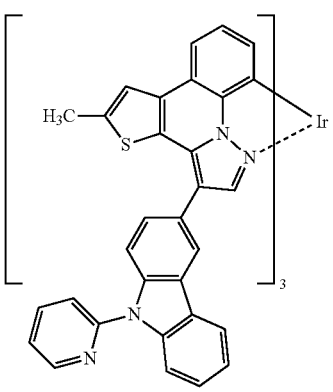
C-95
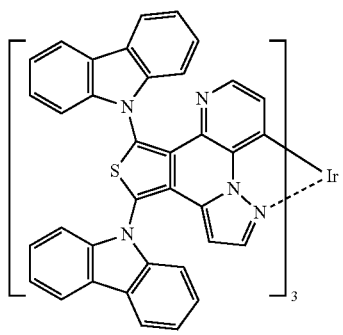
C-96
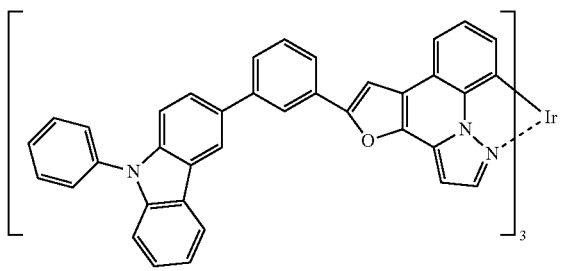
C-97
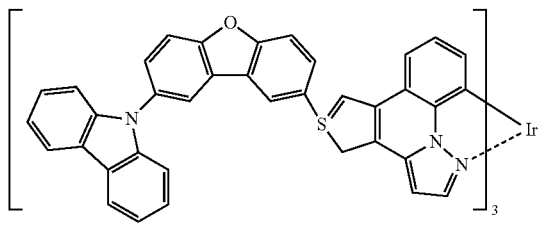
C-98
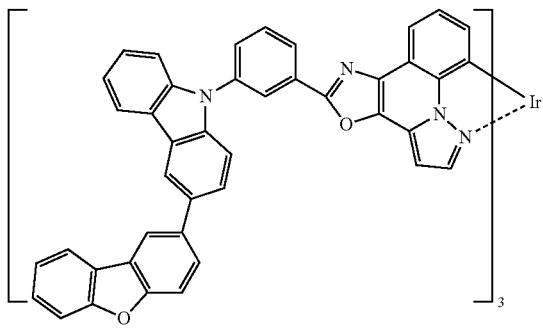
C-99
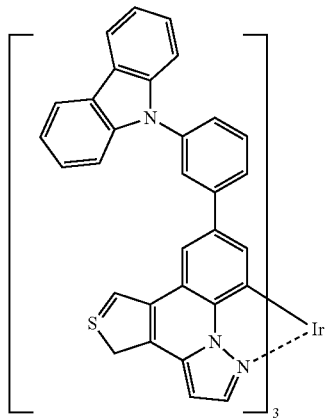
C-100
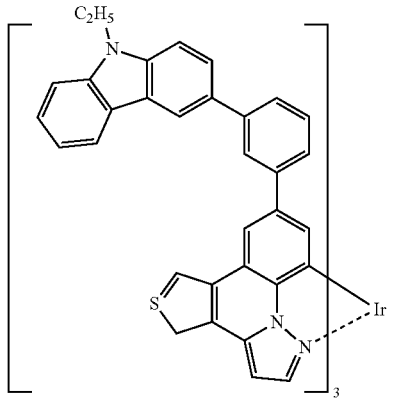

-continued
C-101
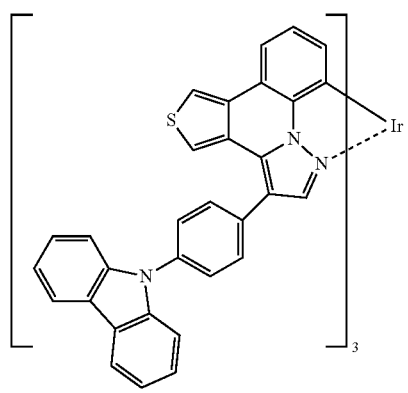
C-102
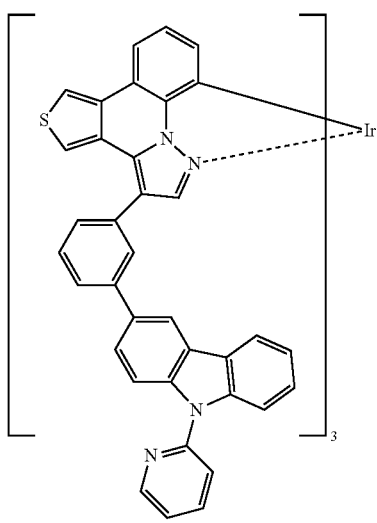
C-103
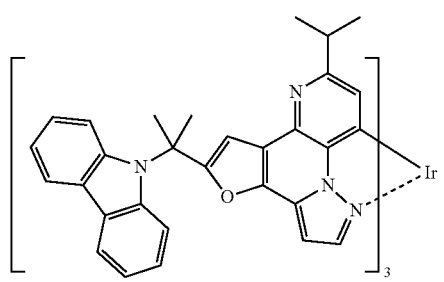
C-104
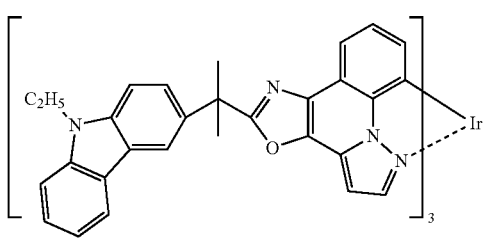
C-105
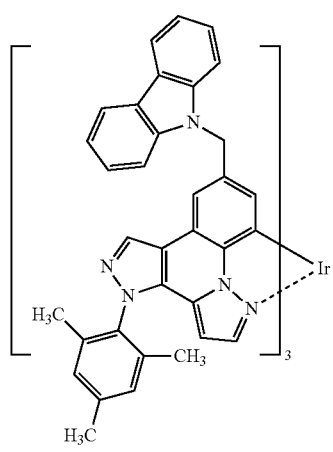
C-106
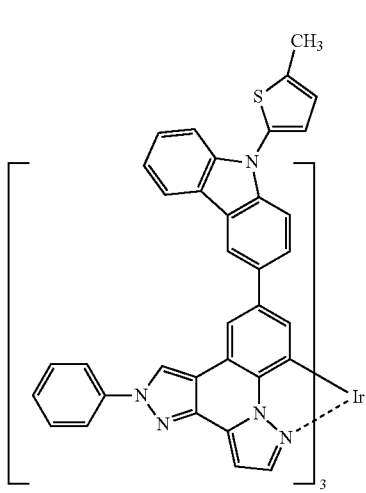

-continued
C-107
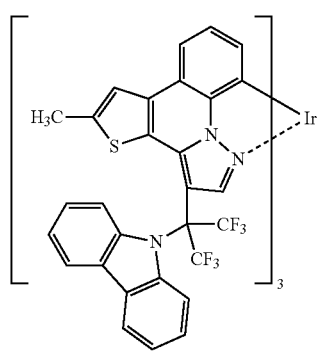
C-108
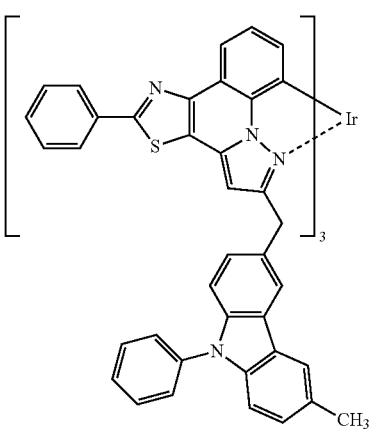
C-11
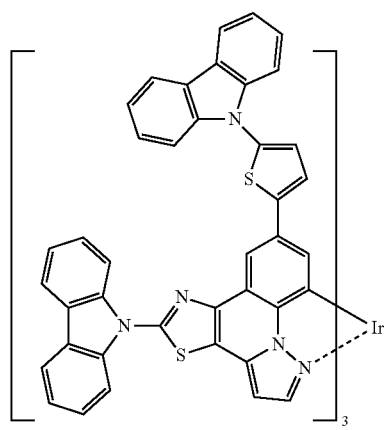
C-109
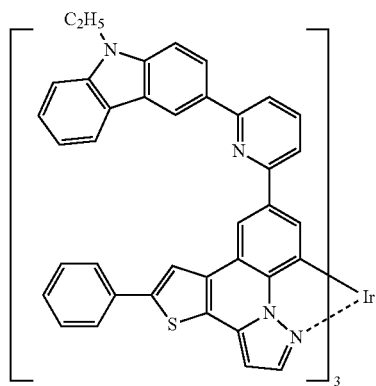
C-111
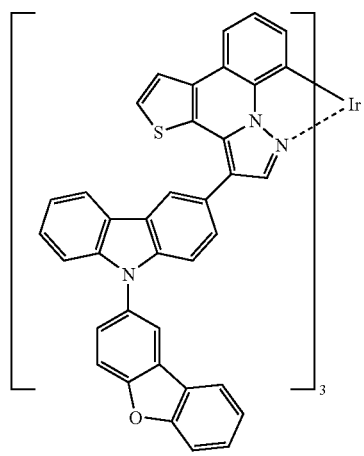
C-112
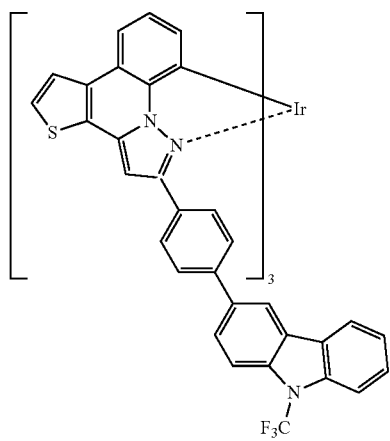

-continued
C-113
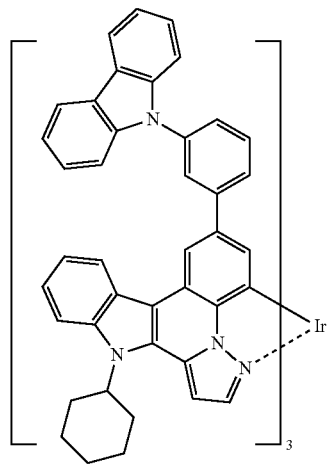
C-114
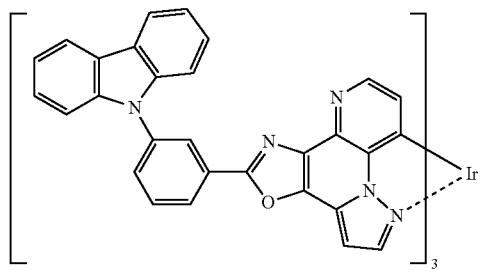
C-115
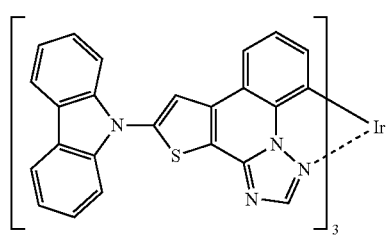
C-116
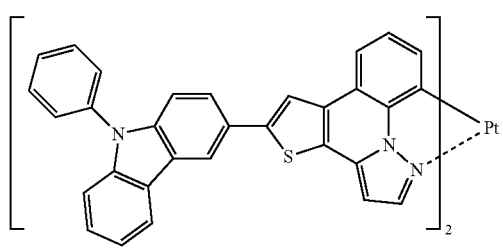
C-117
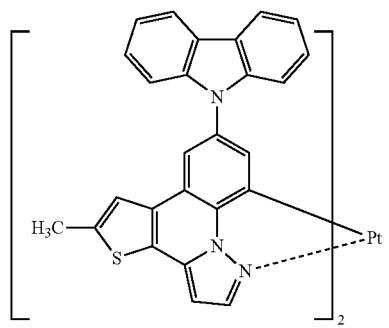
C-118
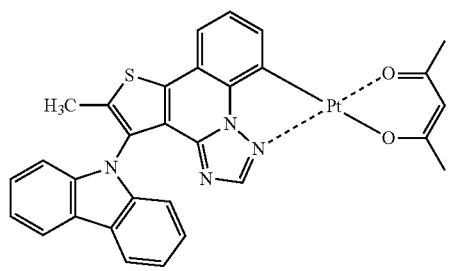
C-119
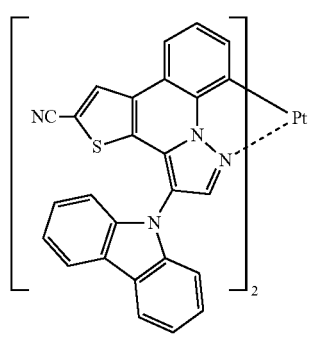
C-120
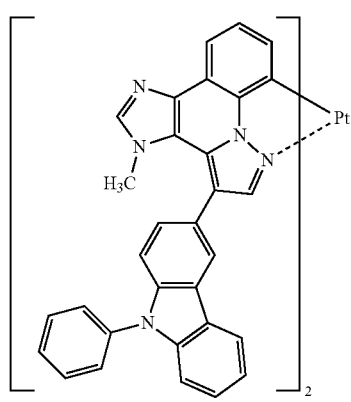

-continued
C-121
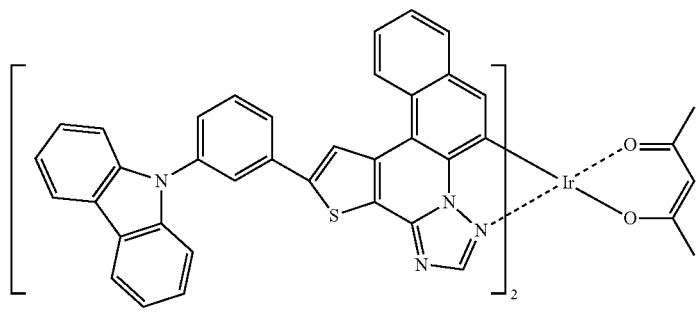
C-122
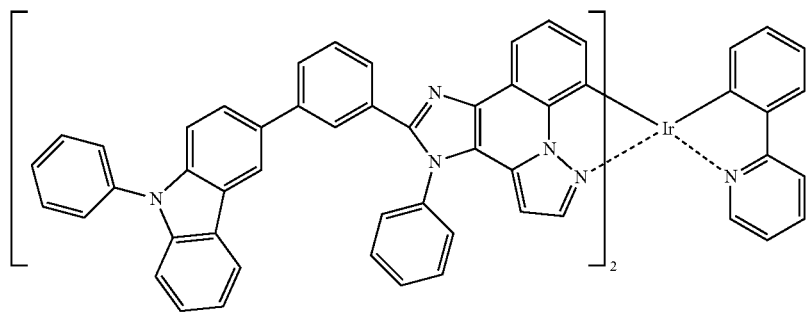
C-123
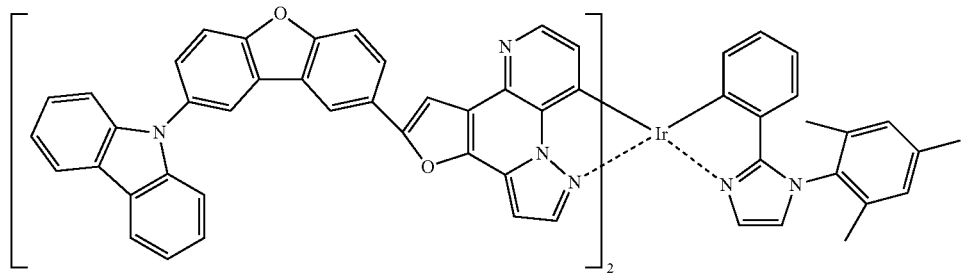
C-124
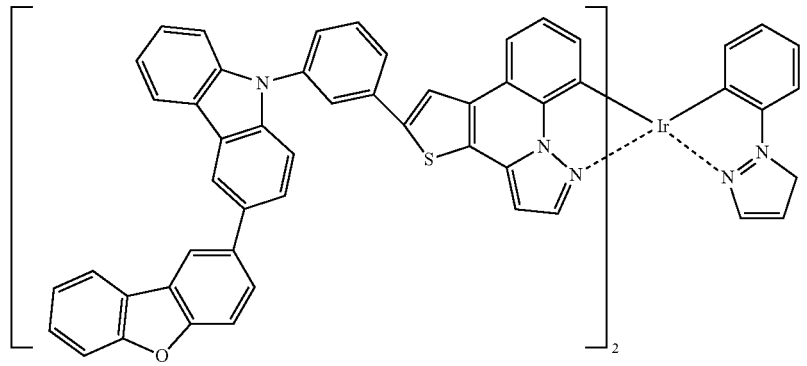
C-125
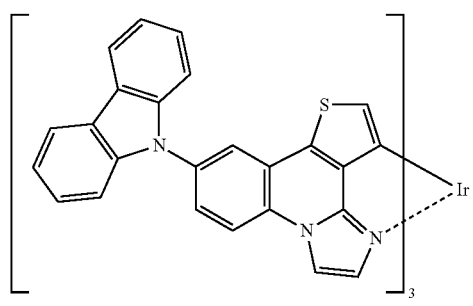
C-126
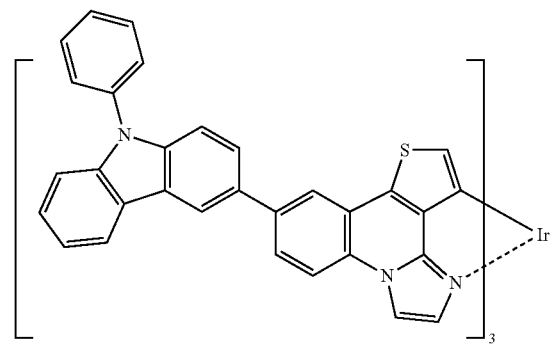

-continued
C-127
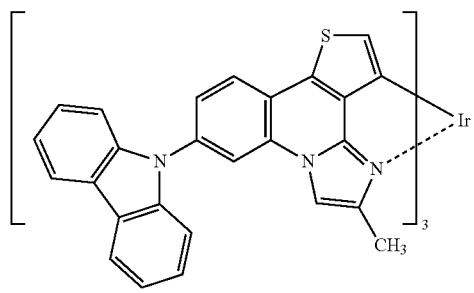
C-128
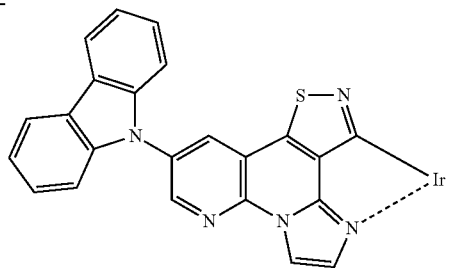
C-129
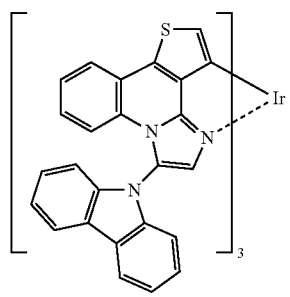
C-130
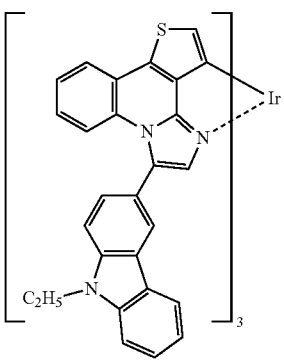
C-131
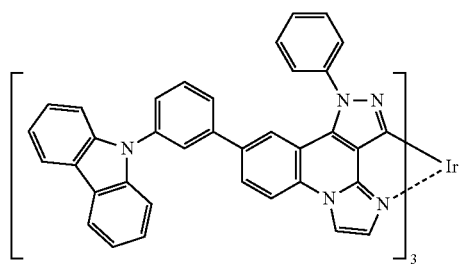
C-132
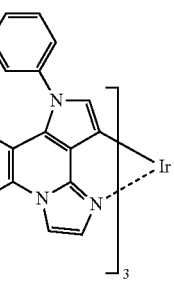
C-133
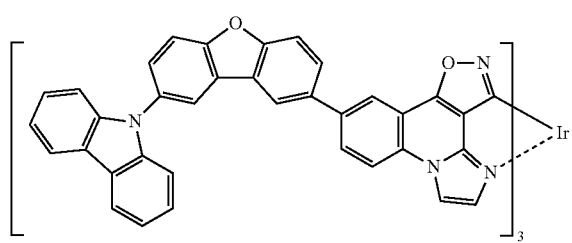
C-134
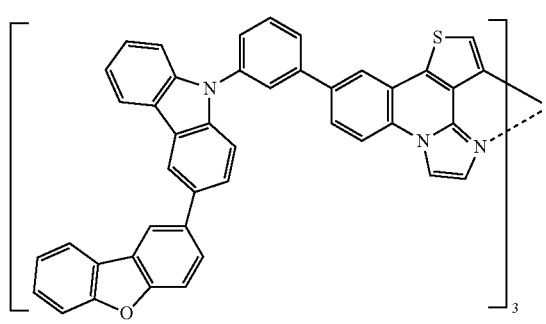
C-135
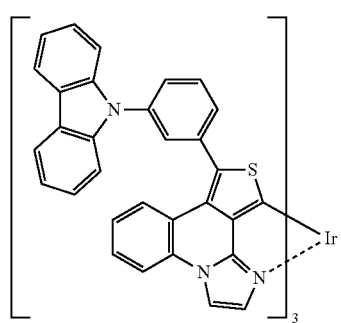
C-136
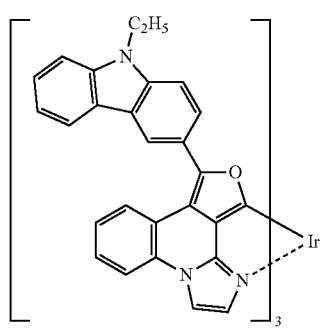

-continued
C-137
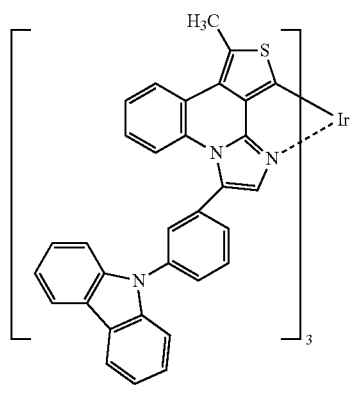
C-138
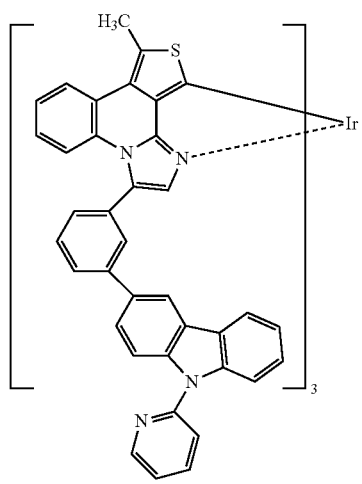
C-139
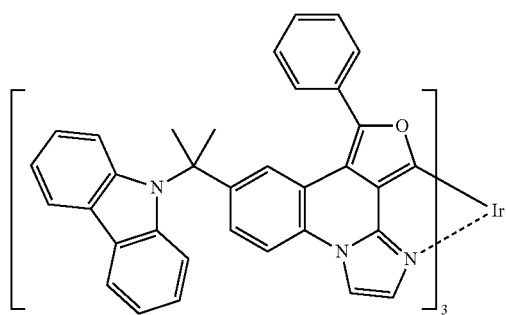
C-140
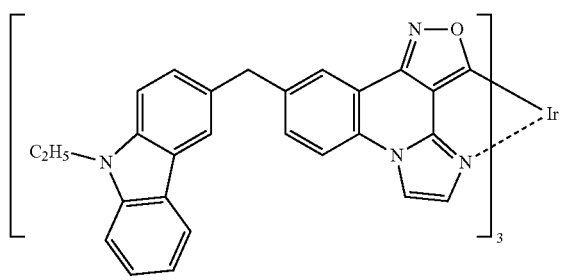
C-141
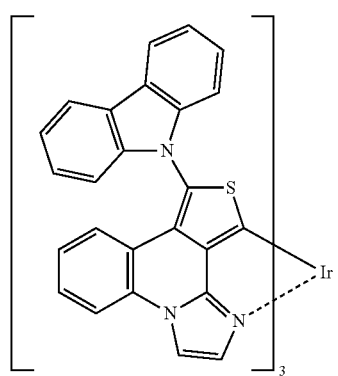
C-142
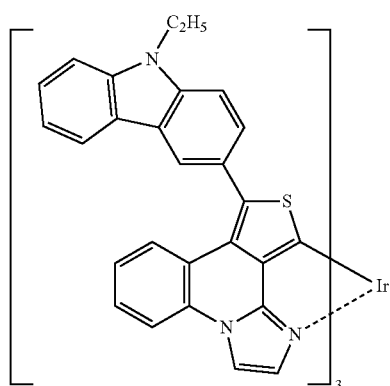

-continued
C-143
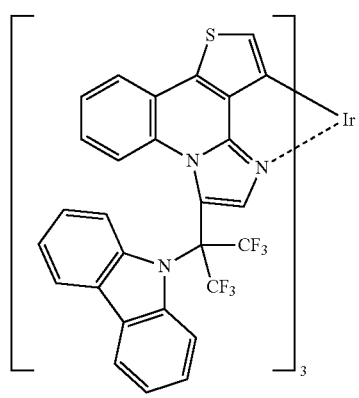
C-144
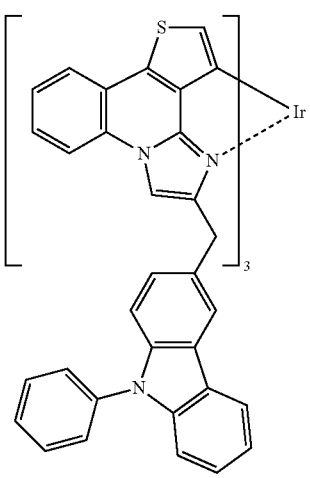
C-145
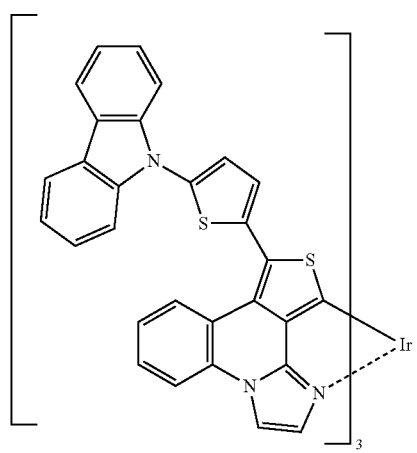
C-146
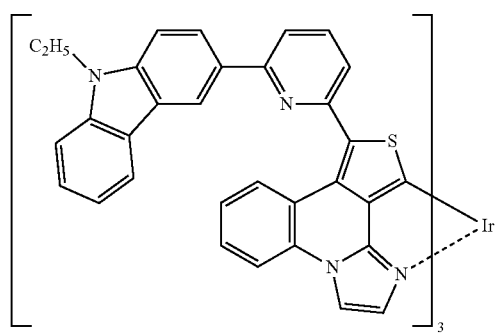
C-147
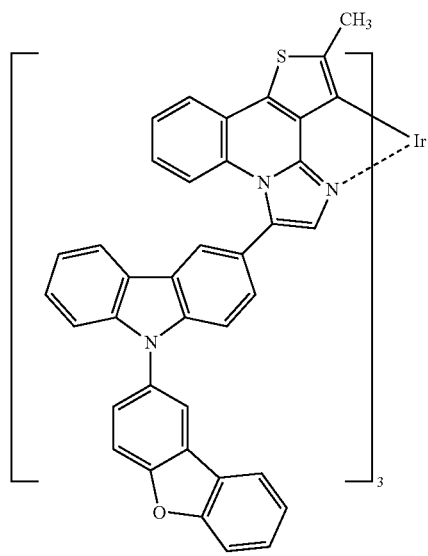
C-148
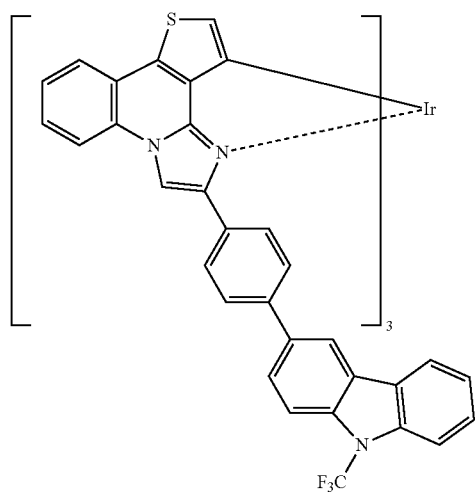

-continued
C-149
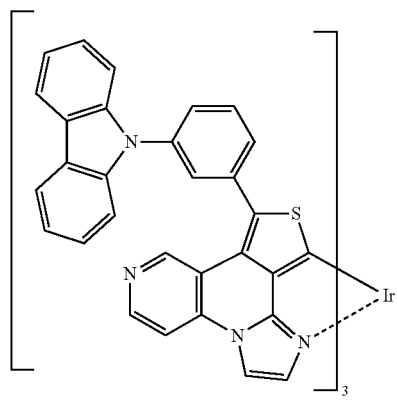
C-150
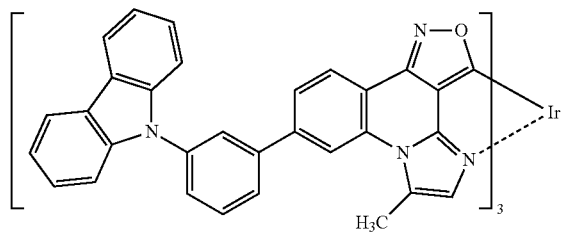
C-151
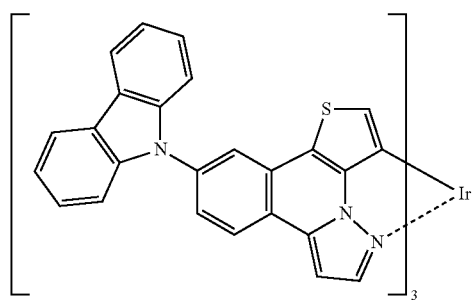
C-152
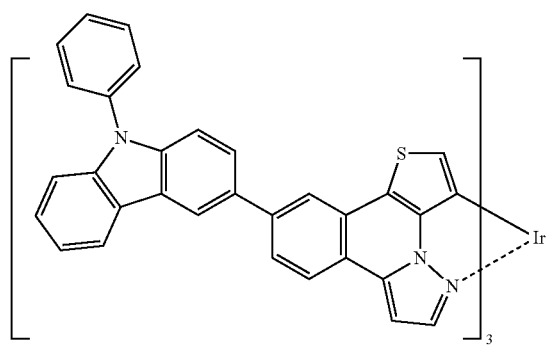
C-153
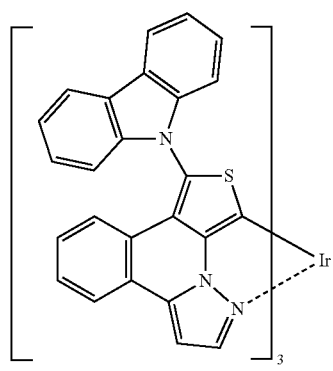
C-154
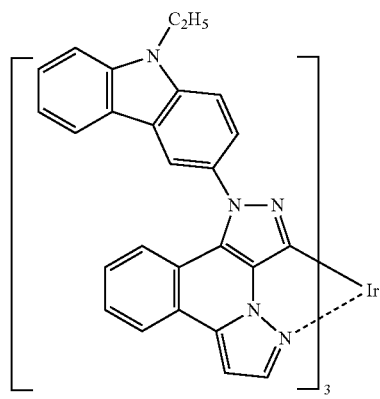

-continued
C-155
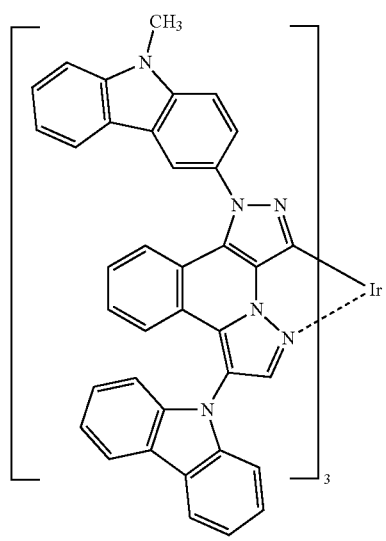
C-156
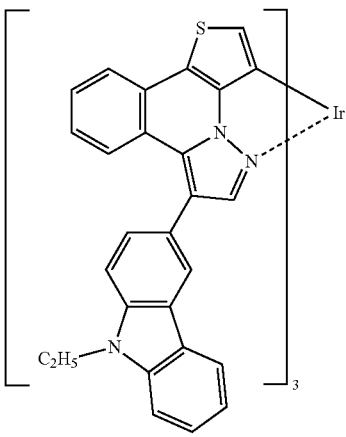
C-157
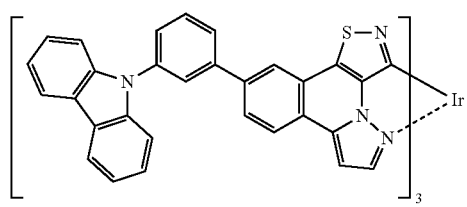
C-158
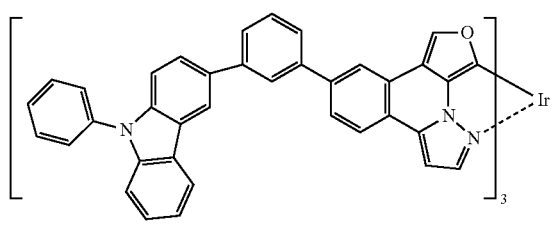
C-159
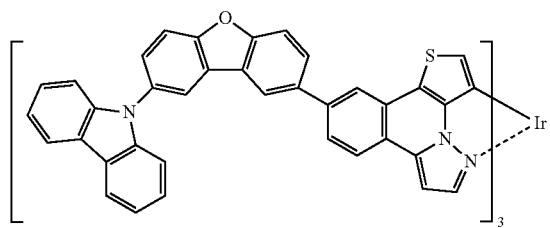
C-160
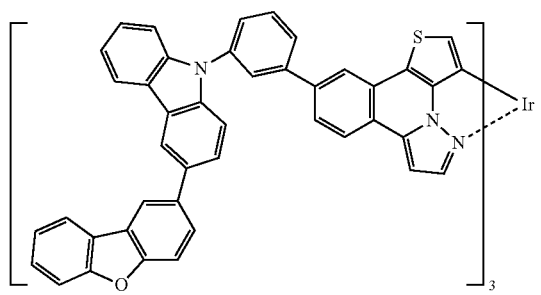
c-161
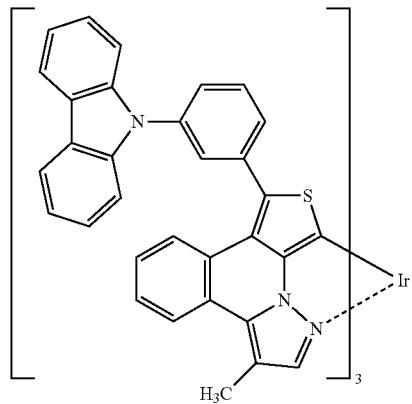
c-162
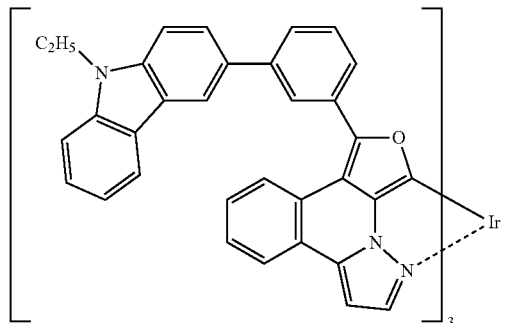

-continued
C-163
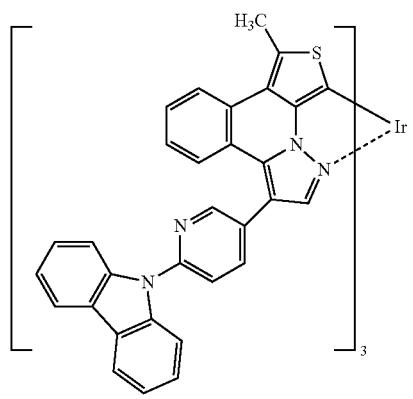
C-164
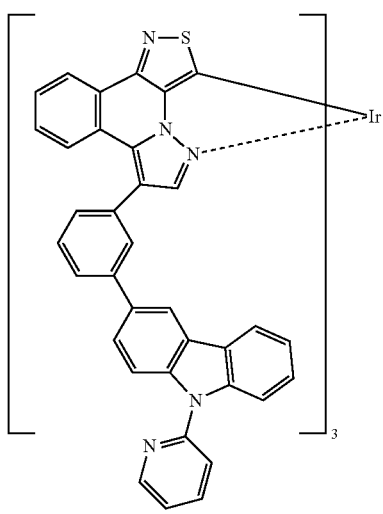
C-165
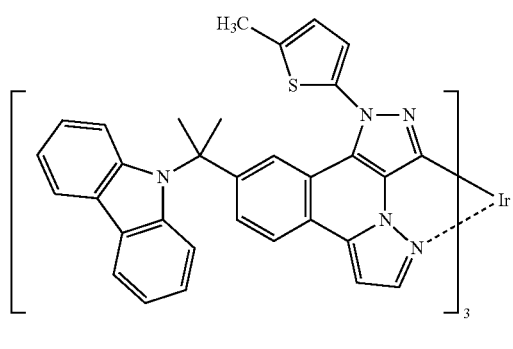
C-166
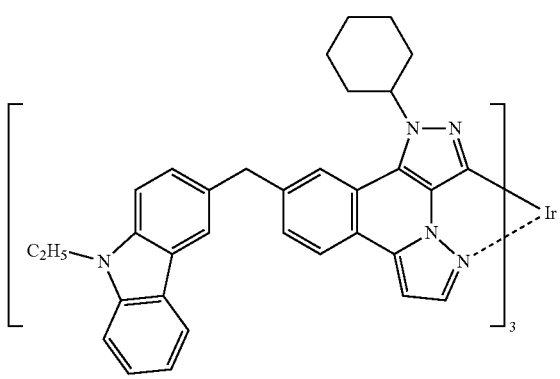
C-167
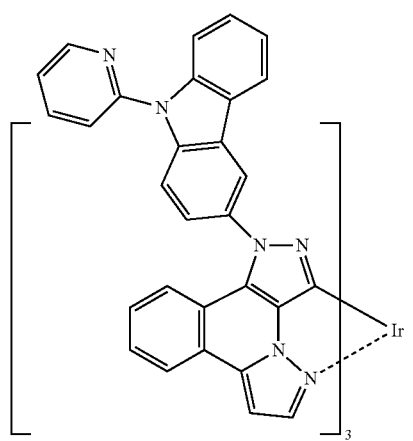
C-168
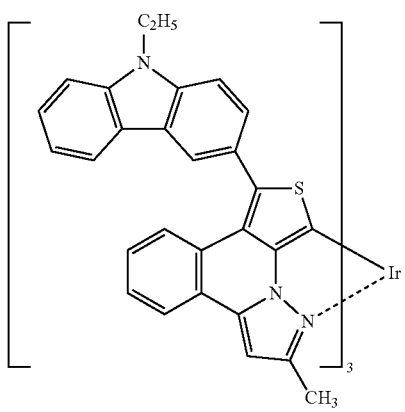

-continued
C-169
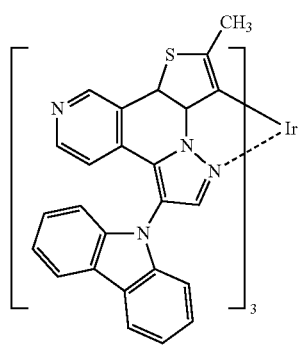
C-170
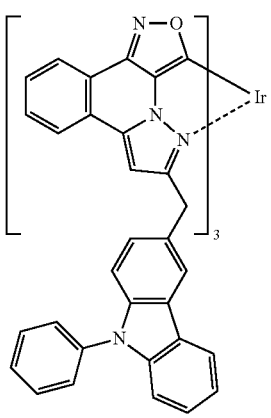
C-171
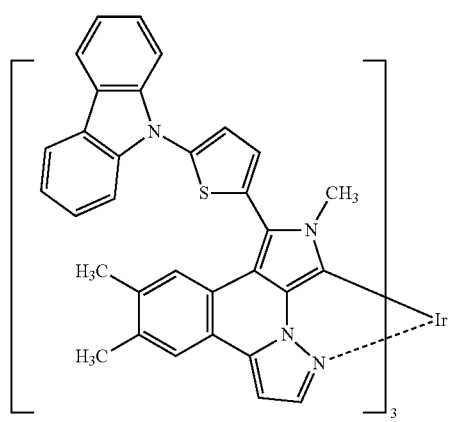
C-172
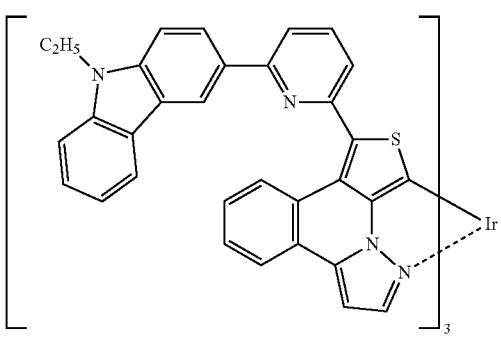
C-173
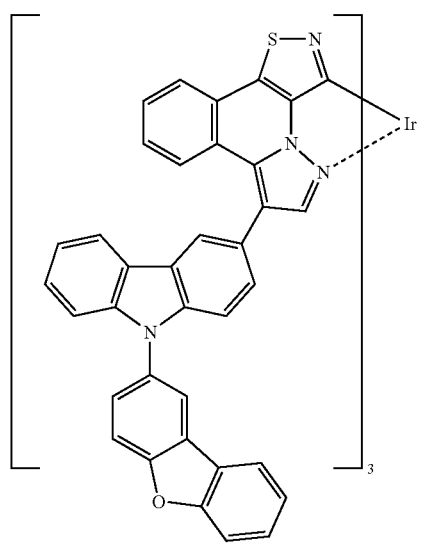
C-174
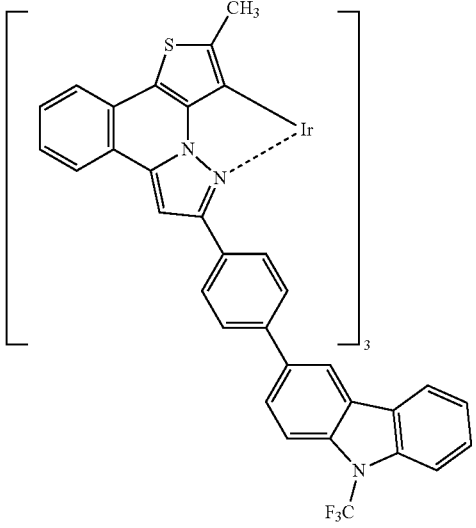

-continued
C-175
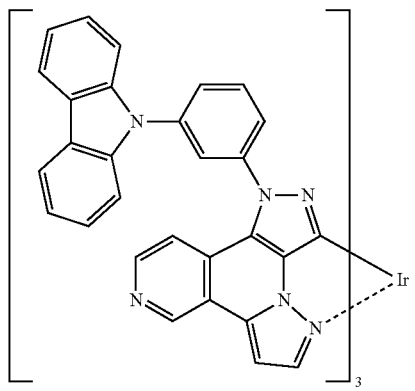
C-176
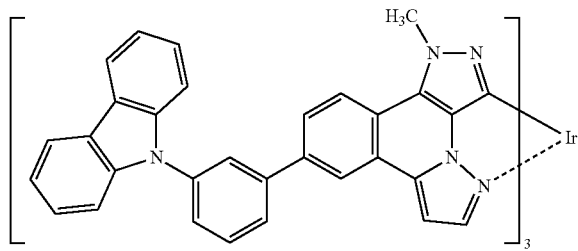
C-177
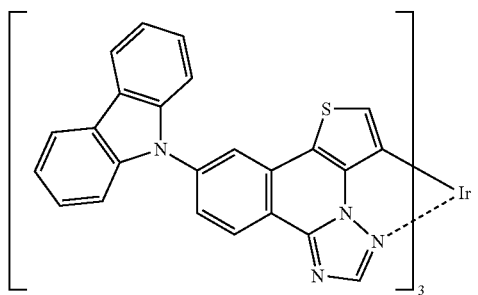
C-178
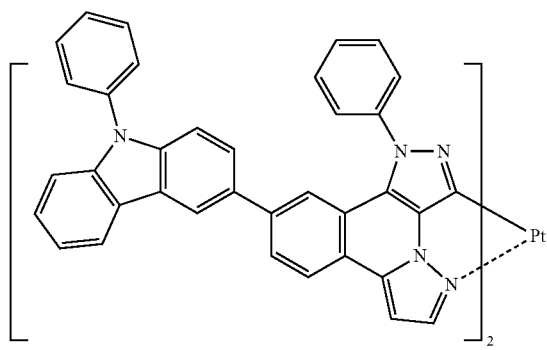
C-179
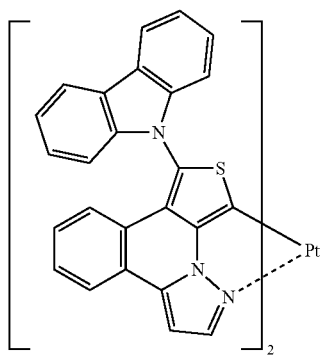
C-180
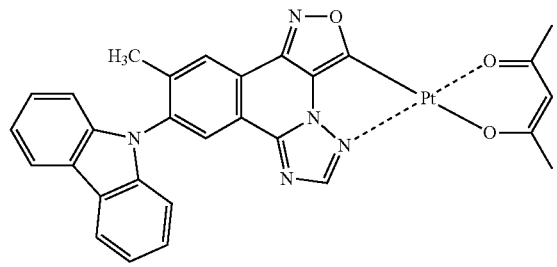
C-181
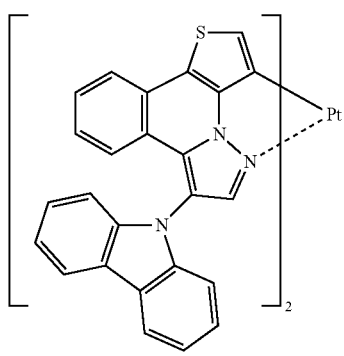
C-182
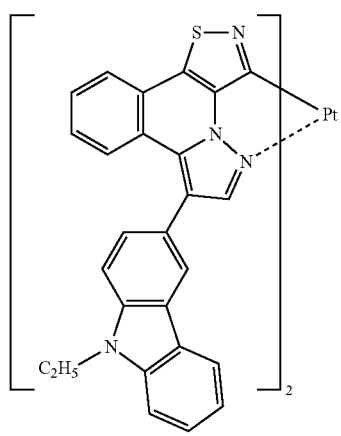

-continued
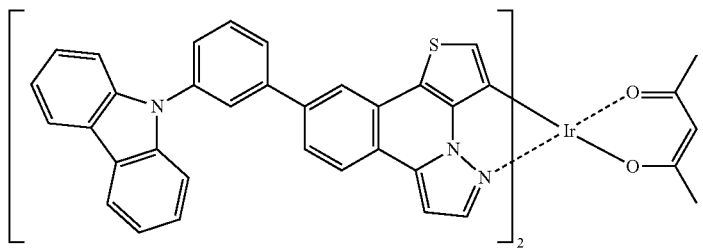
C-183
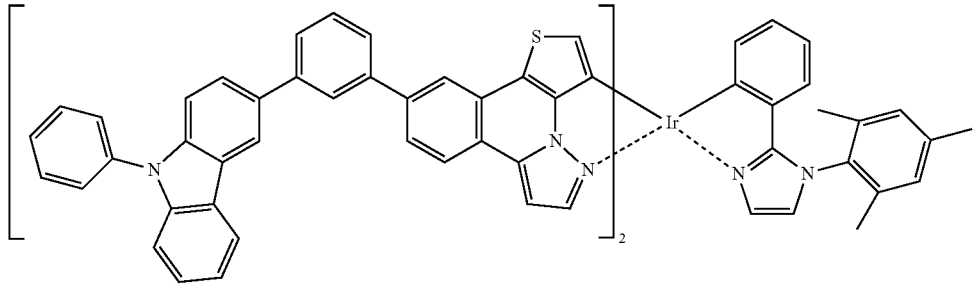
C-184
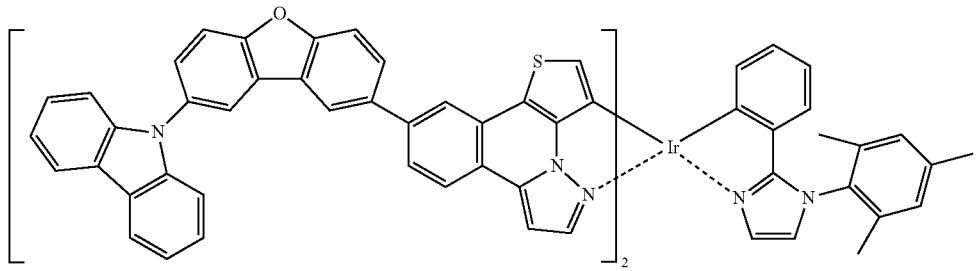
C-185
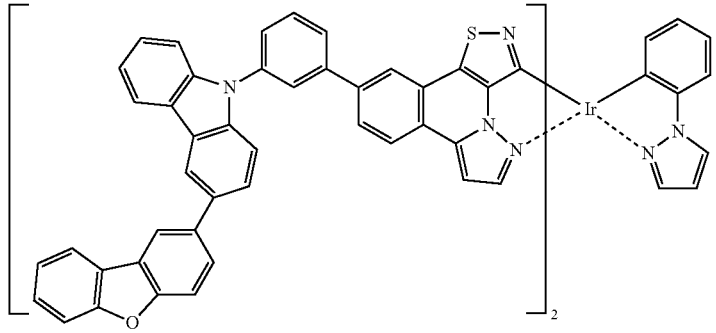
C-186
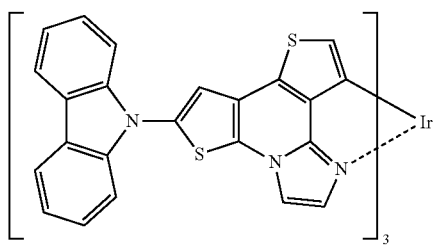
C-187
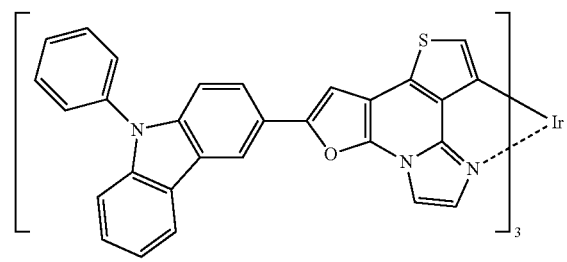
C-188

-continued
C-189
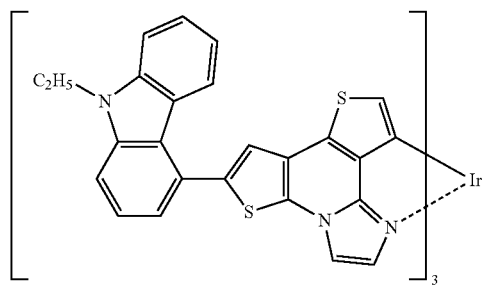
C-190
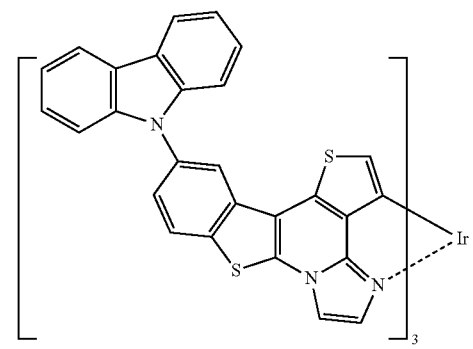
C-191
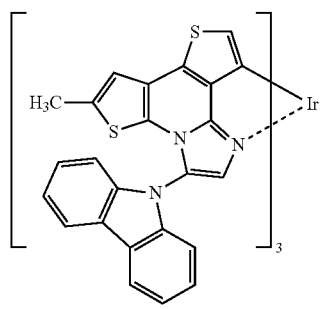
C-192
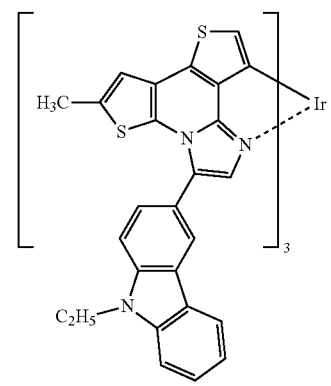
C-193
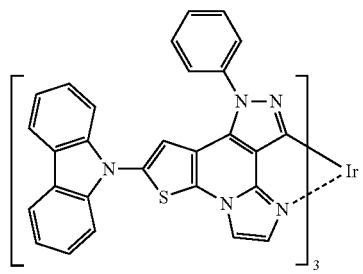
C-194
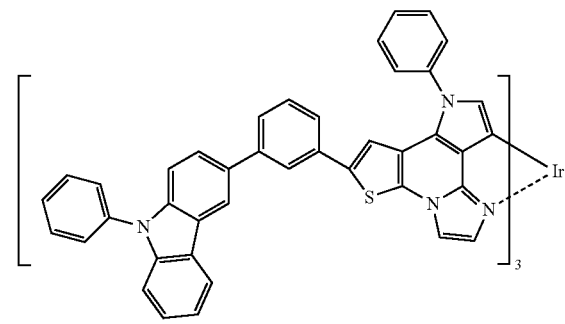
C-195
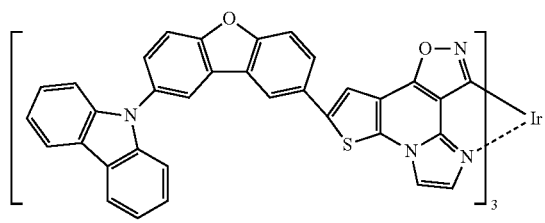
C-196
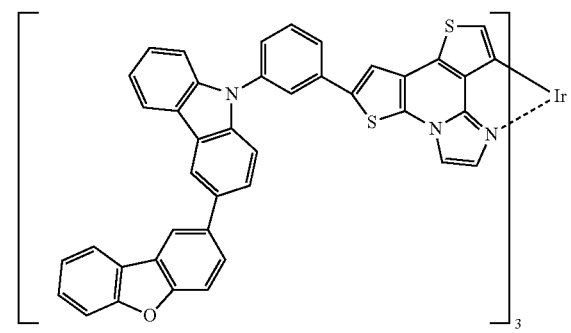

C-197 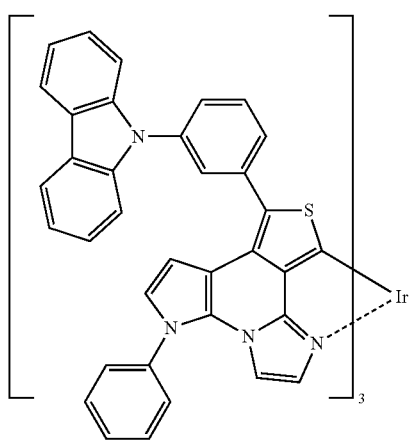
C-198 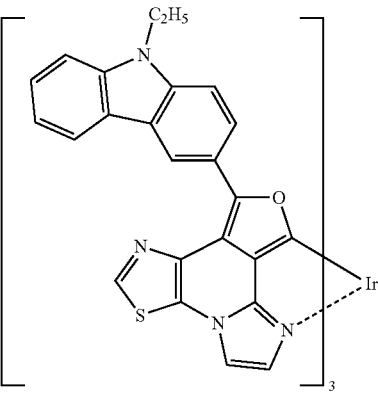
C-199 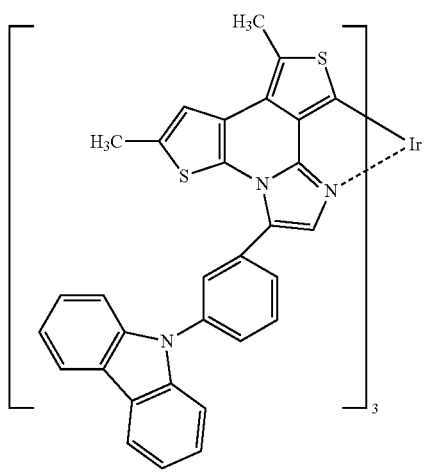
C-200 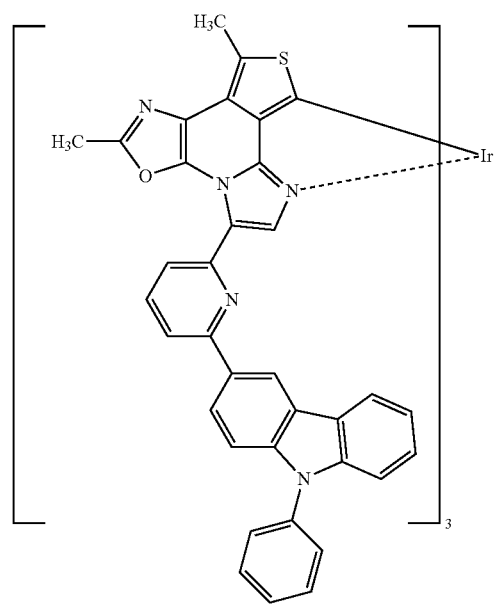
C-201 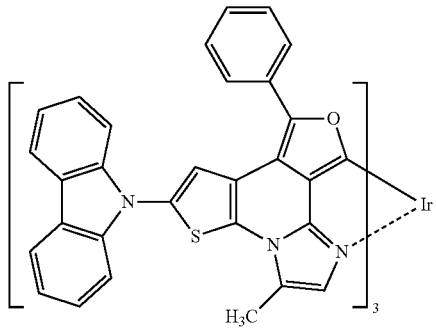
C-202 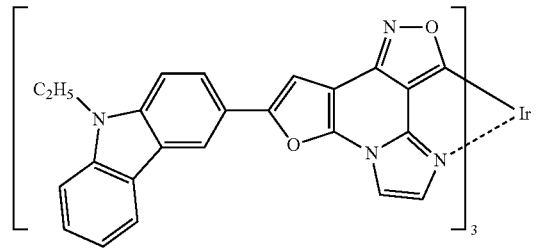

-continued
C-203 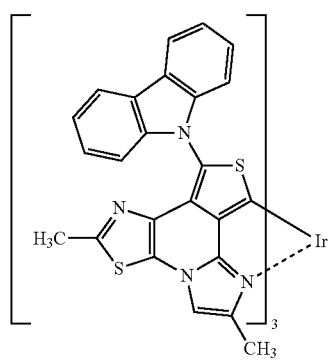
C-204 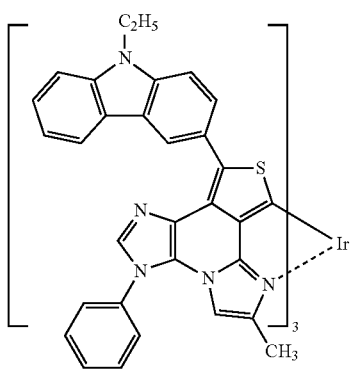
C-205 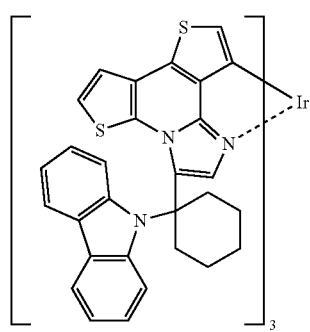
C-206 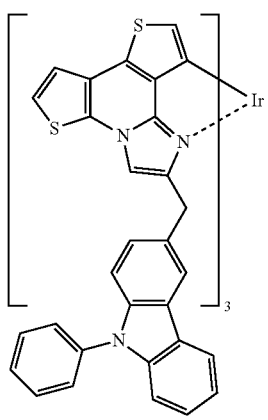
C-207 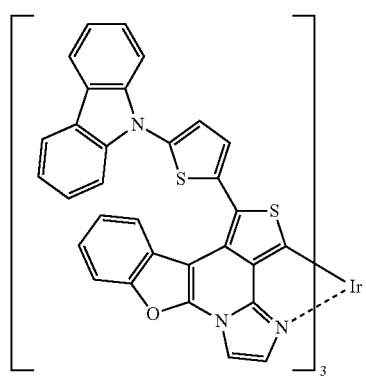
C-208 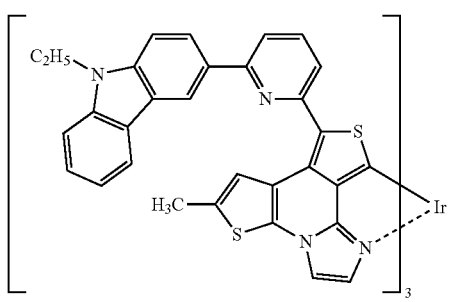

-continued
C-209 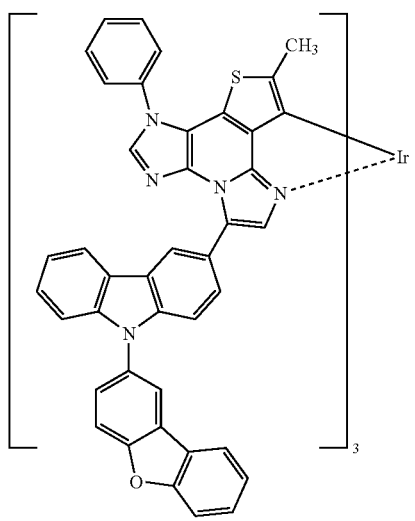
C-210 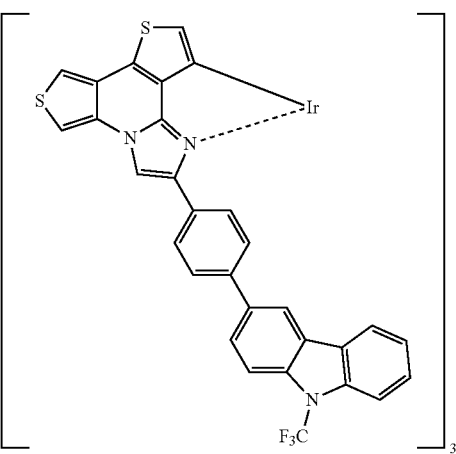
C-211 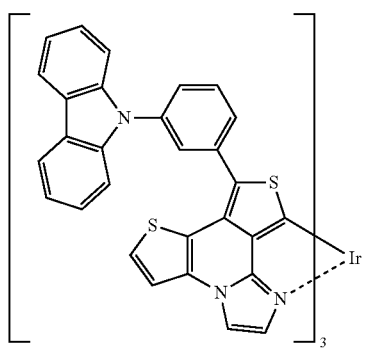
C-212 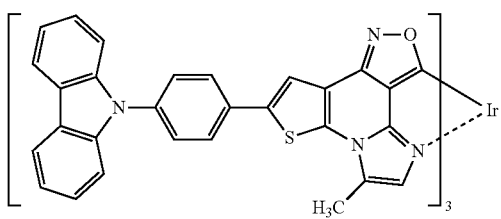
C-213 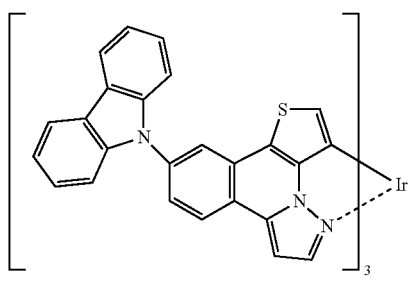
C-214 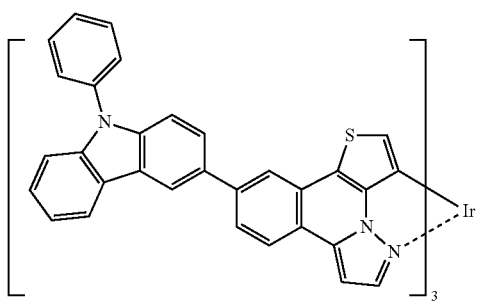
C-215 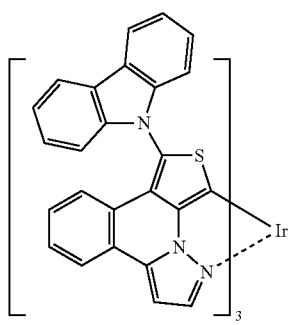
C-216 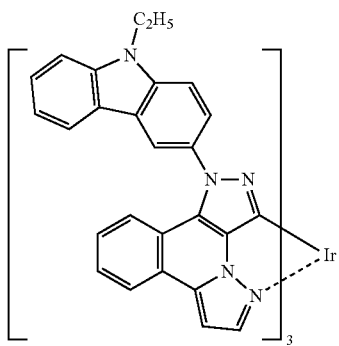

-continued
C-217
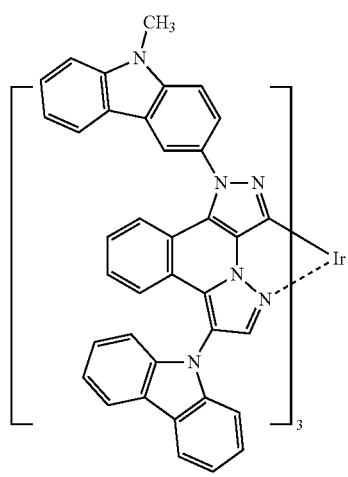
C-218
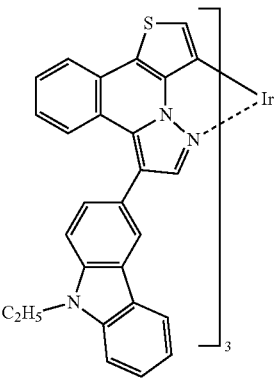
C-219
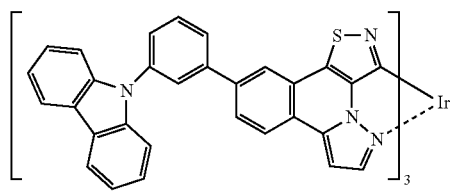
C-220
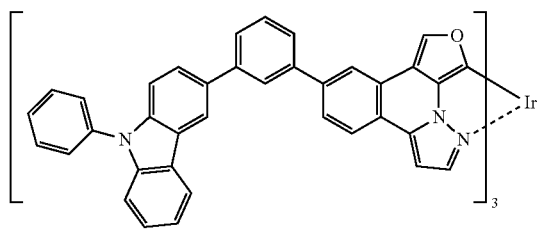
C-221
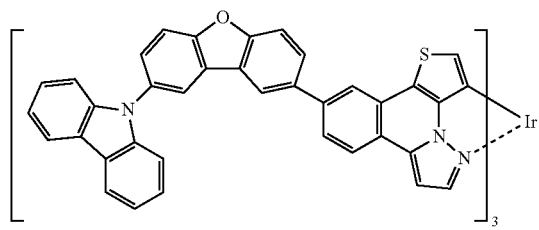
C-222
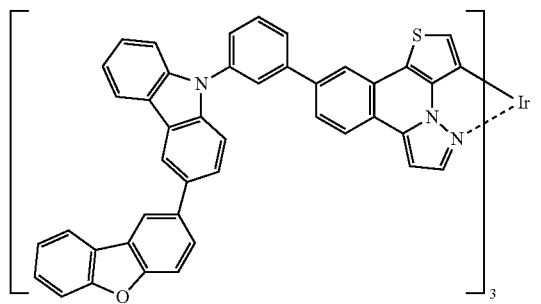
C-223
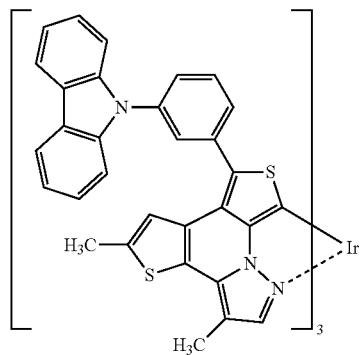
C-224
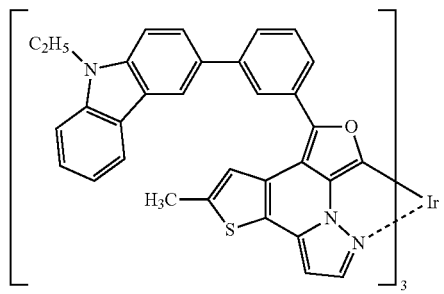

-continued
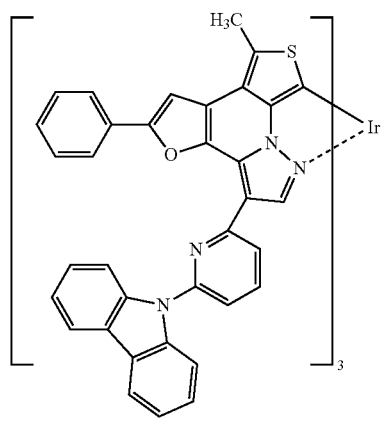
C-225
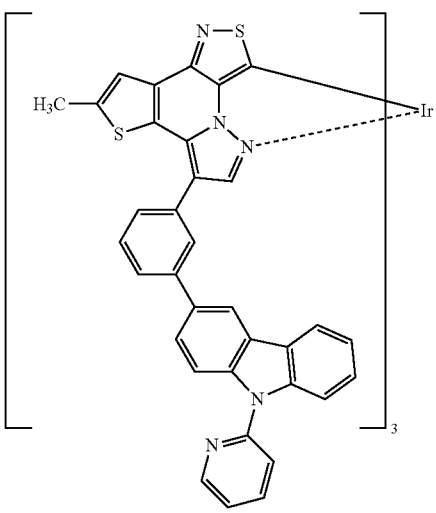
C-226
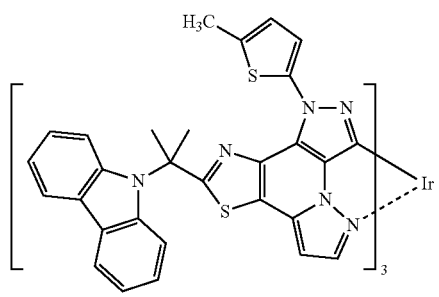
C-227
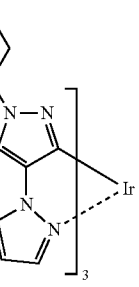
C-228
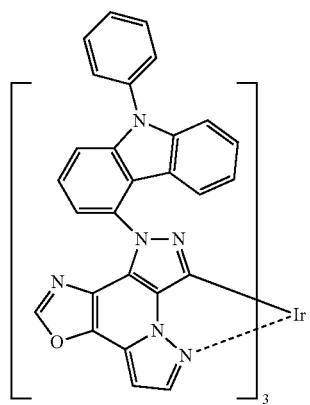
C-229
C-230
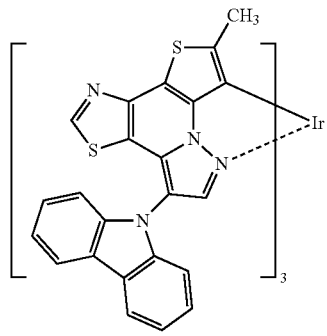
C-231
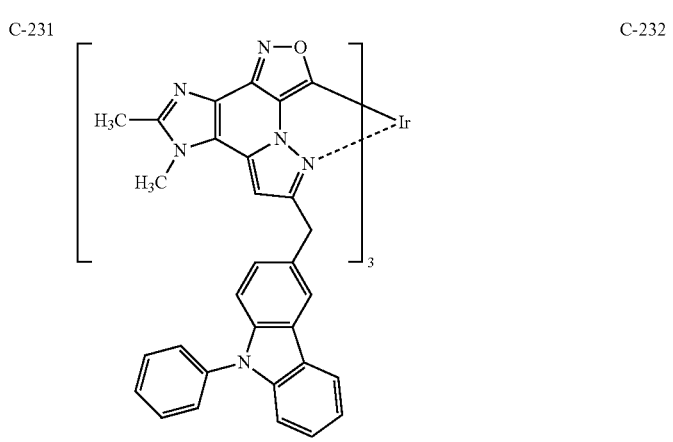
C-232

-continued
C-233
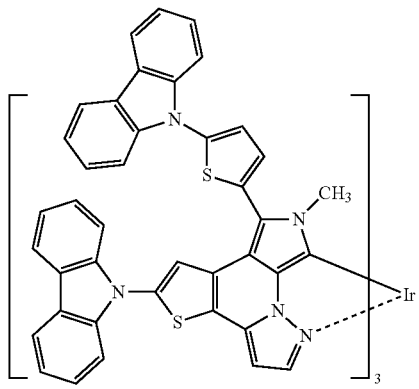
C-234
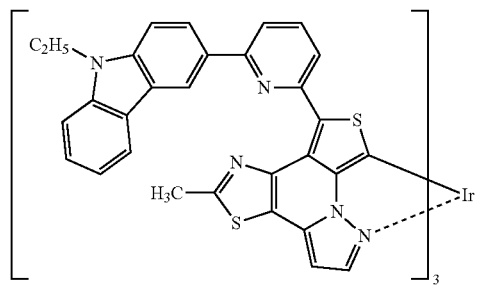
C-235
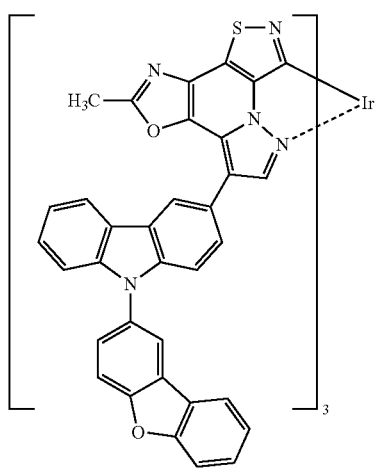
C-236
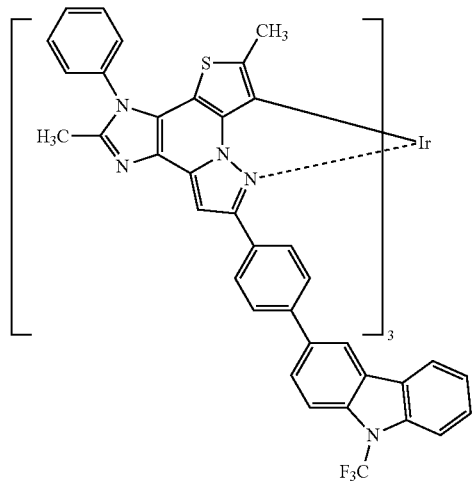
C-237
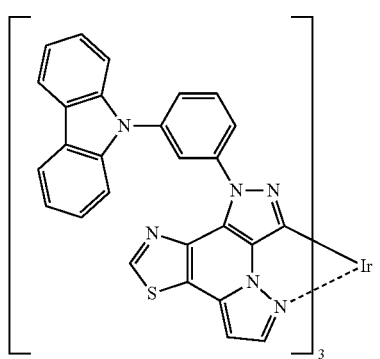
C-238
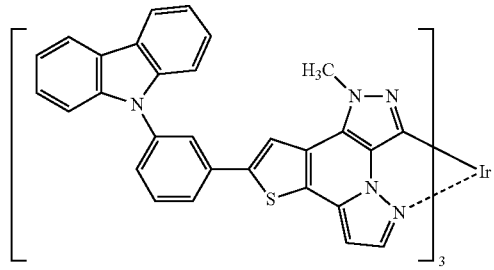
C-239
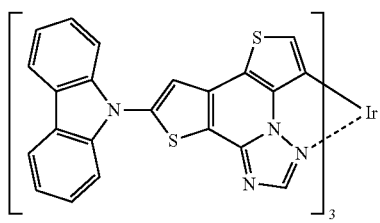
C-240
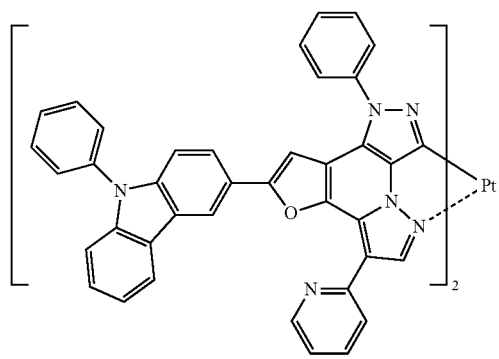

-continued
C-241
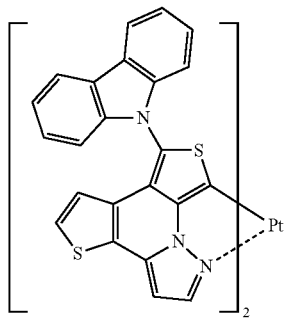
C-242
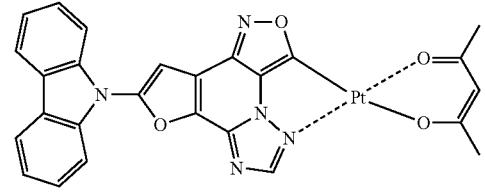
C-243
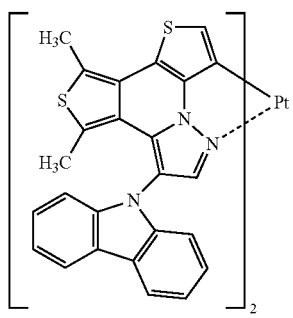
C-244
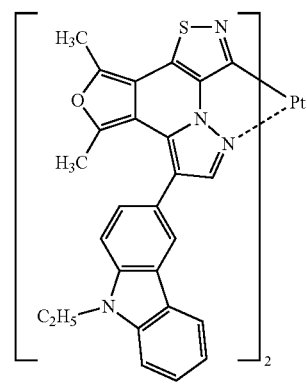
C-245
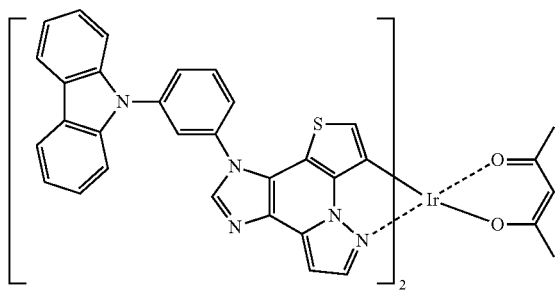
C-246
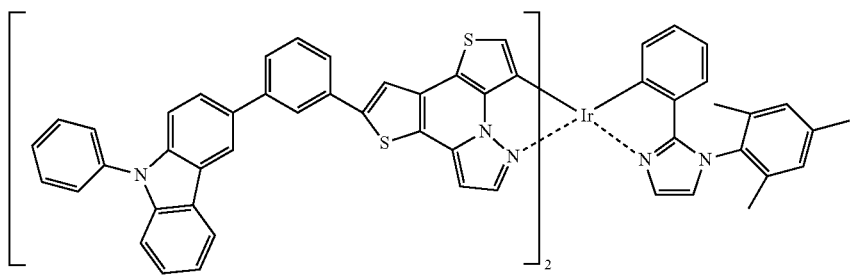
C-247
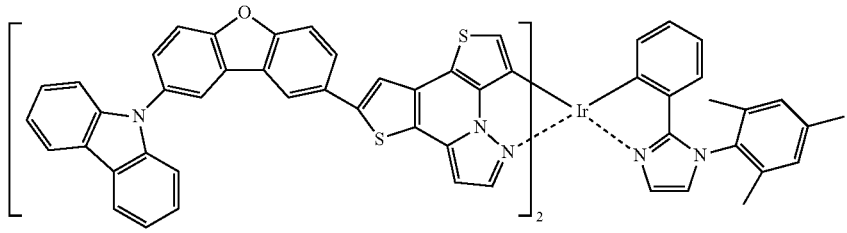

C-248
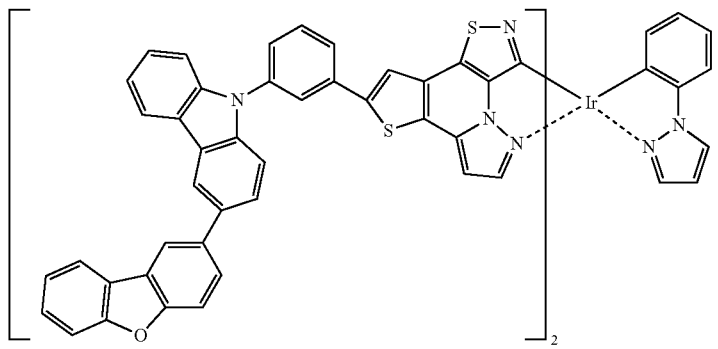
D-1
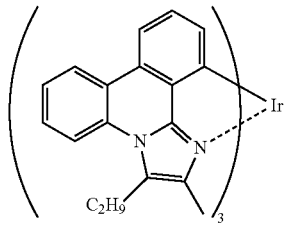
D-2
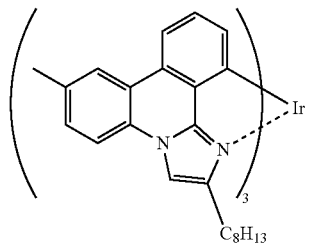
D-3
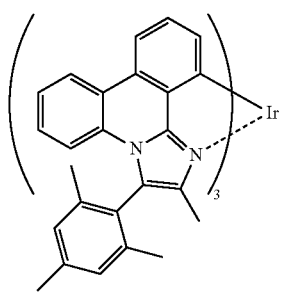
D-4
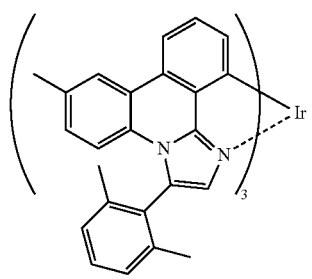
D-5
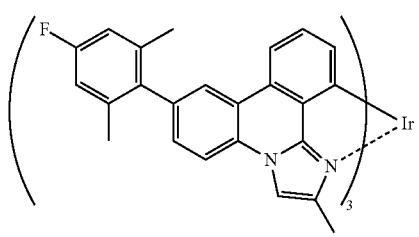
D-6
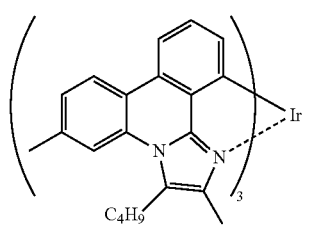
D-7
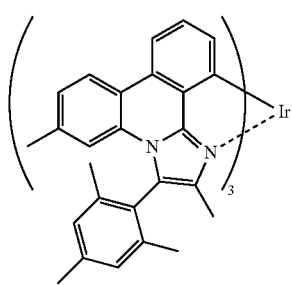
D-8
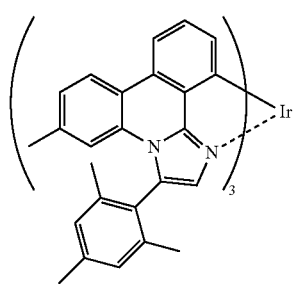

-continued
D-9
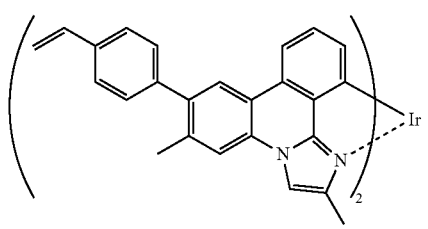
D-10
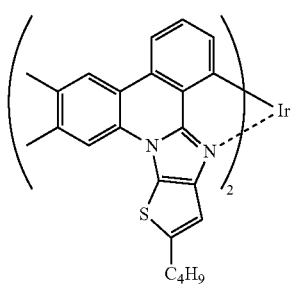
D-12
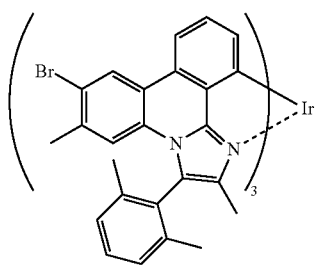
D-11
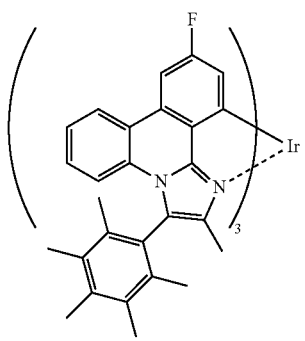
D-13
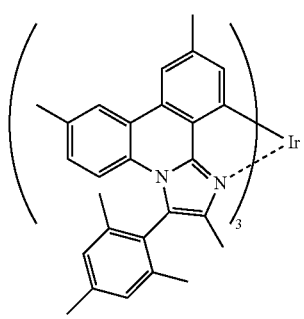
D-14
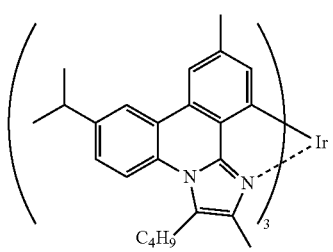
D-15
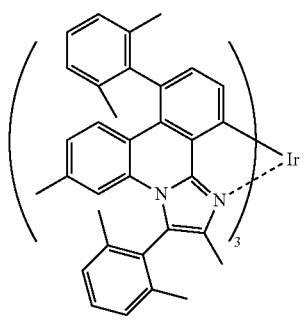
D-16
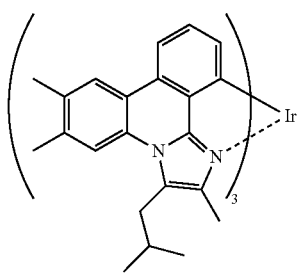
D-17
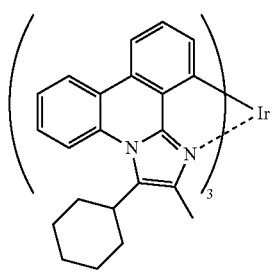
D-18
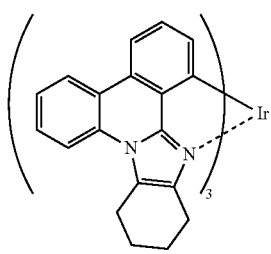

-continued
D-19
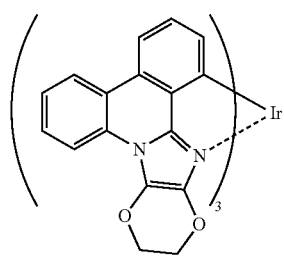
D-20
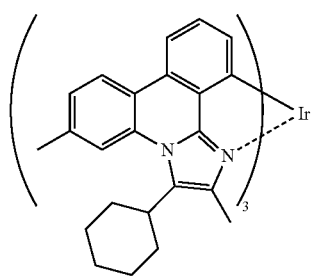
D-21
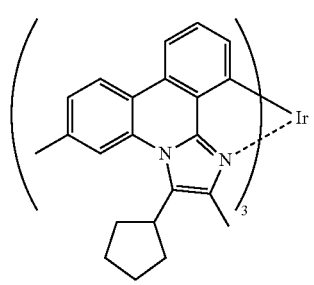
D-22
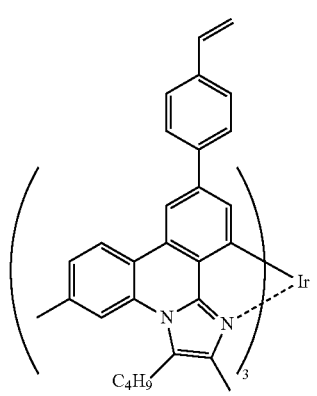
D-23
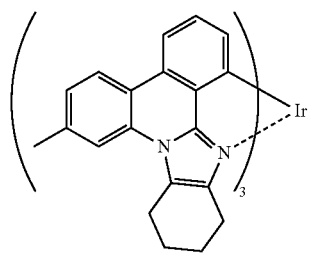
D-24
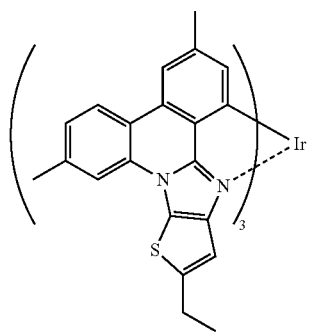
D-25
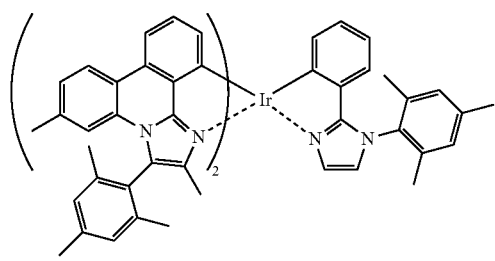
D-26
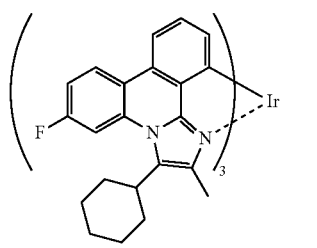
D-27
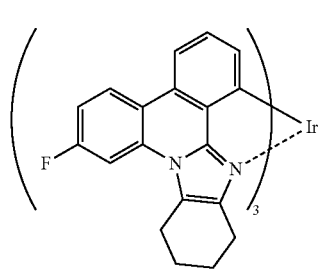
D-28
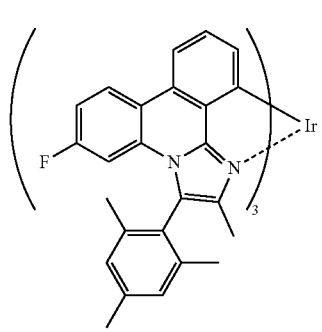

-continued
| | |
|---|---|
| D-29 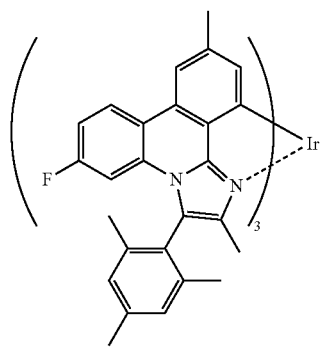 | D-30 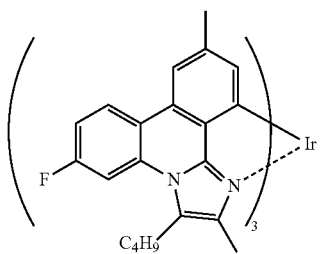 |
| D-31 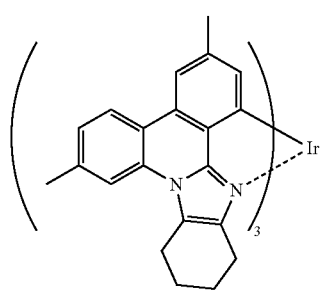 | D-32 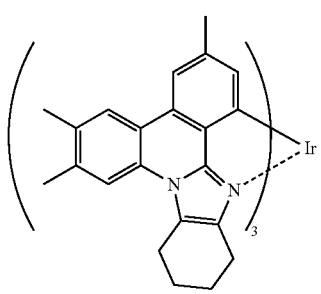 |
| D-33 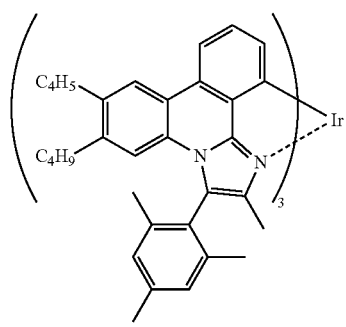 | D-34 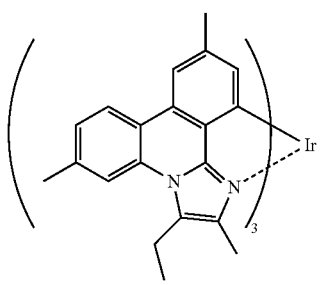 |
| D-35 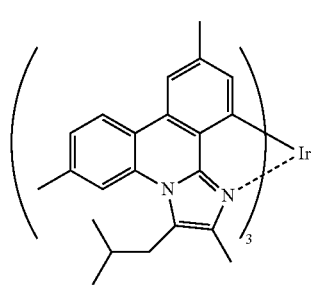 | D-36 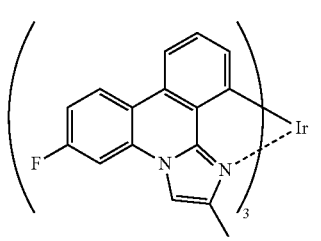 |
| D-37 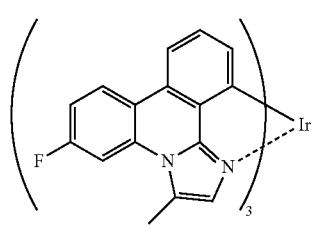 | D-38 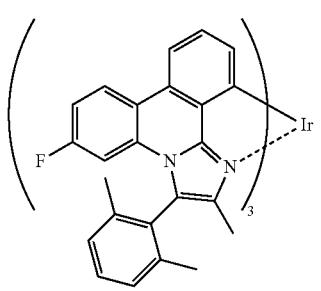 |

-continued
D-39
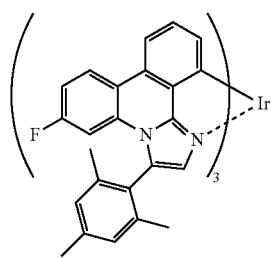
D-40
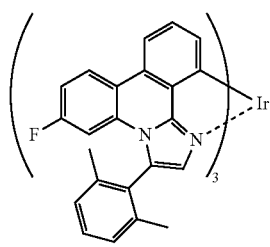
D-41
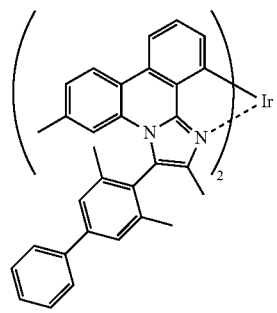
D-42
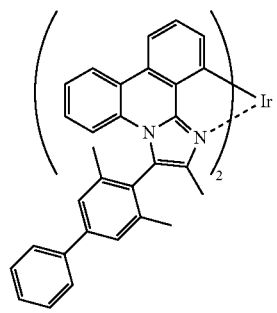
D-43
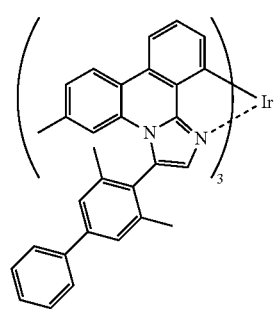
D-44
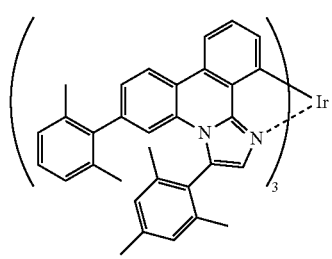
D-45
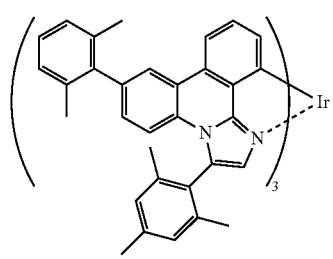
D-46
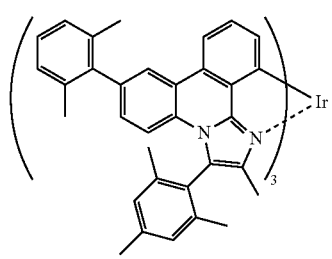
D-47
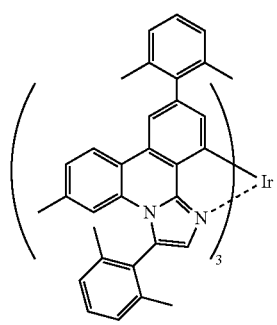
D-48
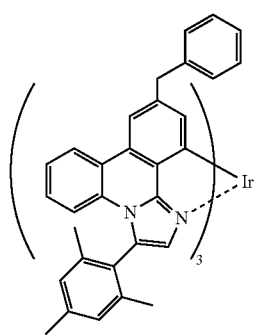

-continued
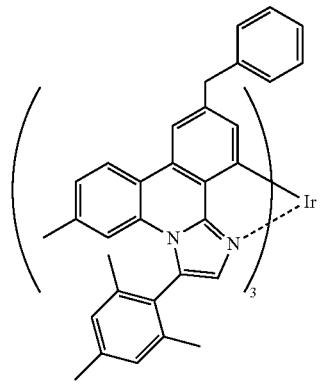
D-49
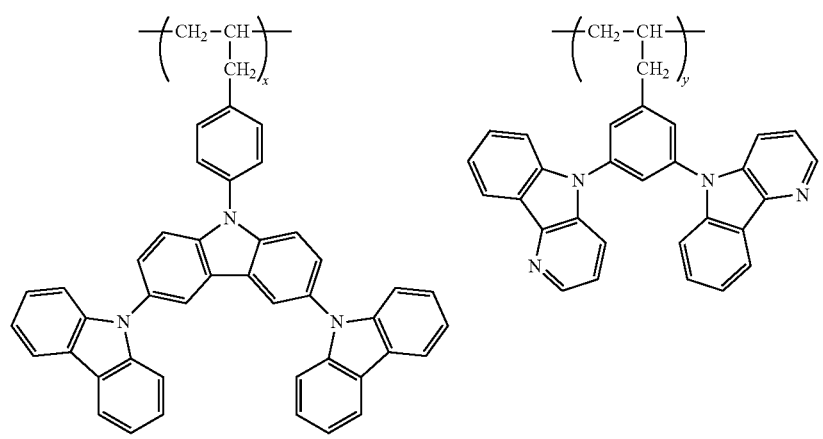
P-201
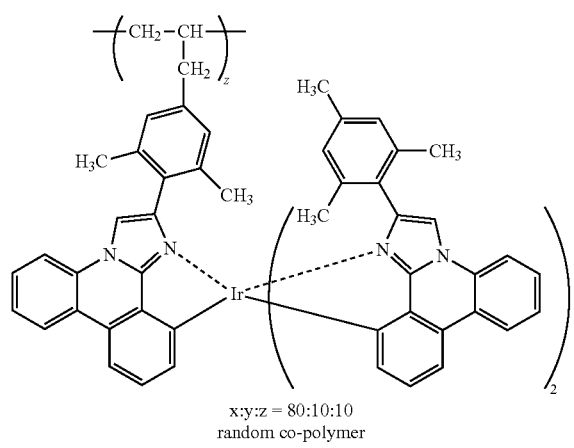
x:y:z = 80:10:10
random co-polymer

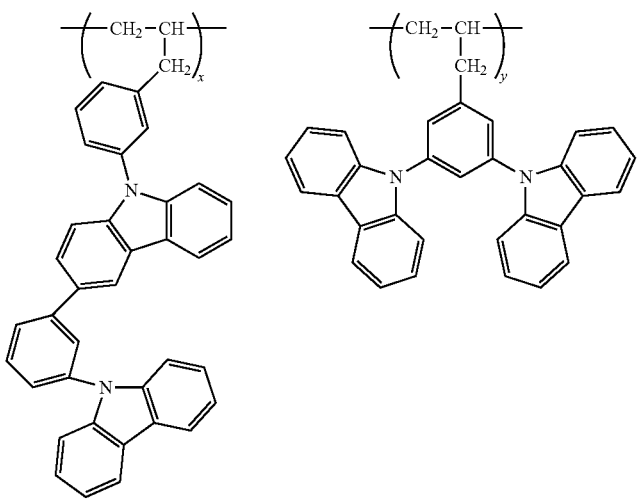
P-202
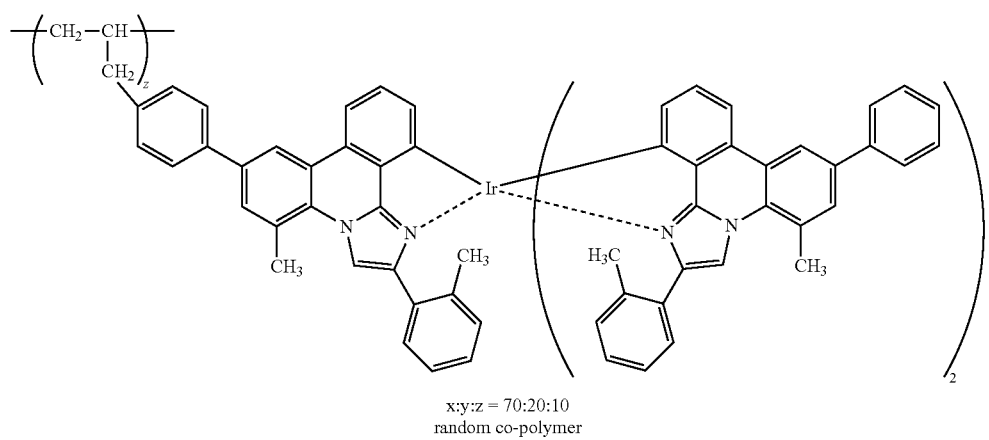
x:y:z = 70:20:10
random co-polymer
P-203
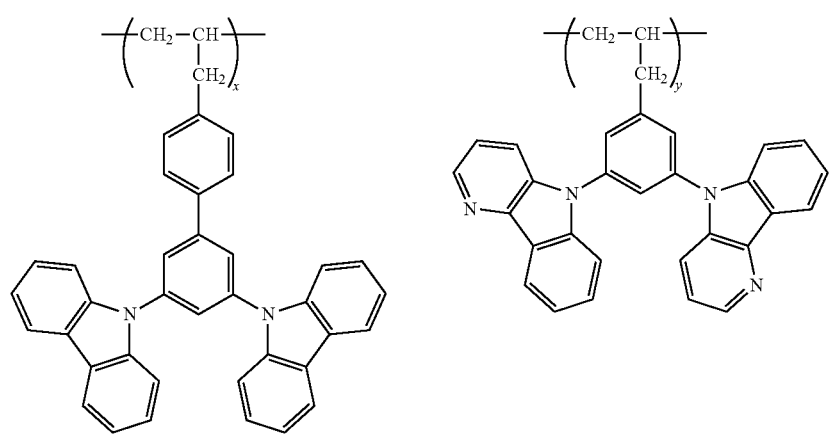

-continued
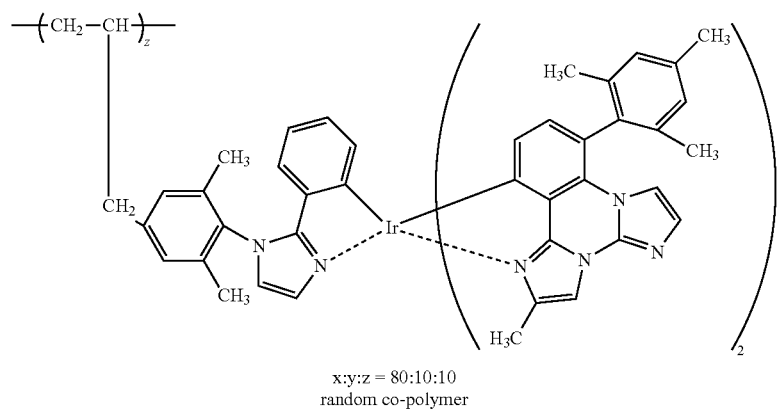
x:y:z = 80:10:10
random co-polymer
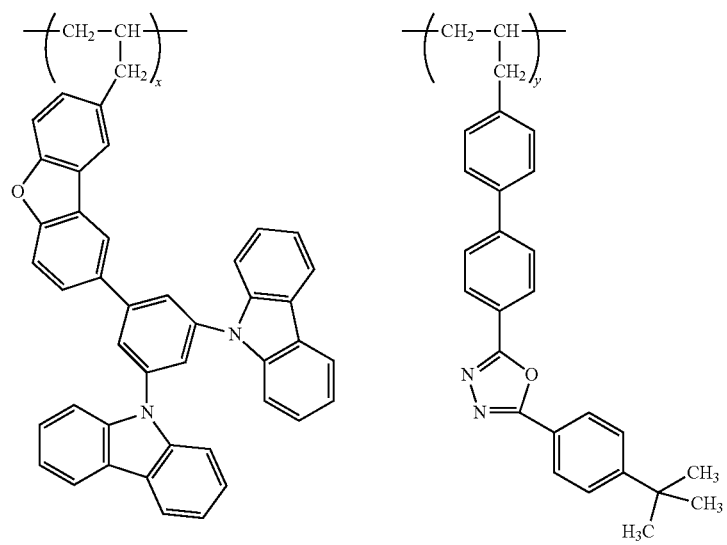
P-204
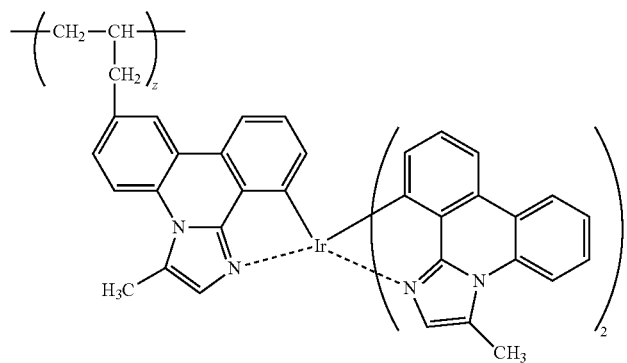
x:y:z = 80:10:10
random co-polymer

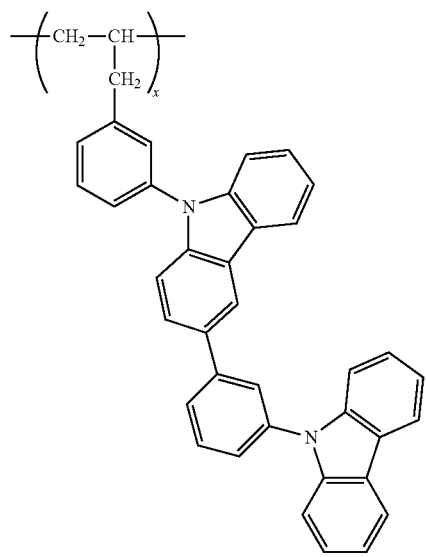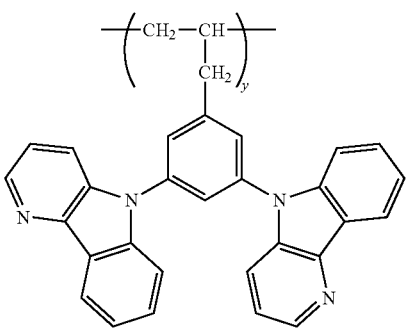
P-205
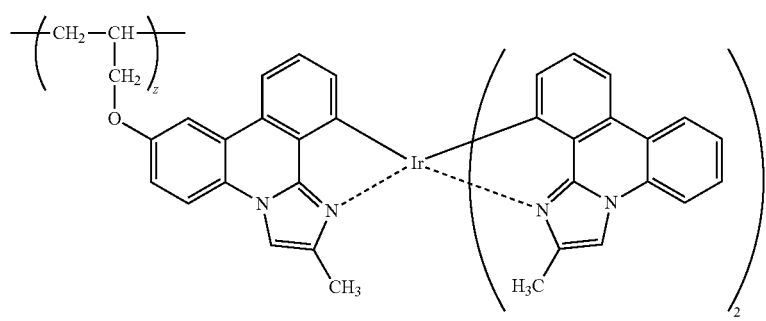
x:y:z = 80:10:10
random co-polymer
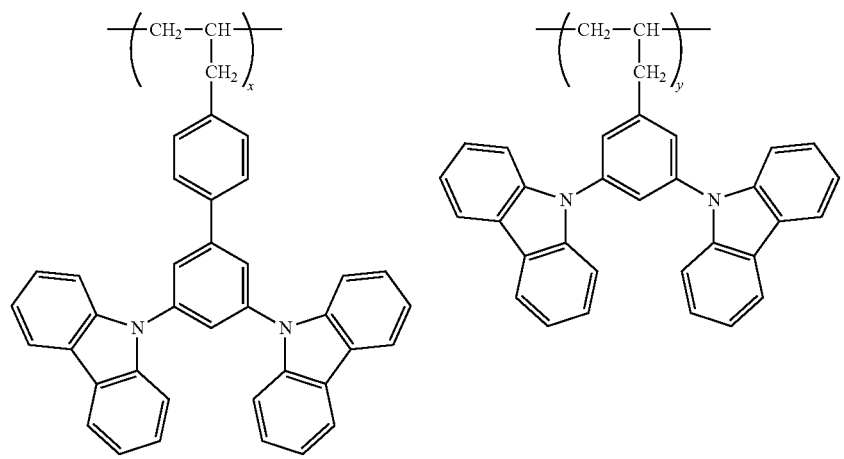
P-206

-continued
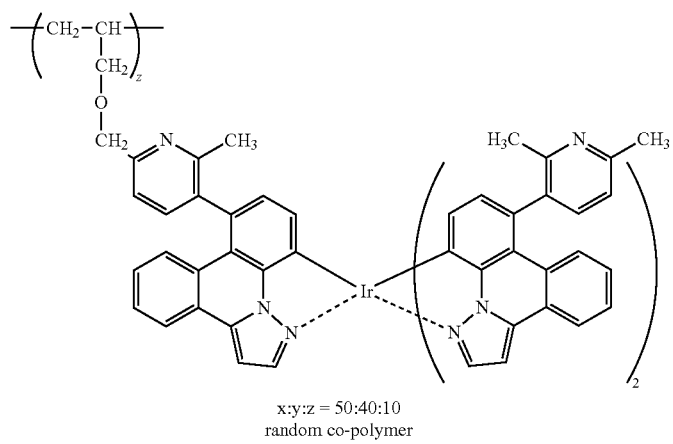
x:y:z = 50:40:10
random co-polymer
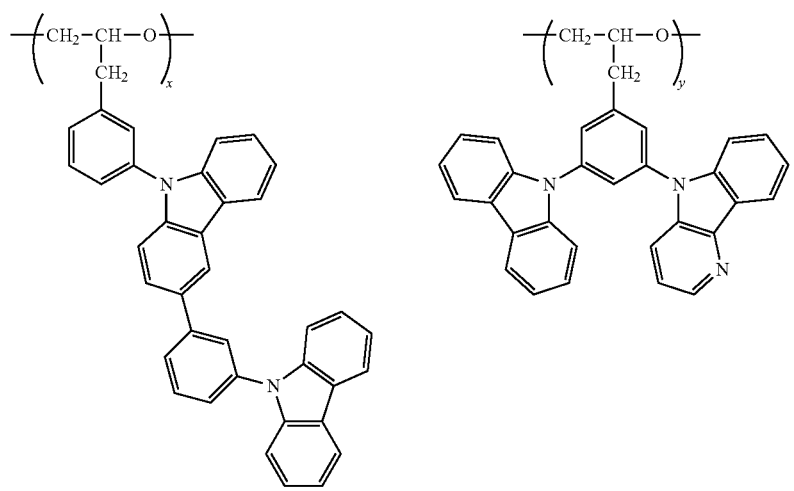
P-207
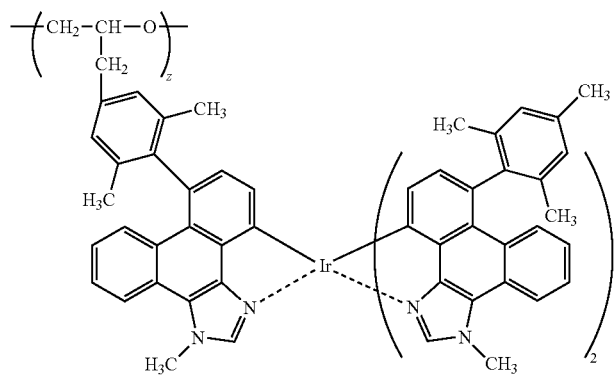
x:y:z = 80:10:10
random co-polymer -continued
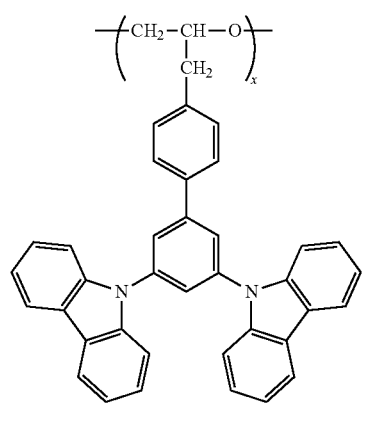 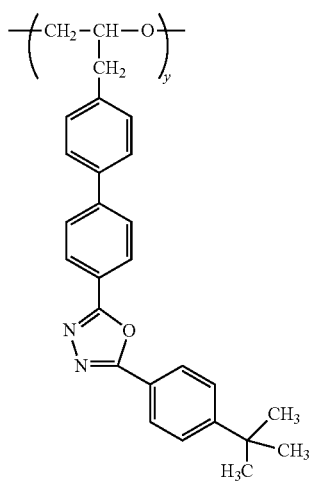
P-208
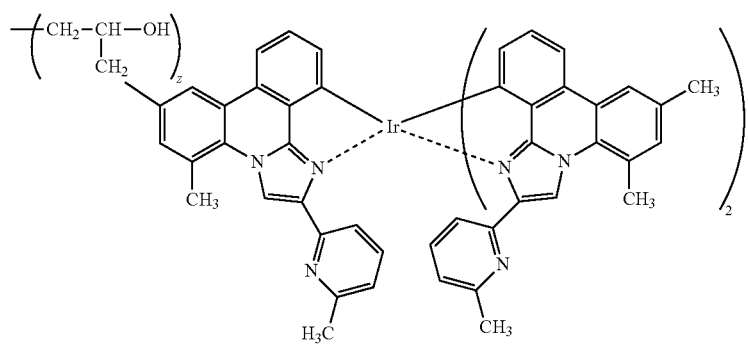
x:y:z = 80:10:10
random co-polymer
P-209
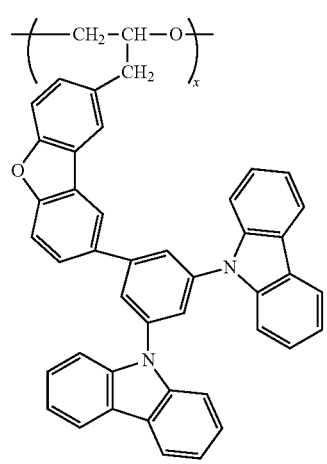 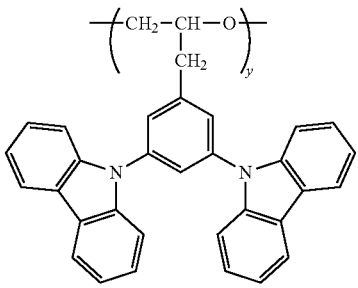

-continued
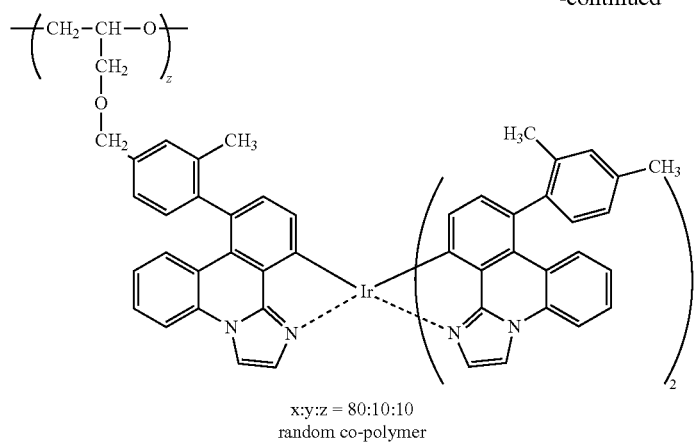
x:y:z = 80:10:10
random co-polymer
P-210
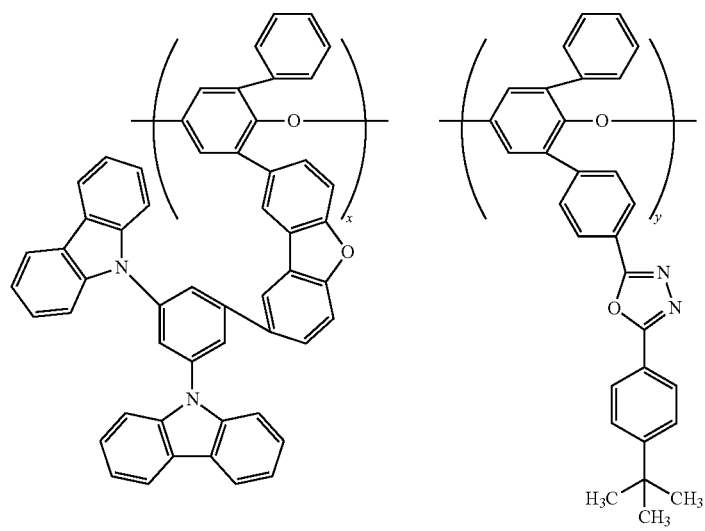
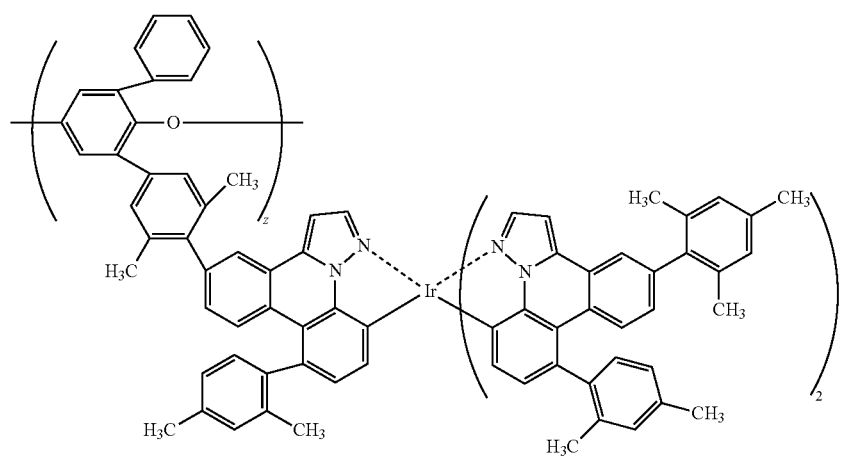
x:y:z = 80:10:10
random co-polymer P-211
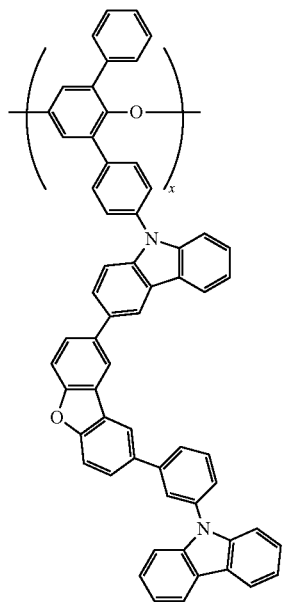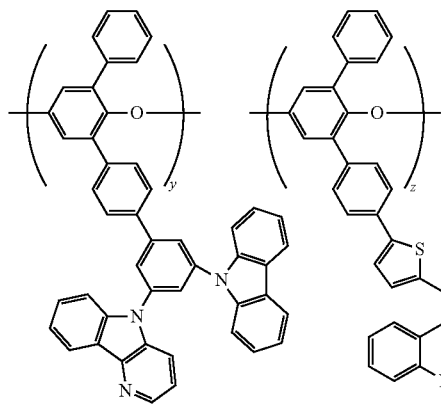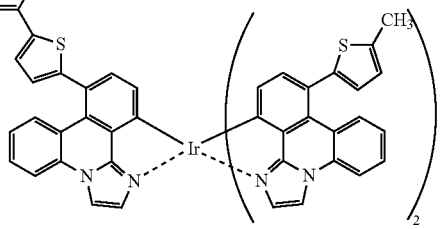
x:y:z = 80:10:10
random co-polymer
P-212
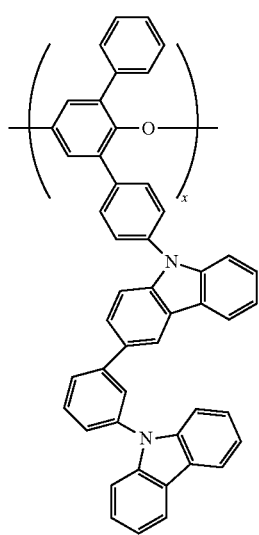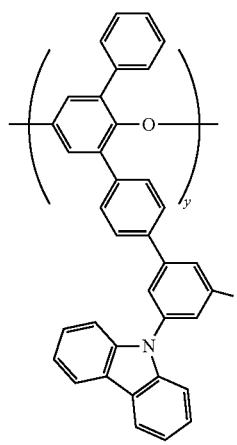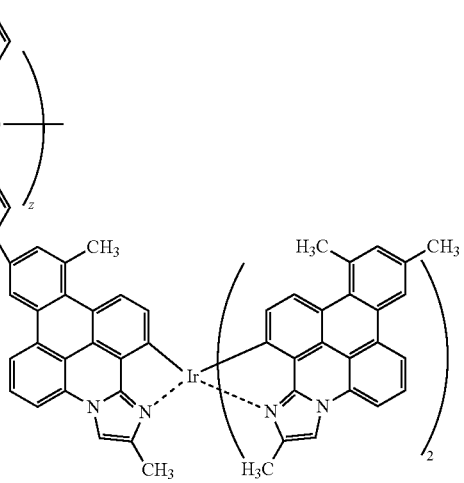
x:y:z = 60:30:10
random co-polymer

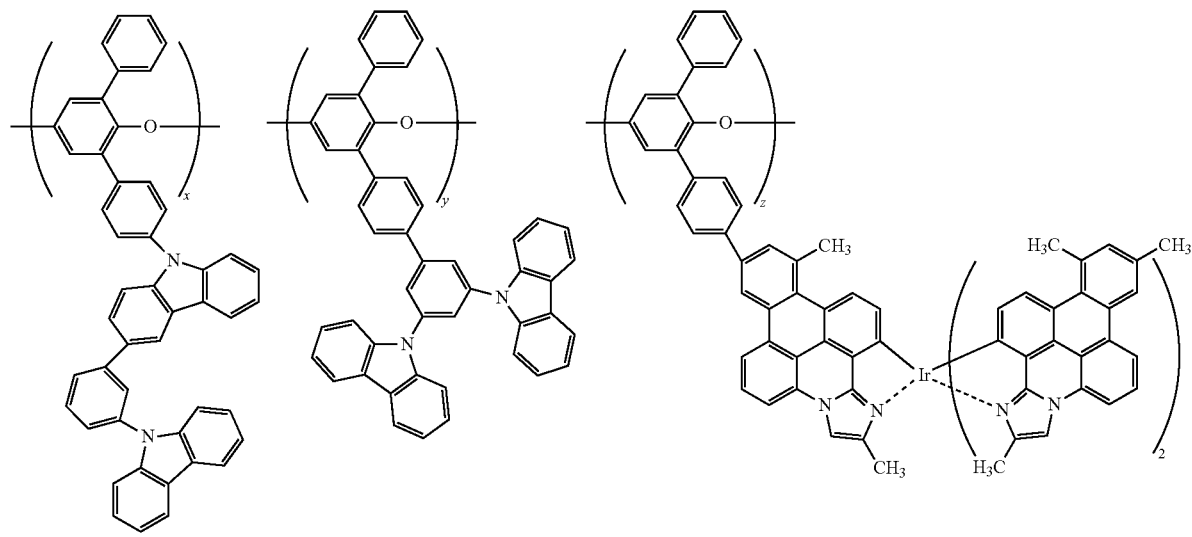
P-212
x:y:z = 60:30:10
random co-polymer
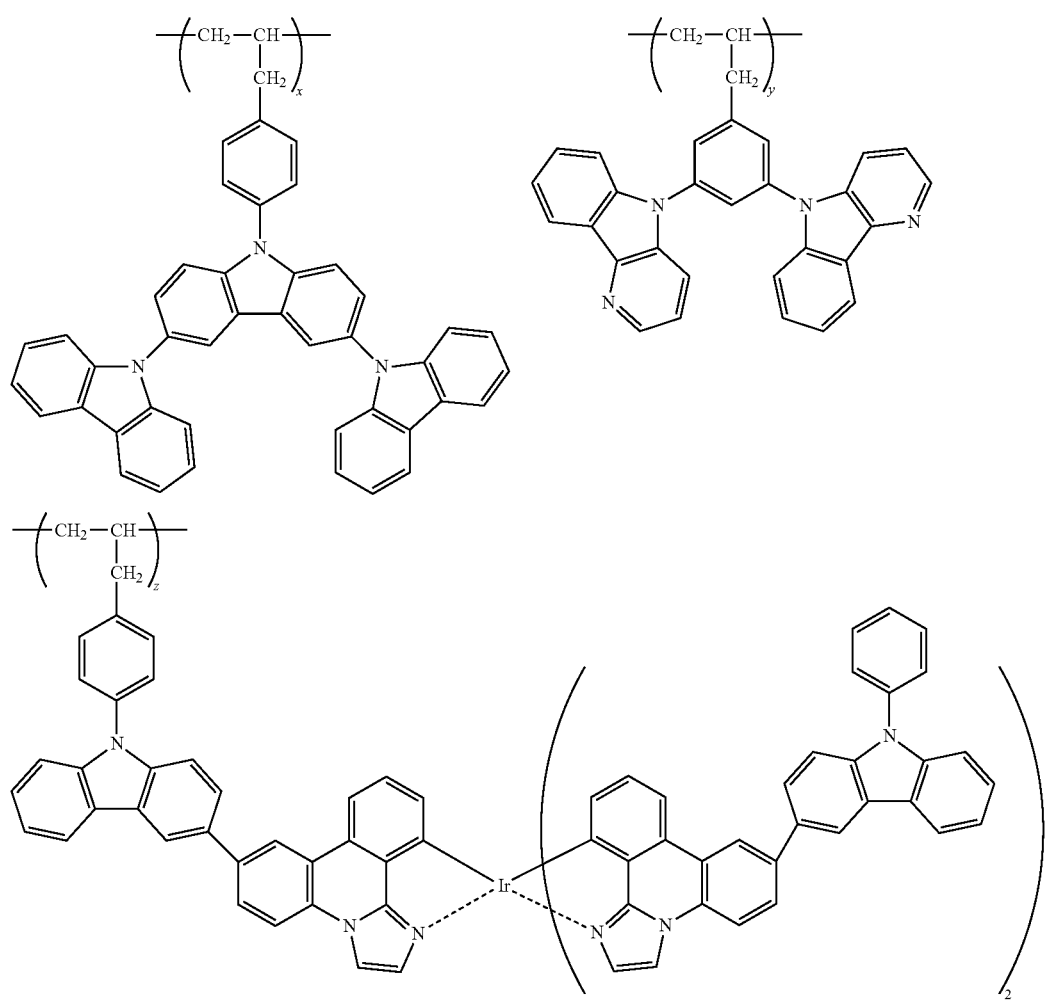
P-213
x:y:z = 70:20:10
random co-polymer

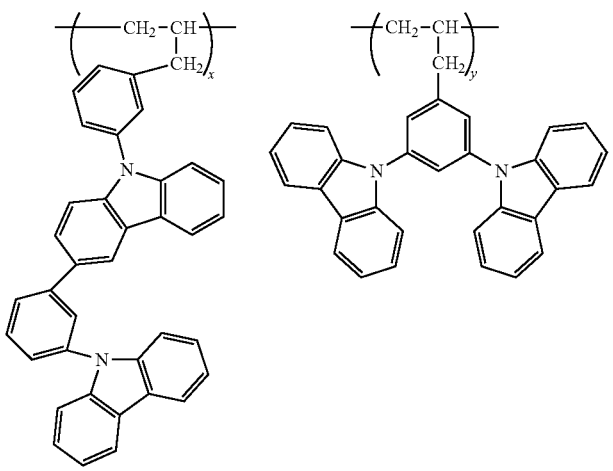
P-214
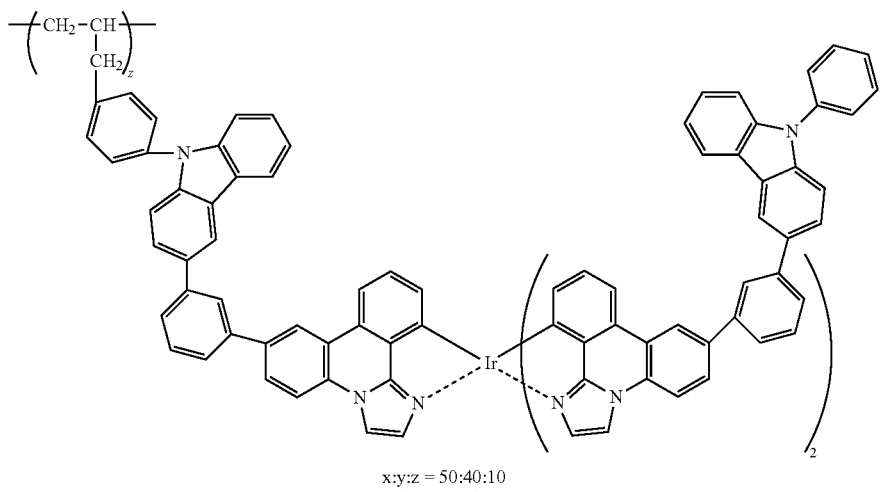
x:y:z = 50:40:10
random co-polymer
P-215
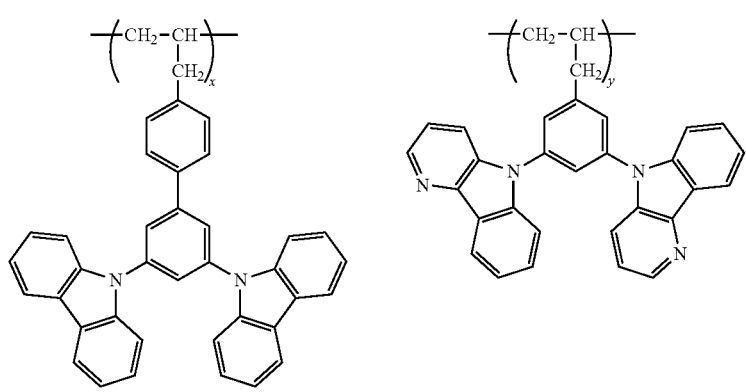

-continued
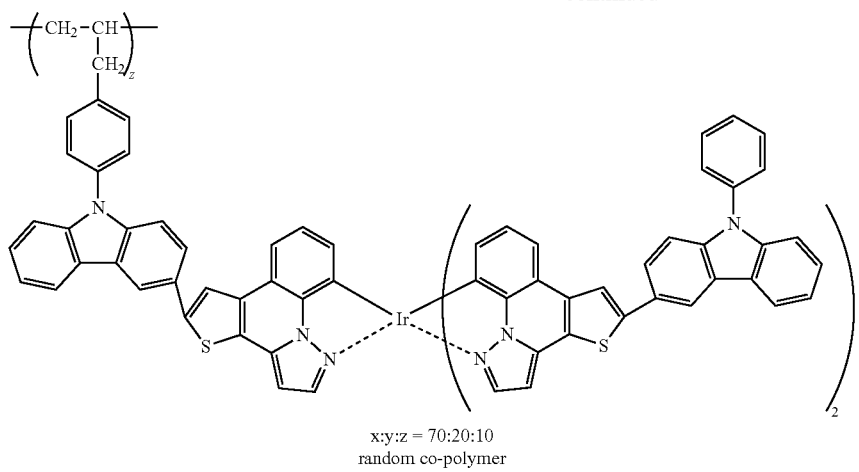
x:y:z = 70:20:10
random co-polymer
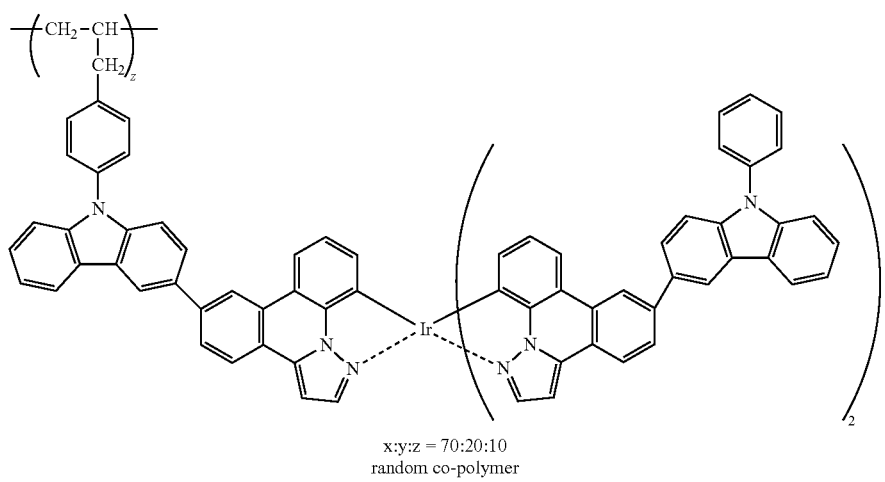
x:y:z = 70:20:10
random co-polymer
P-216
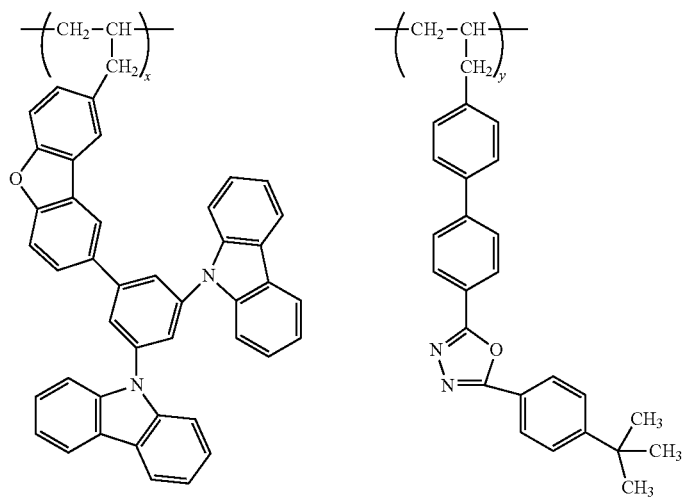

-continued
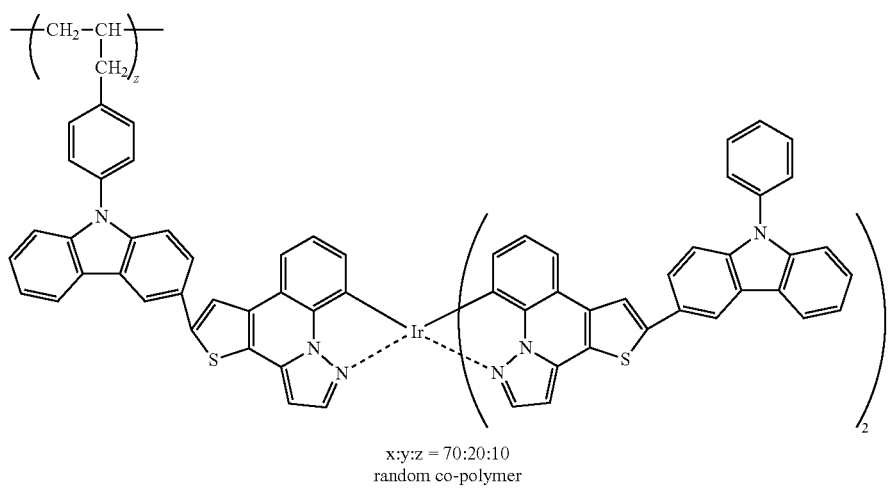
x:y:z = 70:20:10
random co-polymer
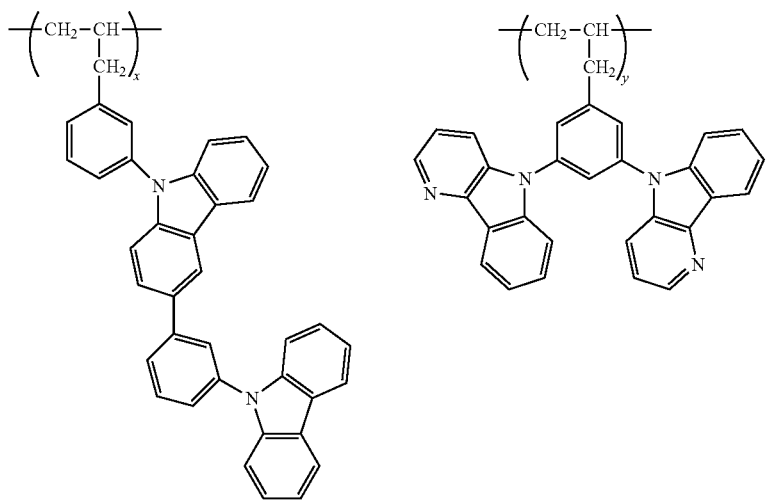
P-217
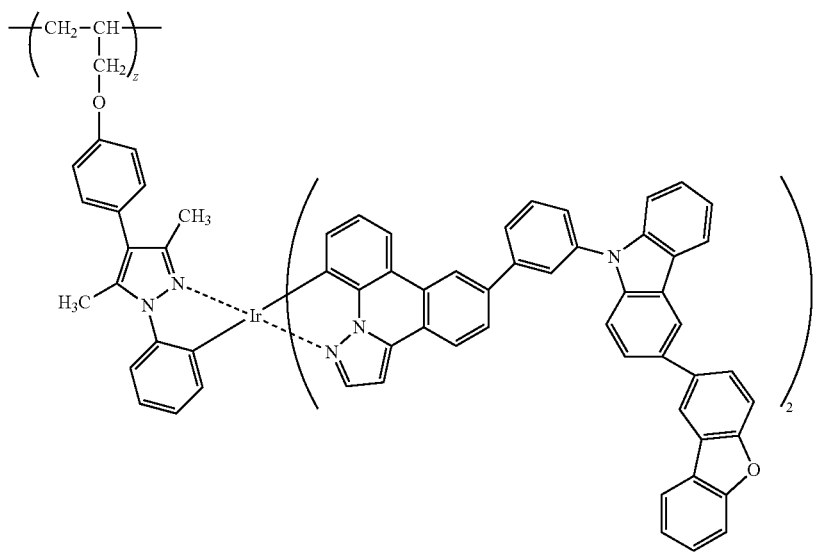
x:y:z = 70:20:10
random co-polymer -continued
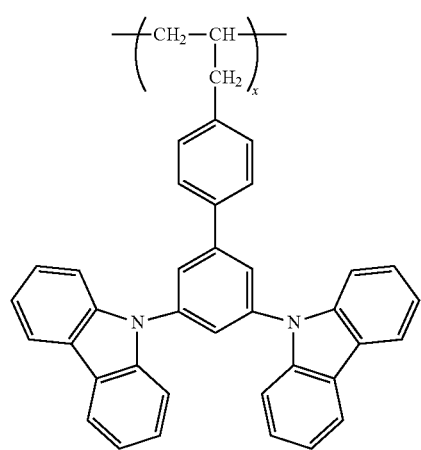 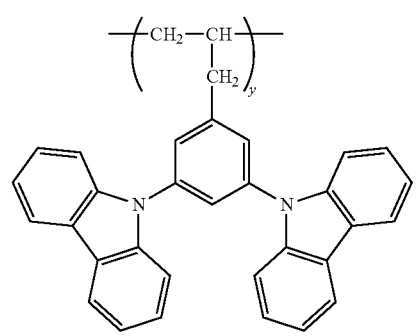
P-218
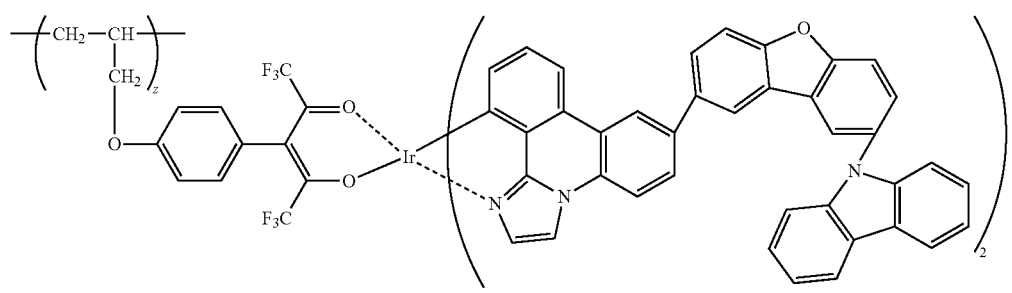
x:y:z = 50:40:10
random co-polymer
P-219
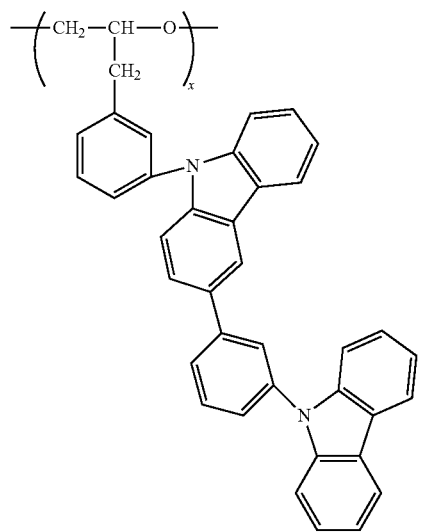 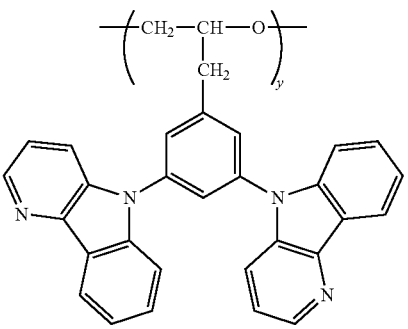

-continued
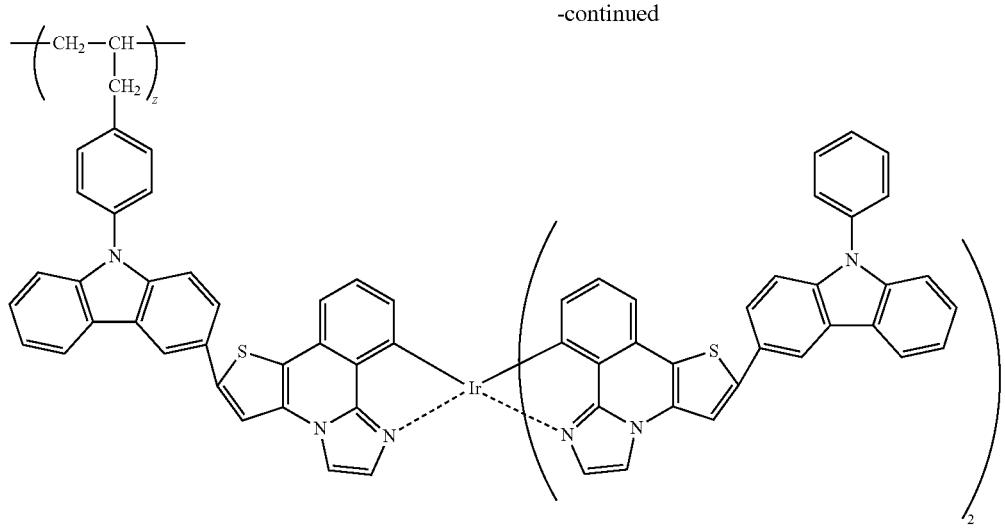
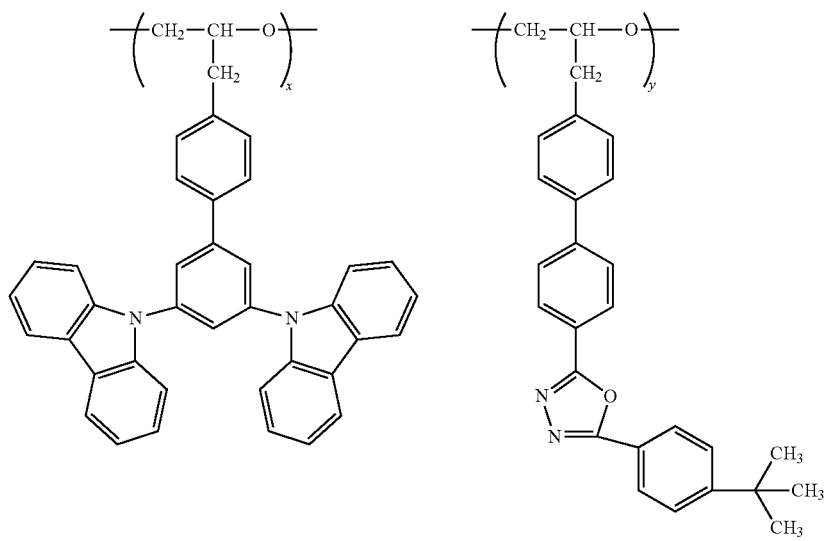
P-220
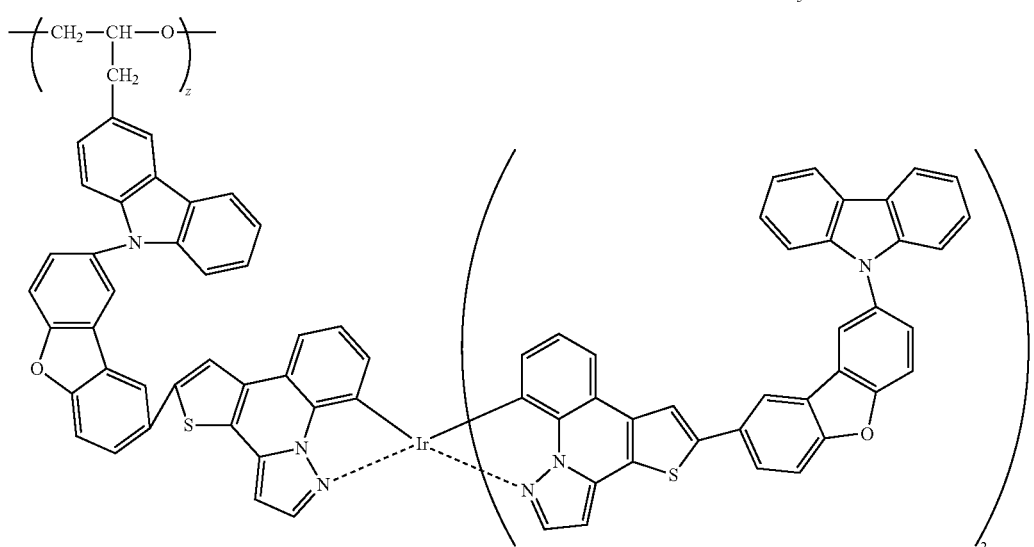

-continued
P-221
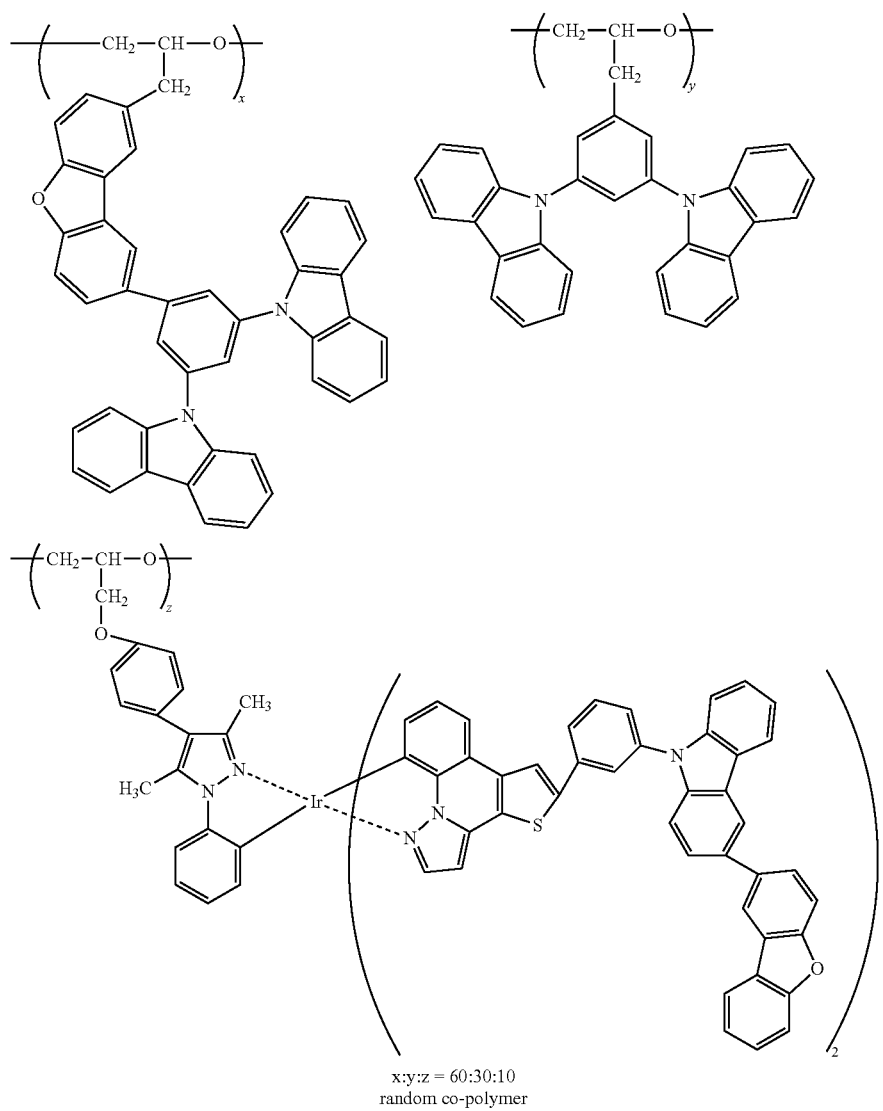
x:y:z = 60:30:10
random co-polymer
P-222
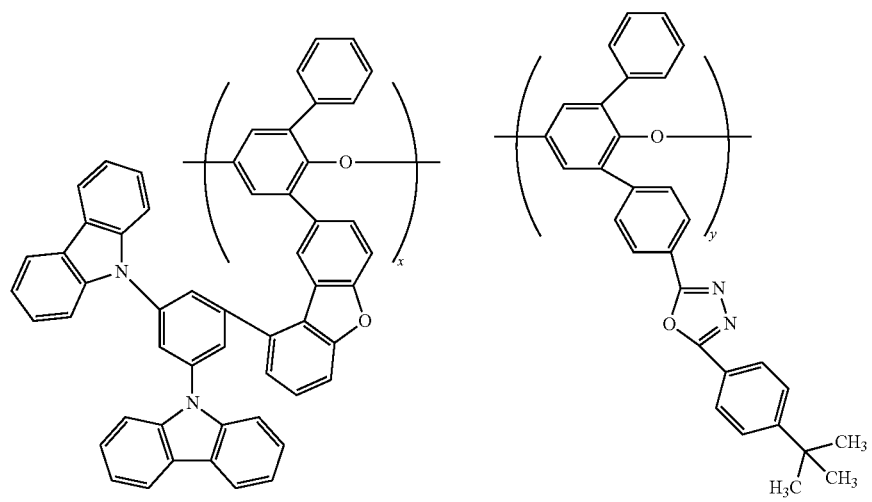

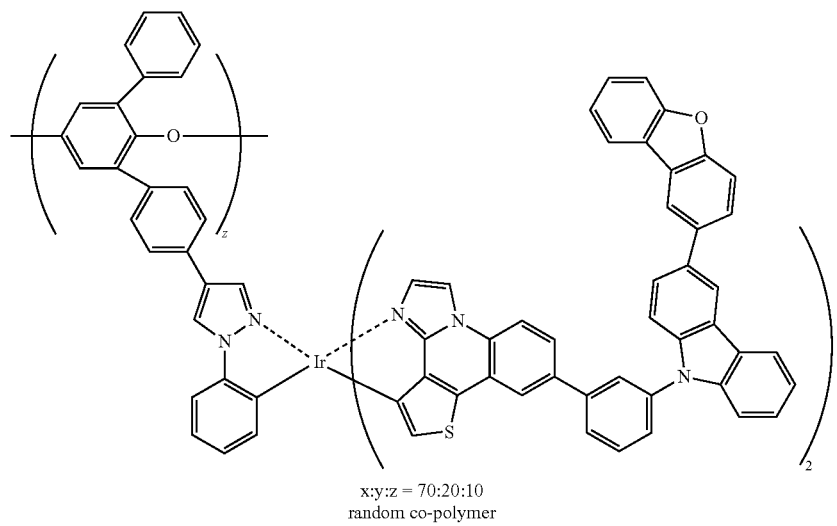
x:y:z = 70:20:10
random co-polymer
P-223
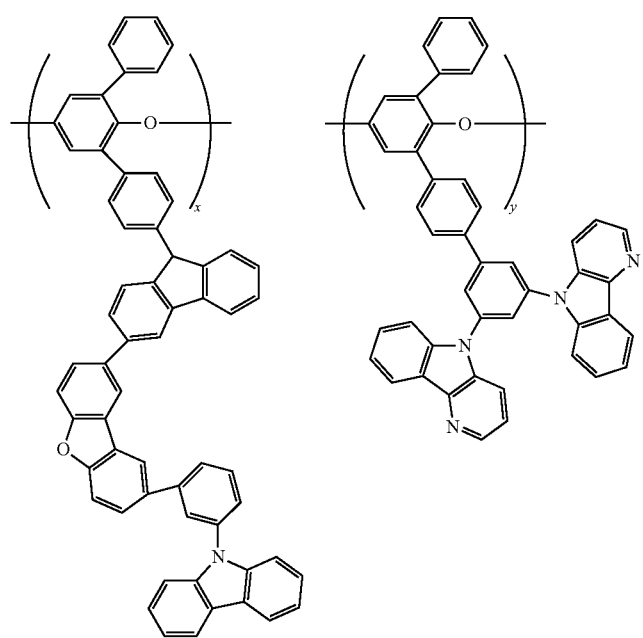

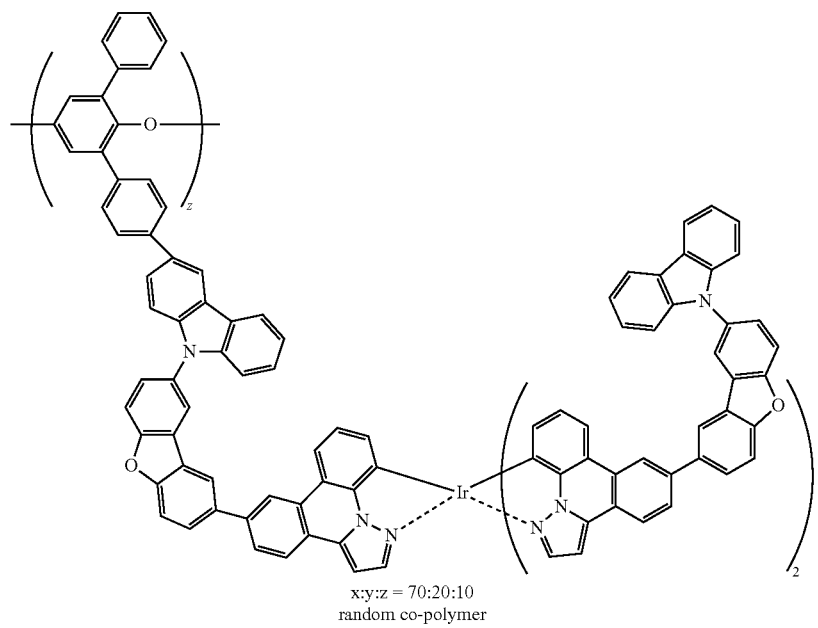
x:y:z = 70:20:10
random co-polymer
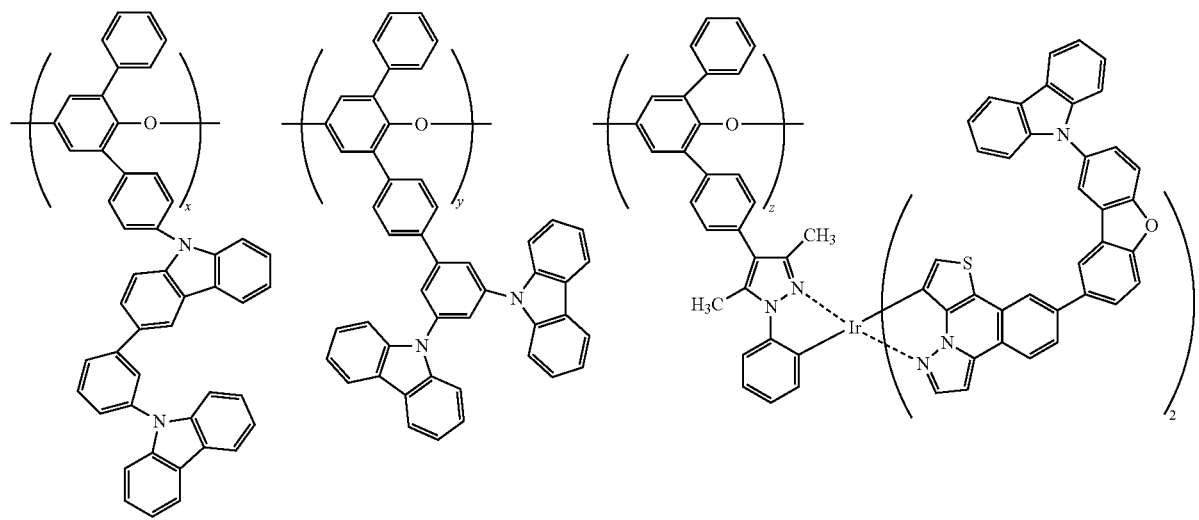
P-224
x:y:z = 60:30:10
random co-polymer -continued
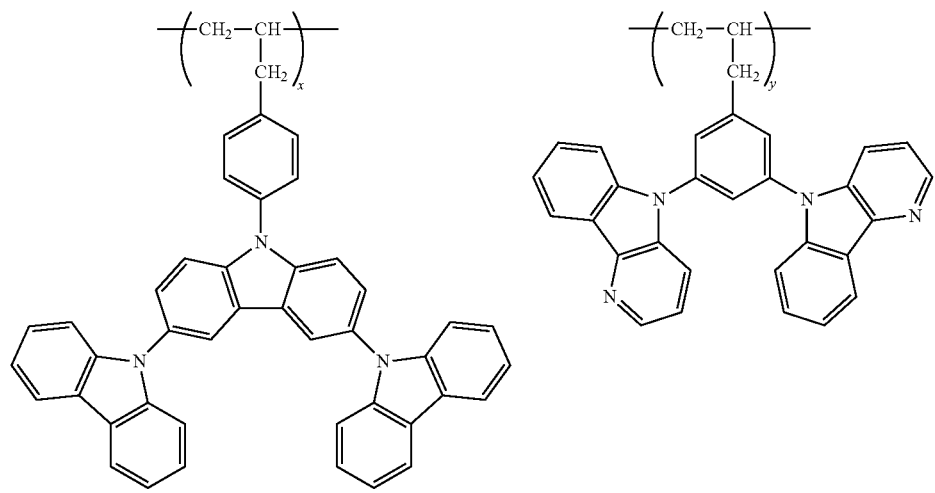
P-225
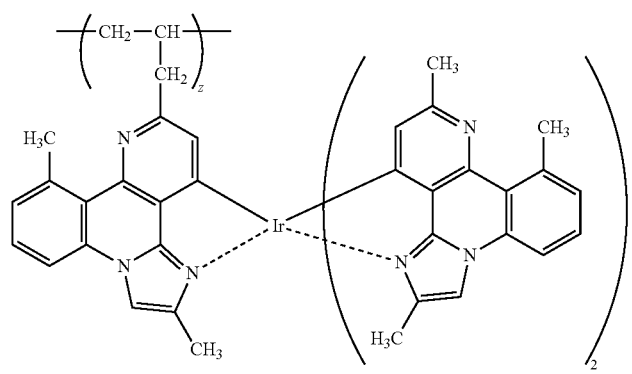
x:y:z = 80:10:10
random co-polymer
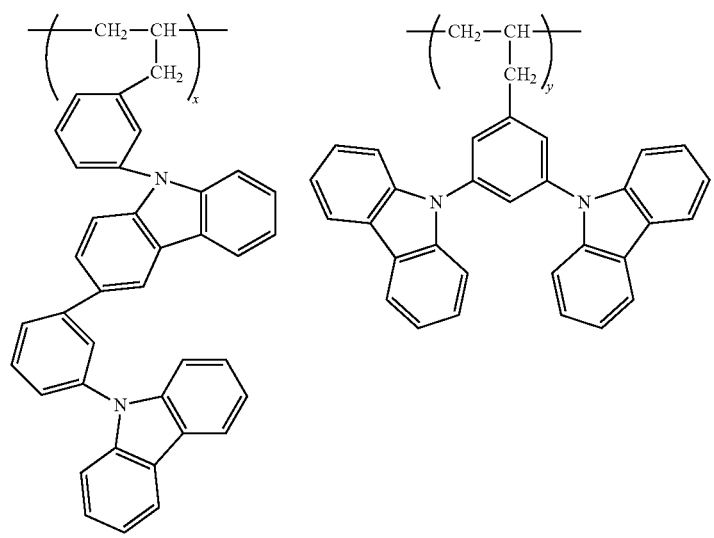
P-226

-continued
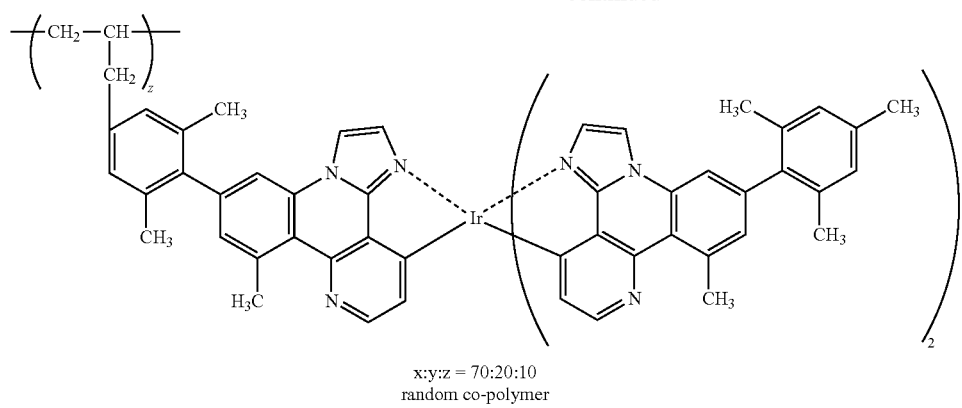
x:y:z = 70:20:10
random co-polymer
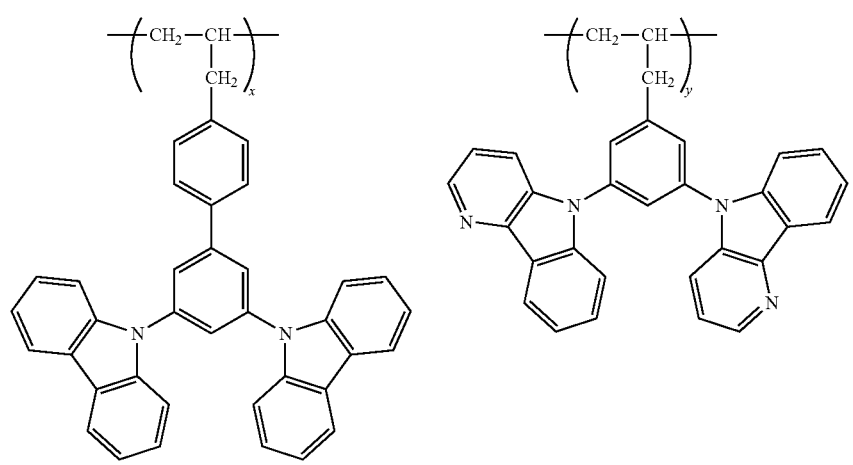
P-227
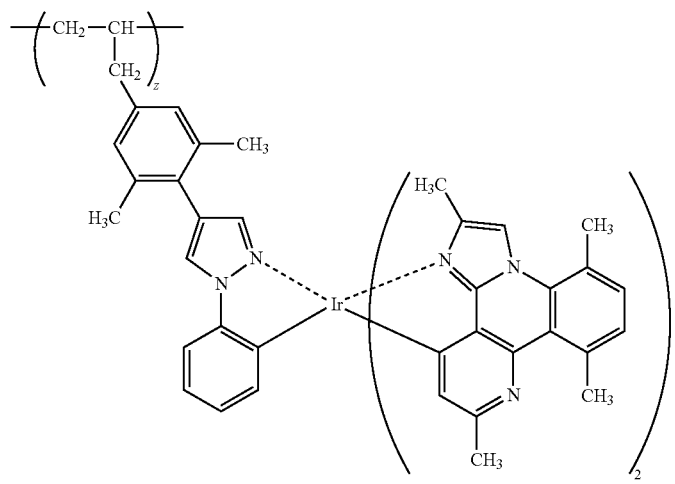

-continued
P-228
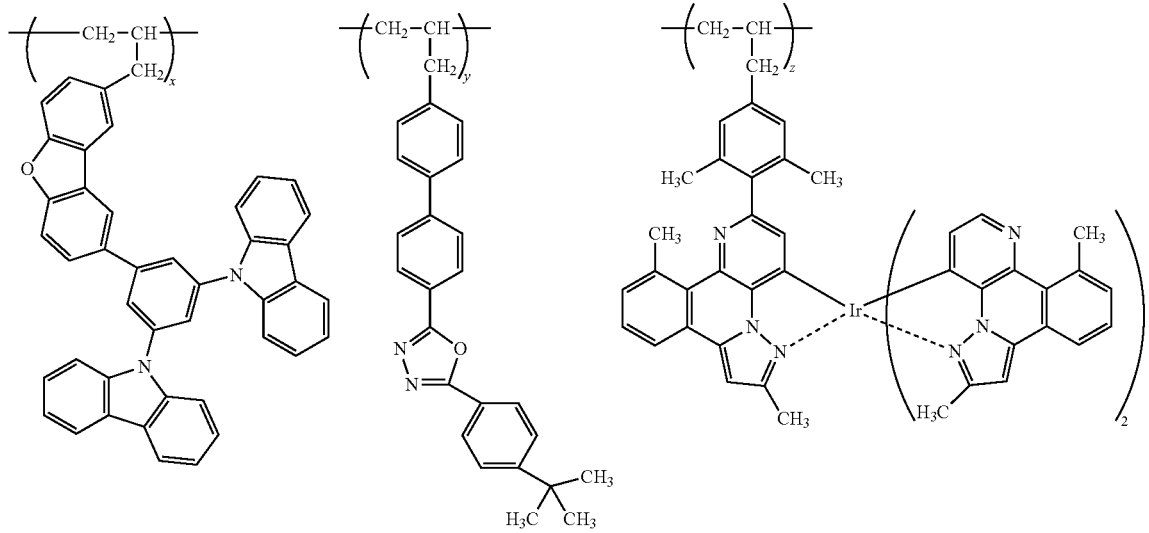
x:y:z = 80:10:10
random co-polymer
P-229
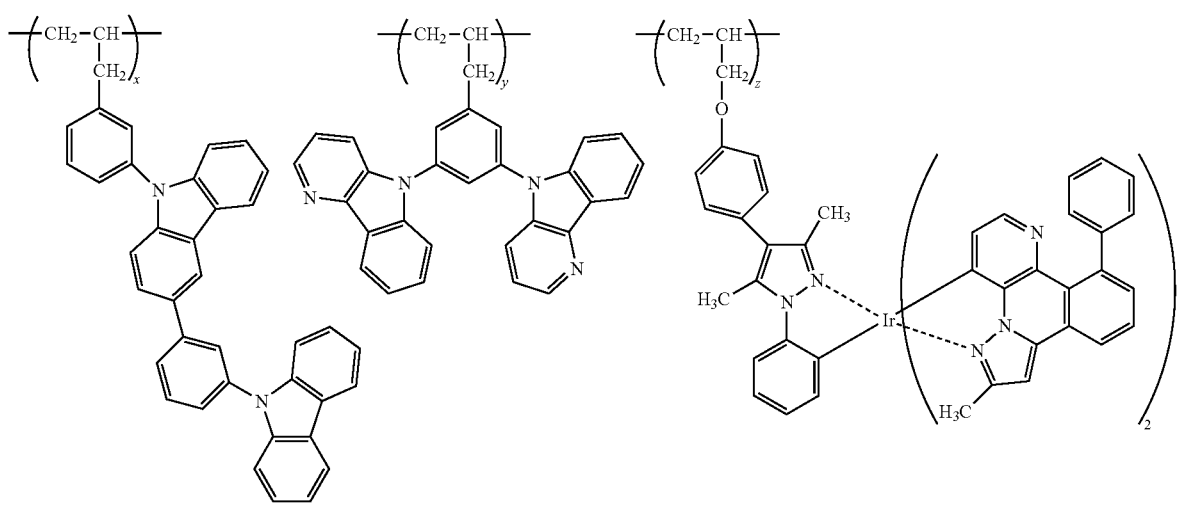
x:y:z = 80:10:10
random co-polymer
P-230
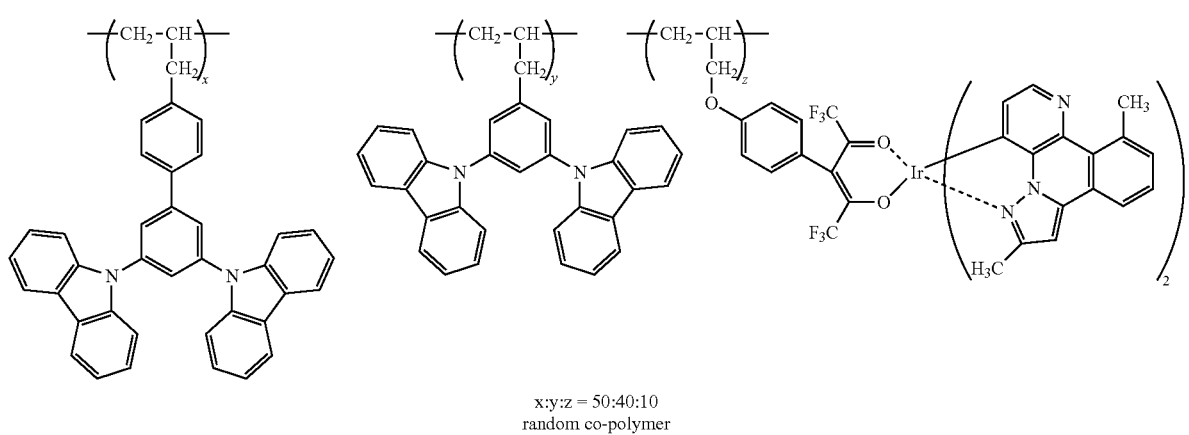
x:y:z = 50:40:10
random co-polymer -continued
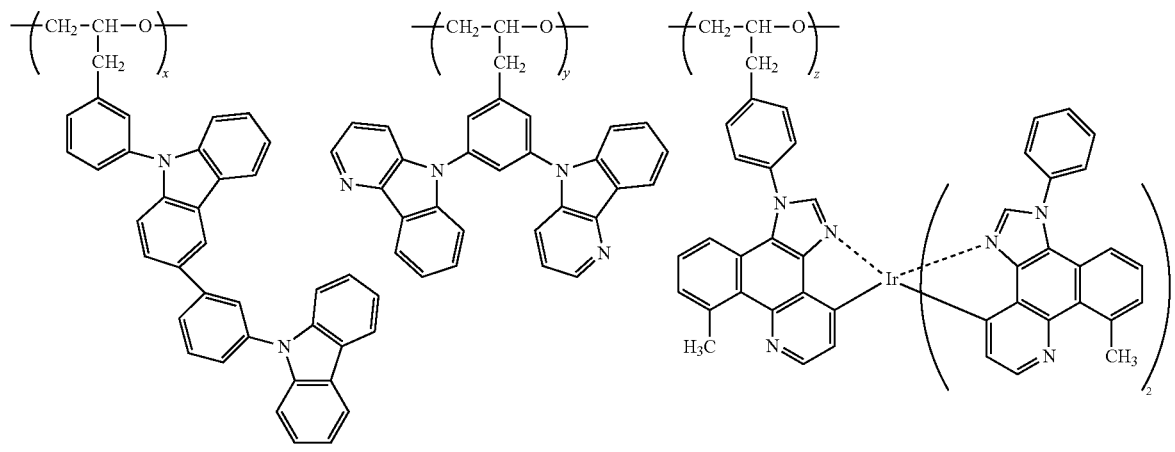
P-231
x:y:z = 80:10:10
random co-polymer
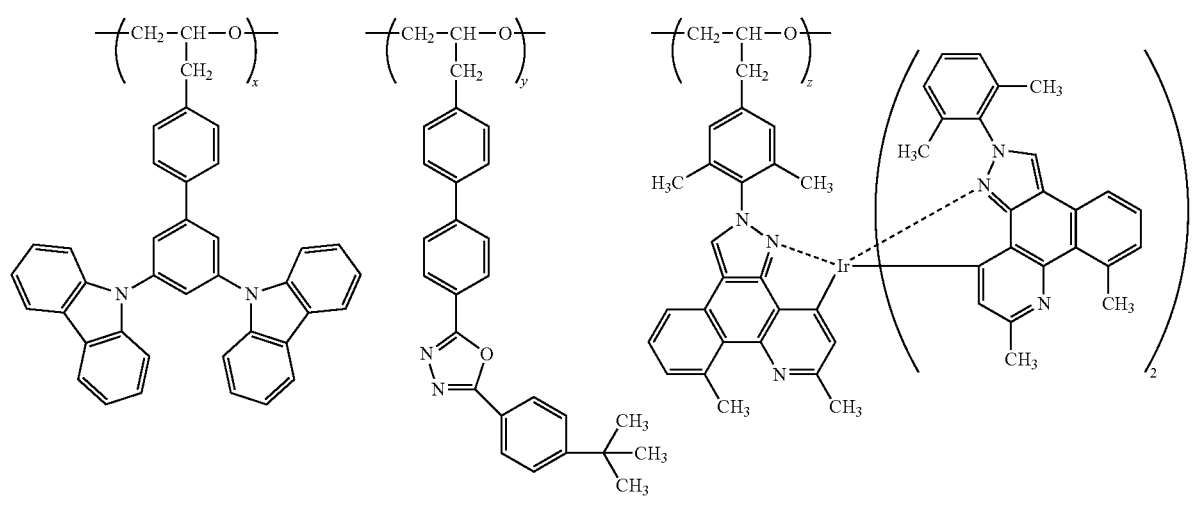
P-232
x:y:z = 80:10:10
random co-polymer
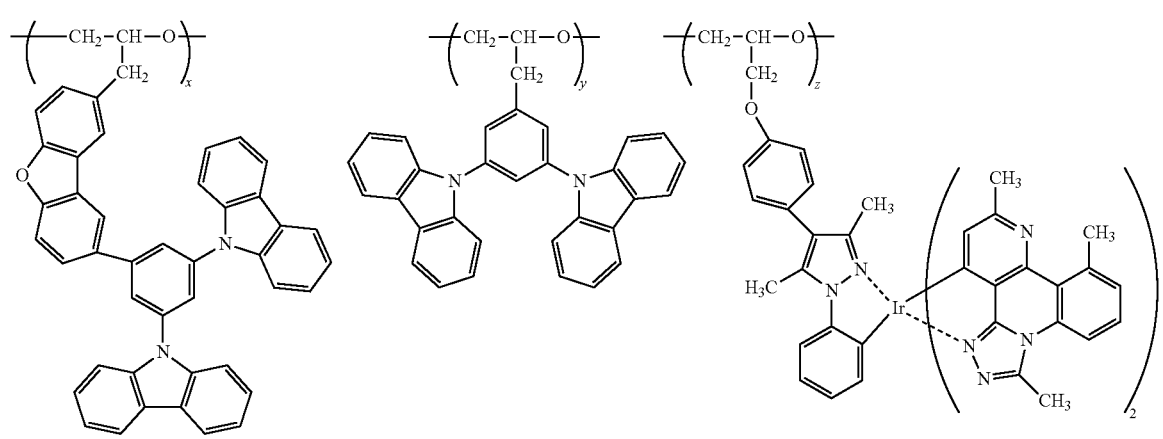
P-233
x:y:z: = 80:10:10
random co-polymer P-234
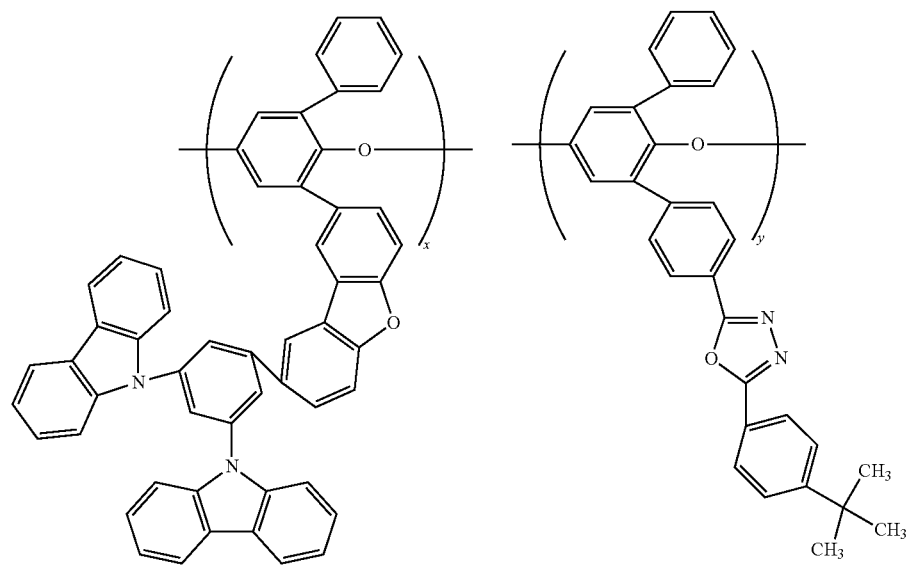
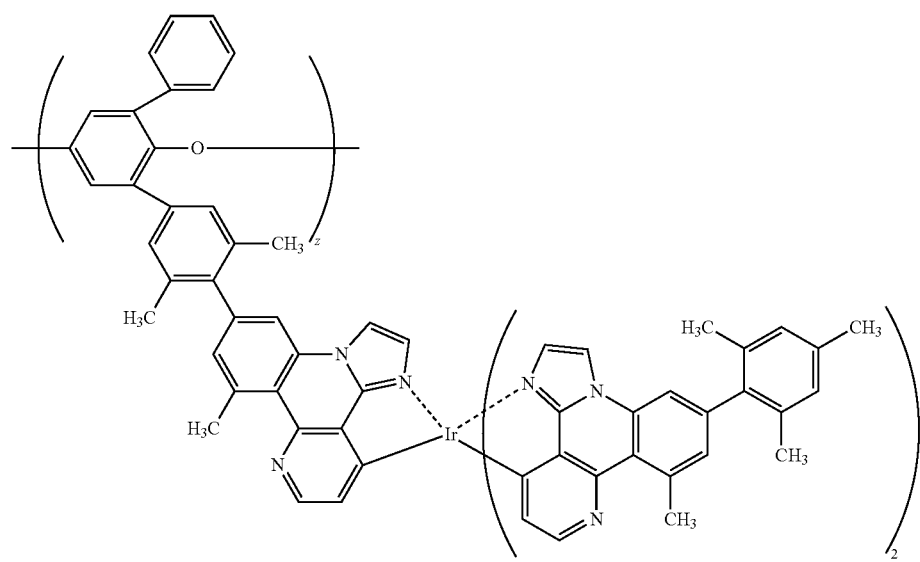
x:y:z = 80:10:10
random co-polymer P-235
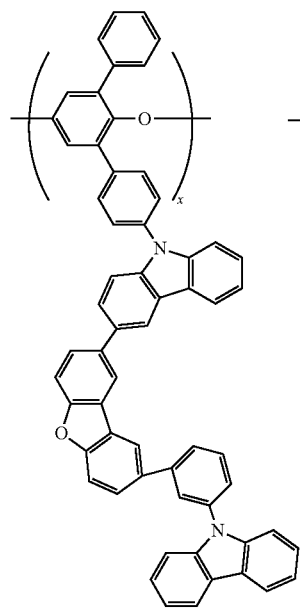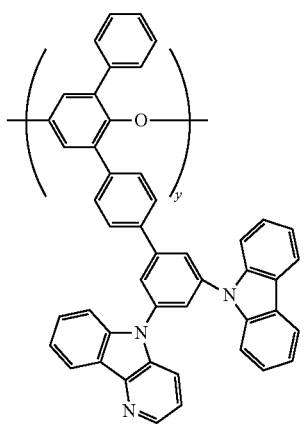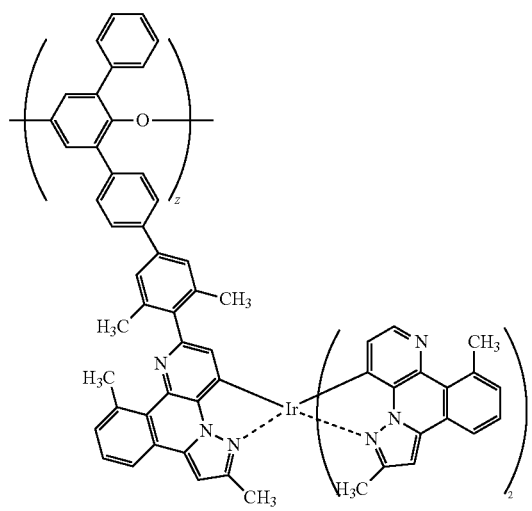
x:y:z = 80:10:10
random co-polymer
P-236
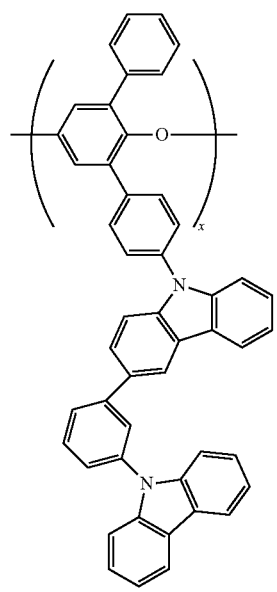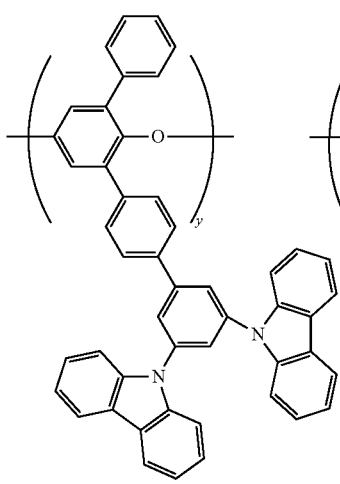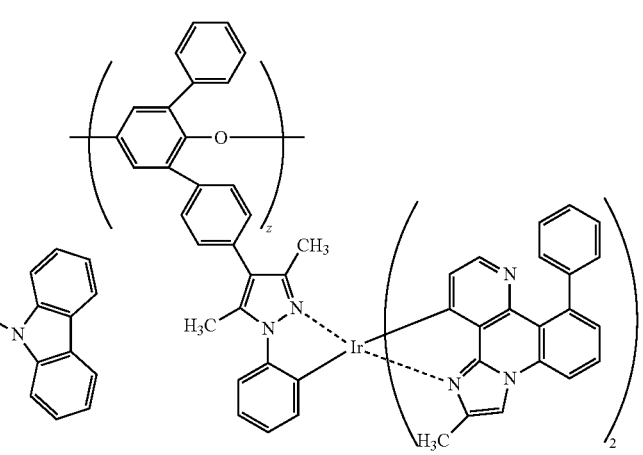
x:y:z = 60:30:10
random co-polymer -continued
P-301
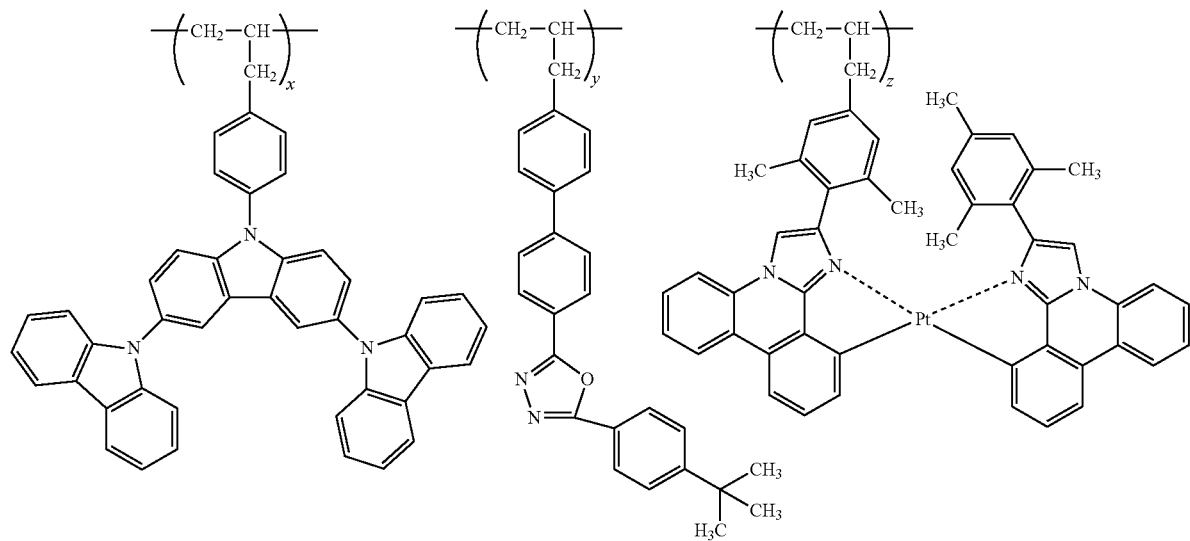
x:y:z = 80:10:10
random co-polymer
P-302
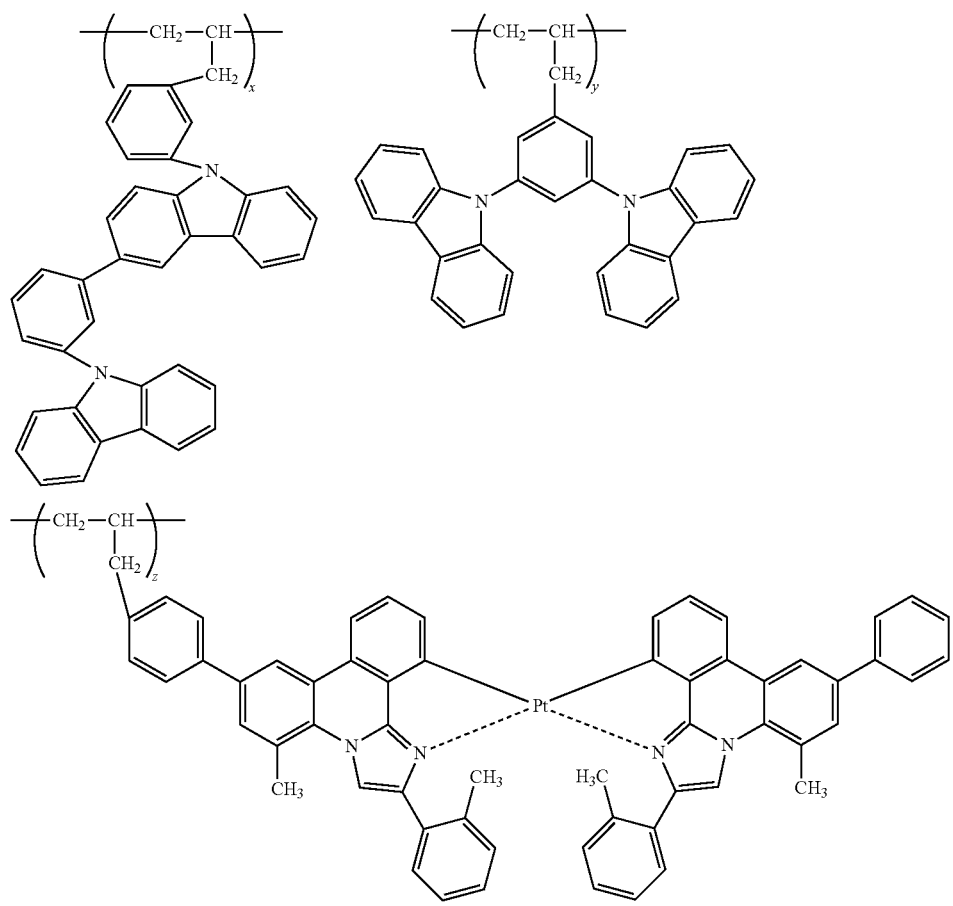
x:y:z = 70:20:10
random co-polymer -continued
P-303
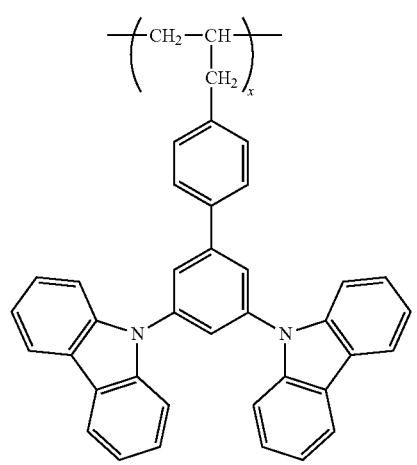
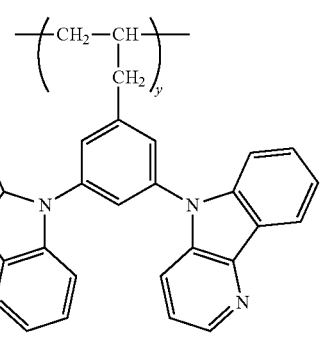
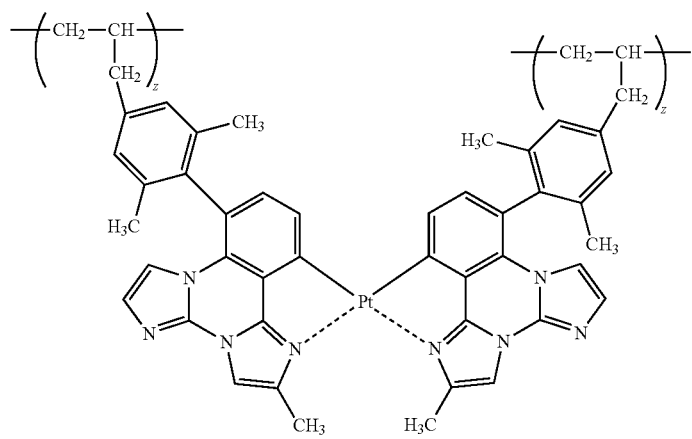
x:y:z = 80:10:10
random co-polymer
P-304
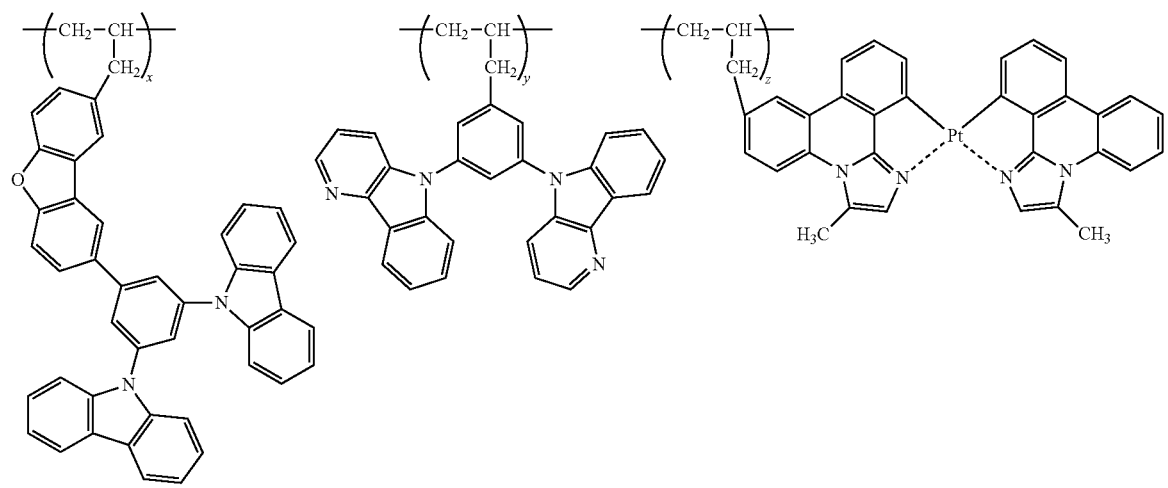
x:y:z = 80:10:10
random co-polymer -continued
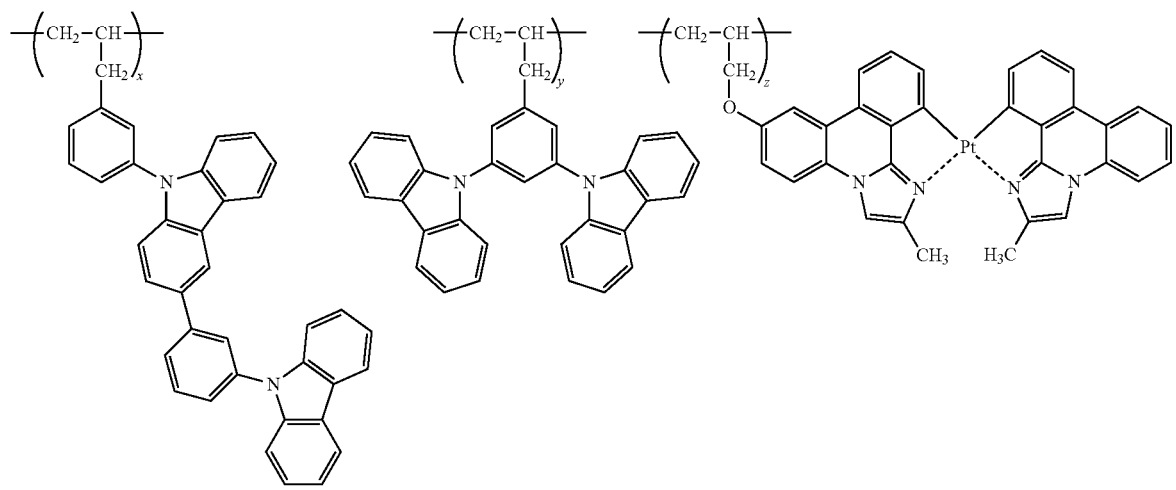
P-305
x:y:z = 50:40:10
random co-polymer
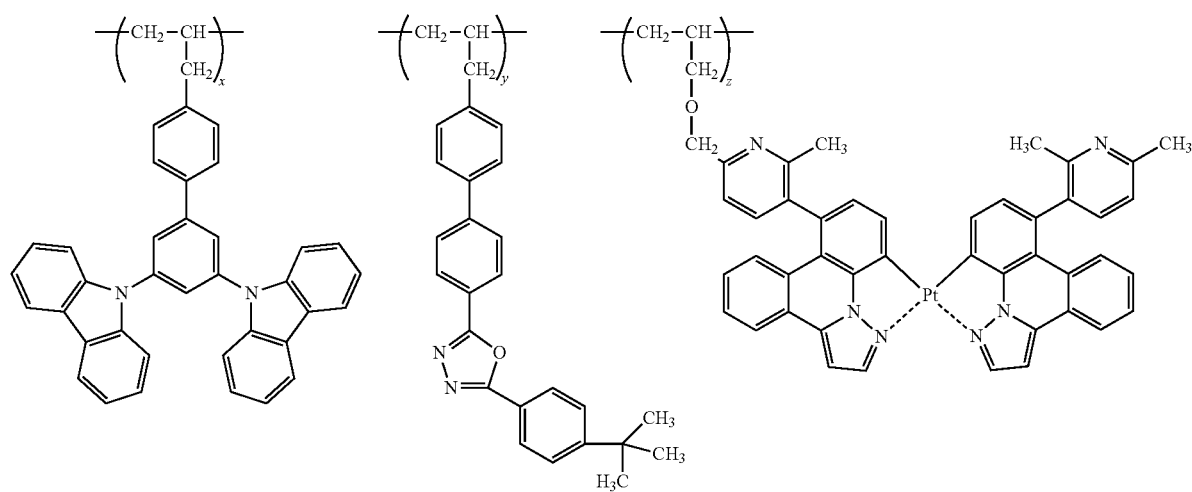
P-306
x:y:z = 80:10:10
random co-polymer -continued
P-307
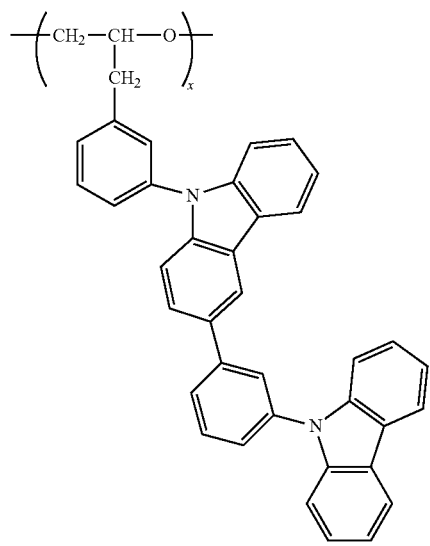
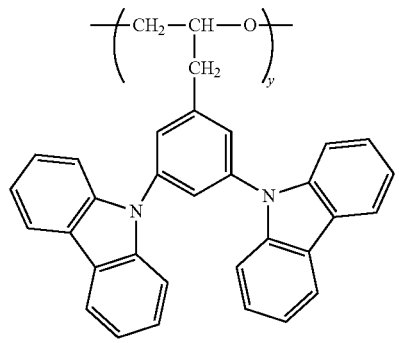
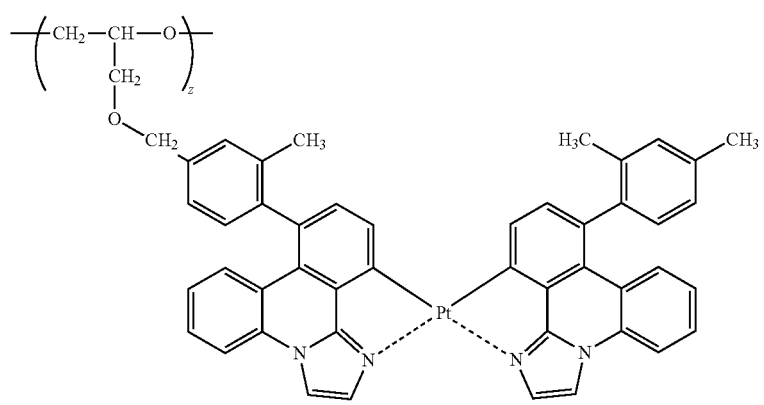
x:y:z = 80:10:10
random co-polymer
P-308
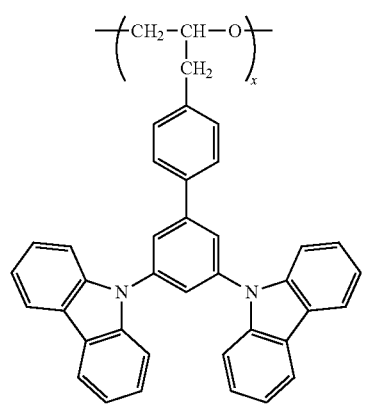
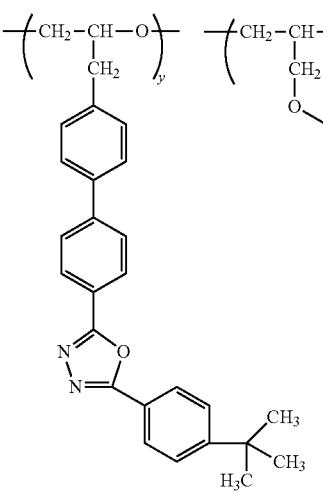
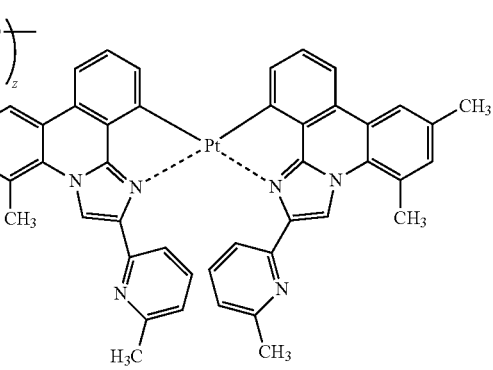
x:y:z = 80:10:10
random co-polymer -continued
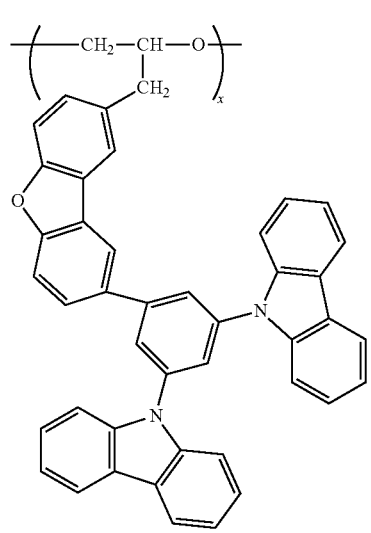
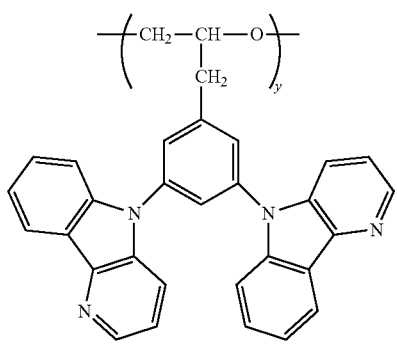
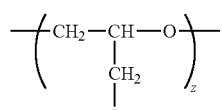
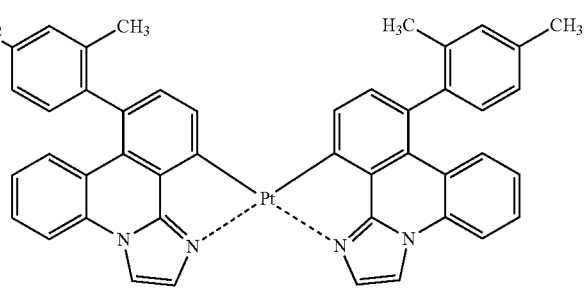
x:y:z = 80:10:10
random co-polymer
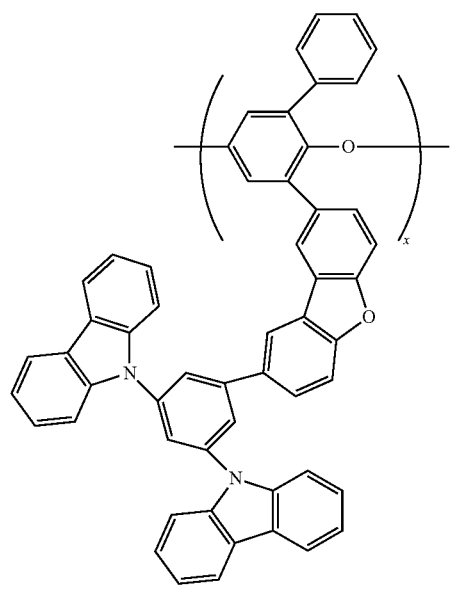
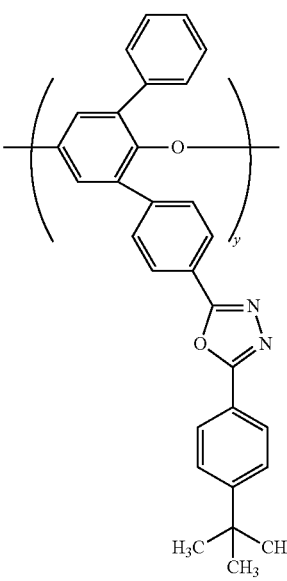
P-309
P-310

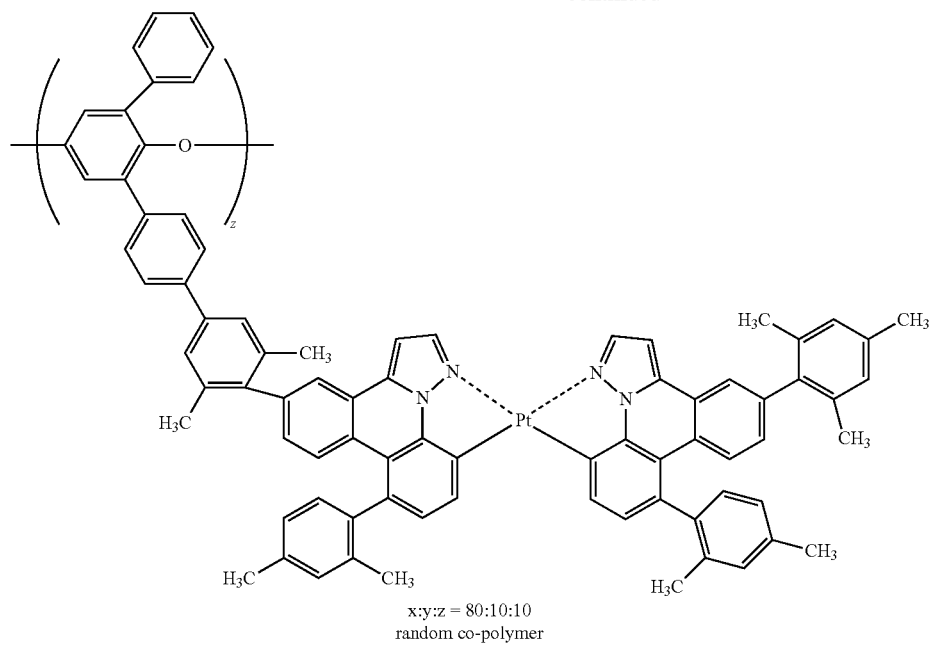
x:y:z = 80:10:10
random co-polymer
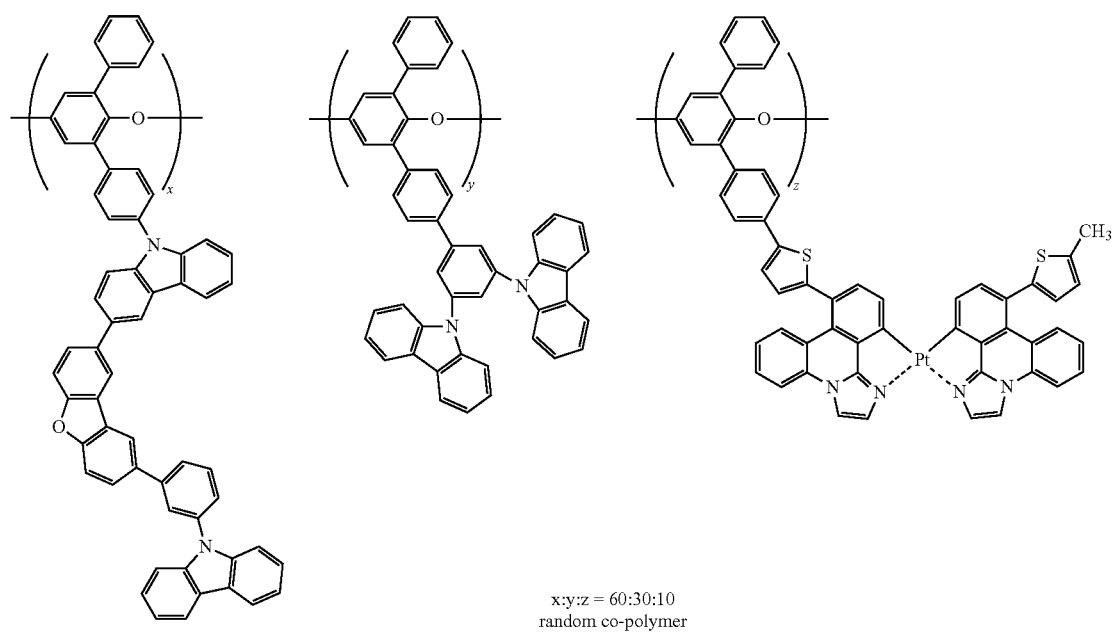
x:y:z = 60:30:10
random co-polymer
P-311

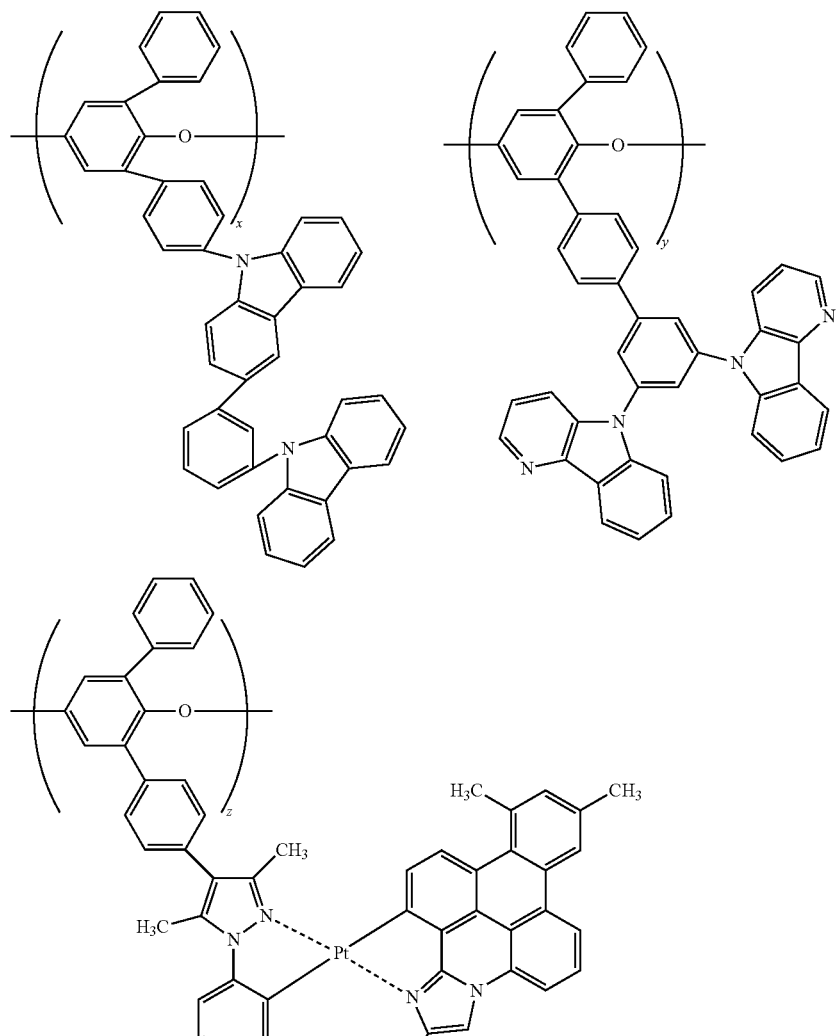
P-312
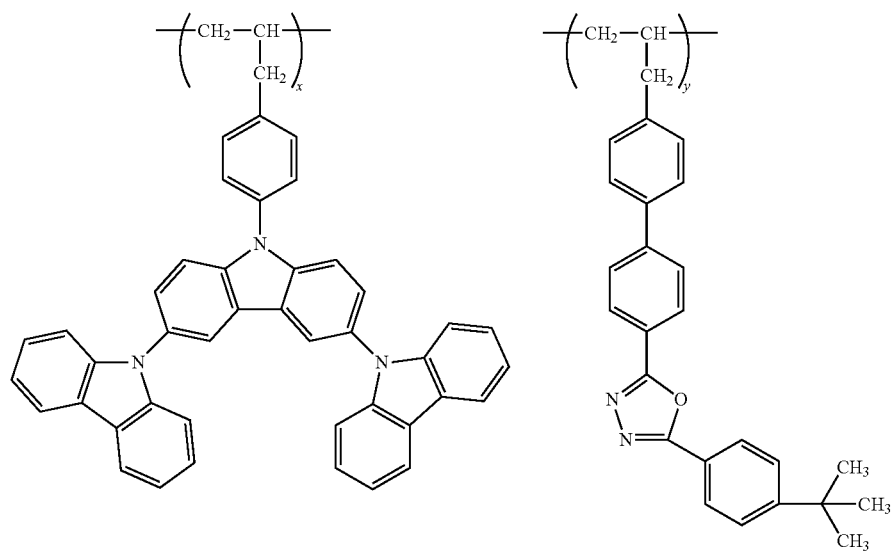
P-313

-continued
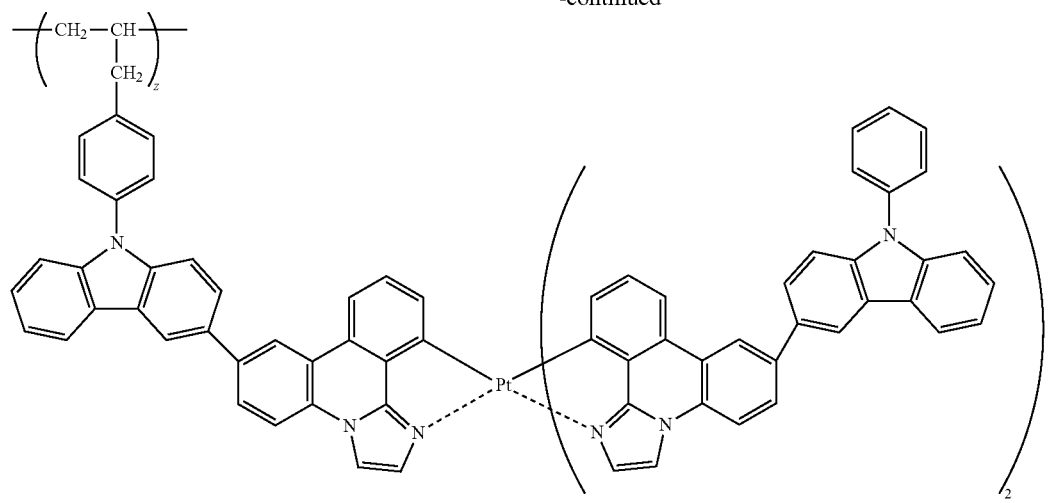
x:y:z = 70:20:10
random co-polymer
P-314
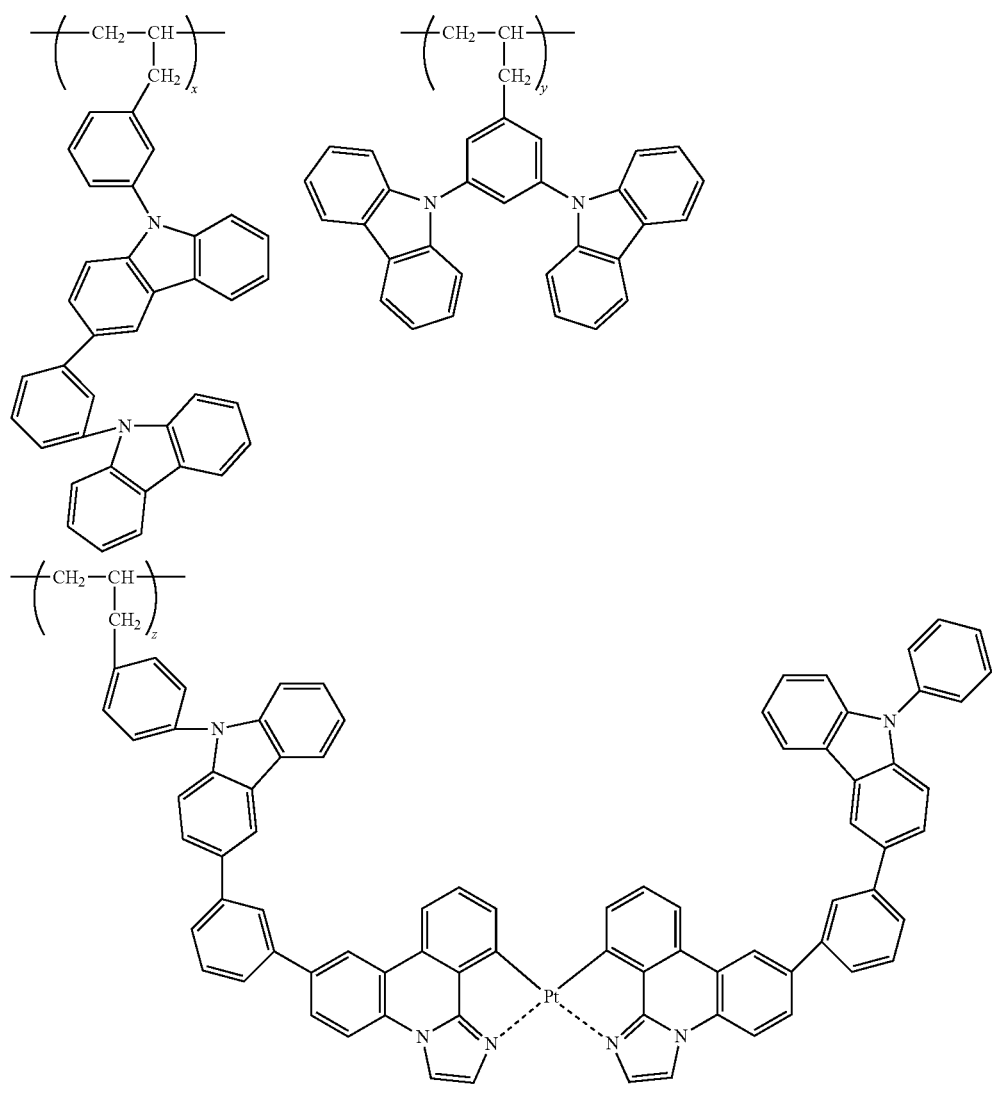
x:y:z = 50:40:10
random co-polymer -continued
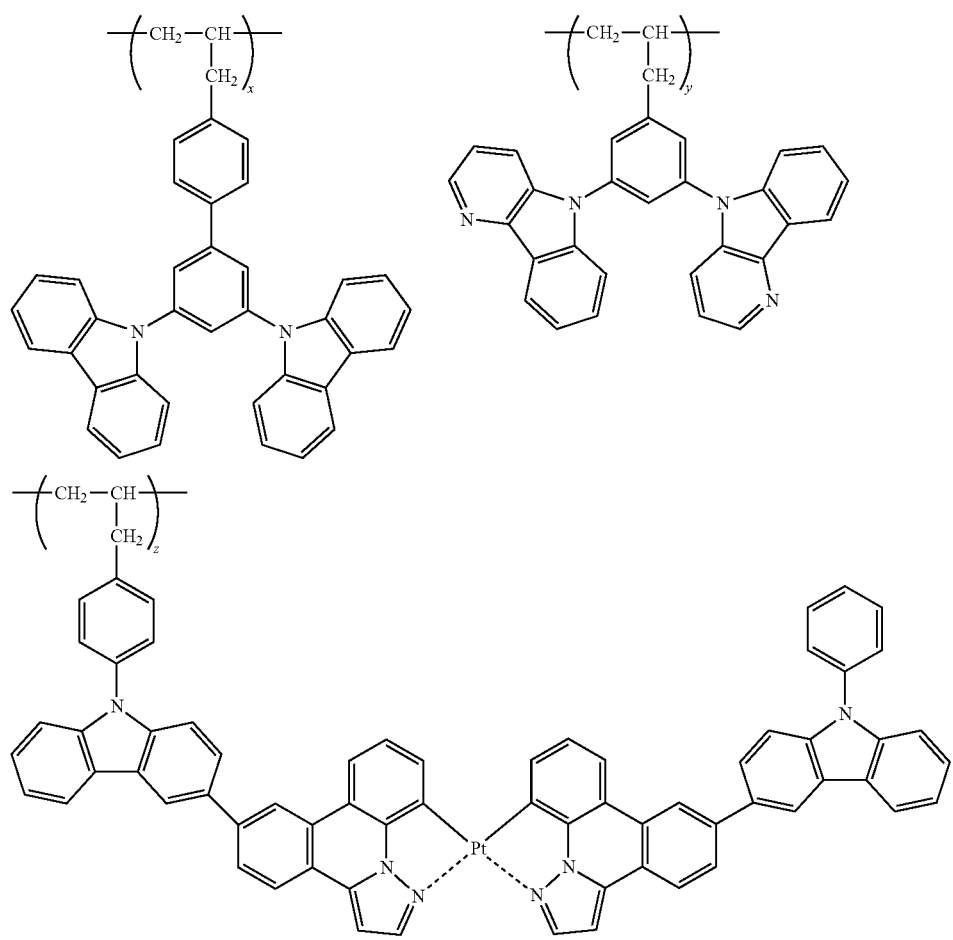
x:y:z = 70:20:10
random co-polymer
P-315
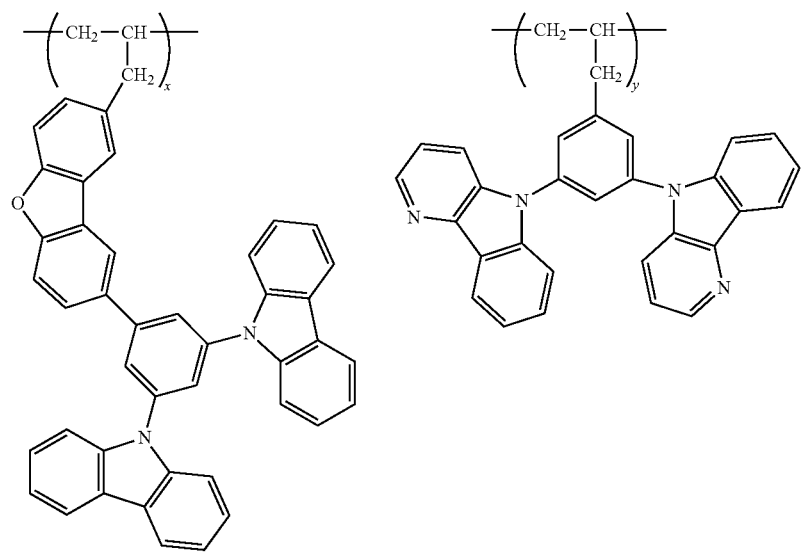
P-316

-continued
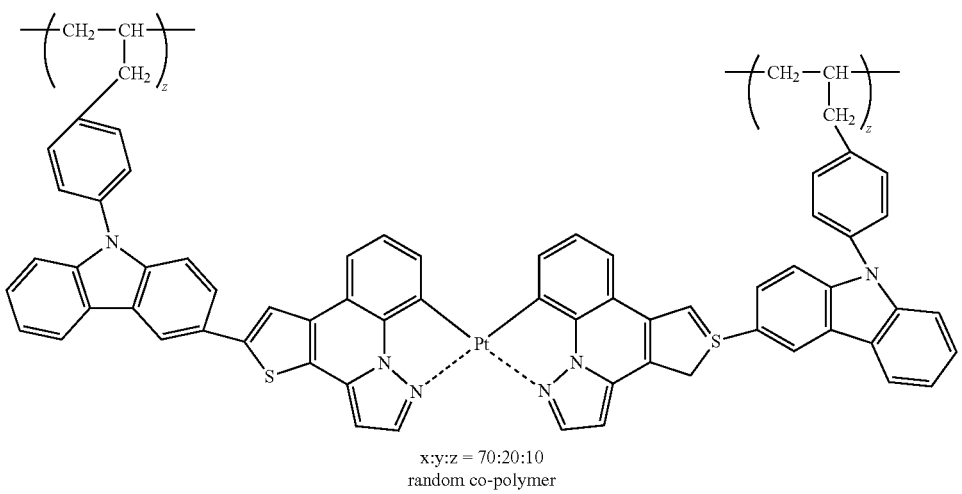
x:y:z = 70:20:10
random co-polymer
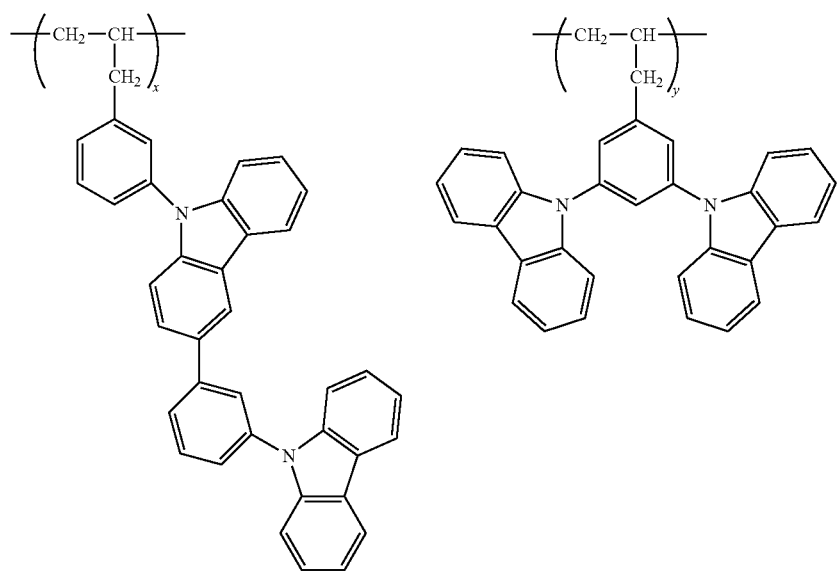
P-317
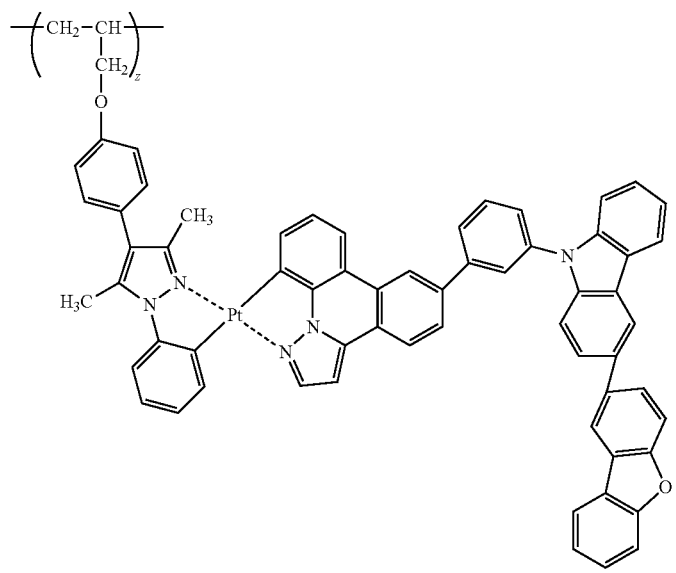
x:y:z = 50:40:10
random co-polymer -continued
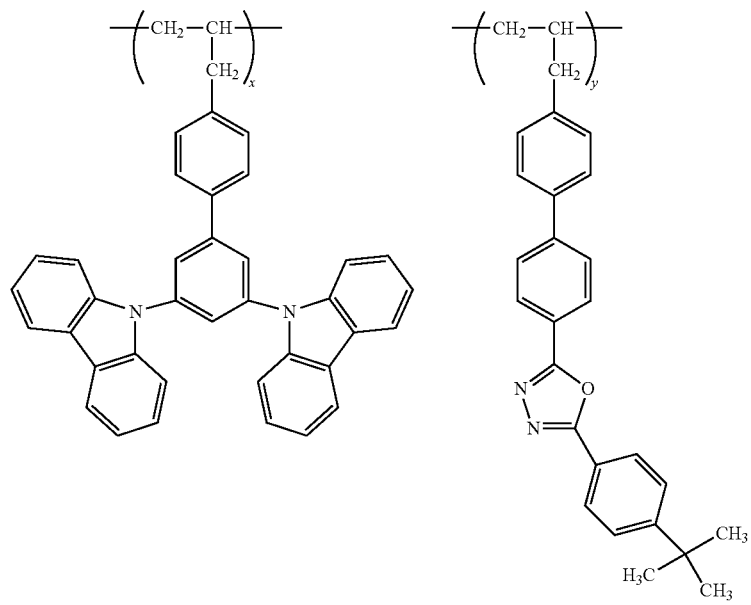
P-318
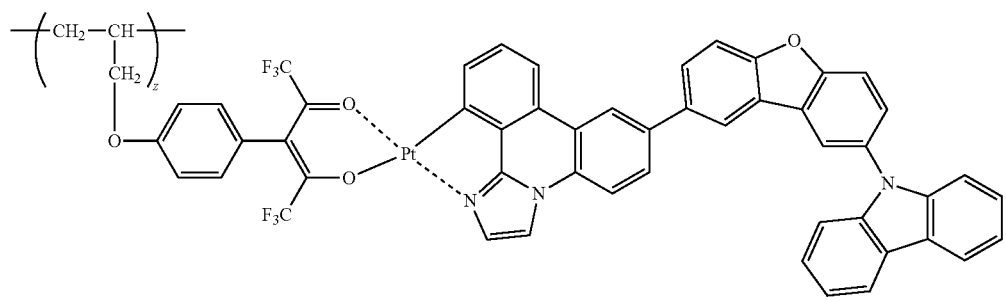
x:y:z = 70:20:10
random co-polymer
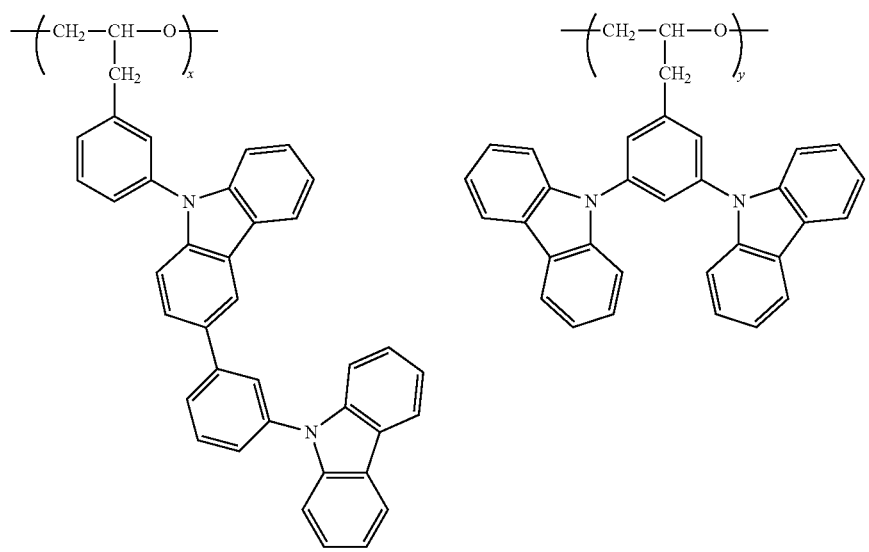
P-319

-continued
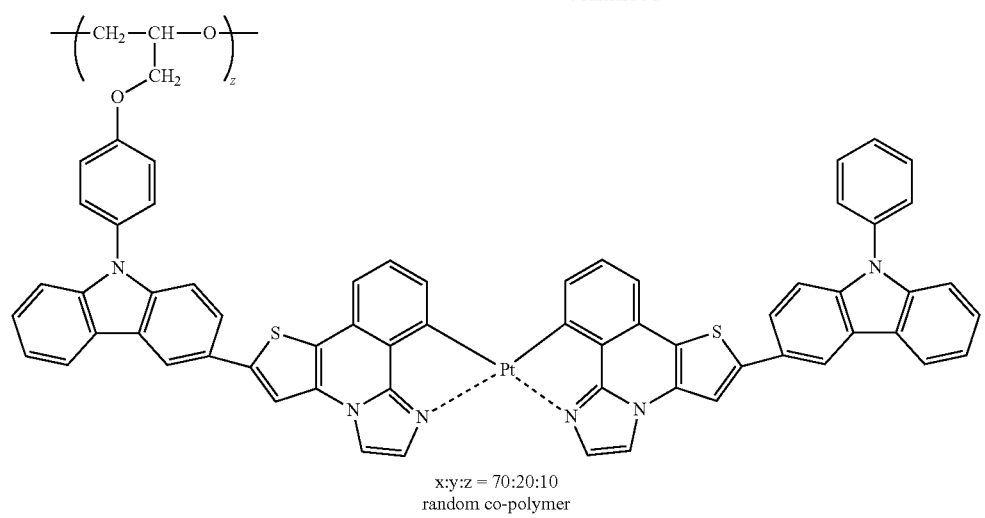
x:y:z = 70:20:10
random co-polymer
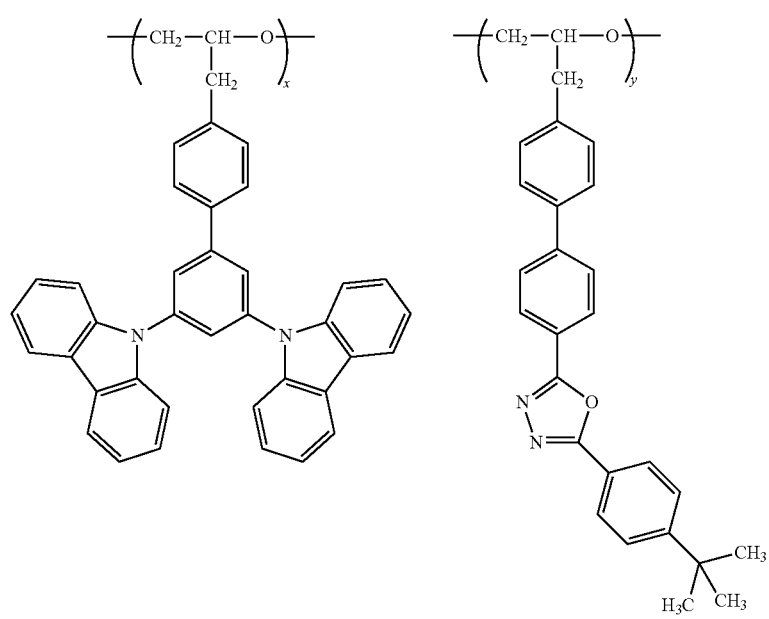
P-320

-continued
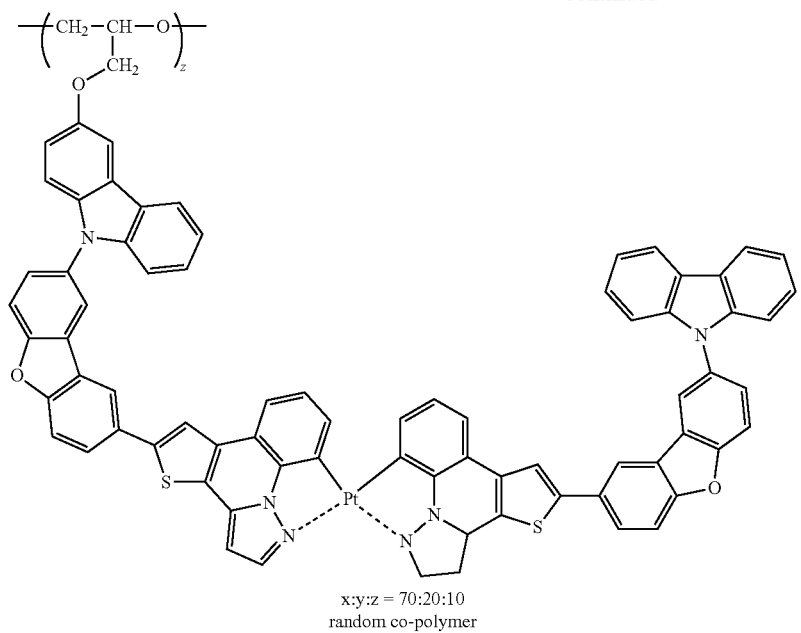
x:y:z = 70:20:10
random co-polymer
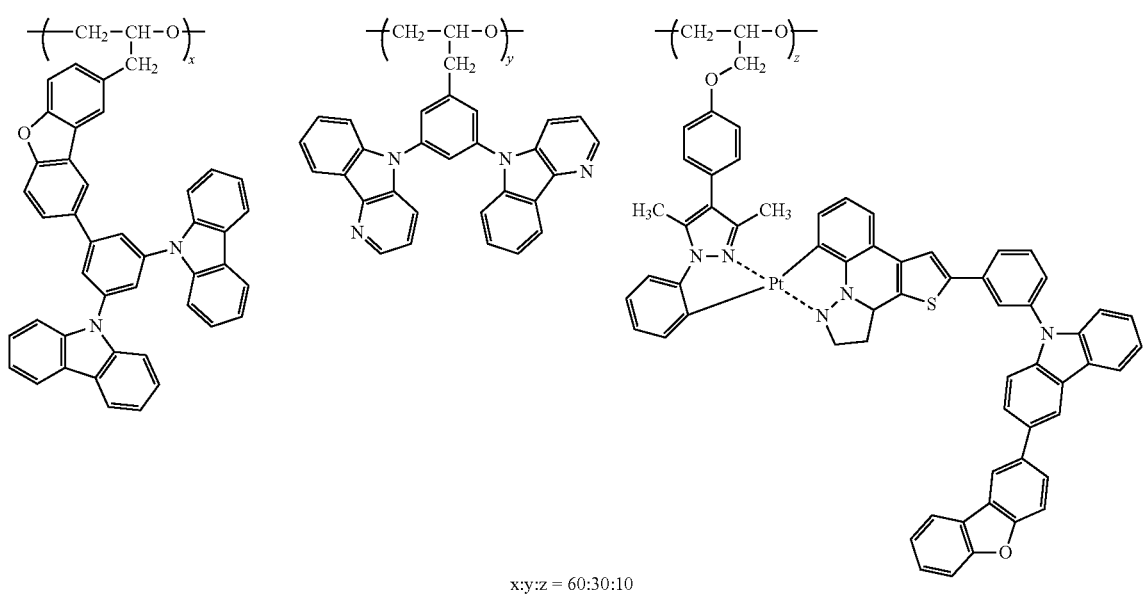
x:y:z = 60:30:10
random co-polymer
P-321

P-322
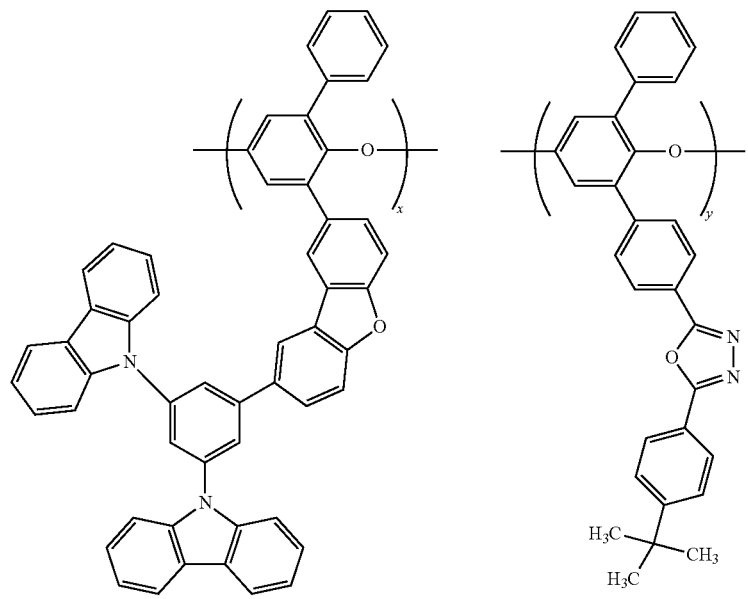
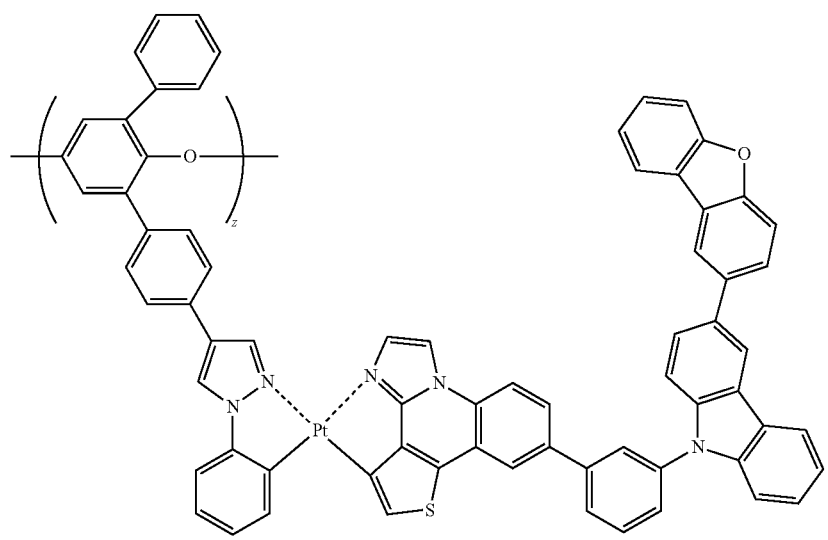
x:y:z = 70:20:10
random co-polymer

-continued
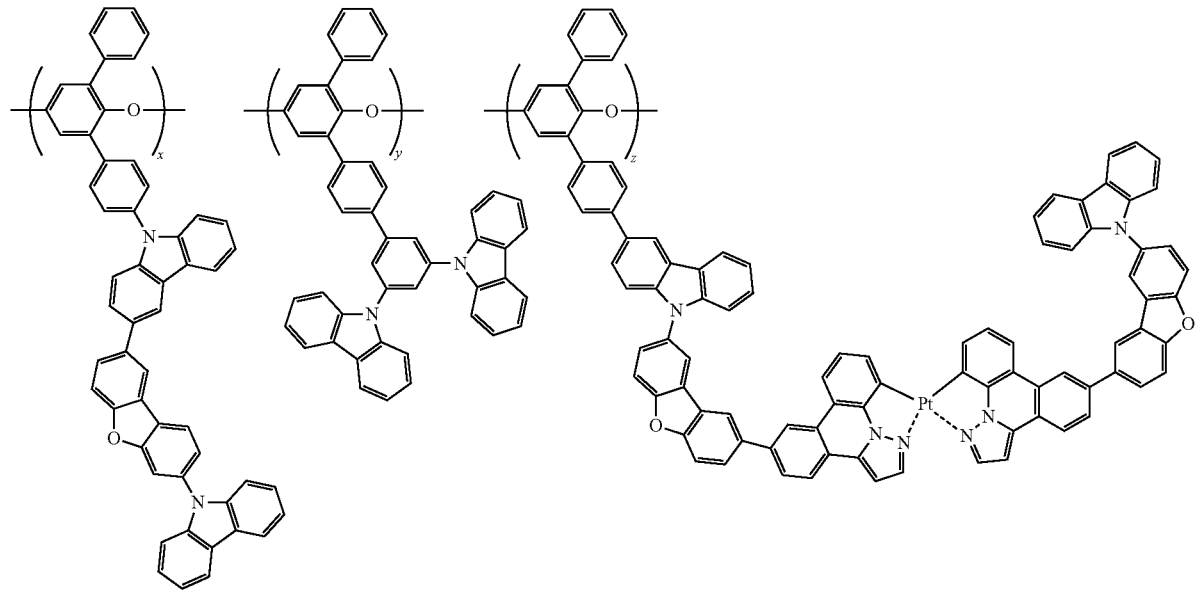
P-323
x:y:z = 70:20:10
random co-polymer
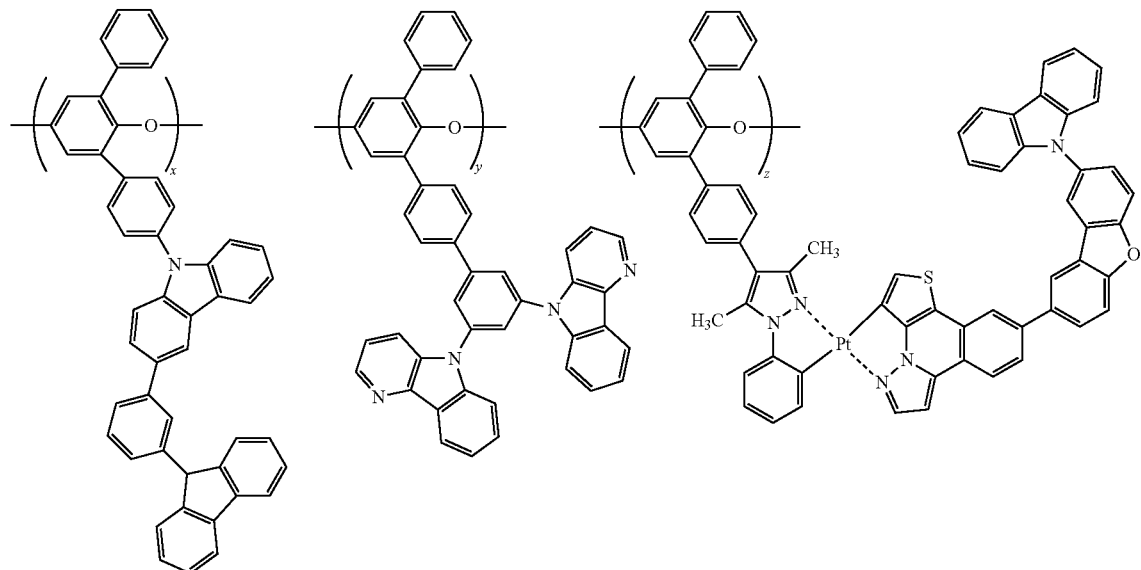
P-324
x:y:z = 60:30:10
random co-polymer -continued
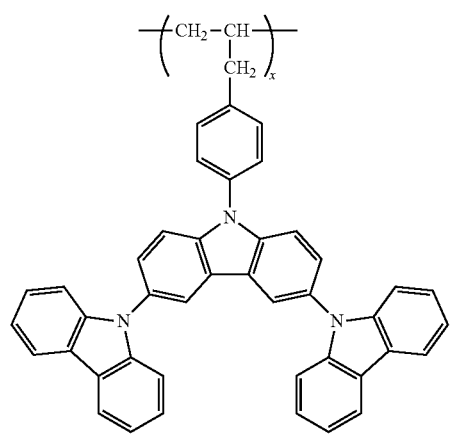
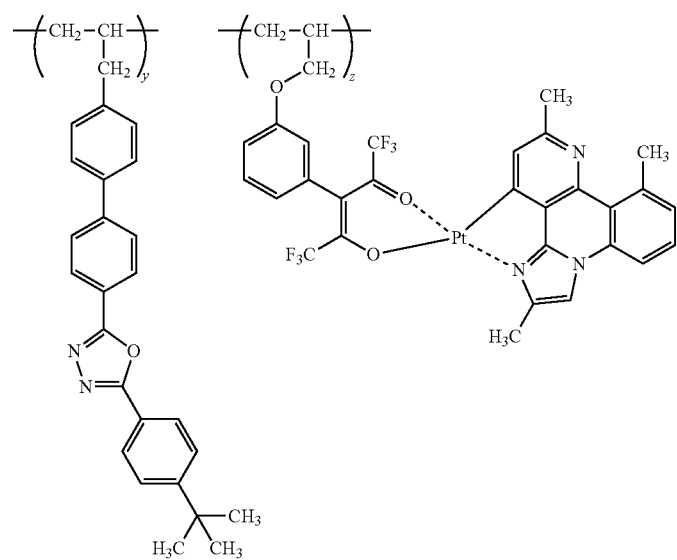
P-325
x:y:z = 80:10:10
random co-polymer
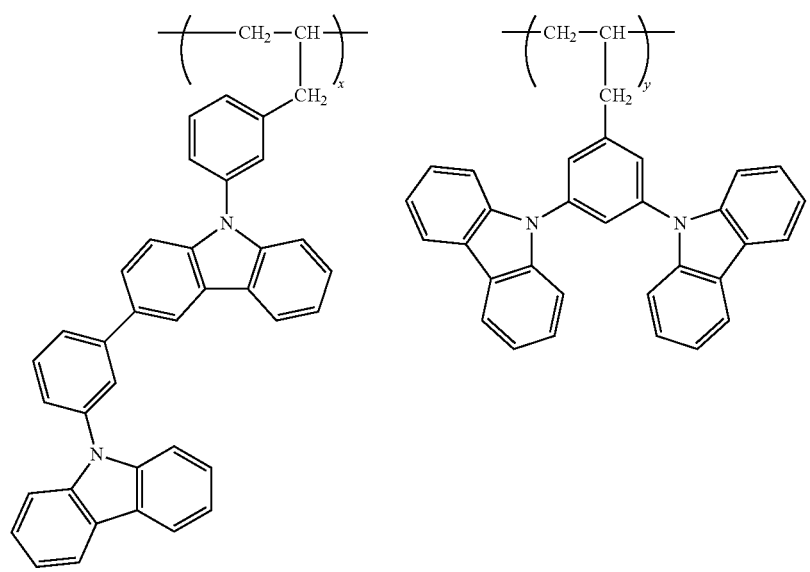
P-326

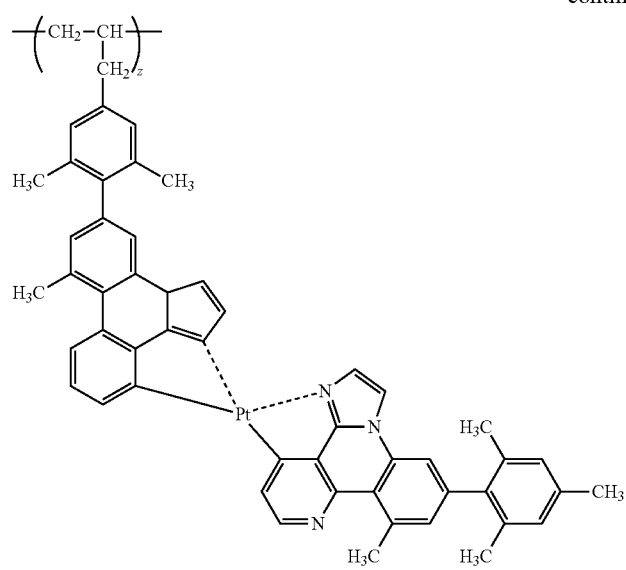
P-327
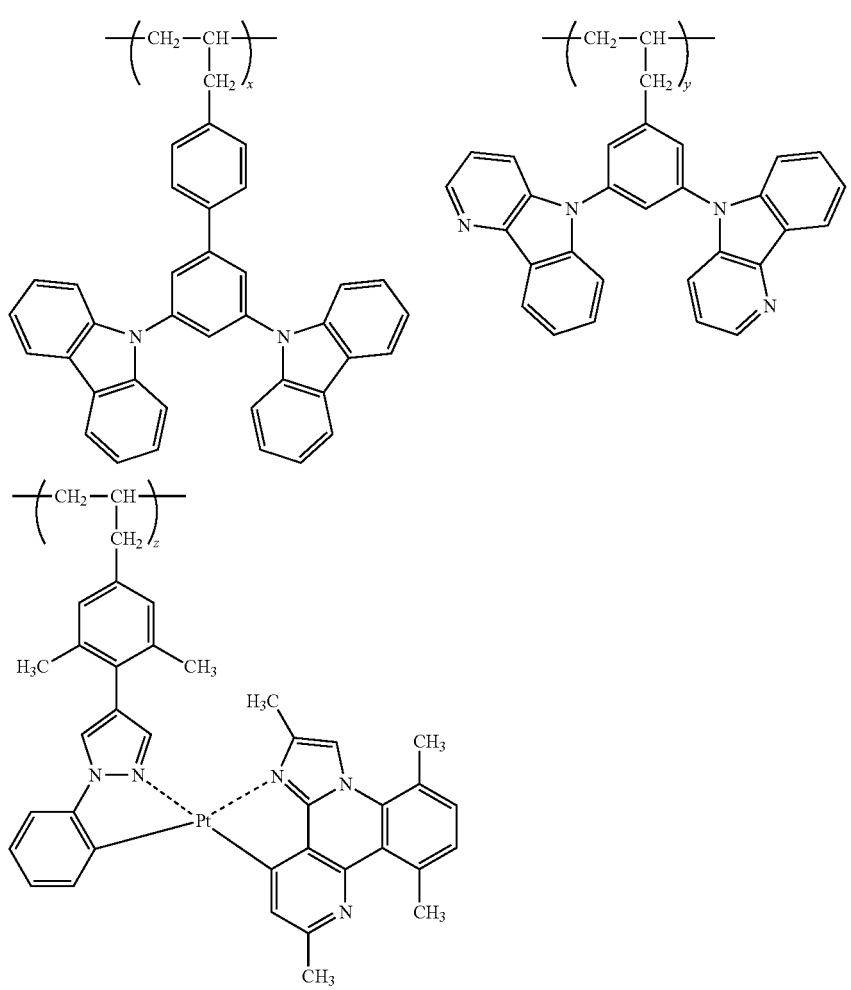

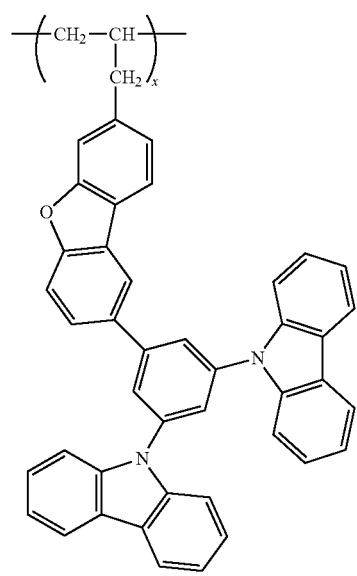
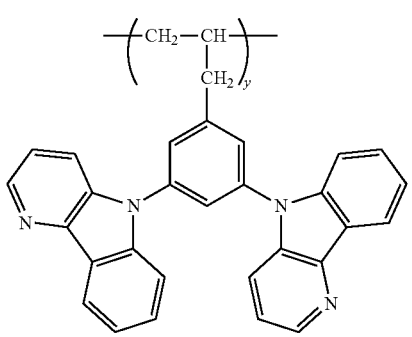
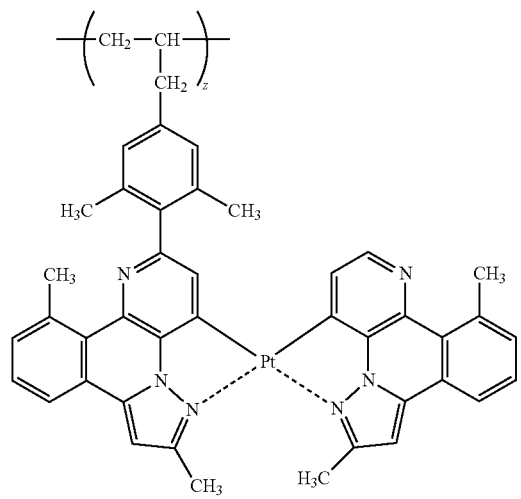
x:y:z = 80:10:10
random co-polymer
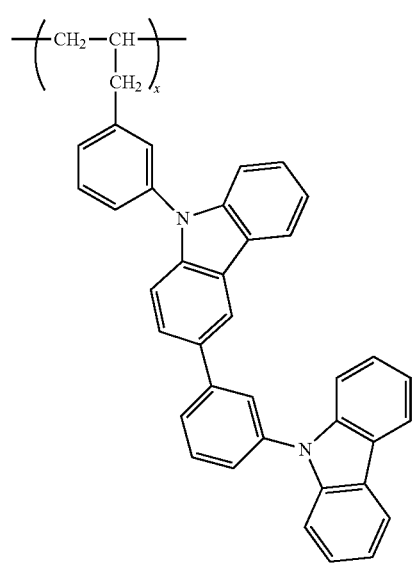
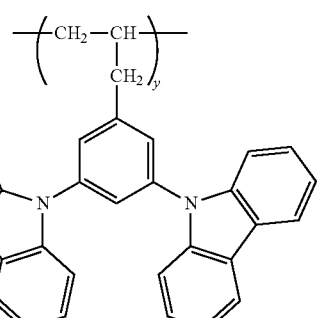
P-328
P-329

-continued
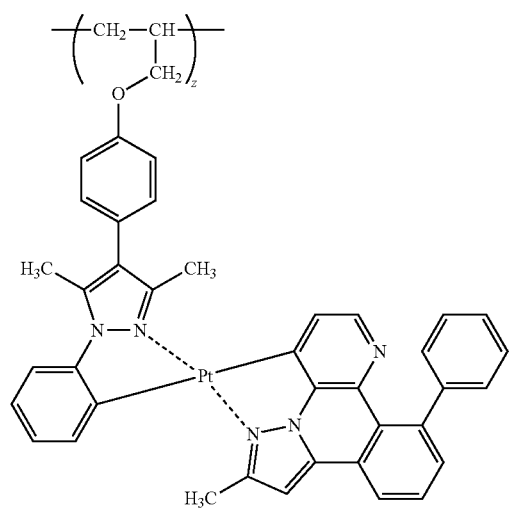
x:y:z = 70:20:10
random co-polymer
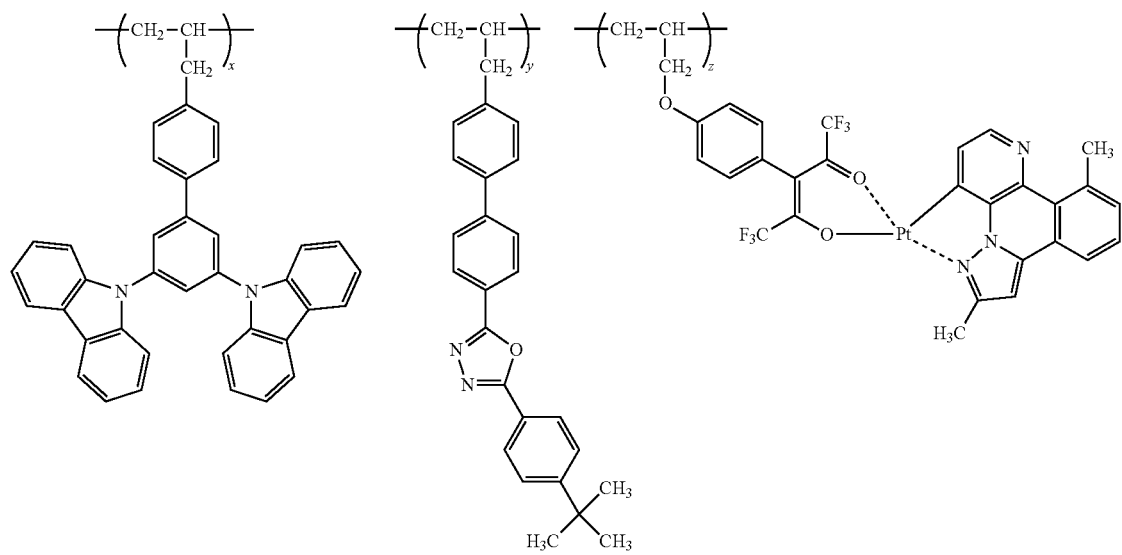
x:y:z = 80:10:10
random co-polymer
P-330

-continued
P-331
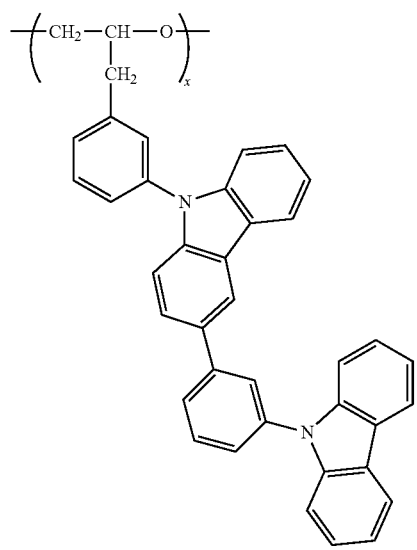
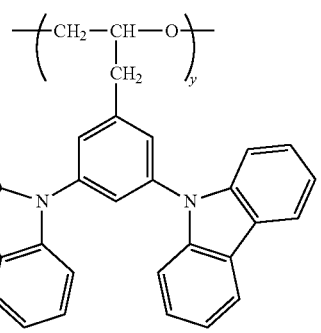
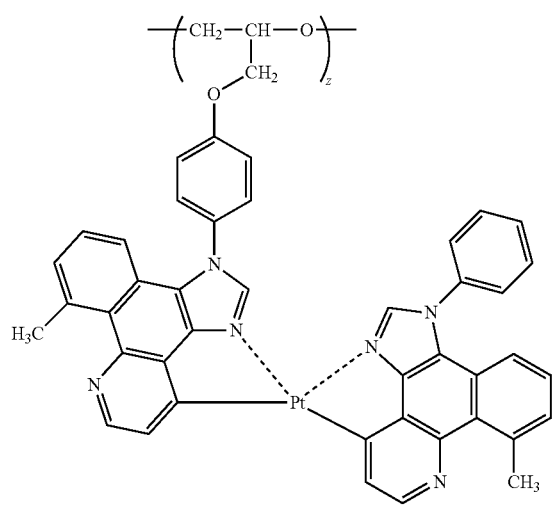
x:y:z = 70:20:10
random co-polymer P-332
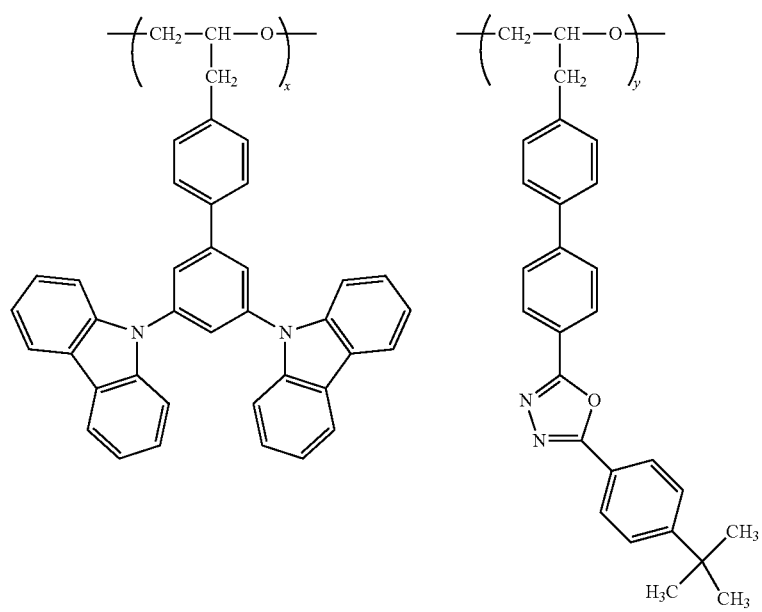
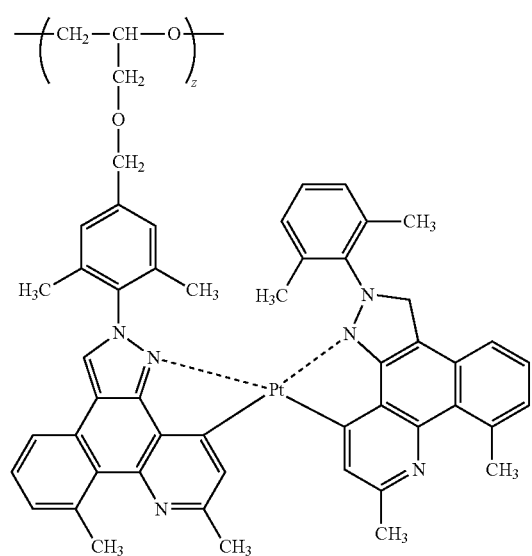
x:y:z = 80:10:10
random co-polymer -continued
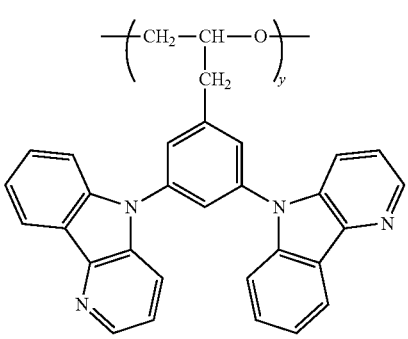
P-333
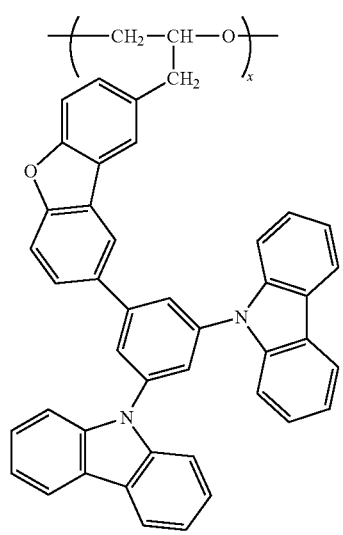
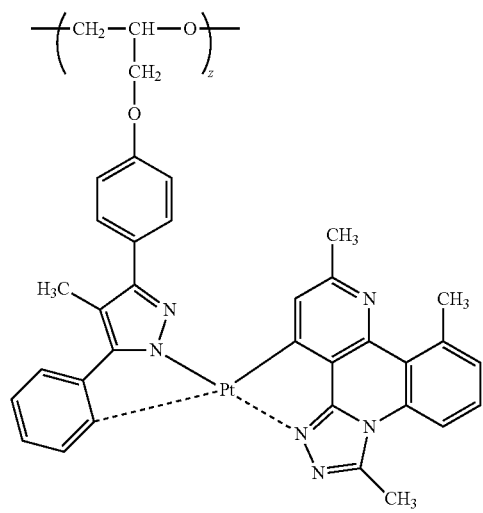
x:y:z = 80:10:10
random co-polymer
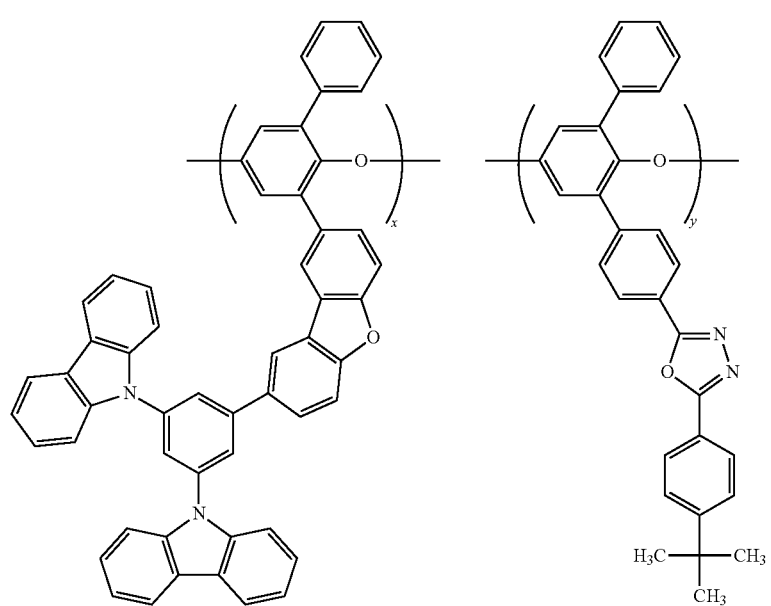
P-334

-continued
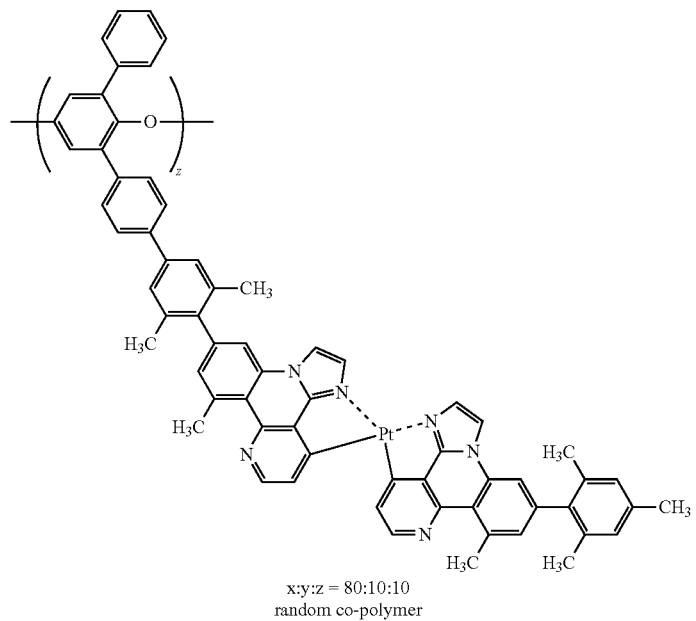
x:y:z = 80:10:10
random co-polymer
P-335
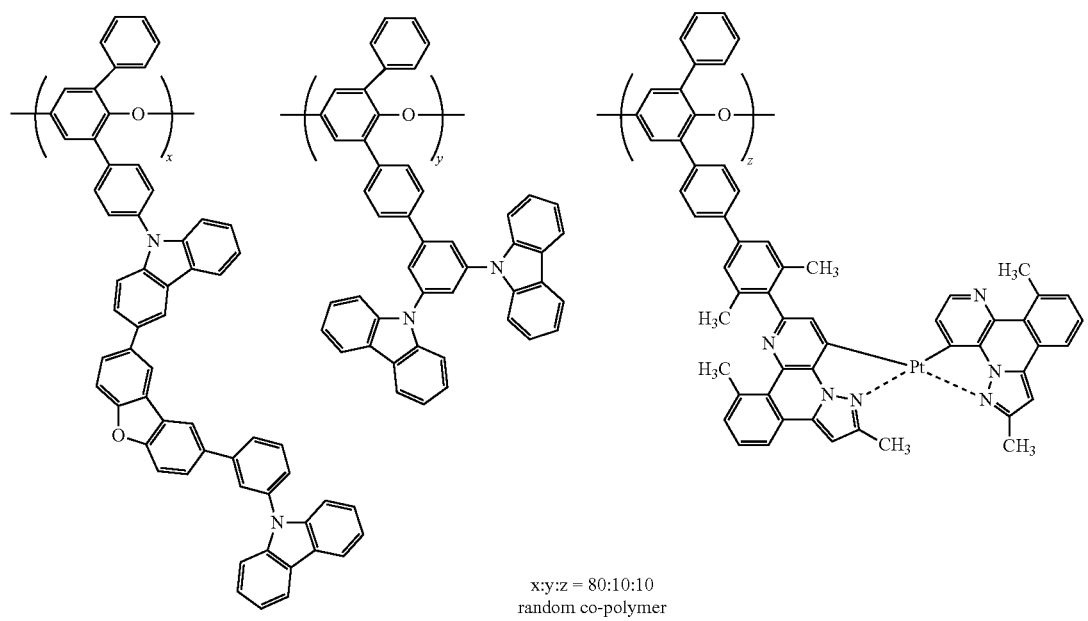
x:y:z = 80:10:10
random co-polymer -continued
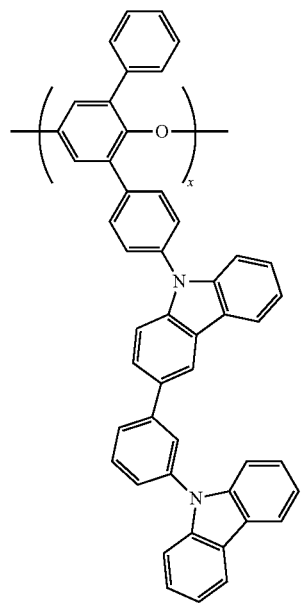 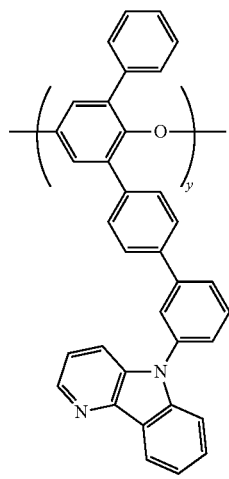 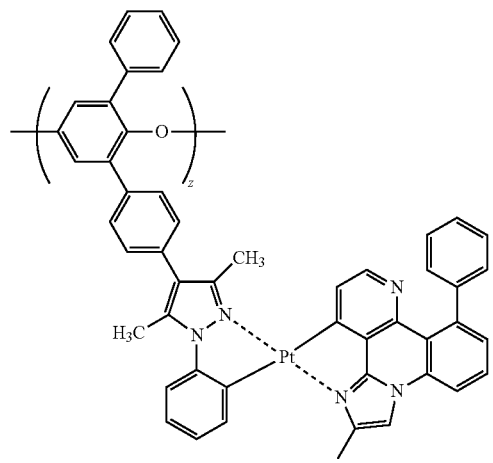
P-336
x:y:z = 80:10:10
random co-polymer
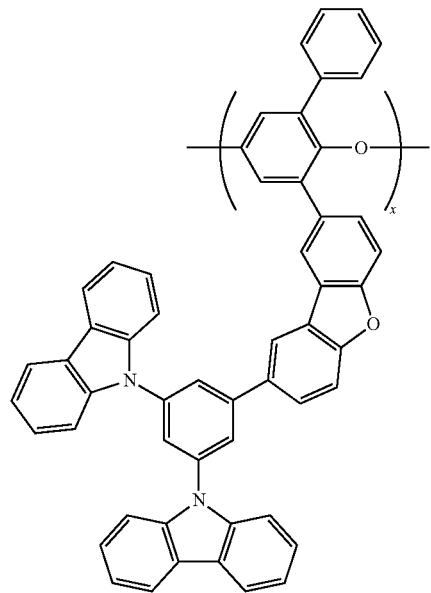 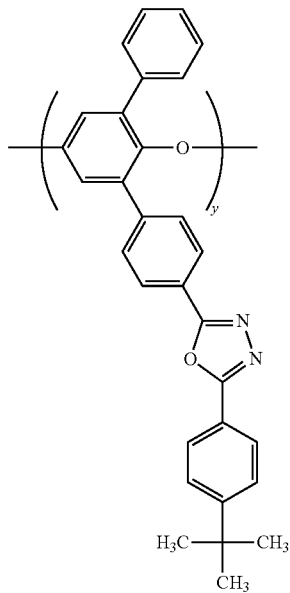
P-337

-continued
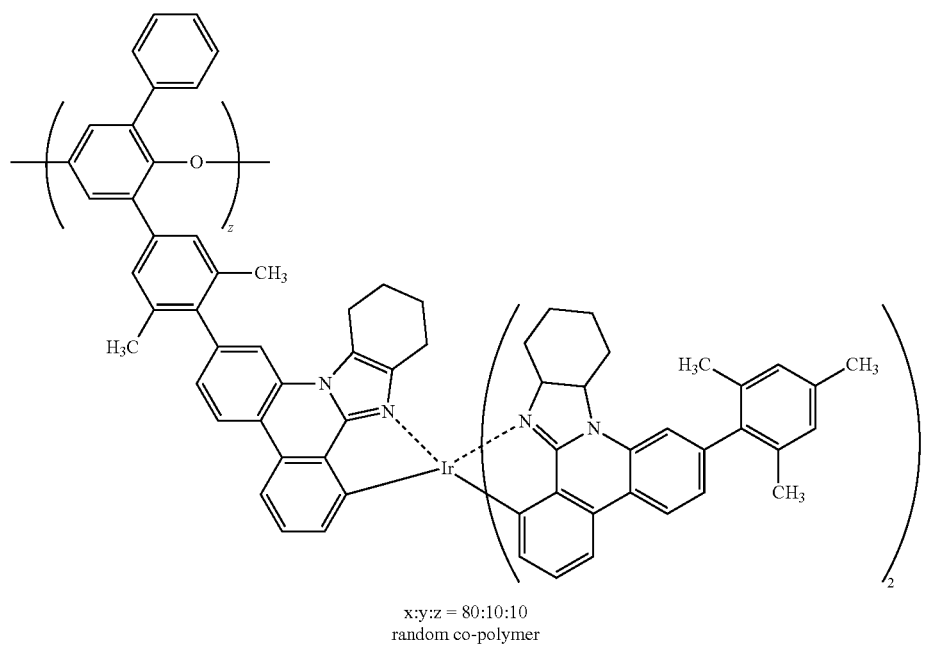
x:y:z = 80:10:10
random co-polymer
P-338
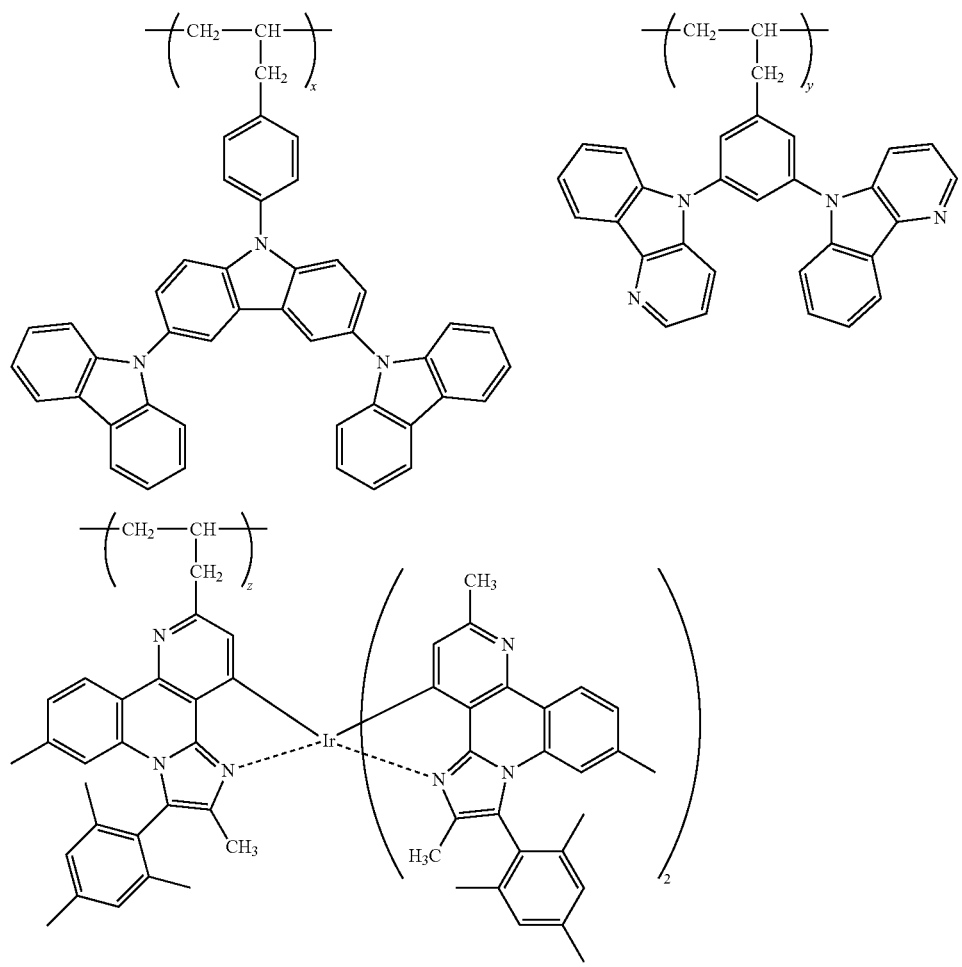
x:y:z = 80:10:10
random co-polymer -continued

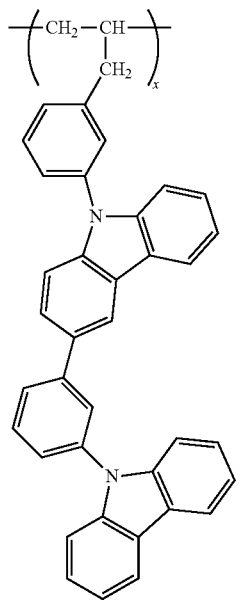 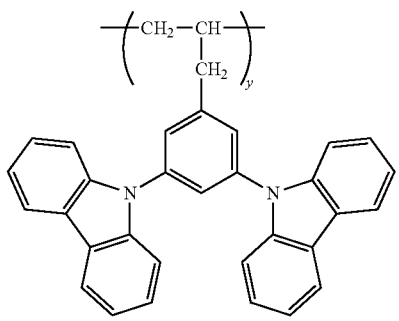

P-339

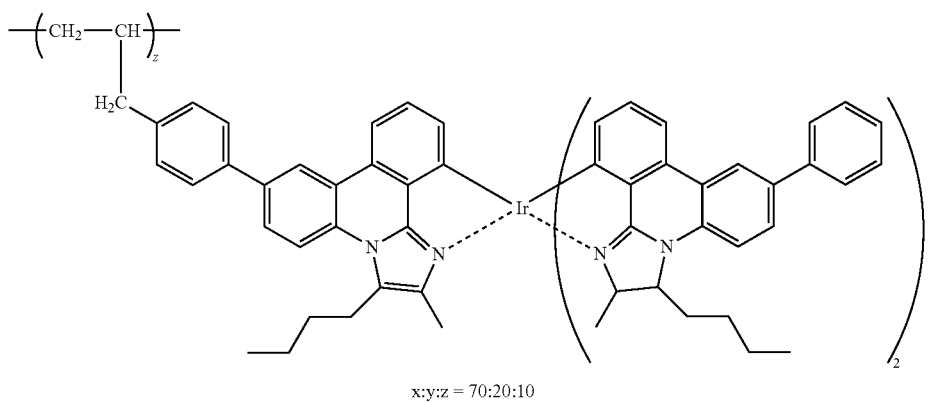

x:y:z = 70:20:10
random co-polymer

Metal complexes according to an organic EL element material of this invention can be synthesized by applying a method described in such as Organic Letter, vol. 3, No. 16, pp. 2579-2581 (2001), Inorganic Chemistry vol. 30, No. 8, pp. 1685-1687 (1991), J. Am. Chem. Soc., vol. 123, p. 4304 (2001), Inorganic Chemistry vol. 40, No. 7, pp. 1704-1711 (2001), Inorganic Chemistry vol. 41, No. 12, pp. 3055-3066 (2002), New Journal of Chemistry, vol. 26, p. 1171 (2002), Organic Letters Vol. 18, No. 3, pp. 415-418 (2006), and reference documents described in these documents.

Examples of metal complexes of the present invention will be described, however, the present invention is not limited to them.

Synthetic Example 1: Preparation of Exemplified Compound A-81

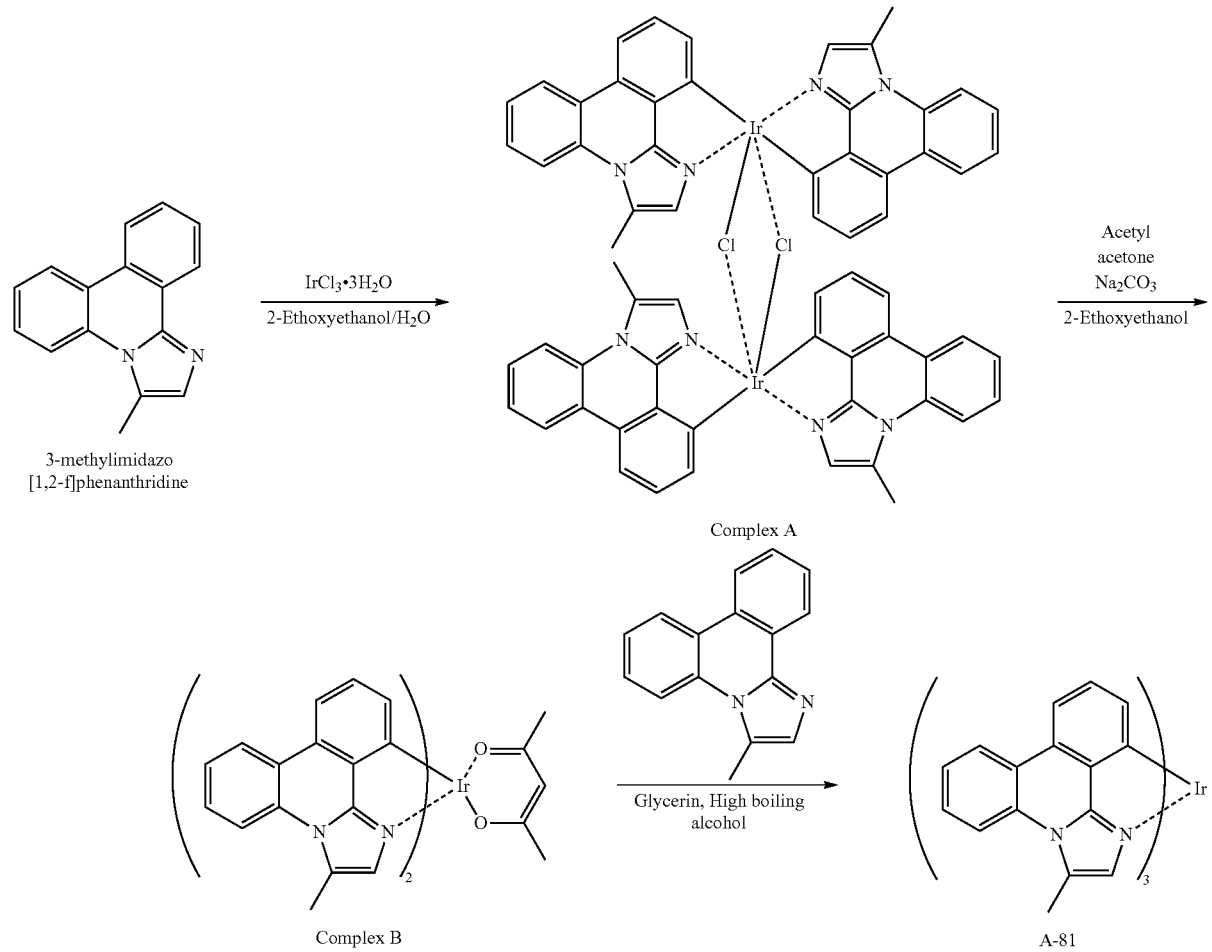

Process 1: Preparation of Complex A

To a four necked 100 ml flask equipped with a nitrogen gas inlet tube, a thermometer and a condenser were placed 0.9 g (0.003875 mol) of 3-methylimidazo[1,2-f]phenanthridine, 13 ml of 2-ethoxyetahnol and 3 ml of water. Then it was set on an oil bath stirrer.

To this were added 0.55 g (0.001560 mol) of $IrCl_3.3H_2O$ and 0.16 g (0.001560 mol) of triethylamine, and then the mixture was heated to reflux at an inner temperature of about 100° C. for 6 hours and to complete the reaction.

After completion of the reaction, the reaction solution was cooled to a room temperature and methanol was added. The precipitated solid was separated by filtration. The obtained solid was washed thoroughly with methanol, and then, it was dried to give 1.05 g (98.1%) of Complex A.

Process 2: Preparation of Complex B

To a four necked 50 ml flask equipped with a nitrogen gas inlet tube, a thermometer and a condenser were placed 1.0 g (0.0007244 mol) of Complex A, 0.29 g of acetylacetone, 1.0 g of sodium carbonate and 24 ml of 2-ethoxyetanhol. Then the flask was set on an oil bath stirrer.

The mixture was heated with stirring under a nitrogen gas atmosphere at inner temperature of about 80° C. for 1.5 hours.

After completion of the reaction, the reaction solution was cooled to a room temperature and methanol was added to the reaction solution. The precipitated crystal was separated by filtration. The obtained crystal was washed with 30 ml of water and 10 ml of methanol, and then, the crystal was dried to give 0.73 g (67.0%) of Complex B.

Process 3: Preparation of Exemplified Compound A-81

To a four necked 50 ml flask equipped with a nitrogen gas inlet tube, a thermometer and an air-cooling tube were placed 0.4 g (0.0005306 mol) of Complex B, 0.37 g of 3-methylimidazo[1,2-f]phenanthridine, 20 ml of glycerin and 20 ml of propylene glycol. Then the flask was set on an oil bath stirrer. The mixture was heated with stirring under a nitrogen gas atmosphere at inner temperature of about 170° C. to 180° C. for 20 hours to complete the reaction.

After completion of the reaction, the reaction solution was cooled to a room temperature and methanol was added, and then dispersed the reaction mixture. The dispersed crystal was separated by filtration to yield 0.37 g of a crude crystal.

The crude crystal was purified with a column chromatography (using developing eluent of dichloromethane). The obtained crystal was purified by dispersing in a heated mixture solvent of tetrahydrofuran and ethyl acetate to give 0.2 g (42.6%) of Exemplified compound A-81.

The structure of the obtained Exemplified compound A-81 was identified with ¹H-NMR (Nuclear Magnetic Resonance spectrum). The measuring conditions, chemical shifts and proton numbers of the peaks of the obtained spectrum are shown in the followings.

¹H-NMR (400 MHz, $CD_2Cl_2$)

Measuring Instrument: JEOL JNM-AL 400 (400 MHz), made by JEOL Ltd.

Attribution of spectrum (Chemical shift δ, proton number, and form of peak): 8.49 (1H, d), 8.27 (1H, d), 7.57 (4H, m), 7.07 (1H, t), 6.80 (1H, s) and 2.89 (3H, s)

In addition, the emission wavelength of Exemplified compound A-81 in the solution was 465 nm (the emission wavelength was measured in dichloromethane.)

In the present invention, the emission wavelength of the exemplified compound was measured as follows:

First, the absorption spectrum of the exemplified compound was measured and the absorption maximum wavelength in the range of 300 nm-350 nm was determined as an excitation light.

The emission wavelength was measured with Fluorophotometer F-4500 (made by Hitachi Ltd.) using the determined excitation light with performing nitrogen babbling.

In addition, although there is no restriction to the solvent which can be used, 2-methyl tetrahydrofuran and dichloromethane are preferably used from the viewpoint of solubility for the compound.

As for the concentration for measurement, it is preferable to be sufficiently diluted. Specifically, it is preferable to measure a sample having a concentration in the range of $10^{-6}$ mol/l to $10^{-4}$ mol/l.

Moreover, although there is no restriction in particular as temperature at the time of measurement, it is preferable to make temperature setting in the range of room temperature to 77K as a usual temperature setting.

Synthetic Example 2: Preparation of Exemplified Compound A-97

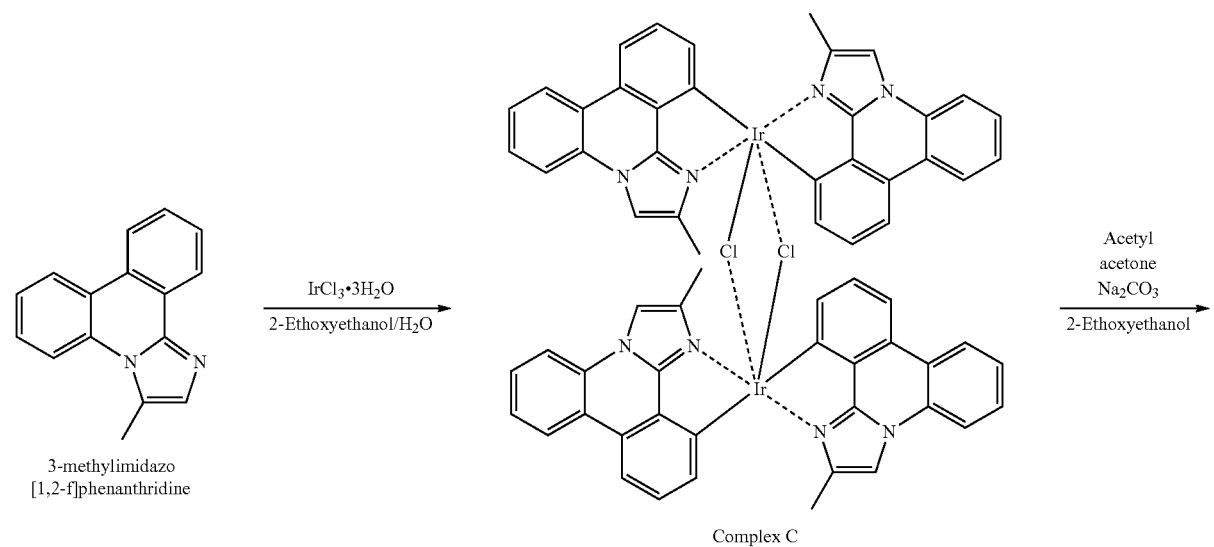

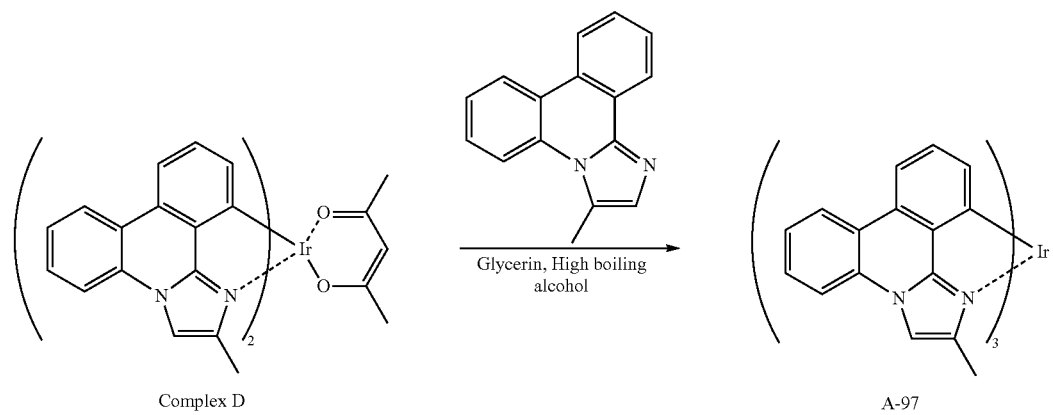

Process 1: Preparation of Complex C

Except having used 1.5 g of 2-methylimidazo[1,2-f]phenanthridine as a starting material instead of 3-methylimidazo[1,2-f]phenanthridine, the reaction and the post processing were performed in the same manner as Process 1 of Synthetic Example 1, and 1.37 g (77.0%) of Complex C was obtained.

Process 2: Preparation of Complex D

Except having used 1.0 g (0.0007244) of Complex C, the reaction and the post processing were performed in the same manner as Process 2 of Synthetic Example 1, and 0.42 g (38.5%) of Complex D was obtained.

Process 3: Preparation of Exemplified Compound A-97

To a four necked 50 ml flask equipped with a nitrogen gas inlet tube, a thermometer and an air-cooling tube were placed 0.386 g (0.0005120 mol) of Complex D, 0.357 g of 2-methylimidazo[1,2-f]phenanthridine and 20 ml of glycerin. Then it was set on an oil bath stirrer. The mixture was heated with stirring under a nitrogen gas atmosphere at inner temperature of about 150° C. for 4.5 hours to complete the reaction.

After completion of the reaction, the reaction solution was cooled to a room temperature and methanol was added, and then dispersed the reaction mixture. The dispersed crystal was separated by filtration to yield 0.38 g of a crude crystal.

The crude crystal was purified with a column chromatography (using developing eluent of dichloromethane). The obtained crystal was purified by dispersing in a heated mixture solvent of tetrahydrofuran and ethyl acetate to give 0.3 g (66.6%) of Exemplified compound A-97.

The structure of the obtained Exemplified compound A-97 was identified with $^1$H-NMR (Nuclear Magnetic Resonance spectrum). The measuring conditions and chemical shifts and proton numbers of the peaks of the obtained spectrum are shown in the followings.

$^1$H-NMR (400 MHz, Tetrahydrofuran-d8)

Measuring Instrument: JEOL JNM-AL 400 (400 MHz), made by JEOL Ltd.

Attribution of spectrum (Chemical shift δ, proton number, and form of peak): 8.48 (1H, d), 7.93 (1H, d), 7.75 (1H,$), 7.64 (1H, d), 7.54 (1H, t), 7.46 (1H, t), 6.95 (1H, t), 6.83 (1H, d) and 1.85 (3H,$).

In addition, the emission wavelength of Exemplified compound A-97 in the solution was 455 nm (the emission wavelength was measured in dichloromethane.)

On of the preferable embodiments of an organic EL element of the present invention is to contain in a light emitting layer, as a phosphorescent dopant (one of the light emitting dopants), the compounds having a partial structure represented by one of the aforesaid Formulas (1) to (4), Formulas (5) to (8), Formulas (9) to (12), or Formulas (13) to (16). However, they may be contained in other constitution layers, which will be described later, of the organic EL element of the present invention than the light emitting layer.

The light emitting layer of the organic EL element of the present invention may be composed of a single layer or multiple layers. However, the two or more phosphorescent dopants of the present invention are preferably contained in the same light emitting layer.

(About the Level of the Highest Occupied Molecular Orbital (HOMO) of Phosphorescence Emitting Metal Complex)

The difference of HOMO levels between the two or more kinds of phosphorescence emitting dopants of the present invention is preferably small from the viewpoints of emitting efficiency and stability such as color shift over time. Specifically, the difference is preferably 0.5 eV or less, and more preferably 0.3 eV or less.

In the present invention, the values of the HOMO and the LUMO levels denote the values obtained by calculations using Gaussian 98 (Gaussian 98, Revision A. 11. 4, M. J. Frisch, et al, Gaussian, Inc., Pittsburgh Pa., 2002), which is software for a molecular orbital calculation, and produced by Gaussian Inc. And the values of the HOMO and the LUMO levels are defined as values (a converted value in eV unit) calculated via structure optimization employing B3LYP/LanL2DZ as a key word. The reason for the calculated value being considered to be valid is that the calculated value obtained by the above method is in good agreement with the experimental one.

<One of Phosphorescence Emitting Metal Complex Among the Two or More Phosphorescence Emitting Metal Complexes>

The one phosphorescence emitting metal complex which is used in combination with a phosphorescence emitting metal complex having a ligand made of a six-membered aromatic compound condensed with three or more rings each having a five or a six-membered aromatic ring can be appropriately selected from the conventionally known compounds used in a light emitting layer of an organic EL element.

The aforesaid phosphorescence emitting metal complex used in combination with is preferably a complex compound having a metal (including a metal ion) of Groups 8 to 10 in the periodic table as a center metal. More preferably, it is an iridium compound, an osmium compound, a platinum compound (a platinum complex compound) or a rare earth complex. Among them, the most preferable is an iridium compound.

Examples of a phosphorescence emitting metal complex which can be used simultaneously are shown in the followings. However, the present invention is not limited to them. These compounds can be prepared with the method described in a literature of, for example, Inorg. Chem., Vol. 40, pages 1704-1711. Blue emitting dopants, green emitting dopants and red emitting dopants can be appropriately selected from these exemplified compounds.

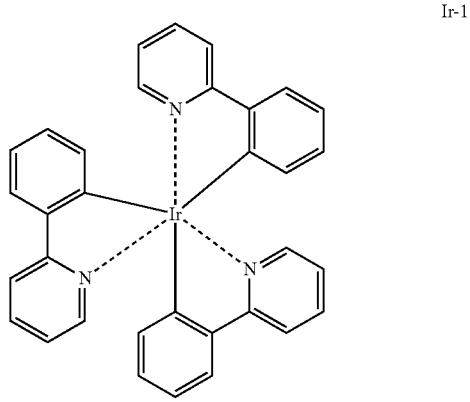

Ir-1

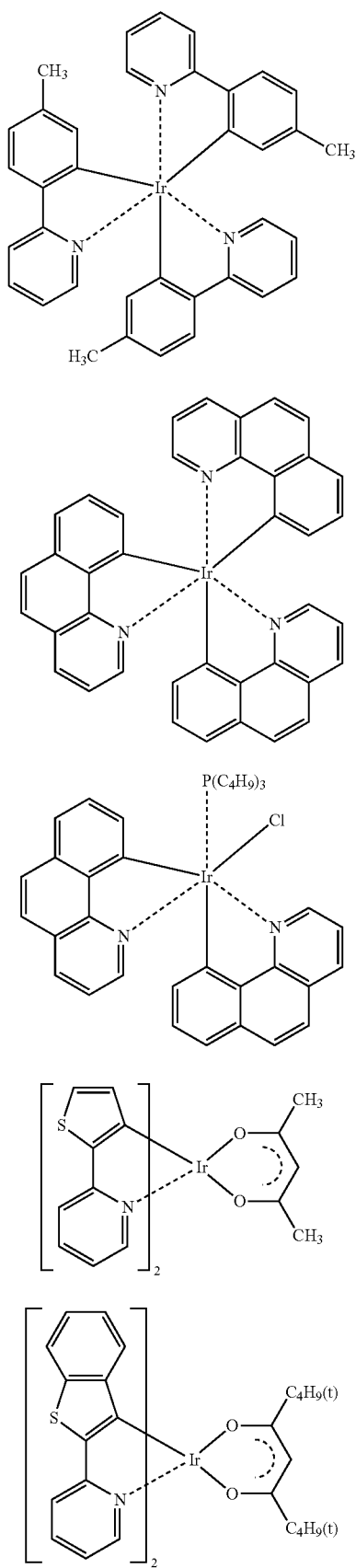
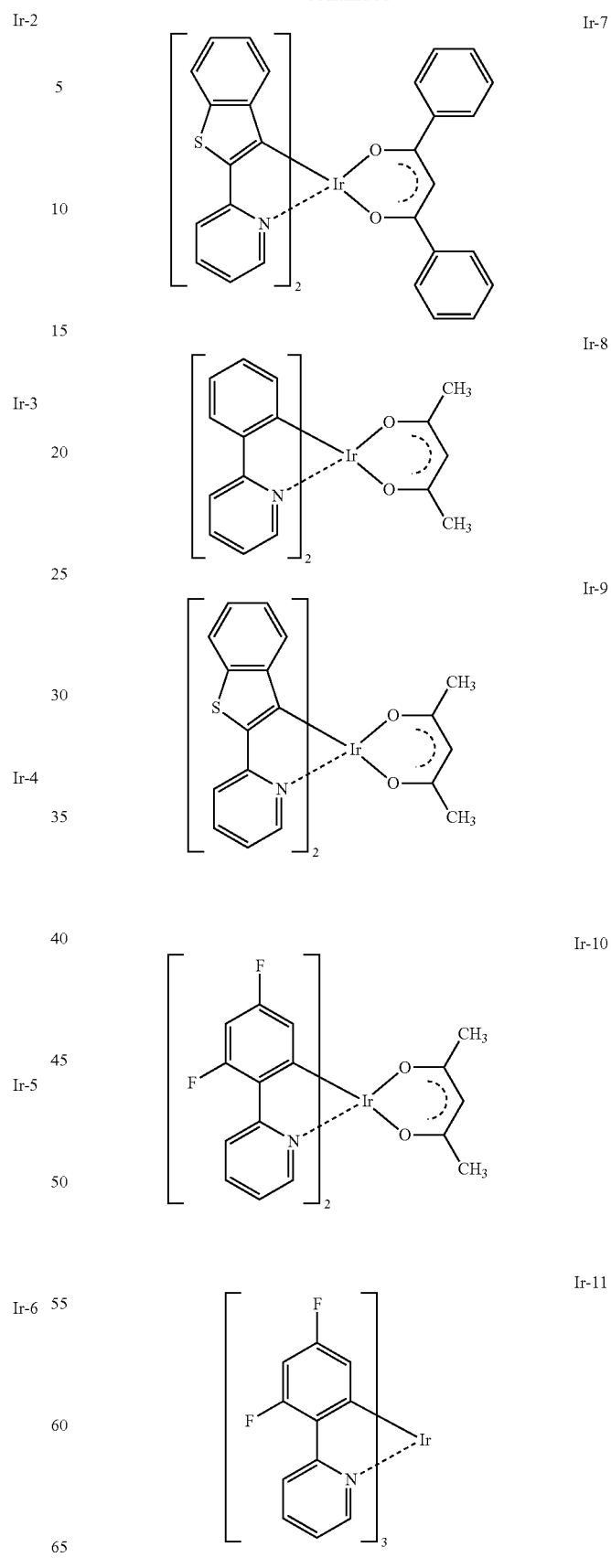

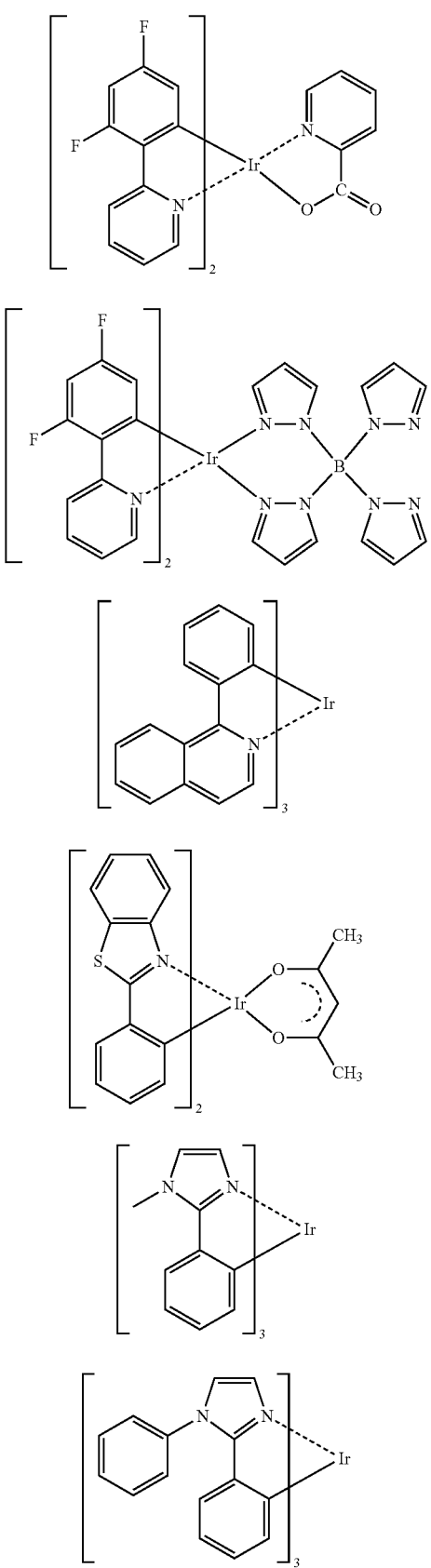

Here, constituting layers of an organic EL element and a light emitting dopant contained in a light emitting layer of the present invention will be detailed.

<Materials for Organic EL Element>

Materials used in an organic EL element of the present invention will be described.

The compound (it is also called also as a metal complex or a metal complex compound) having a partial structure represented by any one of the above-described Formulas (1) to (4), the partial structure represented by any one of the above-described Formulas (5) to (8), the partial structure represented by any one of the above-described Formulas (9) to (12), or the partial structure represented by any one of the above-described Formulas (13) to (16) can be effectively used as a material for producing an organic EL element of the present invention.

A material for producing an organic EL element of the present invention may be used singly or may be used in combination with a conventionally known material for an organic EL element.

<Constituting Layers of Organic EL Element>

Specific examples of a preferable layer constitution of an organic EL element of the present invention are shown below; however, the present invention is not limited thereto.

(i) anode/light emitting layer/electron transport layer/cathode (ii) anode/positive hole transport layer/light emitting layer/electron transport layer/cathode (iii) anode/positive hole transport layer/light emitting layer/positive hole inhibition layer/electron transport layer/cathode (iv) anode/positive hole transport layer/light emitting layer/positive hole inhibition layer/electron transport layer/cathode buffer layer/cathode (v) anode/anode buffer layer/positive hole transport layer/light emitting layer/positive hole inhibition layer/electron transport layer/cathode buffer layer/cathode In the organic EL element of the present invention, the maximum wavelength of light emitted from the blue light emitting layer is preferably within 430-480 nm, and the green light emitting layer is preferably a monochromatic light emitting layer which results in the maximum wavelength of the emitted light within 510-550 nm, while the red light emitting layer is a monochromatic light emitting layer which results in the maximum wavelength of the emitted light in the range of 600-640 nm. Display devices employing these are preferred. Further, a while light emitting layer is acceptable, which is prepared by laminating at least three of these layers. Further, between the light emitting layers may be present a non-light emitting intermediate layer. As the organic EL element of the present invention, preferred is a white light emitting layer, and lighting devices employing these are preferred.

Each of the layers which constitute the organic EL elements of the present invention will now be sequentially detailed.

<Light Emitting Layer>

The light emitting layer of the present invention is a layer, which emits light via recombination of electrons and positive holes injected from an electrode or a layer such as an electron transport layer or a positive hole transport layer. The light emission portion may be present either within the light emitting layer or at the interface between the light emitting layer and an adjacent layer thereof.

The total thickness of the light emitting layer is not particularly limited. However, in view of the layer homogeneity, the minimization of application of unnecessary high voltage during light emission, and the stability enhancement of the emitted light color against the drive electric current, the layer thickness is regulated preferably in the range of 2 nm-5 μm, more preferably in the range of 2 nm-200 nm, but most preferably in the range of 10-20 nm.

With regard to preparation of the light emitting layer, light emitting dopants and host compounds, described below, may be subjected to film formation via a conventional thin filming method such as a vacuum deposition method, a spin coating method, a casting method, an LB method, or an ink-jet method.

It is preferable that the light emitting layer of the organic EL element of the present invention incorporates at least two kinds of compounds: one is a light emitting host compound and other is a light emitting dopant (a phosphorescent dopant (or it is called as a phosphorescence emitting dopant) or a fluorescent dopant).

(Host Compounds (Also Referred to as Light Emitting Hosts)

Host compounds employed in the present invention will now be described.

"Host compounds", as described in the present invention, are defined as compounds, incorporated in a light emitting layer, which result in a weight ratio of at least 20% in the above layer and also result in a phosphorescent quantum yield of the phosphorescence emission of less than 0.1. Further, of compounds incorporated in the light emitting layer, it is preferable that the weight ratio in the aforesaid layer is at least 20%.

An emission host compound of the present invention may be used with plural known host compounds. It is possible to control the transfer of charges by making use of a plurality of host compounds, which results in high efficiency of an organic EL element. In addition, it is possible to mix a different emission lights by making use of a plurality of emission dopants that will be described later. Any required emission color can be obtained thereby.

Further, an emission host of the present invention may be either a low molecular weight compound or a polymer compound having a repeating unit, in addition to a low molecular weight compound provided with a polymerizing group such as a vinyl group and an epoxy group (an evaporation polymerizing emission host).

Examples of a host compound preferably used in the present invention will be shown, however, the present invention is not limited to them.

H-1

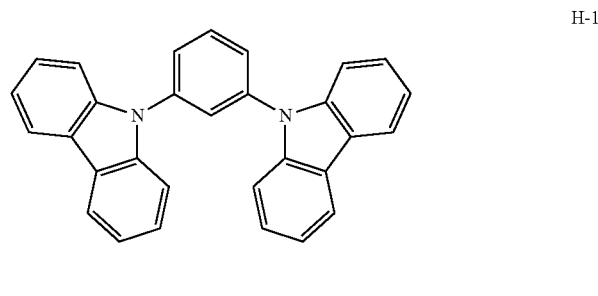

H-2

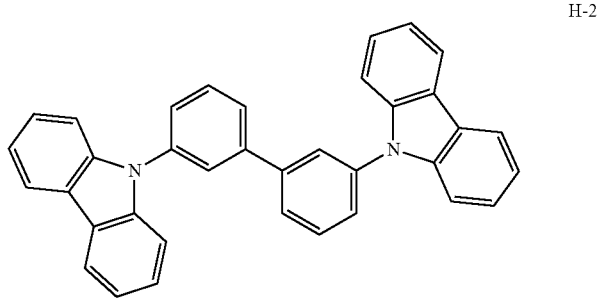

H-3

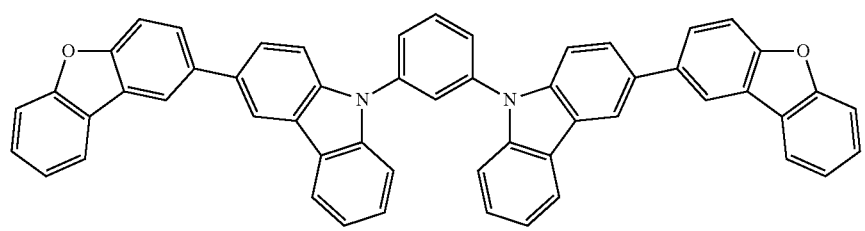

H-4

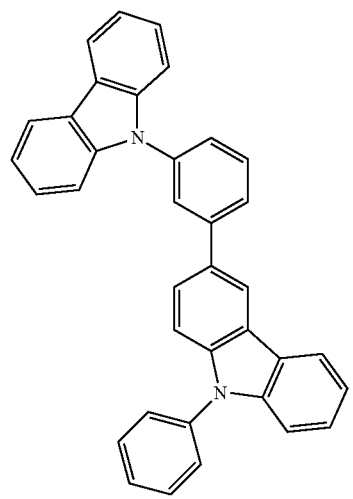

H-5

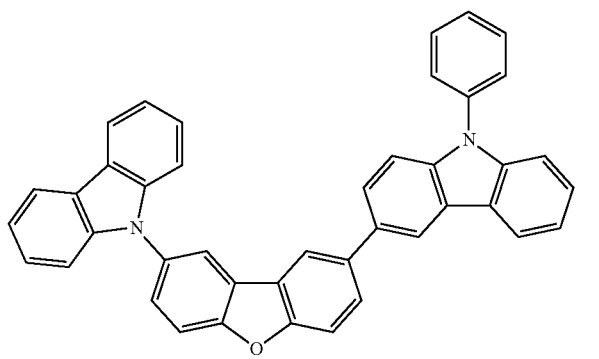

H-6

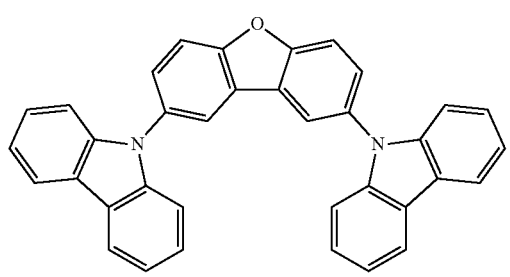

H-7

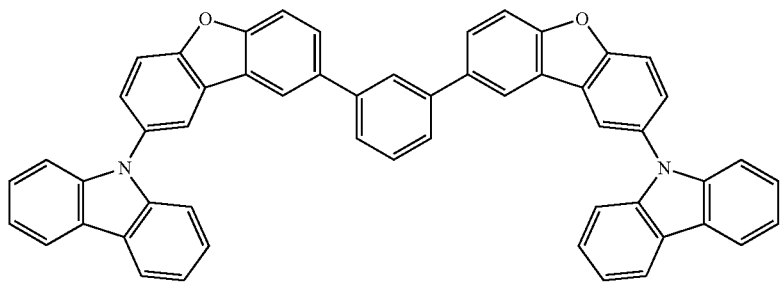

H-8

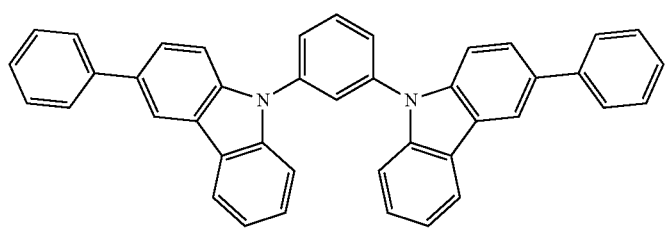

A known emission host which may be jointly used is preferably a compound having a positive hole transporting ability and an electron transporting ability, as well as preventing elongation of an emission wavelength and having a high Tg (a glass transition temperature).

As specific examples of an emission host compounds described in the following Documents are preferable.

For example, JP-A Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837.

(Emission Dopant)

The emission dopant of the present invention will now be described.

As light emitting dopants according to the present invention, it may be employed fluorescent dopants (also referred to as fluorescent compounds) and phosphorescent dopants (also referred to as phosphorescent emitting materials, phosphorescent compounds or phosphorescence emitting compounds). However, in view of production of organic EL elements exhibiting higher light emission efficiency, as light emitting dopants (also referred simply to as light emitting materials) employed in the light emitting layer of the organic EL element and light emitting units in the present invention, it is preferable to simultaneously incorporate the aforesaid host compounds and the phosphorescent dopants.

(Phosphorescent Dopant)

A phosphorescence-emitting dopant of the present invention will be described.

The phosphorescent dopant of the present invention is a compound, wherein emission from an excited triplet state thereof is observed, specifically, emitting phosphorescence at room temperature (25° C.) and exhibiting a phosphorescence quantum yield of at least 0.01 at 25° C. The phosphorescence quantum yield is preferably at least 0.1.

The phosphorescence quantum yield can be determined via a method described in page 398 of Bunko II of Dai 4 Han Jikken Kagaku Koza 7 (Spectroscopy II of 4th Edition Lecture of Experimental Chemistry 7) (1992, published by Maruzen Co., Ltd.). The phosphorescence quantum yield in a solution can be determined using appropriate solvents. However, it is only necessary for the phosphorescent dopant of the present invention to exhibit the above phosphorescence quantum yield using any of the appropriate solvents.

Two kinds of principles regarding emission of a phosphorescent dopant are cited. One is an energy transfer-type, wherein carriers recombine on a host compound on which the carriers are transferred to produce an excited state of the host compound, and then via transfer of this energy to a phosphorescent dopant, emission from the phosphorescence-emitting dopant is realized. The other is a carrier trap-type, wherein a phosphorescence-emitting dopant serves as a carrier trap and then carriers recombine on the phosphorescent dopant to generate emission from the phosphorescent dopant. In each case, the excited state energy of the phosphorescent dopant is required to be lower than that of the host compound.

In the present invention, phosphorescent dopants are appropriately selected from conventional ones employed in the light emitting layer of the organic EL element and simultaneously employed Phosphorescent dopants used in the present invention are preferably complex based compounds incorporating metals in Groups 8-10 in the element periodic table. Of these, more preferred are iridium compounds, osmium compounds, or platinum compounds (being platinum complex based compounds), and rare earth metal complexes, and of these, most preferred are iridium compounds.

The phosphorescent dopants used in the present invention are preferably the aforesaid phosphorescence emitting metal complexes having a ligand made of a six-membered aromatic compound condensed with three or more rings each having a five or a six-membered aromatic ring. Among them, the compounds containing a partial structure represented by one of Formulas (1) to (4) are preferable. Specifically preferred compounds are the exemplified compounds as described above.

Among the two or more phosphorescence emitting metal complexes of the present invention, the other phosphorescence emitting metal complex which is used in combination with the phosphorescence emitting metal complex having a ligand made of a six-membered aromatic compound condensed with three or more rings each having a five or a six-membered aromatic ring can be selected from the conventionally known compounds as described above. However, the present invention is not limited to theme.

The light emitting layer of the present invention contains at least two kinds of phosphorescent dopants, and one of which is a phosphorescence emitting metal complex having a ligand made of a six-membered aromatic compound condensed with three or more rings each having a five or a six-membered aromatic ring. The two or more phosphorescent dopants can be mixed in the same light emitting layer, or they may be incorporated in separate light emitting layers which are laminated. In order to decrease the cost of production, they are preferably incorporated by mixing in the same layer.

The two or more phosphorescent dopants, one of which being a phosphorescence emitting metal complex having a ligand made of a six-membered aromatic compound condensed with three or more rings each having a five or a six-membered aromatic ring, may emit a light having the same hue. It may be possible to select dopants each emitting a light having a different hue.

In an organic EL element of the present invention, since the ratio of light emitting strength between the phosphorescent dopants does not change so much even after prolonged driving, the present invention is specifically effective to restrain the color change when the color is produced by mixed dopants having a different color. Especially, the color change of white color produced by three or more kinds of dopants is so small that it will efficient to produce a light source such as white color illumination. (Fluorescent Dopants (also referred to as Fluorescent Compounds))

As fluorescent dopants, listed are coumarin based dyes, pyran based dyes, cyanine based dyes, croconium based dyes, squarylium based dyes, oxobenzanthracene based dyes, fluorescein based dyes, Rhodamine based dyes, pyrylium based dyes, perylene based dyes, stilbene based dyes, polythiophene based dyes, or rare earth complex based fluorescent materials.

An injection layer, an inhibition layer, and an electron transport layer, which are employed as a constituting layer of the organic EL element of the present invention will now be described.

<Injection Layer: Electron Injection Layer, Positive Hole Injection Layer>

An injection layer is appropriately provided and includes an electron injection layer and a positive hole injection layer, which may be arranged between an anode and an emitting layer or a positive transfer layer, and between a cathode and an emitting layer or an electron transport layer, as described above.

An injection layer is a layer which is arranged between an electrode and an organic layer to decrease an operating voltage and to improve an emission luminance, which is detailed in volume 2, chapter 2 (pp. 123-166) of "Organic EL Elements and Industrialization Front thereof (Nov. 30, 1998, published by N. T. S Corp.)", and includes a positive hole injection layer (an anode buffer layer) and an electron injection layer (a cathode buffer layer).

An anode buffer layer (a positive hole injection layer) is also detailed in such as JP-A 9-45479, 9-260062 and 8-288069, and specific examples include such as a phthalocyanine buffer layer comprising such as copper phthalocyanine, an oxide buffer layer comprising such as vanadium oxide, an amorphous carbon buffer layer, and a polymer buffer layer employing conductive polymer such as polythiophene.

A cathode buffer layer (an electron injection layer) is also detailed in such as JP-A 6-325871, 9-17574 and 10-74586, and specific examples include a metal buffer layer comprising such as strontium and aluminum, an alkali metal compound buffer layer comprising such as lithium fluoride, an alkali earth metal compound buffer layer comprising such as magnesium fluoride, and an oxide buffer layer comprising such as aluminum oxide. The above-described buffer layer (injection layer) is preferably a very thin layer, and the layer thickness is preferably in a range of 0.1 nm-5 μm although it depends on a raw material.

<Inhibition Layer: Positive Hole Inhibition Layer, Electron Inhibition Layer>

An inhibition layer is appropriately provided in addition to the basic constitution layers composed of organic thin layers as described above. Examples are described in such as JP-A Nos. 11-204258 and 11-204359 and p. 273 of "Organic EL Elements and Industrialization Front Thereof (Nov. 30 (1998), published by N. T. S Corp.)" is applicable to a positive hole inhibition (hole block) layer according to the present invention.

A positive hole inhibition layer, in a broad meaning, is provided with a function of electron transport layer, being comprised of a material having a function of transporting an electron but a very small ability of transporting a positive hole, and can improve the recombination probability of an electron and a positive hole by inhibiting a positive hole while transporting an electron.

Further, a constitution of an electron transport layer described later can be appropriately utilized as a positive hole inhibition layer according to the present invention.

The positive hole inhibition layer of the organic EL element of the present invention is preferably arranged adjacent to the light emitting layer.

It is preferable that the positive hole inhibition layer incorporates a carbazole derivative, a carboline derivative, or a diazacarbazole derivative (a diazacarbazole derivative indicates a compound in which one of the carbon atoms constituting the carboline ring is replaced with a nitrogen atom) listed as a host compound described above.

Further, in the present intention, in the case in which a plurality of light emitting layers which differ in a plurality of different emitted light colors, it is preferable that the light emitting layer which results in the shortest wavelength of the emitted light maximum wavelength is nearest to the anode in all light emitting layers. However, in such a case, it is preferable to additionally arrange the positive hole inhibition layer between the aforesaid shortest wavelength layer and the light emitting layer secondly near the anode. Further, at least 50% by weight of the compounds incorporated in the positive hole inhibition layer arranged in the aforesaid position preferably exhibits the ionization potential which is greater by at least 0.3 eV than that of the host compounds of the aforesaid shortest wavelength light emitting layer.

The ionization potential is defined as energy which is necessary to release electrons in the HOMO (being the highest occupied molecular orbital) to the vacuum level, and may be determined via, for example, the method described below.

(1) By employing Gaussian 98 (Gauaaian 98, Revision A. 11. 4, M. J. Frisch, et al. Gaussian 98(Gaussian 98, Revision A. 11. 4, M. J. Frisch, et al, Gaussian, Inc., Pittsburgh h PA, 2002), which is a molecular orbital calculation software, produced by Gaussian Co. in the United State of America, and by employing B3LYP/6-31G* as a key word, the value (in terms of corresponding eV unit) was computed, and it is possible to obtain the ionization potential by rouging off the second decimal point. The background, in which the resulting calculated values are effective, is that the calculated values obtained by the above method exhibit high relationship with the experimental values.

(2) It is possible to determine the ionization potential via a method in which ionization potential is directly determined employing a photoelectron spectrometry. For example, by employing a low energy electron spectrophotometer "Model AC-1", produced by Riken Keiki Co., or appropriately employ a method known as an ultraviolet light electron spectrometry.

On the other hand, the electron inhibition layer, as described herein, has a function of the positive hole transport layer in a broad sense, and is composed of materials having markedly small capability of electron transport, while having capability of transporting positive holes and enables to enhance the recombination probability of electrons and positive holes by inhibiting electrons, while transporting electrons.

Further, it is possible to employ the constitution of the positive hole transport layer, described below, as an electron inhibition layer when needed. The thickness of the positive hole inhibition layer and the electron transport layer according to the present invention is preferably 3-100 nm, but is more preferably 5-30 nm.

<Positive Hole Transport Layer>

A positive hole transport layer contains a material having a function of transporting a positive hole, and in a broad meaning, a positive hole injection layer and an electron inhibition layer are also included in a positive hole transport layer. A single layer of or plural layers of a positive hole transport layer may be provided.

A positive hole transport material is those having any one of a property to inject or transport a positive hole or a barrier property to an electron, and may be either an organic substance or an inorganic substance. For example, listed are a triazole derivative, an oxadiazole derivative, an imidazole derivative, a polyarylalkane derivative, a pyrazolone derivative, a phenylenediamine derivative, an arylamine derivative, an amino substituted chalcone derivative, an oxazole derivatives, a styrylanthracene derivative, a fluorenone derivative, a hydrazone derivative, a stilbene derivative, a silazane derivative, an aniline type copolymer, or conductive polymer oligomer and specifically preferably such as thiophene oligomer.

As a positive hole transport material, those described above can be utilized, however, it is preferable to utilized a porphyrin compound, an aromatic tertiary amine compound and a styrylamine compound, and specifically preferably an aromatic tertiary amine compound.

Typical examples of an aromatic tertiary amine compound and a styrylamine compound include: N,N,N',N'-tetraphenyl-4,4'-diaminophenyl; N,N'-diphenyl-N,N'-bis(3-methylphenyl)-(1,1'-biphenyl)-4,4'-diamine (TDP); 2,2-bis(4-di-p-tolylaminophenyl)propane; 1,1-bis(4-di-p-tolylaminophenyl)cyclohexane; N,N,N',N'-tetra-p-tolyl 4,4'-diaminobiphenyl; 1,1-bis(4-di-p-tolylaminophenyl)-4-phenylcyclohexane; bis(4-dimethylamino-2-methyl) phenylmethane; bis(4-di-p-tolylaminophenyl) phenylmethane; N,N'-diphenyl-N,N'-di(4-methoxyphenyl)-4,4'-diaminobiphenyl; N,N,N',N'-tetraphenyl-4,4'-diaminophenylether; 4,4'-bis(diphenylamino)quadriphenyl; N,N,N-tri(p-tolyl)amine; 4-(di-p-tolylamino)-4'-[4-(di-p-triamino)styryl]stilbene; 4-N, N-diphenylamino-(2-diphenylvinyl)benzene; 3-methoxy-4'-N, N-diphenylaminostilbene; and N-phenylcarbazole, in addition to those having two condensed aromatic rings in a molecule described in U.S. Pat. No. 5,061,569, such as 4,4'-bis[N-(1-naphthyl)-N-phenylamino]biphenyl (NDP), and 4,4',4"-tris[N-(3-methylphenyl)-N-phenylamino]triphenylamine (MDTDATA), in which three of triphenylamine units are bonded in a star burst form, described in JP-A 4-308688.

Polymer materials, in which these materials are introduced in a polymer chain or constitute the main chain of polymer, can be also utilized.

Further, an inorganic compound such as a p type-Si and a p type-SiC can be utilized as a positive hole injection material and a positive hole transport material Further, it is possible to employ so-called p type positive hole transport materials, as described in Japanese Patent Publication Open to Public Inspection (hereinafter referred to as JP-A) No. 11-251067, and J. Huang et al. reference (Applied Physics Letters 80 (2002), p. 139). In the present invention, since high efficiency light emitting elements are prepared, it is preferable to employ these materials.

This positive hole transport layer can be prepared by forming a thin layer made of the above-described positive hole transport material according to a method well known in the art such as a vacuum evaporation method, a spin coating method, a cast method, an inkjet method and a LB method.

The layer thickness of a positive hole transport layer is not specifically limited, however, it is generally 5 nm-5 µm, and preferably 5 nm-200 nm. This positive transport layer may have a single layer structure comprised of one or not less than two types of the above described materials.

Further, it is possible to employ a positive hole transport layer of a higher p property which is doped with impurities. As its example, listed are those described in each of JP-A Nos. 4-297076, 2000-196140, 2001-102175, as well as in J. Appl. Phys., 95, 5773 (2004).

In the present invention, it is preferable to employ a positive hole transport layer of such a high p property, since it is possible to produce an element of lower electric power consumption.

<Electron Transport Layer>

An electron transport layer is comprised of a material having a function to transfer an electron, and an electron injection layer and a positive hole inhibition layer are included in an electron transport layer in a broad meaning. A single layer or plural layers of an electron transport layer may be provided.

Heretofore, when an electron transport layer is composed of single layer and a plurality of layers, electron transport materials (also functioning as a positive hole inhibition material) employed in the electron transport layer adjacent to the cathode side with respect to the light emitting layer, electrons ejected from the cathode may be transported to the light emitting layer. As such materials, any of the conventional compounds may be selected and employed.

Examples of these compounds include such as a nitro-substituted fluorene derivative, a diphenylquinone derivative, a thiopyradineoxide derivative, carbodiimide, a fluorenylidenemethane derivative, anthraquinonedimethane, an anthraquinone derivative, an anthrone derivative and an oxadiazole derivative.

Further, a thiadiazole derivative in which an oxygen atom in the oxadiazole ring of the above-described oxadiazole derivative is substituted by a sulfur atom, and a quinoxaline derivative having a quinoxaline ring which is known as an electron attracting group can be utilized as an electron transport material. Polymer materials, in which these materials are introduced in a polymer chain or these materials form the main chain of polymer, can be also utilized.

Further, a metal complex of a 8-quinolinol derivative such as tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum and bis(8-quinolinol)zinc (Znq); and metal complexes in which a central metal of the aforesaid metal complexes is substituted by In, Mg, Cu, Ca, Sn, Ga or Pb, can be also utilized as an electron transport material.

Further, metal-free or metal phthalocyanine, or those the terminal of which is substituted by an alkyl group and a sulfonic acid group, can be preferably utilized as an electron transport material. Further, distyrylpyrazine derivative, which has been exemplified as a material of an emitting layer, can be also utilized as an electron transport material, and, similarly to the case of a positive hole injection layer and a positive hole transfer layer, an inorganic semiconductor such as an n-type-Si and an n-type-SiC can be also utilized as an electron transport material.

This electron transport layer can be prepared by forming a thin layer made of the above-described electron transport material according to a method well known in the art such as a vacuum evaporation method, a spin coating method, a cast method, an inkjet method and a LB method.

The layer thickness of an electron transport layer is not specifically limited; however, it is generally 5 nm-5 µm, and preferably 5 nm-200 nm. This electron transport layer may have a single layer structure comprised of one or not less than two types of the above described materials.

Further, it is possible to employ an electron transport layer doped with impurities, which exhibits high n property. Examples thereof include those, described in JP-A Nos. 4-297076, 10-270172, 2000-196140, 2001-102175, as well as J. Appl. Phys., 95, 5773 (2004).

The present invention is preferable since by employing an electron transport layer of such a high n property electron transport layer, it is possible to preparer an element of further lowered electric power consumption.

<Anode>

As an anode according to an organic EL element of the present invention, those comprising metal, alloy, a conductive compound, which is provided with a large work function (not less than 4 eV), and a mixture thereof as an electrode substance are preferably utilized. Specific examples of such an electrode substance include a conductive transparent material such as metal like Au, CuI, indium tin oxide (ITO), $SnO_2$ and ZnO.

Further, a material such as IDIXO ($In_2O_3$—ZnO), which can prepare an amorphous and transparent electrode, may be also utilized.

As for an anode, these electrode substances may be made into a thin layer by a method such as evaporation or spattering and a pattern of a desired form may be formed by means of photolithography, or in the case of requirement of pattern precision is not so severe (not less than 100 µm), a pattern may be formed through a mask of a desired form at the time of evaporation or spattering of the above-described substance.

Alternatively, when coatable materials such as organic electrically conductive compounds are employed, it is possible to employ a wet system filming method such as a printing system or a coating system.

When emission is taken out of this anode, the transmittance is preferably set to not less than 10% and the sheet resistance as an anode is preferably not more than a few hundreds $\Omega/\square$. Further, although the layer thickness depends on a material, it is generally selected in a range of 10-1,000 nm and preferably of 10-200 nm.

<Cathode>

On the other hand, as a cathode according to the present invention, metal, alloy, a conductive compound and a mixture thereof, which have a small work function (not more than 4 eV), are utilized as an electrode substance. Specific examples of such an electrode substance includes such as sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture and rare earth metal.

Among them, with respect to an electron injection property and durability against such as oxidation, preferable are a mixture of electron injecting metal with the second metal which is stable metal having a work function larger than electron injecting metal, such as a magnesium/silver mixture, a magnesium/aluminum mixture, a magnesium/indium mixture, an aluminum/aluminum oxide ($Al_2O_3$) mixture and a lithium/aluminum mixture, and aluminum.

As for a cathode, these electrode substances may be made into a thin layer by a method such as evaporation or spattering.

Further, the sheet resistance as a cathode is preferably not more than a few hundreds $\Omega/\square$ and the layer thickness is generally selected in a range of 10-1,000 nm and preferably of 10-200 nm.

Herein, to transmit emission, either one of an anode or a cathode of an organic EL element is preferably transparent or translucent to improve the mission luminance.

Further, after forming, on the cathode, the above metals at a film thickness of 1-20 nm, it is possible to prepare a transparent or translucent cathode in such a manner that electrically conductive transparent materials are prepared thereon. By applying the above, it is possible to produce an element in which both anode and cathode are transparent.

<Substrate>

A substrate according to an organic EL element of the present invention is not specifically limited with respect to types of such as glass and plastics. They me be transparent or opaque.

However, a transparent substrate is preferable when the emitting light is taken from the side of substrate. Substrates preferably utilized includes such as glass, quartz and transparent resin film. A specifically preferable substrate is resin film capable of providing an organic EL element with a flexible property.

Resin film includes such as: polyesters such as polyethylene terephthalate (PET) and polyethylene naphthalate (PEN); polyethylene, polypropyrene; cellulose esters or their derivatives such as cellophane, cellulose diacetate, cellulose triacetate, cellulose acetate butylate, cellulose acetate propionate (CAP), cellulose acetate phthalate (TAC) and cellulose nitrate; polyvinylidene chloride, polyvinyl alcohol, polyethylene vinyl alcohol, syndiotactic polystyrene, polycarbonate, norbornene resin, polymethylpentene, polyether ketone, polyimide, polyether sulfone (PES), polyphenylene sulfide, polysulfones, polyetherimide, polyether ketone imide, polyamide, fluororesin, Nylon, polymethylmethacrylate, acrylic resin, polyacrylate; and cycloolefine resins such as ARTON (produced by JSR Co. Ltd.) and APEL (produce by Mitsui Chemicals, Inc.)

On the surface of a resin film, formed may be a film incorporating inorganic and organic compounds or a hybrid film of both. Barrier films are preferred at a water vapor permeability (25±0.5° C., and relative humidity (90±2)% RH) of at most 0.01 g/(m$^2$·24 h), determined based on JIS K 7129-1992. Further, high barrier films are preferred at an oxygen permeability of at most $1\times10^{-3}$ ml/(m$^2$·24 h·MPa), and at a water vapor permeability of at most $10^{-5}$ g/(m$^2$·24 h), determined based on JIS K 7126-1987.

As materials forming a barrier film, employed may be those which retard penetration of moisture and oxygen, which deteriorate the element. For example, it is possible to employ silicon oxide, silicon dioxide, and silicon nitride. Further, in order to improve the brittleness of the aforesaid film, it is more preferable to achieve a laminated layer structure of inorganic layers and organic layers. The laminating order of the inorganic layer and the organic layer is not particularly limited, but it is preferable that both are alternatively laminated a plurality of times.

Barrier film forming methods are not particularly limited, and examples of employable methods include a vacuum deposition method, a sputtering method, a reactive sputtering method, a molecular beam epitaxy method, a cluster ion beam method, an ion plating method, a plasma polymerization method, a plasma CVD method, a laser CVD method, a thermal CVD method, and a coating method. Of these, specifically preferred is a method employing an atmospheric pressure plasma polymerization method, described in JP-A No. 2004-68143.

Examples of opaque support substrates include metal plates such aluminum or stainless steel, films, opaque resin substrates, and ceramic substrates.

The external extraction efficiency of light emitted by the organic EL element of the present invention is preferably at least 1% at room temperature, but is more preferably at least 5%.

External extraction quantum yield (%)=the number of photons emitted by the organic EL element to the exterior/ the number of electrons fed to organic EL element Further, even by simultaneously employing color hue improving filters such as a color filter, simultaneously employed may be color conversion filters which convert emitted light color from the organic EL element to multicolor by employing fluorescent materials. When the color conversion filters are employed, it is preferable that λmax of light emitted by the organic EL element is at least 480 nm.

<Sealing>

As sealing means employed in the present invention, listed may be, for example, a method in which sealing members, electrodes, and a supporting substrate are subjected to adhesion via adhesives.

The sealing members may be arranged to cover the display region of an organic EL element, and may be an engraved plate or a flat plate. Neither transparency nor electrical insulation is limited.

Specifically listed are glass plates, polymer plate-films, metal plates, and films. Specifically, it is possible to list, as glass plates, soda-lime glass, barium-strontium containing glass, lead glass, aluminosilicate glass, borosilicate glass, bariumborosilicate glass, and quartz.

Further, listed as polymer plates may be polycarbonate, acryl, polyethylene terephthalate, polyether sulfide, and polysulfone. As a metal plate, listed are those composed of at least one metal selected from the group consisting of stainless steel, iron, copper, aluminum magnesium, nickel, zinc, chromium, titanium, molybdenum, silicon, germanium, and tantalum, or alloys thereof.

In the present invention, since it is possible to convert the element to a thin film, it is possible to preferably employ a metal film.

Further, the oxygen permeability of the polymer film is preferably at most $1\times10^{-3}$ ml/(m$^2$·24 h·MPa), determined by the method based on JIS K 7126-1987, while its water vapor permeability (at 25±0.5° C. and relative humidity (90±2)%) is at most $10^{-5}$ g/(m$^2$·24 h), determined by the method based on JIS K 7129-1992.

Conversion of the sealing member into concave is carried out employing a sand blast process or a chemical etching process.

In practice, as adhesives, listed may be photo-curing and heat-curing types having a reactive vinyl group of acrylic acid based oligomers and methacrylic acid, as well as moisture curing types such as 2-cyanoacrylates.

Further listed may be thermal and chemical curing types (mixtures of two liquids) such as epoxy based ones. Still further listed may be hot-melt type polyamides, polyesters, and polyolefins. Yet further listed may be cationically curable type ultraviolet radiation curable type epoxy resin adhesives.

In addition, since an organic EL element is occasionally deteriorated via a thermal process, those are preferred which enable adhesion and curing between room temperature and 80° C. Further, desiccating agents may be dispersed into the aforesaid adhesives. Adhesives may be applied onto sealing portions via a commercial dispenser or printed on the same in the same manner as screen printing.

Further, it is appropriate that on the outside of the aforesaid electrode which interposes the organic layer and faces the support substrate, the aforesaid electrode and organic layer are covered, and in the form of contact with the support substrate, inorganic and organic material layers are formed as a sealing film. In this case, as materials forming the aforesaid film may be those which exhibit functions to retard penetration of those such as moisture or oxygen which results in deterioration. For example, it is possible to employ silicon oxide, silicon dioxide, and silicon nitride.

Still further, in order to improve brittleness of the aforesaid film, it is preferable that a laminated layer structure is formed, which is composed of these inorganic layers and layers composed of organic materials. Methods to form these films are not particularly limited. It is possible to employ, for example, a vacuum deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a thermal CVD method, and a coating method.

In a gas phase and a liquid phase, it is preferable to inject inert gases such as nitrogen or argon, and inactive liquids such as fluorinated hydrocarbon or silicone oil into the space between the sealing member and the surface region of the organic EL element. Further, it is possible to form vacuum. Still further, it is possible to enclose hygroscopic compounds in the interior.

Examples of hygroscopic compounds include metal oxides (for example, sodium oxide, potassium oxide, calcium oxide, barium oxide, magnesium oxide, and aluminum oxide); sulfates (for example, sodium sulfate, calcium sulfate, magnesium sulfate, and cobalt sulfate); metal halides (for example, calcium chloride, magnesium chloride, cesium fluoride, tantalum fluoride, cerium bromide, magnesium bromide, barium iodide, and magnesium iodide); perchlorates (for example, barium perchlorate and magnesium perchlorate). In sulfates, metal halides, and perchlorates, suitably employed are anhydrides.

<Protective Film and Protective Plate>

The aforesaid sealing film on the side which nips the organic layer and faces the support substrate or on the outside of the aforesaid sealing film, a protective or a protective plate may be arranged to enhance the mechanical strength of the element. Specifically, when sealing is achieved via the aforesaid sealing film, the resulting mechanical strength is not always high enough, whereby it is preferable to arrange the protective film or the protective plate described above. Usable materials for these include glass plates, polymer plate-films, and metal plate-films which are similar to those employed for the aforesaid sealing. However, in terms of light weight and a decrease in thickness, it is preferable to employ polymer films.

<Light Extraction>

It is generally known that an organic EL element emits light in the interior of the layer exhibiting the refractive index (being about 1.7-about 2.1) which is greater than that of air, whereby only about 15-about 20% of light generated in the light emitting layer is extracted.

This is due to the fact that light incident to an interface (being an interface of a transparent substrate to air) at an angle of θ which is at least critical angle is not extracted to the exterior of the element due to the resulting total reflection, or light is totally reflected between the transparent electrode or the light emitting layer and the transparent substrate, and light is guided via the transparent electrode or the light emitting layer, whereby light escapes in the direction of the element side surface.

Means to enhance the efficiency of the aforesaid light extraction include, for example, a method in which roughness is formed on the surface of a transparent substrate, whereby total reflection is minimized at the interface of the transparent substrate to air (U.S. Pat. No. 4,774,435), a method in which efficiency is enhanced in such a manner that a substrate results in light collection (JP-A No. 63-314795), a method in which a reflection surface is formed on the side of the element (JP-A No. 1-220394), a method in which a flat layer of a middle refractive index is introduced between the substrate and the light emitting body and an antireflection film is formed (JP-A No. 62-172691), a method in which a flat layer of a refractive index which is equal to or less than the substrate is introduced between the substrate and the light emitting body (JP-A No. 2001-202827), and a method in which a diffraction grating is formed between the substrate and any of the layers such as the transparent electrode layer or the light emitting layer (including between the substrate and the outside) (JP-A No. 11-283751).

In the present invention, it is possible to employ these methods while combined with the organic EL element of the present invention. Of these, it is possible to appropriately employ the method in which a flat layer of a refractive index which is equal to or less than the substrate is introduced between the substrate and the light emitting body and the method in which a diffraction grating is formed between the substrate and any of the layers such as the transparent electrode layer or the light emitting layer (including between the substrate and the outside).

By combining these means, the present invention enables the production of elements which exhibit higher luminance or excel in durability.

When a low refractive index medium of a thickness, which is greater than the wavelength of light, is formed between the transparent electrode and the transparent substrate, the extraction efficiency of light emitted from the transparent electrode to the exterior increases as the refractive index of the medium decreases.

As materials of the low refractive index layer, listed are, for example, aerogel, porous silica, magnesium fluoride, and fluorine based polymers. Since the refractive index of the transparent substrate is commonly about 1.5-about 1.7, the refractive index of the low refractive index layer is preferably at most approximately 1.5, but is more preferably at most 1.35.

Further, thickness of the low refractive index medium is preferably at least two times the wavelength in the medium. The reason is that when the thickness of the low refractive index medium reaches nearly the wavelength of light so that electromagnetic waves oozed via evernescent enter into the substrate, effects of the low refractive index layer are lowered.

The method in which the interface which results in total reflection or a diffraction grating is introduced in any of the media is characterized in that light extraction efficiency is significantly enhanced.

The above method works as follows. By utilizing properties of the diffraction grating capable of changing the light direction to the specific direction different from diffraction via so-called Bragg diffraction such as primary diffraction or secondary diffraction of the diffraction grating, of light emitted from the light emitting layer, light, which is not emitted to the exterior due to total reflection between layers, is diffracted via introduction of a diffraction grating between any layers or in a medium (in the transparent substrate and the transparent electrode) so that light is extracted to the exterior.

It is preferable that the introduced diffraction grating exhibits a two-dimensional periodic refractive index. The reason is as follows. Since light emitted in the light emitting layer is randomly generated to all directions, in a common one-dimensional diffraction grating exhibiting a periodic refractive index distribution only in a certain direction, light which travels to the specific direction is only diffracted, whereby light extraction efficiency is not sufficiently enhanced.

However, by changing the refractive index distribution to a two-dimensional one, light, which travels to all directions, is diffracted, whereby the light extraction efficiency is enhanced.

As noted above, a position to introduce a diffraction grating may be between any layers or in a medium (in a transparent substrate or a transparent electrode). However, a position near the organic light emitting layer, where light is generated, is desirous.

In this case, the cycle of the diffraction grating is preferably about ½-about 3 times the wavelength of light in the medium.

The preferable arrangement of the diffraction grating is such that the arrangement is two-dimensionally repeated in the form of a square lattice, a triangular lattice, or a honeycomb lattice.

<Light Collection Sheet>

Via a process to arrange a structure such as a micro-lens array shape on the light extraction side of the organic EL element of the present invention or via combination with a so-called light collection sheet, light is collected in the specific direction such as the front direction with respect to the light emitting element surface, whereby it is possible to enhance luminance in the specific direction.

In an example of the micro-lens array, square pyramids to realize a side length of 30 μm and an apex angle of 90 degrees are two-dimensionally arranged on the light extraction side of the substrate. The side length is preferably 10-100 μm. When it is less than the lower limit, coloration results due to generation of diffraction effects, while when it exceeds the upper limit, the thickness increases undesirably.

It is possible to employ, as a light collection sheet, for example, one which is put into practical use in the LED backlight of liquid crystal display devices. It is possible to employ, as such a sheet, for example, the luminance enhancing film (BEF), produced by Sumitomo 3M Limited.

As shapes of a prism sheet employed may be, for example, Δ shaped stripes of an apex angle of 90 degrees and a pitch of 50 μm formed on a base material, a shape in which the apex angle is rounded, a shape in which the pitch is randomly changed, and other shapes.

Further, in order to control the light radiation angle from the light emitting element, simultaneously employed may be a light diffusion plate-film. For example, it is possible to employ the diffusion film (LIGHT-UP), produced by Kimoto Co., Ltd.

<Preparation Method of Organic EL Element>

As one example of the preparation method of the organic EL element of the present invention, the preparation method of the organic EL element composed of anode/positive hole injection layer/positive hole transport layer/light emitting layer/electron transport layer/electron injection layer/cathode will be described.

Initially, a thin film composed of desired electrode substances, for example, anode substances is formed on an appropriate base material to reach a thickness of at most 1 μm but preferably 10-200 nm, employing a method such as vapor deposition or sputtering, whereby an anode is prepared.

Subsequently, on the above, formed are organic compound thin layers including a positive hole injection layer, a positive hole transport layer, a light emitting layer, a positive hole inhibition layer, an electron transport layer, and an electron injection layer, which are organic EL element materials.

Methods to form each of these layers include, as described above, a vapor deposition method and a wet process (a spin coating method, a casting method, an ink-jet method, and a printing method). In the present invention, in view of easy formation of a homogeneous film and rare formation of pin holes, preferred is film formation via the coating method such as the spin coating method, the ink-jet method, or the printing method.

As liquid media which are employed to dissolve or disperse organic metal complexes according to the present invention, employed may be, for example, ketones such as methyl ethyl ketone or cyclohexanone, fatty acid esters such as ethyl acetate, halogenated hydrocarbons such as dichlorobenzene, aromatic hydrocarbons such as toluene, xylene, mesitylene, and cyclohexylbenzene, aliphatic hydrocarbons such as cyclohexane, decaline, and dodecane, and organic solvents such as DMF or DMSO.

Further, with regard to dispersion methods, it is possible to achieve dispersion employing dispersion methods such as ultrasonic waves, high shearing force dispersion or media dispersion.

After forming these layers, a thin layer composed of cathode materials is formed on the above layers via a method such as vapor deposition or sputtering so that the film thickness reaches at most 1 μm, but is preferably in the range of 50-200 nm, whereby a cathode is arranged, and the desired organic EL element is prepared.

Further, by reversing the preparation order, it is possible to achieve preparation in order of a cathode, an electron injection layer, an electron transport layer, a light emitting layer, a positive hole transport layer, a positive hole injection layer, and an anode.

When direct current voltage is applied to the multicolor display device prepared as above, the anode is employed as +polarity, while the cathode is employed as −polarity. When 2-40 V is applied, it is possible to observe light emission. Further, alternating current voltage may be applied. The wave form of applied alternating current voltage is not specified.

<Application>

It is possible to employ the organic EL element of the present invention as display devices, displays, and various types of light emitting sources. Examples of light emitting sources include, but are not limited to lighting apparatuses (home lighting and car lighting), clocks, backlights for liquid crystals, sign advertisements, signals, light sources of light memory media, light sources of electrophotographic copiers, light sources of light communication processors, and light sources of light sensors.

It is effectively employed especially as backlights of liquid crystal display devices and lighting sources.

If needed, the organic EL element of the present invention may undergo patterning via a metal mask or an ink-jet printing method during film formation. When the patterning is carried out, only an electrode may undergo patterning, an electrode and a light emitting layer may undergo patterning, or all element layers may undergo patterning. During preparation of the element, it is possible to employ conventional methods.

Figure 4:
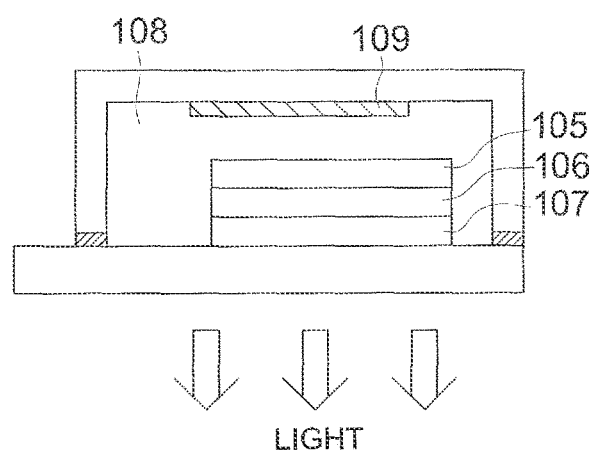
FIG. 4 is a schematic cross-sectional view of a lighting device.

Color of light emitted by the organic EL element of the present invention and compounds according to the present invention is specified as follows. In FIG. 4.16 on page 108 of "Shinpen Shikisai Kagaku Handbook (New Edition Color Science Handbook)" (edited by The Color Science Association of Japan, Tokyo Daigaku Shuppan Kai, 1985), values determined via a spectroradiometric luminance meter CS-1000 (produced by Konica Minolta Sensing Inc.) are applied to the CIE chromaticity coordinate, whereby the color is specified.

Further, when the organic EL element of the present invention is a white element, "white", as described herein, means that when 2-degree viewing angle front luminance is determined via the aforesaid method, chromaticity in the CIE 1931 Color Specification System is within the region of X=0.33±0.07 and Y=0.33±0.07.

EXAMPLES

The present invention will now be described with reference to examples, however the present invention is not limited thereto.

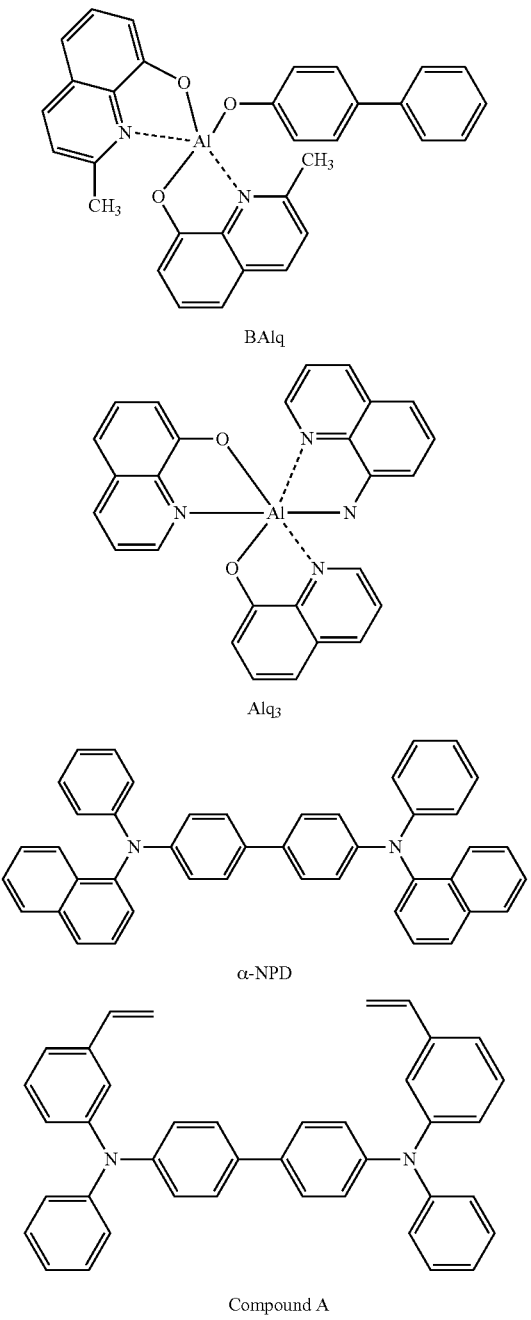

BAlq

Alq$_3$

α-NPD

Compound A

Example 1

Preparation of Organic EL Element 1-1

Patterning was applied to a substrate (NA45 produced by NH Techno Glass Corp.) on which a 100 nm film of ITO (indium tin oxide) was formed, as a anode, on the above 100 mm×100 mm×1.1 mm glass substrate. Thereafter, the above transparent support substrate provided with the ITO transparent electrode underwent ultrasonic washing with isopropyl alcohol, dried via desiccated nitrogen gas, and underwent UV ozone washing for 5 minutes.

The resulting transparent support substrate was fixed via the substrate holder of a commercial vacuum deposition apparatus. Separately, 200 mg of α-NPD was placed in a molybdenum resistance heating boat, 200 mg of H-1 as a host compound was placed in another molybdenum resistance heating boat, 200 mg of BAlq was placed in further another molybdenum resistance heating boat, 100 mg of Ir-1 was placed in yet another molybdenum resistance heating boat, 100 mg of Ir-12 was placed in yet another molybdenum resistance heating boat, and 200 mg of Alq$_3$ was placed in still yet another molybdenum resistance heating boat, and the resulting boats were fitted in the vacuum deposition apparatus.

Subsequently, after reducing the pressure of the vacuum tank to 4×10$^{-4}$ Pa, the aforesaid heating boat, in which α-NPD was placed, was heated via application of electric current and deposition was carried out onto the transparent support substrate at a deposition rate of 0.1 nm/second, whereby a 40 nm thick positive hole transport layer was arranged.

Further, the aforesaid heating boats in which H-1, Ir-12 and Ir-1 were placed respectively, were heated via application of electric current and vapor deposition rates of H-1 (emission host), Ir-12 (dopant) and Ir-1 (dopant) were controlled to be 100:5:0.6, whereby a 30 nm thick light emitting layer was arranged.

Further, the aforesaid heating boat, in which BAlq was placed, was heated via application of electric current and deposition was carried out onto the aforesaid light emitting layer at a deposition rate of 0.1 nm/second, whereby a 10 nm thick positive hole inhibition layer was arranged.

Further, the aforesaid heating boat, in which Alq$_3$ was placed, was heated via application of electric current and deposition was carried out onto the aforesaid positive hole inhibition layer at a deposition rate of 0.1 nm/second, whereby a 40 nm thick electron transport layer was arranged.

The substrate during deposition had a room temperature.

Subsequently, 0.5 nm lithium fluoride and 110 nm aluminum were deposited to form a cathode, whereby Organic EL Element 1-1 was prepared.

The non-light emitting surface of each of the organic EL elements was covered with a glass case, and a 300 μm thick glass substrate was employed as a sealing substrate. An epoxy based light curable type adhesive (LUXTRACK LC0629B produced by Toagosei Co., Ltd.) was employed in the periphery as a sealing material. The resulting one was superimposed on the aforesaid cathode to be brought into close contact with the aforesaid transparent support substrate, and curing and sealing were carried out via exposure of UV radiation onto the glass substrate side, whereby the lighting device shown in FIGS. 3 and 4 was formed, followed by evaluation.

Figure 3:
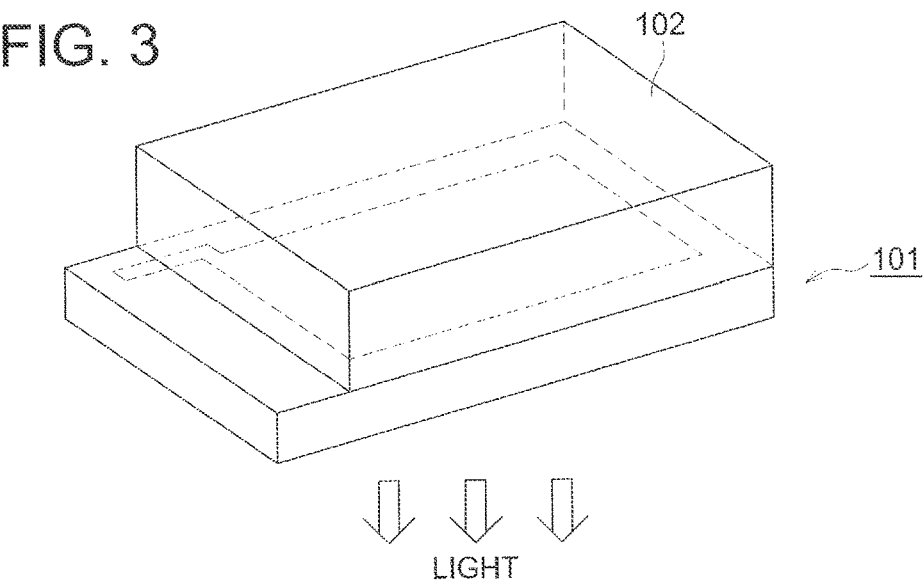
FIG. 3 is a schematic drawing of a lighting device.

FIG. 3 is a schematic view of a lighting device and Organic EL Element 101 is covered with glass cover 102

(incidentally, sealing by the glass cover was carried out in a globe box under nitrogen ambience (under an ambience of high purity nitrogen gas at a purity of at least 99.999%) so that Organic EL Element 101 was not brought into contact with atmosphere.

FIG. 4 is a cross-sectional view of a lighting device, and in FIG. 4, 105 represents a cathode, 106 represents an organic EL layer, and 107 represents a glass substrate fitted with a transparent electrode. Further, the interior of glass cover 102 is filled with nitrogen gas 108 and water catching agent 109 is provided.

<Preparation of Organic EL Elements 1-2 Through 1-12>

Organic EL Elements 1-2 through 1-12 were prepared in the same manner as Organic EL Element 1-1, except that the dopant material was replaced as is listed in Table 1.

<Evaluation of Organic EL Elements 1-1 Through 1-12>

Prepared Organic EL Elements 1-1 through 1-12 were evaluated. Table 1 shows the results.

<External Extraction Quantum Efficiency>

Constant electric current of 2.5 mA/cm$^2$ was applied to the prepared organic EL element at 23° C. under an ambience of desiccated nitrogen gas, and the external extraction quantum efficiency (%) was determined. A spectroradiometric luminance meter CS-1000 (produced by Konica Minolta Sensing Inc.) was employed for the above determination.

The external extraction quantum efficiency in Table 1 was represented by the relative value when the external extraction quantum efficiency of Organic EL Element 1-1 was set to be 100.

(Lifetime)

When Organic EL element was driven at a constant electric current of 2.5 mA/cm$^2$, the time which was required for a decease in one half of the luminance immediately after the initiation of light emission (being the initial luminance) was determined, and the resulting value was employed as an index of the lifetime in terms of a half lifetime ($\tau 0.5$).

A spectroradiometric luminance meter CS-1000 (produced by Konica Minolta Sensing Inc.) was employed for the above determination. Further, the lifetime in Table 1 is represented by a relative value when the lifetime of Organic EL Element 1-1 was set to be 100. Table 1 shows the results.

(Color Shift)

The coordinate values in the CIE color coordinate of Organic EL element prior to the lifetime evaluation and after subjected to the lifetime evaluation were measured. The distance in x and y coordinates of these two values were determined as a relative value when the distance of Organic EL Element 1-1 was set to be 100.

The obtained results are shown in Table 1.

TABLE 1

| Element No. | Light emitting dopant | Vapor evaporation ratio | Quantum efficiency | Life-time | Color shift | Re-marks |
|---|---|---|---|---|---|---|
| 1-1 | Ir-12/Ir-1 | 5/0.6 | 100 | 100 | 100 | Comp. |
| 1-2 | Ir-12/Ir-14 | 5/1.6 | 90 | 95 | 102 | Comp. |
| 1-3 | Ir-16/Ir-1 | 5/0.6 | 101 | 130 | 90 | Comp. |
| 1-4 | (1)/Ir-1 | 5/0.6 | 150 | 230 | 20 | Inv. |
| 1-5 | (1)/Ir-14 | 5/0.6 | 148 | 240 | 25 | Inv. |
| 1-6 | A-81/Ir-14 | 5/0.6 | 162 | 289 | 15 | Inv. |
| 1-7 | A-97/Ir-17 | 5/0.6 | 155 | 210 | 17 | Inv. |
| 1-8 | (4)/Ir-1 | 5/0.6 | 143 | 205 | 23 | Inv. |
| 1-9 | A-100/Ir-1 | 5/0.6 | 132 | 222 | 21 | Inv. |

TABLE 1-continued

| Element No. | Light emitting dopant | Vapor evaporation ratio | Quantum efficiency | Life-time | Color shift | Re-marks |
|---|---|---|---|---|---|---|
| 1-10 | C-81/Ir-1 | 5/0.6 | 128 | 198 | 31 | Inv. |
| 1-11 | A-203/Ir-1 | 5/0.6 | 138 | 252 | 18 | Inv. |
| 1-12 | (3)/Ir-1 | 5/0.6 | 133 | 203 | 35 | Inv. |

Inv.: present invention, Comp.: comparative example

As can be seen from Table 1, Organic EL elements of the present invention achieved high external extraction quantum efficiency, and long lifetime, and small color shift compared with comparative examples.

Example 2

Preparation of Organic EL Element 2-1

The electrode of the transparent electrode substrate underwent patterning in an area of 20 mm×20 mm, and, a 25 nm thick α-NPD film was formed thereon as a positive hole injection/transport layer in the same manner as Example 1. Further, electric current was independently applied to each of the aforesaid heating boat in which H-1 was placed and the boat in which Ir-14 was placed, and vapor deposition was carried out to result in a film thickness of 12 nm, while regulating the vapor deposition rate of H-1 (light emitting host) to Ir-14 (light emitting dopant) to be 100:5, respectively, whereby a red light emitting layer was arranged.

Further, electric current was applied to heating boat containing Ir-1 while regulating the vapor deposition rate of H-1 to Ir-1 to be 100:6, respectively, and resulting in a film thickness of 10 nm, whereby a green light emitting layer was arranged.

Further, by regulating the vapor deposition rate of H-1 to Ir-12 to be 100:6, respectively, vapor deposition was carried out to make a film having a thickness of 15 nm, whereby a blue light emitting layer was arranged.

Subsequently, a 10 nm BAlq film was formed, whereby a positive hole inhibition layer was arranged. Further, a 40 nm Alq$_3$ film was formed, whereby an electron transport layer was arranged.

Subsequently, in the same manner as Example 1, square shaped perforated stainless steel mask having the almost same shape as the transparent electrode was arranged on the electron transport layer, and a 0.5 nm lithium fluoride film as a cathode buffer layer and a 150 nm aluminum film as a cathode were formed via vapor deposition.

The obtained element was provided with a sealing container prepared in the same manner and having the same structure as Example 1, and Organic EL element 2-1 was prepared.

<Preparation of Organic EL Elements 2-2>

Organic EL Elements 2-2 was prepared in the same manner as Organic EL Element 2-1, except that the light emitting dopant Ir-12 was replaced with A-81 which is a phosphorescence emitting metal complex of the present invention.

The obtained Organic EL Elements 2-1 and 2-2 exhibited almost white light. After making them emitted for a prolonged time, the light emitted from Organic EL Elements 2-1 increased yellow hue, while the light emitted from Organic EL Elements 2-2 was not changed.

Example 3

Preparation of White Light Emitting Element and White Light Lighting Device

Patterning was applied to a substrate (NA45 produced by NH Techno Glass Corp.) on which a 100 nm film of ITO (indium tin oxide) was formed, as a anode, on the above 100 mm×100 mm×1.1 mm glass substrate. Thereafter, the above transparent support substrate provided with the ITO transparent electrode underwent ultrasonic washing with isopropyl alcohol, dried via desiccated nitrogen gas, and underwent UV ozone washing for 5 minutes.

On the transparent support substrate thus prepared was applied a 70% solution of poly(3,4-ethylenedioxythiphene)-polystyrene sulfonate (PEDOT/PSS, Baytron P Al 4083 made by Bayer AG.) diluted with water by using a spin coating method (3,000 rpm, for 30 seconds) to form a film and then it was dried at 200° C. for one hour. A first positive hole transport layer having thickness of 30 nm was prepared.

The aforesaid substrate was transferred under an atmosphere of nitrogen, and a solution containing 50 mg of Compound A and 10 ml of toluene was applied on the first positive hole transport layer by using a spin coating method (1,000 rpm, for 30 seconds) to form a film. The film was irradiated with UV rays for 180 seconds so as to achieve photopolymerization and cross-linking, and then it was subjected to a vacuum drying at 60° C. A second positive hole transport layer was thus prepared.

Then, by using a solution of H-5 (60 mg), Exemplified compound (80) (3.0 mg) and Ir-9 (3.0 mg) dissolved in 6 ml of toluene, a film was formed by using a spin coating method (1,000 rpm, for 30 seconds). A light emitting layer was thud prepared.

Next, the aforesaid substrate was fixed in a substrate holder of a vacuum deposition apparatus, and then, 200 mg of BAlq was placed in a molybdenum resistance heating boat and it was fitted in the vacuum deposition apparatus.

Subsequently, after reducing the pressure of the vacuum tank to $4 \times 10^{-4}$ Pa, the aforesaid heating boat, in which BAlq was placed, was heated via application of electric current and deposition was carried out onto the transparent support substrate at a deposition rate of 0.1 nm/second, whereby a 40 nm thick positive hole transport layer was arranged.

The substrate during deposition had a room temperature.

Subsequently, 0.5 nm lithium fluoride and 110 nm aluminum were deposited to form a cathode, whereby a white light emitting organic EL element was prepared.

An electric current was applied to the organic EL element thus prepared. It was proved that the organic EL element emitted a light of almost white and it can be used for a lighting device.

The invention claimed is:

1. A method for producing an organic electroluminescent element comprising a light emitting layer sandwiched between an anode and a cathode,
the method comprising a step of:
preparing the light emitting layer with a wet process using an organic solvent selected from the group consisting of a ketone, a fatty acid ester, a halogenated hydrocarbon, an aromatic hydrocarbon, an aliphatic hydrocarbon, dimethylformamide (DMF) and dimethylsulfoxide (DMSO),
wherein the light emitting layer emits a white light and contains at least two phosphorescence emitting metal complexes, provided that one of the phosphorescence emitting metal complexes has a partial structure represented by one of the following Formulas (1) to (4):

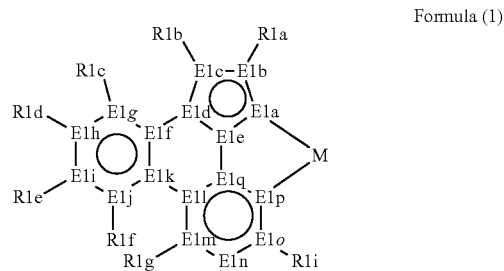

Formula (1)

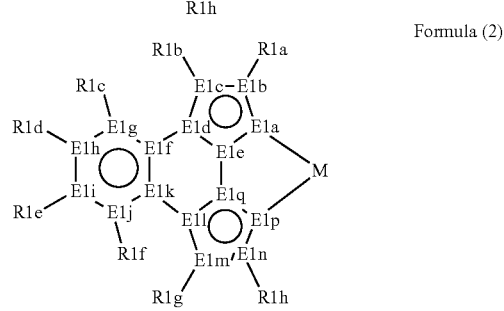

Formula (2)

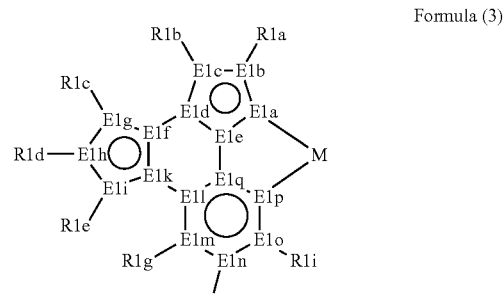

Formula (3)

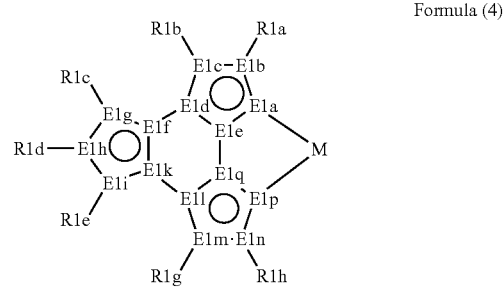

Formula (4)

wherein,
in Formula (1): E1a represents a nitrogen atom; E1b and E1c represent a carbon atom, a nitrogen atom, an oxygen atom or a sulfur atom; E1d and E1e represent a carbon atom or a nitrogen atom; E1f represents a carbon atom; E1g to E1j represent a carbon atom or a nitrogen atom; E1k and E1l represent a carbon atom; E1m to E1o represent a carbon atom or a nitrogen atom; E1p and E1q represent a carbon atom; R1a and R1b represent a hydrogen atom or a substituent when E1b and E1c represent the carbon atom or the nitrogen atom having a bond of —N<, R1a and R1b represent null when E1b and E1c represent the nitrogen atom having a bond of —N═, the oxygen atom or the sulfur atom; and
R1c to R1i represent a hydrogen atom or a substituent; and M represents a transition metal of Group 8 to Group 10 in the periodic table, in Formula (2): E1a represents a nitrogen atom; E1b and E1c represent a carbon atom, a nitrogen atom, an oxygen atom or a sulfur atom; E1d and E1e represent a carbon atom or a nitrogen atom; E1f represents a carbon atom; E1g to E1j represent a carbon atom or a nitrogen atom; E1k represents a carbon atom; E1l represents a carbon atom or a nitrogen atom; E1m and E1n represent a carbon atom, a nitrogen atom, an oxygen atom or a sulfur atom; E1p represents a carbon atom; E1q represents a carbon atom or nitrogen atom;

R1a, R1b, R1g and R1h represent a hydrogen atom or a substituent when E1b, E1c, E1m and E1n represent the carbon atom or the nitrogen atom having a bond of —N<, R1a, R1b, R1g and R1h represent null when E1b, E1c, E1m and E1n represent the nitrogen atom having a bond of —N=, the oxygen atom or the sulfur atom; and R1c to R1f represent a hydrogen atom or a substituent; and M represents a transition metal of Group 8 to Group 10 in the periodic table, in Formula (3): E1a represents a nitrogen atom; E1b and E1c represent a carbon atom, a nitrogen atom, an oxygen atom or a sulfur atom; E1d and E1e represent a carbon atom or a nitrogen atom; E1f and E1k represent a carbon atom or a nitrogen atom; E1g to E1i represent a carbon atom, a nitrogen atom an oxygen atom or a sulfur atom; E1l represents a carbon atom; E1m to E1o represent a carbon atom or a nitrogen atom; E1p and E1q represent a carbon atom;

R1a, R1b, R1c, R1d and R1e represent a hydrogen atom or a substituent when E1b, E1c, E1g, E1h and E1i represent the carbon atom or the nitrogen atom having a bond of —N<, R1a, R1b, R1c, R1d and R1e represent null when E1b, E1c, E1g, E1h and E1i represent the nitrogen atom having a bond of —N=, the oxygen atom or the sulfur atom; and R1g to R1i represent a hydrogen atom or a substituent; and M represents a transition metal of Group 8 to Group 10 in the periodic table, in Formula (4): E1a represents a nitrogen atom; E1b and E1c represent a carbon atom, a nitrogen atom, an oxygen atom or a sulfur atom; E1d and E1e represent a carbon atom or a nitrogen atom; E1f and E1k represent a carbon atom or a nitrogen atom; E1g to E1i represent a carbon atom, a nitrogen atom, an oxygen atom or a sulfur atom; E1l represents a carbon atom or a nitrogen atom; E1m and E1n represent a carbon atom, a nitrogen atom, an oxygen atom or a sulfur atom; E1p represents a carbon atom; E1q represents a carbon atom or nitrogen atom;

R1a to R1e, R1g and R1h represent a hydrogen atom or a substituent when E1b, E1c, E1g, E1h, E1i, E1m and E1n represent the carbon atom or the nitrogen atom having a bond of —N<, R1a to R1e, R1g and R1h represent null when E1b, E1c, E1g, E1h, E1i, E1m and E1n represent the nitrogen atom having a bond of —N=, the oxygen atom or the sulfur atom; and M represents a transition metal of Group 8 to Group 10 in the periodic table, wherein the two phosphorescence emitting metal complexes each emits a light of a different hue, and the phosphorescence emitting metal complex having the partial structure represented by one of Formulas (1) to (4) emits a blue light, and wherein a difference of highest occupied molecular orbitals (HOMO) of the at least two phosphorescence emitting metal complexes is 0.5 eV or less.

2. The method for producing the organic electroluminescent element of claim 1,
wherein the light emitting layer comprises at least two light emitting layers, each of the at least two light emitting layers is made by the wet process, and a different one of the at least two phosphorescence emitting metal complexes is contained in a different one of the at least two light emitting layers.

3. The method for producing the organic electroluminescent element of claim 1,
wherein M represents platinum or iridium.

4. A display device comprising the organic electroluminescent element produced by the method of claim 1.

5. A lighting device comprising the organic electroluminescent element produced by the method of claim 1.

6. An organic electroluminescent element comprising a light emitting layer sandwiched between an anode and a cathode,
wherein the light emitting layer is prepared with a wet process using an organic solvent selected from the group consisting of a ketone, a fatty acid ester, a halogenated hydrocarbon, an aromatic hydrocarbon, an aliphatic hydrocarbon, dimethylformamide (DMF) and dimethylsulfoxide (DMSO),
wherein the light emitting layer emits a white light and contains at least two phosphorescence emitting metal complexes, provided that one of the phosphorescence emitting metal complexes has a partial structure represented by one of the following Formulas (1) to (4):

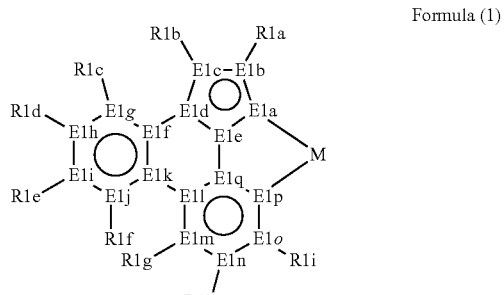

Formula (1)

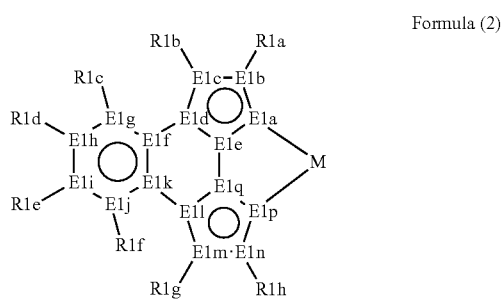

Formula (2)

Formula (3)

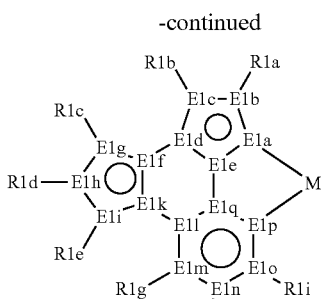

Formula (4)

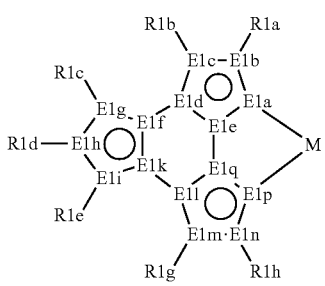

wherein, in Formula (1): E1a represents a nitrogen atom; E1b and E1c represent a carbon atom, a nitrogen atom, an oxygen atom or a sulfur atom; E1d and E1e represent a carbon atom or a nitrogen atom; E1f represents a carbon atom; E1g to E1j represent a carbon atom or a nitrogen atom; E1k and E1l represent a carbon atom; E1m to E1o represent a carbon atom or a nitrogen atom; E1p and E1q represent a carbon atom; R1a and R1b represent a hydrogen atom or a substituent when E1b and E1c represent the carbon atom or the nitrogen atom having a bond of —N<, R1a and R1b represent null when E1b and E1c represent the nitrogen atom having a bond of —N=, the oxygen atom or the sulfur atom; and R1c to R1i represent a hydrogen atom or a substituent; and M represents a transition metal of Group 8 to Group 10 in the periodic table, in Formula (2): E1a represents a nitrogen atom; E1b and E1c represent a carbon atom, a nitrogen atom, an oxygen atom or a sulfur atom; E1d and E1e represent a carbon atom or a nitrogen atom; E1f represents a carbon atom; E1g to E1j represent a carbon atom or a nitrogen atom; E1k represents a carbon atom; E1l represents a carbon atom or a nitrogen atom; E1m and E1n represent a carbon atom, a nitrogen atom, an oxygen atom or a sulfur atom; E1p represents a carbon atom; E1q represents a carbon atom or nitrogen atom;

R1a, R1b, R1g and R1h represent a hydrogen atom or a substituent when E1b, E1c, E1m and E1n represent the carbon atom or the nitrogen atom having a bond of —N<, R1a, R1b, R1g and R1h represent null when E1b, E1c, E1m and E1n represent the nitrogen atom having a bond of —N=, the oxygen atom or the sulfur atom; and R1c to R1f represent a hydrogen atom or a substituent; and M represents a transition metal of Group 8 to Group 10 in the periodic table, in Formula (3): E1a represents a nitrogen atom; E1b and E1c represent a carbon atom, a nitrogen atom, an oxygen atom or a sulfur atom; E1d and E1e represent a carbon atom or a nitrogen atom; E1f and E1k represent a carbon atom or a nitrogen atom; E1g to E1i represent a carbon atom, a nitrogen atom, an oxygen atom or a sulfur atom; E1l represents a carbon atom; E1m to E1o represent a carbon atom or a nitrogen atom; E1p and E1q represent a carbon atom;

R1a, R1b, R1c, R1d and R1e represent a hydrogen atom or a substituent when E1b, E1c, E1g, E1h and E1i represent the carbon atom or the nitrogen atom having a bond of —N<, R1a, R1b, R1c, R1d and R1e represent null when E1b, E1c, E1g, E1h and E1i represent the nitrogen atom having a bond of —N=, the oxygen atom or the sulfur atom; and R1g to R1i represent a hydrogen atom or a substituent; and M represents a transition metal of Group 8 to Group 10 in the periodic table, in Formula (4): E1a represents a nitrogen atom; E1b and E1c represent a carbon atom, a nitrogen atom, an oxygen atom or a sulfur atom; E1d and E1e represent a carbon atom or a nitrogen atom; E1f and E1k represent a carbon atom or a nitrogen atom; E1g to E1i represent a carbon atom, a nitrogen atom, an oxygen atom or a sulfur atom; E1l represents a carbon atom or a nitrogen atom; E1m and E1n represent a carbon atom, a nitrogen atom, an oxygen atom or a sulfur atom; E1p represents a carbon atom; E1q represents a carbon atom or nitrogen atom;

R1a to R1e, R1g and R1h represent a hydrogen atom or a substituent when E1b, E1c, E1g, E1h, E1i, E1m and E1n represent the carbon atom or the nitrogen atom having a bond of —N<, R1a to R1e, R1g and R1h represent null when E1b, E1c, E1g, E1h, E1i, E1m and E1n represent the nitrogen atom having a bond of —N=, the oxygen atom or the sulfur atom; and M represents a transition metal of Group 8 to Group 10 in the periodic table, wherein the two phosphorescence emitting metal complexes each emits a light of a different hue, and the phosphorescence emitting metal complex having the partial structure represented by one of Formulas (1) to (4) emits a blue light, and wherein a difference of highest occupied molecular orbitals (HOMO) of the at least two phosphorescence emitting metal complexes is 0.5 eV or less.

* * * * *